(12) United States Patent
Hinner et al.

(10) Patent No.: US 10,526,384 B2
(45) Date of Patent: Jan. 7, 2020

(54) INTERLEUKIN-17A-SPECIFIC AND INTERLEUKIN-23-SPECIFIC BINDING POLYPEPTIDES AND USES THEREOF

(71) Applicant: PIERIS PHARMACEUTICALS GMBH, Freising-Weihenstephan (DE)

(72) Inventors: Marlon Hinner, Munich (DE); Laurent Audoly, Toulouse (FR); Martin Huelsmeyer, Roemerberg (DE); Kristian Jensen, Vienna (AT); Gabriele Matschiner, Munich (DE); Shane Olwill, Freising (DE); Alexander Wiedenmann, Neufahm bei Freising (DE); Andrea Allersdorfer, Geisenhausen (DE)

(73) Assignee: Pieris Pharmaceuticals GmbH, Freising-Weihenstephan (DE)

( * ) Notice: Subject to any disclaimer, the term of this patent is extended or adjusted under 35 U.S.C. 154(b) by 0 days.

(21) Appl. No.: 14/442,924

(22) PCT Filed: Nov. 20, 2013

(86) PCT No.: PCT/EP2013/074224
§ 371 (c)(1),
(2) Date: May 14, 2015

(87) PCT Pub. No.: WO2014/076321
PCT Pub. Date: May 22, 2014

(65) Prior Publication Data
US 2015/0344538 A1  Dec. 3, 2015

Related U.S. Application Data

(60) Provisional application No. 61/727,988, filed on Nov. 19, 2012.

(30) Foreign Application Priority Data

Mar. 26, 2013  (EP) ..................... 13001538

(51) Int. Cl.
| | | |
|---|---|---|
| A61K 38/17 | (2006.01) | |
| C07K 14/47 | (2006.01) | |
| G01N 33/68 | (2006.01) | |
| C07K 14/54 | (2006.01) | |
| A61K 38/16 | (2006.01) | |
| C07K 14/00 | (2006.01) | |
| C07K 19/00 | (2006.01) | |
| A61K 38/00 | (2006.01) | |

(52) U.S. Cl.
CPC .......... *C07K 14/4703* (2013.01); *A61K 38/16* (2013.01); *C07K 14/00* (2013.01); *C07K 14/47* (2013.01); *C07K 14/54* (2013.01); *C07K 19/00* (2013.01); *G01N 33/6869* (2013.01); *A61K 38/00* (2013.01); *C07K 2318/20* (2013.01); *C07K 2319/00* (2013.01); *G01N 2333/54* (2013.01)

(58) Field of Classification Search
None
See application file for complete search history.

(56) References Cited

U.S. PATENT DOCUMENTS

| | | |
|---|---|---|
| 5,728,553 A | 3/1998 | Goodey et al. |
| 5,849,576 A | 12/1998 | Skerra et al. |
| 6,099,517 A | 8/2000 | Daugherty |
| 6,103,493 A | 8/2000 | Skerra et al. |
| 6,123,936 A | 9/2000 | Platz et al. |
| 6,177,074 B1 | 1/2001 | Glue et al. |
| 6,403,564 B1 | 6/2002 | Ganguly et al. |
| 6,500,930 B2 | 12/2002 | Adamson |
| 6,620,413 B1 | 9/2003 | De Sauvage et al. |
| 6,696,245 B2 | 2/2004 | Winter et al. |
| 7,250,297 B1 | 7/2007 | Beste et al. |
| 7,252,998 B2 | 8/2007 | Skerra et al. |

(Continued)

FOREIGN PATENT DOCUMENTS

| | | |
|---|---|---|
| DE | 4417598 A1 | 12/1995 |
| DE | 19641876 A1 | 4/1998 |

(Continued)

OTHER PUBLICATIONS

Pieris AG's presentation: Pieris Presents Data and Reveals Targets for Anticalin® Bispecific PRS-190 at European Antibody Congress (Nov. 29, 2012.*
Hohlbaum and Skerra, "Anticalins (R): the lipocalin family as a novel protein scaffold for the development of next-generation immunotherapies", Expert Review of Clinical Immunology, Future Drugs Ltd., vol. 3, No. 4, pp. 491-501, 2007.
International Search Report dated Apr. 30, 2014 issued in PCT/EP2013/074224.
Schlehuber and Skerra, "Anticalins as an alternative to antibody technology," Expert Opinion on Biological Therapy, vol. 5., No. 11, pp. 1453-1462, Jan. 2005.
Skerra, "Alternative binding proteins: Anticalins—harnessing the structural plasticity of the lipocalin ligand pocket to engineer novel binding activites," FEBS Journal, vol. 275, No. 11, pp. 2677-2683, Jun. 2008.

(Continued)

*Primary Examiner* — Dong Jiang
(74) *Attorney, Agent, or Firm* — Brenda H. Jarrell; Brian E. Reese; Choate, Hall & Stewart, LLP

(57) ABSTRACT

The present invention relates to novel, specific-binding therapeutic and/or diagnostic polypeptides directed against the target of Swiss Prot Q16552 and novel, specific-binding therapeutic and/or diagnostic polypeptides directed against the target of Swiss Prot Q9NPF7. In addition, the present invention relates to novel, specific-binding therapeutic and/or diagnostic polypeptides directed against one or both of Swiss Prot Q16552 and Swiss Prot Q9NPF7. The invention also relates to nucleic acid molecules encoding such polypeptides and to methods for generation of such polypeptides and nucleic acid molecules. In addition, the invention is directed to compositions comprising the polypeptides, and therapeutic and/or diagnostic uses of these polypeptides.

16 Claims, 26 Drawing Sheets

Figure 1:
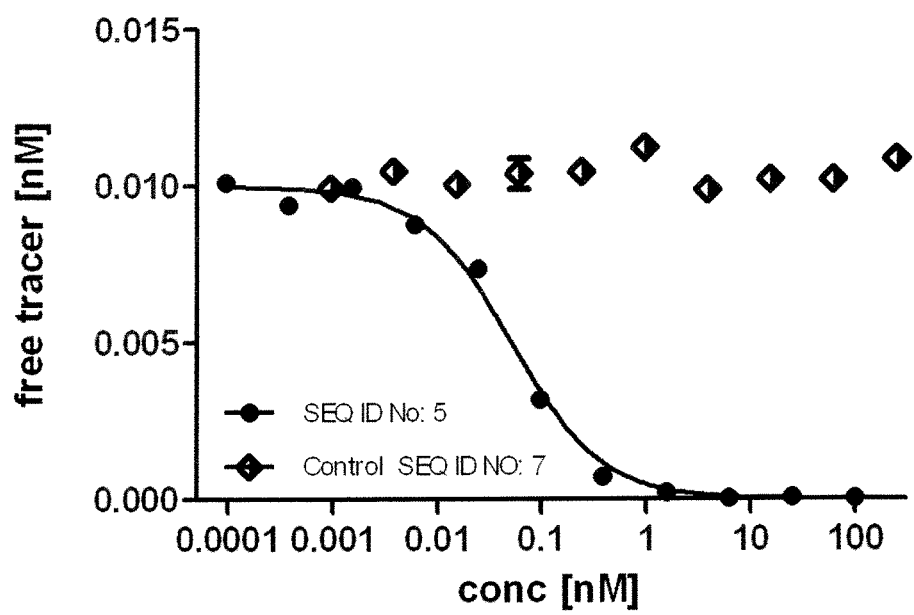

Specification includes a Sequence Listing.

(56) References Cited

U.S. PATENT DOCUMENTS

| | | | | |
|---|---|---|---|---|
| 8,313,924 | B2* | 11/2012 | Jensen | C07K 14/47 |
| | | | | 435/320.1 |
| 8,986,951 | B2* | 3/2015 | Hohlbaum | C07K 14/435 |
| | | | | 435/320.1 |
| 9,051,382 | B2 | 6/2015 | Trentmann et al. | |
| 9,260,492 | B2 | 2/2016 | Matschiner et al. | |
| 9,549,968 | B2 | 1/2017 | Skerra et al. | |
| 2003/0069395 | A1 | 4/2003 | Sato et al. | |
| 2006/0058510 | A1 | 3/2006 | Skerra et al. | |
| 2006/0088908 | A1 | 4/2006 | Skerra et al. | |
| 2013/0079286 | A1 | 3/2013 | Skerra et al. | |
| 2017/0107266 | A1 | 4/2017 | Hinner et al. | |
| 2017/0114109 | A1 | 4/2017 | Skerra et al. | |
| 2017/0166615 | A1 | 6/2017 | Matschiner et al. | |
| 2017/0369542 | A1 | 12/2017 | Trentmann et al. | |
| 2018/0016312 | A1 | 1/2018 | Bel Aiba et al. | |
| 2018/0141988 | A1 | 5/2018 | Hinner et al. | |
| 2018/0148484 | A1 | 5/2018 | Hinner et al. | |

FOREIGN PATENT DOCUMENTS

| | | |
|---|---|---|
| DE | 19742706 A1 | 4/1999 |
| DE | 19926068 C1 | 1/2001 |
| EP | 0 330 451 A2 | 8/1989 |
| EP | 0 361 991 A2 | 4/1990 |
| JP | 2005503829 A | 2/2005 |
| JP | 2007284351 A | 11/2007 |
| WO | WO-96/23879 A1 | 8/1996 |
| WO | WO-98/16873 A1 | 4/1998 |
| WO | WO-99/16873 A1 | 4/1999 |
| WO | WO-99/064016 A1 | 12/1999 |
| WO | WO-00/075308 A1 | 12/2000 |
| WO | WO-03/029462 A1 | 4/2003 |
| WO | WO-03/029463 A2 | 4/2003 |
| WO | WO-03/029471 A1 | 4/2003 |
| WO | WO-2005/019254 A1 | 3/2005 |
| WO | WO-2005/019255 A1 | 3/2005 |
| WO | WO-2005/019256 A2 | 3/2005 |
| WO | WO-2006/056464 A2 | 6/2006 |
| WO | WO-2007/038619 A2 | 4/2007 |
| WO | WO-2007/147019 A2 | 12/2007 |
| WO | WO-2007/149032 A1 | 12/2007 |
| WO | WO-2008/103432 A1 | 8/2008 |
| WO | WO-2009/043933 A1 | 4/2009 |
| WO | WO-2009/052390 A1 | 4/2009 |
| WO | WO-2009/156456 A1 | 12/2009 |
| WO | WO-2012/156219 A1 | 11/2012 |
| WO | WO-2014/076321 A1 | 5/2014 |

OTHER PUBLICATIONS

Skerra, "Anticalins as alternative binding proteins for therapeutic use," Current Opinion in Molecular Therapeutics, Current Drugs, vol. 9, No. 4, pp. 336-344, Aug. 2007.
Skerra, "Anticalins: a new class of engineered ligand-binding proteins with antibody-like properties", Reviews in Molecular Biotechnology, vol. 74, No. 4, pp. 257-275, Jun. 2001.
Weiss and Lowman, "Anticalins versus antibodies: made to order binding proteins for small molecules," Chemistry and Biology, Current Biology, vol. 7, No. 8, Aug. 2000.
"Chain A Crystal Structure of Siderocalin (Ngal, Lipocalin 2) Complexed With Trencam-3,2-Hopo, A Cepabactin Analogue," GenBank Accession No. 1X71_A, Sep. 24, 2008.
Altschul, S. et al., Gapped BLAST and PSI-BLAST: a new generation of protein database search programs, Nucl. Acids Res.. 1997, 25(17):3389-3402.
Amstutz, P. et al., In vitro display technologies: novel developments and applications, Curr. Opin. Biotechnol., 2001, 12:400-405.
Bachmann, Barbara J., Linkage Map of *Escherichia coli* K-12. Edition 8, Microbial. Rev., Jun. 1990, 54(2):130-197.
Beck, et al., Nucleotide Sequence and Genome Organisation of Filamentous Bacteriophages f1 and fd, Gene, vol. 16, pp. 35-58, 1981.
Beste, G. et al., Small antibody-like proteins with prescribed ligand specificities derived from the lipocalin fold, Proc. Natl. Acad. Sci. USA, Mar. 1999, 96:1898-1903.
Bittker, J. et al., Nucleic acid evolution and minimization by nonhomologous random recombination, Nat. Biotechnol., Oct. 2002, 20:1024-1029.
Bos et al., OctoDEX.TM.—Controlled Release of Pharmaceutical Proteins from Hydrogels, Business Briefing: Pharmatech, 2003:1-6.
Breustedt, D. et al., Comparative ligand-binding analysis of ten human lipocalins, Biochim. Biophys. Acta, 2006, 1764:161-173.
Broders, O et al., Hyperphage. Improving antibody presentation in phage display, Methods Mol. Biol., 2003, 205:295-302.
Brody et al., Active and Passive Immunotherapy for Neurodegenerative Disorders, Annu. Rev. Neurosci., 2008, 31:175-193.
Bruckdorfer, T., et al., From Production of Peptides in Milligram Amounts for Research to Multi-Tons Quantities for Drugs of the Future, Curr. Pharm. Biotechnol., 2004, 5:29-43.
Bullock, W. et al., XL1-Blue: A High Efficiency Plasmid Transforming recA *Escherichia coli* Strain with Beta-Galactosidase Selection, Biotechniques, 1987, 5(4):376-378.
Bundgaard, J.R. et al., Molecular Cloning and Expression of A cDNA Encode NGAL: A Lipocalin Expressed in Human Neutrophils, Biochemical and Biophysical Research Communications, Aug. 15, 1994, pp. 1468-1475, vol. 202, No. 3, XP002036694.
Carnemolla et al., Phage Antibodies with PAN-Species Recognition of the Oncofoetal Angiogenesis Marker Fibronectin ED-B Domain, Int. J. Cancer, 1996, 68:397-405.
Chan et al., The primary structure of rat α 2μ globulin-related protein, Nucleic Acids Research, vol. 16, No. 23, pp. 11368, 1988.
Coles, et al., The Solution Structure and Dynamics of Human Neutrophil Gelatinase-associated Lipocalin, J. Mol. Biol., vol. 289, pp. 139-157, 1999.
Dennis, M. et al., Albumin Binding as a General Strategy for Improving the Pharmacokinetics of Proteins, J. Biol. Chem., Sep. 20, 2002, 277(38):35035-35043.
Dodel et al., Immunotherapy for Alzheimer's disease, Lancet Neurology, Apr. 2003, 2:215-220.
Ebbinghaus et al., Diagnostic and Therapeutic Applications of Recombinant Antibodies: Targeting the Extra-Domain B of Fibronectin, A Marker of Tumor Angiogenesis, Curr. Pharm. Des., 2004, 10:1537-1549.
Fitzgerald, Kevin, In Vitro Display Technologies—New Tools for Drug Discovery, Reviews, vol. 5, No. 6, pp. 253-258, Jun. 2000.
Fling, S. and Gregerson, D., Peptide and Protein Molecular Weight Determination by Electrophoresis Using a High-Molarity Tris Buffer System without Urea, Anal. Biochem., 1986, 155:83-88.
Flower, Darren R., The lipocalin protein family: structure and function, Biochem. J., 1996, 318:1-14.
Frank, Ronald, The SPOT-synthesis technique Synthetic Peptide arrays on membrane supports—principles and applications, J. Immunol. Methods, 2002, 267:13-26.
Fuerteges, F. and Abuchowski, A., The Clinical Efficacy of Poly(Ethylene Glycol)—Modified Proteins,: J. Control. Release, 1990, 11:139-148.
Fujii, Phage display and beyond antibody—molecular target by antibody molecule, Seikagaku, 2010, vol. 82, No. 8, pp. 710-726, Abstract.
Gaillard, P. et al., Diphtheria toxin receptor-targeted brain drug delivery, International Congress Series., 2005, 1277:185-198.
Gaillard, P. et al., Targeted delivery across the blood-brain barrier, Expert Opin Drug Deliv., 2005, 2(2):299-309.
Gasteiger et al., ExPASy: the proteomics server for in-depth protein knowledge and analysis, Nucleic Acids Res., 2003, 31(13):3784-3788.
Goetz, D. et al., Ligand Preference Inferred from the Structure of Neutrophil Gelatinase Associated Lipocalin, Biochemistry, 2000, 39:1935-1941.
Gronwall et al., Selection and characterization of Affibody ligands binding to Alzheimer amyloid β peptides, J. Biotechnol., 2007, 128:162-183.
Haass et al., Soluble protein oligomers in neurodegeneration: lessons from the Alzheimer's amyloid β-peptide, Nat. Rev. Mol. Cell. Biol., Feb. 2007, 8:101-112.

(56) References Cited

OTHER PUBLICATIONS

Hengen, Paul N., Methods and Reagents, Trends Biochem. Sci., vol. 21, pp. 75-76, 1996.
Hoess, Ronald H., Phage Display of Peptides and Protein Domains, Structural Biology, vol. 3, pp. 572-279, 1993.
Holzfeind, P. et al., Structural Organization of the Gene Encoding the Human Lipocalin Tear Prealbumin and Synthesis of the Recombinant Protein in *Escherichia coli*, Gene, vol. 139, pp. 177-183, 1994.
Hortschansky et al., The aggregation Kinetics of Alzheimer's β-amyloid peptide is controlled by stochastic nucleation, Protein Sci., 2005, 14:1753-1759.
Hoyer, W. et al., Stabilization of a β-hairpin in monomeric Alzheimer's amyloid-β peptide inhibits amyloid formation, Proc. Natl. Acad. Sci. USA, Apr. 1, 2008, 105(13):5099-5104.
International Search report issued in Application No. PCT/EP2015/061034 dated Dec. 21, 2015.
Karlsson et al., Kinetic analysis of monoclonal antibody-antigen interactions with a new biosensor based analytical system, J. Immunol. Methods, 1991, 145:229-240.
Kaspar et al., Fibronectin as target for tumor therapy, Int. J. Cancer, 2006, 118:1331-1339.
Khurana et al., Mechanism of thioflavin T binding to amyloid fibrils, J. Struct. Biol., 2005, 151:229-238.
Kim, H. et al., High-Affinity Recognition of Lanthanide(III) Chelate Complexes by a Reprogrammed Human Lipocalin 2, J. Am. Chem. Soc., 2009, 131:3565-3576.
Kjelsden, L. et al., Human Neutrophil Gelatinase-Associated Lipocalin and Homologous Proteins in Rat and Mouse, Biochimica et Biophysica Acta, vol. 1482, pp. 272-283, 2000.
Konig, T. and Skerra, A., Use of an albumin-binding domain for the selective immobilization of recombinant capture antibody fragments on ELISA plates, J. Immunol. Methods, 1998, 218:73-83.
Korean Office Action issued in corresponding application No. 10-2012-7017730 dated Jul. 28, 2018 with English translation.
Kraulis, et al., The Serum Albumin-Binding Domain of Streptococcal Protein G is a Three-Helical Bundle: A Heteronuclear NMR Study, FEBS Letters, vol. 378, pp. 190-194, 1996.
Leahy et al., Crystallization of a Fragment of Human Fibronectin: Introduction of Methionine by Site-Directed Mutagenesis to Allow Phasing via Selenomethionine, Proteins, 1994, 19:48-54.
Lichtlen et al., Antibody-based approaches in Alzheimer's research: safety, pharmacokinetics, metabolism, and analytical tools, J. Neurochem., 2007, 104:859-874.
Lohrengel, B. et al., Expression and Purification of Woodchuck Tumour Necrosis Factor Alpha, Cytokine, vol. 12, No. 6, pp. 573-577, Jun. 2000.
Low, N. et al., Mimicking Somatic Hypermutation: Affinity Maturation of Antibodies Displayed on Bacteriophage Using a Bacterial Mutator Strain, J. Mol. Biol., vol. 260, pp. 359-368, 1996.
Lowman, H.B. Bacteriophage display and discovery of peptides leads for drug development, Annu. Rev. Biophys. Biomol. Struct., 1997, 26:401-424.
Mateo, C. et al., Removal of Amphipathic Epitopes from Genetically Engineered Antibodies: Production of Modified Immunoglobulins with Reduced Immunogenicity, Hybridoma, 2000, 19(6):463-471.
Meidan et al., Emerging Technologies in Transdermal Therapeutics, Am. J. Ther., 2004, 11(4):312-316.
Moretto et al., Conformation-sensitive Antibodies against Alzheimer Amyloid-β by Immunization with a Thioredoxin-constrained B-cell Epitope Peptide, J. Biol. Chem., 2007, 282(15):11436-11445.
Murakami, H. et al., Random insertion and deletion of arbitrary number of bases for codon-based random mutation of DNAs, Nat. Biotechnol., Jan. 2002, 20:76-81.
Notice of Reasons for Rejections dated Jan. 20, 2015 issued in Japanese Application No. 2012-542505, with English translation.
Osborn, B. et al., Pharmacokinetic and Pharmacodynamic Studies of a Human Serum Albumin-Interferon-α Fusion Protein in Cynomolgus Monkeys, J. Pharmacol. Exp. Ther., 2002, 303(2):540-548.

Paine et al., The Lipocalin website, Elsevier Science B.V., Biochimica et Biophysica Acta 1482, pp. 351-352, 2000.
Papiz, et al., The Structure of Beta-Lactoglobulin and Its Similarity to Plasma Retinol-Binding Protein, Nature, vol. 324, pp. 383-385, 1986.
Pervaiz, et al., Homology and Structure-Function Correlations Between α1-Acid Glycoprotein and Serum Retinol-Binding Protein and Its Relatives, 1987, Department of Biochemistry, University of Miami School of Medicine.
Pini et al., Design and Use of a Phage Display Library, J. Biol. Chem., Aug. 21, 1998, 273(34):21769-21776.
Pini, A. et al., Phage Display and Colony Filter Screening for High-Throughput Selection of Antibody Libraries, Comb. Chem. High Throughput Screen., 2002, 5:503-510.
Pujuguet et al., Expression of Fibronectin ED-A$^{30}$ and ED-B$^+$ Isoforms by Human and Experimental Colorectal Cancer, Am. J. Pathol., Feb. 1996, 148(2):579-592.
Redl, Bernhard, Human tear lipocalin, Biochim. Biophys. Acta, 2000, 1482:241-248.
Roberts, Richard W., Totally In Vitro Protein Selection Using mRNA-Protein Fusions and Ribosome Display, Current Opinion in Chemical Biology, vol. 3, pp. 268-273, 1999.
Rodi, D. and Makowski, L., Phage-display technology—finding a needle in a vast molecular haystack, Curr. Opin. Biotechnol., 1999, 10:87-93.
Schlehuber, S. and Skerra, A. et al., Duocalins, engineered ligand-binding proteins with dual specificity derived from the lipocalin fold, Biol. Chem., Sep. 2001, 382:1335-1342.
Schlehuber, S. et al., A Novel Type of Receptor Protein, Based on the Lipocalin Scaffold, with Specificity for Digoxigenin, J. Mol. Biol., 2000, 297:1105-1120.
Schliemann et al., Antibody-based targeting of the tumor vasculature, Biochim. Biophys. Acta, 2007, 1776:175-192.
Schmidt et al., The Strep-tag system for one-step purification and high-affinity detection of capturing of proteins, Nat. Protoc., 2007, 2(6):1528-1535.
Schmidt, T. et al., Molecular Interaction Between the Strep-tag Affinity Peptide and its Cognate Target, Streptavidin, J. Mol. Biol., 1996, 255:753-766.
Schoepfer, Ralf, The pRSET Family of T7 Promoter Expression Vectors for *Escherichia coli*, Gene, vol. 124, pp. 83-85, 1993.
Schonfeld, D. et al., An engineered lipocalin specific for CTLA-4 reveals a combining site with structural and conformational features similar to antibodies, PNAS, May 19, 2009, 106(20):8198-8203.
Skerra, 'Anticalins': a new class of engineered ligand-binding proteins with antibody-like properties; Reviews in Molecular Biotechnology, 74(4): 257-275 (Jun. 2001).
Skerra, Arne, Anticalins as alternative binding proteins for therapeutic use, Current Opinion in Molecular Therapeutics, 2007, 9(4):336-344.
Skerra, Arne, Use of the tetracycline promoter for the tightly regulated production of a murine antibody fragment in *Escherichia coli*, Gene, 1994, 151:131-135.
Skerra, et al., Filter Screening of Antibody Fab Fragments Secreted From Individual Bacterial Colonies: Specific Detection of Antigen Binding with a Two-Membrane System, Anal. Biochem., vol. 196, pp. 151-155, 1991.
Skerra, S., et al., Lipocalins as a scaffold, Elsevier Science B.V., Biochimica et Biophysica Acta 1482, pp. 337-350, 2000.
Stoesz, S. et al., Overexpression of neu-related lipocalin (NRL) in neu-initiated but not ras or chemically initiated rat mammary carcinomas, Oncogene (1995), 11, pp. 2233-2241.
Studier, F.W., and Moffatt, B.A., Use of Bacteriophage T7 RNA Polymerase to Direct Selective High-level Expression of Cloned Genes, J. Mol. Biol., 1986, 189:113-130.
Tartof et al., Improved Media for Growing Plasmid and Cosmid Clones, Focus, Bethesda Research Laboratory, 1987, 9(2):12.
Tulasne, D. et al., C-Terminal Peptide of Thrombospondin-1 Includes Platelet Aggregation Through the Fc Receptor γ-Chain-Associated Signaling Pathway and by Agglutination, Blood, vol. 98, No. 12, pp. 3346-3352, Dec. 1, 2001.

(56) References Cited

OTHER PUBLICATIONS

Vajo, Z. and Duckworth, W., Genetically Engineered Insulin Analogs: Diabetes in the New Millenium, Pharmacol. Rev., 2000, 52(1):1-9.

Venturi, M. et al., High Level Production of Functional Antibody Fab Fragments in an Oxidizing Bacterial Cytoplasm, J. Mol. Biol., 2002, 315:1-8.

Virnekas et al., Trinucleotide phosphoramidites: ideal reagents for the synthesis of mixed oligonucleotides for random mutagenesis, Nucleic Acids Res, 1994, 22(25):5600-5607.

Vogt, M. and Skerra, A., Construction of an Artificial Receptor Protein ("Anticalin") Based on the Human Apolipoprotein D, ChemBioChem, 5: 191-199 (2004).

Voss, et al., Mutagenesis of a Flexible Loop in Streptavidin Leads to Higher Affinity for the Strep-Tag II Peptide and Improved Performance in Recombinant Protein Purification, Protein Engineering, vol. 10, No. 8, pp. 975-982, 1997.

Wang et al., Expanding the Genetic Code of *Escherichia coli*, Science, Apr. 20, 2001, 292:498-500.

Wang et al., Expanding the genetic code, Chem. Comm., 2002, 1:1-11.

Wang, A. M. et al., Molecular Cloning of the Complementary DNA for Human Tumor Necrosis Factor, Science, vol. 228, pp. 149-154, 1985 (Abstract).

Wells, J. et al., Rapid Evolution of Peptide and Protein Binding Properties In Vitro, Current Opinion in Structural Biology, vol. 2, pp. 597-604, 1992.

Wilson, D. et al., The use of mRNA display to select high-affinity protein-binding peptides, Proc. Natl. Acad. Sci. USA, Mar. 27, 2001, 98(7):3750-3755.

Yanisch-Perron, C. et al., Improved M13 phage cloning vectors and host strains: nucleotide sequences of the M13mp18 and pUC19 vectors, Gene, 1985, 33:103-119.

Zaccolo, M. et al., An Approach to Random Mutagenesis of DNA Using Mixtures of Triphosphate Derivatives of Nucleoside Analogues, J. Mal. Biol., 1996, 255:589-603.

Zardi, L. et al., Transformed human cells produce a new fibronectin isoform by preferential alternative splicing of a previously unobserved exon, EMBO J, 6(8):2337-42 (1987).

\* cited by examiner

Figure 16

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| SEQ ID NO:1 | H | H | L | L | A | S | D | E | E | - | Q | D | V | S | A | T | W | Y | L | K | A | M | T | V | D | R |
| SEQ ID NO:2 | H | | | | A | S | D | E | E | - | Q | D | V | S | A | T | W | Y | L | K | A | M | T | V | D | F |
| SEQ ID NO:3 | | | | | A | S | D | E | E | - | Q | D | V | S | A | T | W | Y | L | K | A | M | T | V | D | F |
| SEQ ID NO:4 | | | | | A | S | D | E | E | - | Q | D | V | S | A | T | W | Y | L | K | A | M | T | V | D | F |
| SEQ ID NO:5 | | | | | A | S | D | E | E | - | Q | D | V | S | A | T | W | Y | L | K | A | M | T | V | D | W |
| SEQ ID NO:6 | | | | | A | S | D | E | E | - | Q | D | V | S | G | T | W | Y | L | K | A | M | T | V | D | R |
| SEQ ID NO:7 | | | | | A | S | D | E | E | - | Q | D | V | S | A | T | W | Y | L | K | A | M | T | V | D | W |
| SEQ ID NO:12 | | | | | A | S | D | E | E | - | Q | D | V | S | G | T | W | Y | L | K | A | M | T | V | D | W |
| SEQ ID NO:13 | | | | | A | S | D | E | E | - | Q | D | V | S | G | T | W | Y | L | K | A | M | T | V | D | W |
| SEQ ID NO:14 | | | | | A | S | D | E | E | - | Q | D | V | S | G | T | W | Y | L | K | A | M | T | V | D | Y |

| | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 |
|---|---|---|---|---|---|---|---|---|---|---|---|---|---|---|---|---|---|---|---|---|---|---|---|---|---|---|---|---|---|---|---|---|---|---|---|---|---|---|
| | E | F | P | E | M | N | L | E | S | V | T | P | M | T | L | T | T | L | E | G | G | N | L | E | A | K | V | T | M | L | I | S | G | R | C | Q | E | V |
| | W | C | S | G | V | H | E | E | S | V | T | P | M | T | L | T | T | L | E | G | G | N | L | E | A | K | V | T | M | D | - | G | G | F | L | Q | E | V |
| | W | C | S | G | I | - | H | E | S | V | T | P | M | T | L | T | T | L | E | G | G | N | L | E | A | K | V | T | M | D | I | A | G | F | L | Q | E | V |
| | W | C | S | G | I | H | D | E | S | V | T | P | M | T | L | T | T | L | E | G | G | N | L | E | A | K | V | T | M | D | - | G | G | F | L | Q | E | F |
| | W | C | S | G | I | H | E | P | S | V | T | P | M | T | L | T | T | L | E | G | G | N | L | E | A | K | V | T | M | P | - | R | G | F | L | Q | E | F |
| | Q | C | C | P | E | - | - | - | D | E | S | V | T | P | M | T | L | T | T | L | E | G | G | N | L | E | A | K | V | T | M | L | - | S | G | L | W | E | E |
| | E | F | - | T | W | D | D | L | E | S | V | T | P | M | T | L | T | T | L | E | G | G | N | L | E | A | K | V | T | M | - | - | F | G | R | S | E | V |
| | Q | C | T | P | E | M | N | L | E | S | V | T | P | M | T | L | T | T | L | E | G | G | N | L | E | A | K | V | T | - | P | T | F | G | L | A | Q | E |
| | V | C | A | F | D | D | D | P | S | V | T | P | M | T | L | T | T | L | E | G | G | N | L | E | A | K | V | T | - | P | T | F | G | L | Y | E | E | E |
| | G | C | N | H | P | S | - | W | S | V | T | P | M | T | L | T | T | L | E | G | G | N | L | E | A | K | V | T | M | Y | W | E | G | S | R | Q | E | D |

Figure 16 (cont')

Sequence alignment (positions 65–140). All sequences share a common identity across most columns; residue differences noted where visible.

Positions 65–102:

| Seq | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 |
|---|---|---|---|---|---|---|---|---|---|---|---|---|---|---|---|---|---|---|---|---|---|---|---|---|---|---|---|---|---|---|---|---|---|---|---|---|---|---|
| 1 | K | A | V | L | E | K | T | D | E | P | G | K | Y | T | A | D | G | G | K | H | V | A | Y | – | – | R | S | H | V | K | D | H | Y | – | F | Y | C | E |
| 2 | K | A | V | L | E | K | T | D | E | P | G | K | Y | T | A | D | G | G | K | H | V | A | Y | – | – | R | S | H | V | K | D | H | Y | – | F | Y | S | E |
| 3 | K | A | V | L | E | K | T | D | E | P | G | K | Y | T | A | D | G | G | K | H | V | A | Y | – | – | R | S | H | V | K | D | H | Y | – | F | Y | S | E |
| 4 | K | A | V | L | E | K | T | D | E | P | G | K | Y | T | A | D | G | G | K | H | V | A | Y | – | – | R | S | H | V | K | D | H | Y | – | F | Y | S | E |
| 5 | K | A | V | L | E | K | T | D | E | P | G | K | Y | T | A | D | G | G | K | H | V | A | Y | – | – | R | S | H | V | K | D | H | Y | – | F | Y | S | E |
| 6 | K | A | V | L | E | K | T | D | E | P | G | K | Y | T | A | D | G | G | K | H | V | A | Y | – | – | R | S | H | V | K | D | H | Y | – | F | Y | S | E |
| 7 | K | A | V | L | E | K | T | D | E | P | G | K | Y | T | A | D | G | G | K | H | V | A | Y | – | – | R | S | H | V | K | D | H | Y | – | F | Y | S | E |
| 8 | K | A | V | L | E | K | T | D | E | P | G | K | Y | T | A | D | G | G | K | H | V | A | Y | – | – | R | S | H | V | K | D | H | Y | – | F | Y | S | E |
| 9 | K | A | V | L | E | K | T | D | E | P | G | K | Y | T | A | D | G | G | K | H | V | A | Y | – | – | R | S | H | V | K | D | H | Y | – | F | Y | S | E |

Positions 103–140:

| Seq | 103 | 104 | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 |
|---|---|---|---|---|---|---|---|---|---|---|---|---|---|---|---|---|---|---|---|---|---|---|---|---|---|---|---|---|---|---|---|---|---|---|---|---|---|---|
| 1 | G | E | L | H | G | K | P | V | R | G | V | K | L | V | G | R | D | P | K | N | N | L | E | A | L | E | D | F | E | K | A | A | G | A | R | G | L | S |
| 2 | G | D | C | P | G | L | P | V | P | G | V | W | L | V | G | R | D | P | K | N | N | L | E | A | L | E | D | F | E | K | A | A | G | A | R | G | L | S |
| 3 | G | D | C | P | G | – | P | V | P | G | V | W | L | V | G | R | D | P | K | N | N | L | E | A | L | E | D | F | E | K | A | A | G | A | R | G | L | S |
| 4 | G | D | C | P | D | S | P | V | P | G | V | W | L | V | G | R | D | P | K | N | N | L | E | A | L | E | D | F | E | K | A | A | G | A | R | G | L | S |
| 5 | G | D | C | P | G | – | P | V | P | G | V | W | L | V | G | R | D | P | K | N | N | L | E | A | L | E | D | F | E | K | A | A | G | A | R | G | L | S |
| 6 | G | A | C | Y | G | Q | P | V | P | G | V | W | L | V | G | R | D | P | K | N | N | L | E | A | L | E | D | F | E | K | A | A | G | A | R | G | L | S |
| 7 | G | E | C | H | W | K | P | V | P | G | V | W | L | V | G | R | D | P | K | N | N | L | E | A | L | E | D | F | E | K | A | A | G | A | R | G | L | S |
| 8 | G | R | C | W | G | R | P | V | P | G | V | W | L | V | G | R | D | P | K | N | N | L | E | A | L | E | D | F | E | K | A | A | G | A | R | G | L | S |
| 9 | G | A | C | H | G | H | P | V | P | G | V | W | L | V | G | R | D | P | K | N | N | L | E | A | L | E | D | F | E | K | A | A | G | A | R | G | L | S |

Figure 16 (cont')

| 141 | 142 | 143 | 144 | 145 | 146 | 147 | 148 | 149 | 150 | 151 | 152 | 153 | 154 | 155 | 156 | 157 | 158 | 159 | 160 | 161 | 162 | 163 | 164 | 165 | 166 |
|---|---|---|---|---|---|---|---|---|---|---|---|---|---|---|---|---|---|---|---|---|---|---|---|---|---|
| T | E | S | – | L | – | P | R | Q | S | E | T | C | S | P | G | S | D |   |   |   |   |   |   |   |   |
| T | E | S | – | L | – | P | R | Q | S | E | T | S | S | P | G |   |   |   |   |   |   |   |   |   |   |
| T | E | S | – | L | – | P | R | Q | S | E | T | S | S | P | G |   |   |   |   |   |   |   |   |   |   |
| T | E | S | – | L | – | P | R | Q | S | E | T | S | S | P | G |   |   |   |   |   |   |   |   |   |   |
| T | E | S | – | L | – | P | R | Q | S | E | T | S | S | P | G |   |   |   |   |   |   |   |   |   |   |
| T | E | S | – | L | – | P | R | Q | S | E | T | S | S | P | G |   |   |   |   |   |   |   |   |   |   |
| T | E | S | – | L | – | P | R | Q | S | E | T | S | S | P | G |   |   |   |   |   |   |   |   |   |   |
| T | E | S | – | L | – | P | R | Q | S | E | T | S | S | P | G |   |   |   |   |   |   |   |   |   |   |
| T | E | S | – | L | – | P | R | Q | S | E | T | S | S | P | G |   |   |   |   |   |   |   |   |   |   |

Figure 17

| Position | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|
| SEQ ID NO:8  | Q | D | S | T | S | D | L | - | P | A | P | L | L | S | K | V | P | L | Q | Q | N | F | Q | D | N | Q | F | Q | G | K | W | Y | V | V | G | L | A |
| SEQ ID NO:9  | Q | D | S | T | S | D | L | - | P | A | P | L | L | S | K | V | P | L | Q | Q | N | F | Q | D | N | Q | F | H | G | K | W | Y | V | V | G | M | A |
| SEQ ID NO:10 | Q | D | S | T | S | D | L | - | P | A | P | L | L | S | K | V | P | L | Q | Q | N | F | Q | D | N | Q | F | H | G | K | W | Y | V | V | G | L | A |
| SEQ ID NO:11 | Q | D | S | T | S | D | L | - | P | A | P | L | L | S | K | V | P | L | Q | Q | N | F | Q | D | N | Q | F | Q | G | K | W | Y | V | V | G | L | A |
| SEQ ID NO:15 | Q | D | S | T | S | D | L | - | P | A | P | L | L | S | K | V | P | L | Q | Q | N | F | Q | D | N | Q | F | H | G | K | W | Y | V | V | G | E | A |

| Position | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 |
|---|---|---|---|---|---|---|---|---|---|---|---|---|---|---|---|---|---|---|---|---|---|---|---|---|---|---|---|---|---|---|---|---|---|---|---|---|---|
| SEQ ID NO:8  | G | N | A | - | L | R | E | D | K | D | P | P | K | M | Y | A | T | - | Y | E | L | K | E | D | K | S | Y | N | V | T | S | V | L | F | R | K | K |
| SEQ ID NO:9  | G | N | L | M | L | R | E | D | K | D | P | P | K | M | S | A | T | - | Y | E | L | K | E | D | K | S | Y | N | V | T | W | V | D | F | R | F | K |
| SEQ ID NO:10 | G | N | T | - | L | R | E | D | K | D | P | P | K | M | E | A | T | - | Y | E | L | K | E | D | K | S | Y | N | V | T | S | V | D | F | - | I | M |
| SEQ ID NO:11 | G | N | A | - | L | R | E | D | K | D | P | P | Q | M | Y | A | T | - | Y | E | L | K | E | D | K | S | Y | N | V | T | S | V | L | F | R | K | K |
| SEQ ID NO:15 | G | N | - | - | L | R | E | D | K | D | P | P | R | M | T | A | T | - | Y | E | L | K | E | D | K | S | Y | N | V | T | R | V | E | F | G | V | K |

| Position | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 |
|---|---|---|---|---|---|---|---|---|---|---|---|---|---|---|---|---|---|---|---|---|---|---|---|---|---|---|---|---|---|---|---|---|---|---|---|---|---|
| SEQ ID NO:8  | K | C | D | Y | W | I | R | T | F | V | P | G | C | Q | P | G | E | F | T | L | G | N | I | K | S | Y | P | G | L | T | S | Y | L | V | R | V | V |
| SEQ ID NO:9  | K | C | K | Y | Q | I | G | T | F | V | P | G | S | Q | P | G | E | F | T | L | G | G | - | K | S | M | P | G | M | T | S | F | L | V | R | V | V |
| SEQ ID NO:10 | K | C | W | Y | F | I | T | T | F | V | P | G | S | Q | P | G | E | F | T | L | G | H | - | K | S | M | P | G | M | T | S | Y | L | V | R | V | V |
| SEQ ID NO:11 | K | C | D | Y | W | I | R | T | F | V | P | G | S | Q | P | G | E | F | T | L | G | N | I | K | S | Y | P | G | L | T | S | Y | L | V | R | V | V |
| SEQ ID NO:15 | T | Y | K | Y | Q | I | G | T | F | V | P | G | S | Q | P | G | E | F | T | L | G | G | - | K | S | M | P | G | M | T | S | F | L | V | R | V | V |

Figure 17 (cont')

| | 112 | 113 | 114 | 115 | 116 | 117 | 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 |
|---|---|---|---|---|---|---|---|---|---|---|---|---|---|---|---|---|---|---|---|---|---|---|---|---|---|---|---|---|---|---|---|---|---|---|---|---|---|
| SEQ ID NO: 8 | S | T | N | Y | N | Q | H | A | M | V | F | F | K | K | V | S | Q | N | R | E | Y | F | K | I | T | L | Y | G | R | T | K | E | L | T | S | E | L |
| SEQ ID NO: 9 | S | T | N | Y | N | Q | H | A | M | V | F | F | K | Y | Y | Y | Q | N | R | E | Y | F | E | I | T | L | Y | G | R | T | K | E | L | T | S | E | L |
| SEQ ID NO: 10 | S | T | N | Y | N | Q | H | A | M | V | F | F | K | Y | Y | Y | Q | N | R | E | F | F | E | I | T | L | Y | G | R | T | K | E | L | T | S | E | L |
| SEQ ID NO: 11 | S | T | N | Y | N | Q | H | A | M | V | F | F | K | K | V | S | Q | N | R | E | Y | F | K | I | T | L | Y | G | R | T | K | E | L | T | S | E | L |
| SEQ ID NO: 15 | S | T | N | Y | N | Q | H | A | M | V | F | F | K | Y | Y | Y | Q | N | R | E | Y | F | E | I | T | L | Y | G | R | T | K | E | L | T | S | E | L |

| | 149 | 150 | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 |
|---|---|---|---|---|---|---|---|---|---|---|---|---|---|---|---|---|---|---|---|---|---|---|---|---|---|---|---|---|---|---|
| SEQ ID NO: 8 | K | E | N | F | I | R | F | S | K | S | L | G | L | P | E | N | H | I | V | F | P | V | P | I | D | Q | C | I | D | G |
| SEQ ID NO: 9 | K | E | N | F | I | R | F | S | K | S | L | G | L | P | E | N | H | I | V | F | P | V | P | I | D | Q | C | I | D | G |
| SEQ ID NO: 10 | K | E | N | F | I | R | F | S | K | S | L | G | L | P | E | N | H | I | V | F | P | V | P | I | D | Q | C | I | D | G |
| SEQ ID NO: 11 | K | E | N | F | I | R | F | S | K | S | L | G | L | P | E | N | H | I | V | F | P | V | P | I | D | Q | C | I | D | G |
| SEQ ID NO: 15 | K | E | N | F | I | R | F | S | K | S | L | G | L | P | E | N | H | I | V | F | P | V | P | I | D | Q | A | I | D | G |

SEQUENCE LISTING

```
<160> NUMBER OF SEQ ID NOS: 58

<210> SEQ ID NO 1
<211> LENGTH: 158
<212> TYPE: PRT
<213> ORGANISM: human
<220> FEATURE:
<223> OTHER INFORMATION: Human tear lipocalin

<400> SEQUENCE: 1

His His Leu Leu Ala Ser Asp Glu Glu Ile Gln Asp Val Ser Gly Thr
1               5                   10                  15

Trp Tyr Leu Lys Ala Met Thr Val Asp Arg Glu Phe Pro Glu Met Asn
            20                  25                  30

Leu Glu Ser Val Thr Pro Met Thr Leu Thr Thr Leu Glu Gly Gly Asn
        35                  40                  45

Leu Glu Ala Lys Val Thr Met Leu Ile Ser Gly Arg Cys Gln Glu Val
    50                  55                  60

Lys Ala Val Leu Glu Lys Thr Asp Glu Pro Gly Lys Tyr Thr Ala Asp
65                  70                  75                  80

Gly Gly Lys His Val Ala Tyr Ile Ile Arg Ser His Val Lys Asp His
                85                  90                  95

Tyr Ile Phe Tyr Cys Glu Gly Glu Leu His Gly Lys Pro Val Arg Gly
            100                 105                 110

Val Lys Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155
```

```
<210> SEQ ID NO 2
<211> LENGTH: 152
<212> TYPE: PRT
<213> ORGANISM: Artificial
<220> FEATURE:
<223> OTHER INFORMATION: Mutein of human tear lipocalin

<400> SEQUENCE: 2

Ala Ser Asp Glu Glu Ile Gln Asp Val Ser Gly Thr Trp Tyr Leu Lys
1               5                   10                  15

Ala Met Thr Val Asp Phe Trp Cys Ser Gly Val His Glu Glu Ser Val
            20                  25                  30

Thr Pro Met Thr Leu Thr Thr Leu Glu Gly Gly Asn Leu Glu Ala Lys
        35                  40                  45

Val Thr Met Asp Ile Gly Gly Phe Leu Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Asp Cys Pro Gly Leu Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 3
<211> LENGTH: 151
<212> TYPE: PRT
<213> ORGANISM: Artificial
<220> FEATURE:
<223> OTHER INFORMATION: Mutein of human tear lipocalin

<400> SEQUENCE: 3

Ala Ser Asp Glu Glu Ile Gln Asp Val Ser Gly Thr Trp Tyr Leu Lys
1               5                   10                  15

Ala Met Thr Val Asp Phe Trp Cys Ser Gly Ile His Asp Glu Ser Val
            20                  25                  30

Thr Pro Met Thr Leu Thr Thr Leu Glu Gly Gly Asn Leu Glu Ala Lys
        35                  40                  45

Val Thr Met Asp Ile Ala Gly Phe Leu Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Asp Cys Pro Gly Pro Val Pro Gly Val Trp Leu Val Gly
            100                 105                 110

Arg Asp Pro Lys Asn Asn Leu Glu Ala Leu Glu Asp Phe Glu Lys Ala
        115                 120                 125

Ala Gly Ala Arg Gly Leu Ser Thr Glu Ser Ile Leu Ile Pro Arg Gln
    130                 135                 140

Ser Glu Thr Ser Ser Pro Gly
```

145        150

<210> SEQ ID NO 4
<211> LENGTH: 152
<212> TYPE: PRT
<213> ORGANISM: Artificial
<220> FEATURE:
<223> OTHER INFORMATION: Mutein of human tear lipocalin

<400> SEQUENCE: 4

Ala Ser Asp Glu Glu Ile Gln Asp Val Ser Gly Thr Trp Tyr Leu Lys
1               5                   10                  15

Ala Met Thr Val Asp Phe Trp Cys Ser Gly Ile His Glu Glu Ser Val
            20                  25                  30

Thr Pro Met Thr Leu Thr Thr Leu Glu Gly Gly Asn Leu Glu Ala Lys
        35                  40                  45

Val Thr Met Asp Ile Arg Gly Phe Leu Gln Glu Phe Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Asp Cys Pro Asp Ser Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 5
<211> LENGTH: 151
<212> TYPE: PRT
<213> ORGANISM: Artificial
<220> FEATURE:
<223> OTHER INFORMATION: Mutein of human tear lipocalin

<400> SEQUENCE: 5

Ala Ser Asp Glu Glu Ile Gln Asp Val Ser Gly Thr Trp Tyr Leu Lys
1               5                   10                  15

Ala Met Thr Val Asp Phe Trp Cys Ser Gly Ile His Glu Glu Ser Val
            20                  25                  30

Thr Pro Met Thr Leu Thr Thr Leu Glu Gly Gly Asn Leu Glu Ala Lys
        35                  40                  45

Val Thr Met Asp Ile Glu Gly Phe Leu Gln Glu Phe Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Asp Cys Pro Gly Pro Val Pro Gly Val Trp Leu Val Gly
            100                 105                 110

Arg Asp Pro Lys Asn Asn Leu Glu Ala Leu Glu Asp Phe Glu Lys Ala
        115                 120                 125

Ala Gly Ala Arg Gly Leu Ser Thr Glu Ser Ile Leu Ile Pro Arg Gln
    130                 135                 140

Ser Glu Thr Ser Ser Pro Gly
145                 150

<210> SEQ ID NO 6
<211> LENGTH: 152
<212> TYPE: PRT
<213> ORGANISM: Artificial
<220> FEATURE:
<223> OTHER INFORMATION: Mutein of human tear lipocalin

<400> SEQUENCE: 6

Ala Ser Asp Glu Glu Ile Gln Asp Val Ser Gly Thr Trp Tyr Leu Lys
1               5                   10                  15

Ala Met Thr Val Asp Trp Gln Cys Thr Trp Asp Asp Pro Ser Val
            20                  25                  30

Thr Pro Met Thr Leu Thr Thr Leu Glu Gly Gly Asn Leu Glu Ala Lys
            35                  40                  45

Val Thr Met Pro Ile Phe Gly Leu Trp Gln Glu Glu Lys Ala Val Leu
        50                  55                  60

Glu Lys Thr Asp Glu Pro Gly Lys Tyr Thr Ala Asp Gly Gly Lys His
65              70                  75                  80

Val Ala Tyr Ile Ile Arg Ser His Val Lys Asp His Tyr Ile Phe Tyr
                85                  90                  95

Ser Glu Gly Ala Cys Tyr Gly Gln Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 7
<211> LENGTH: 152
<212> TYPE: PRT
<213> ORGANISM: Artificial
<220> FEATURE:
<223> OTHER INFORMATION: Mutein of human tear lipocalin

<400> SEQUENCE: 7

Ala Ser Asp Glu Glu Ile Gln Asp Val Ser Gly Thr Trp Tyr Leu Lys
1               5                   10                  15

Ala Met Thr Val Asp Arg Glu Cys Pro Glu Met Asn Leu Glu Ser Val
            20                  25                  30

Thr Pro Met Thr Leu Thr Thr Leu Glu Gly Gly Asn Leu Glu Ala Lys
            35                  40                  45

Val Thr Met Leu Ile Ser Gly Arg Ser Gln Glu Val Lys Ala Val Leu
        50                  55                  60

Glu Lys Thr Asp Glu Pro Gly Lys Tyr Thr Ala Asp Gly Gly Lys His
65              70                  75                  80

Val Ala Tyr Ile Ile Arg Ser His Val Lys Asp His Tyr Ile Phe Tyr
                85                  90                  95

Ser Glu Gly Glu Cys His Gly Lys Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

```
Gln Ser Glu Thr Ser Ser Pro Gly
145                 150

<210> SEQ ID NO 8
<211> LENGTH: 178
<212> TYPE: PRT
<213> ORGANISM: human
<220> FEATURE:
<223> OTHER INFORMATION: Human Lipocalin 2 (hNGAL)

<400> SEQUENCE: 8

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 9
<211> LENGTH: 178
<212> TYPE: PRT
<213> ORGANISM: Artificial
<220> FEATURE:
<223> OTHER INFORMATION: Mutein of hNGAL

<400> SEQUENCE: 9

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Met Ala Gly Asn Leu Met Leu Arg Glu Asp Lys Asp Pro
        35                  40                  45

Thr Lys Met Ser Ala Thr Ile Tyr Glu Leu Lys Glu Asp Lys Ser Tyr
    50                  55                  60

Asn Val Thr Trp Val Asp Phe Arg Phe Lys Lys Cys Lys Tyr Gln Ile
65                  70                  75                  80

Gly Thr Phe Val Pro Gly Ser Gln Pro Gly Glu Phe Thr Leu Gly Gly
                85                  90                  95

Ile Lys Ser Met Pro Gly Met Thr Ser Phe Leu Val Arg Val Val Ser
            100                 105                 110
```

Thr Asn Tyr Asn Gln His Ala Met Val Phe Lys Tyr Val Tyr Gln
            115                 120                 125

Asn Arg Glu Tyr Phe Glu Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 10
<211> LENGTH: 178
<212> TYPE: PRT
<213> ORGANISM: Artificial
<220> FEATURE:
<223> OTHER INFORMATION: Mutein of hNGAL

<400> SEQUENCE: 10

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Thr Ile Leu Arg Glu Asp Lys Asp Pro
        35                  40                  45

Asp Lys Met Glu Ala Thr Ile Tyr Glu Leu Lys Glu Asp Lys Ser Tyr
    50                  55                  60

Asn Val Thr Ser Val Asp Phe Ile Met Lys Lys Cys Trp Tyr Phe Ile
65                  70                  75                  80

Thr Thr Phe Val Pro Gly Ser Gln Pro Gly Glu Phe Thr Leu Gly His
                85                  90                  95

Ile Lys Ser Met Pro Gly Met Thr Ser Phe Leu Val Arg Val Val Ser
            100                 105                 110

Thr Asn Tyr Asn Gln His Ala Met Val Phe Phe Lys Tyr Val Tyr Gln
        115                 120                 125

Asn Arg Glu Phe Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 11
<211> LENGTH: 178
<212> TYPE: PRT
<213> ORGANISM: Artificial
<220> FEATURE:
<223> OTHER INFORMATION: Mutein of hNGAL

<400> SEQUENCE: 11

Gln Asp Ser Thr Ser Asp Leu Ile Pro Ala Pro Pro Leu Ser Lys Val
1               5                   10                  15

Pro Leu Gln Gln Asn Phe Gln Asp Asn Glu Phe His Gly Lys Trp Tyr
            20                  25                  30

Val Val Gly Leu Ala Gly Asn Ala Ile Leu Arg Glu Asp Lys Asp Pro
        35                  40                  45

```
Gln Lys Met Tyr Ala Thr Ile Tyr Glu Leu Lys Glu Asp Lys Ser Tyr
     50                  55                  60

Asn Val Thr Ser Val Leu Phe Arg Lys Lys Cys Asp Tyr Trp Ile
 65                  70                  75                  80

Arg Thr Phe Val Pro Gly Ser Gln Pro Gly Glu Phe Thr Leu Gly Asn
                 85                  90                  95

Ile Lys Ser Tyr Pro Gly Leu Thr Ser Tyr Leu Val Arg Val Val Ser
             100                 105                 110

Thr Asn Tyr Asn Gln His Ala Met Val Phe Phe Lys Lys Val Ser Gln
         115                 120                 125

Asn Arg Glu Tyr Phe Lys Ile Thr Leu Tyr Gly Arg Thr Lys Glu Leu
 130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                 165                 170                 175

Asp Gly

<210> SEQ ID NO 12
<211> LENGTH: 152
<212> TYPE: PRT
<213> ORGANISM: Artificial
<220> FEATURE:
<223> OTHER INFORMATION: Mutein of human tear lipocalin

<400> SEQUENCE: 12

Ala Ser Asp Glu Glu Ile Gln Asp Val Ser Gly Thr Trp Tyr Leu Lys
 1                5                  10                  15

Ala Met Thr Val Asp Trp Gln Cys Thr Trp Ala Asp Glu Pro Ser Val
                 20                  25                  30

Thr Pro Met Thr Leu Thr Thr Leu Glu Gly Gly Asn Leu Glu Ala Lys
             35                  40                  45

Val Thr Ile Pro Thr Phe Gly Leu Ala Glu Glu Lys Ala Val Leu
         50                  55                  60

Glu Lys Thr Asp Glu Pro Gly Lys Tyr Thr Ala Asp Gly Gly Lys His
 65                  70                  75                  80

Val Ala Tyr Ile Ile Arg Ser His Val Lys Asp His Tyr Ile Phe Tyr
                 85                  90                  95

Ser Glu Gly Arg Cys Trp Gly Arg Pro Val Pro Gly Val Trp Leu Val
             100                 105                 110

Gly Arg Asp Pro Lys Asn Asn Leu Glu Ala Leu Glu Asp Phe Glu Lys
         115                 120                 125

Ala Ala Gly Ala Arg Gly Leu Ser Thr Glu Ser Ile Leu Ile Pro Arg
 130                 135                 140

Gln Ser Glu Thr Ser Ser Pro Gly
145                 150

<210> SEQ ID NO 13
<211> LENGTH: 152
<212> TYPE: PRT
<213> ORGANISM: Artificial
<220> FEATURE:
<223> OTHER INFORMATION: Mutein of human tear lipocalin

<400> SEQUENCE: 13

Ala Ser Asp Glu Glu Ile Gln Asp Val Ser Gly Thr Trp Tyr Leu Lys
 1                5                  10                  15
```

```
Ala Met Thr Val Asp Trp Val Cys Ala Phe Asp Asp Pro Ser Val
            20                  25                  30

Thr Pro Met Thr Leu Thr Thr Leu Glu Gly Gly Asn Leu Glu Ala Lys
        35                  40                  45

Val Thr Ile Pro Thr Phe Gly Leu Tyr Gln Glu Glu Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Ala Cys His Gly His Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150
```

```
<210> SEQ ID NO 14
<211> LENGTH: 152
<212> TYPE: PRT
<213> ORGANISM: Artificial
<220> FEATURE:
<223> OTHER INFORMATION: Mutein of human tear lipocalin

<400> SEQUENCE: 14
```

```
Ala Ser Asp Glu Glu Ile Gln Asp Val Ser Gly Thr Trp Tyr Leu Lys
1               5                   10                  15

Ala Met Thr Val Asp Tyr Gly Cys Asn His Pro Ser Ile Trp Ser Val
            20                  25                  30

Thr Pro Met Thr Leu Thr Thr Leu Glu Gly Gly Asn Leu Glu Ala Lys
        35                  40                  45

Val Thr Met Tyr Trp Glu Gly Ser Arg Gln Glu Asp Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe
                85                  90                  95

Tyr Ser Glu Gly Ile Cys Glu Gly Ala Pro Val Pro Gly Val Trp
            100                 105                 110

Leu Val Gly Arg Asp Pro Lys Asn Asn Leu Glu Ala Leu Glu Asp
        115                 120                 125

Phe Glu Lys Ala Ala Gly Ala Arg Gly Leu Ser Thr Glu Ser Ile
    130                 135                 140

Leu Ile Pro Arg Gln Ser Glu Thr Ser Ser Pro Gly
                145                 150
```

```
<210> SEQ ID NO 15
<211> LENGTH: 178
<212> TYPE: PRT
<213> ORGANISM: Artificial
<220> FEATURE:
<223> OTHER INFORMATION: Mutein of hNGAL

<400> SEQUENCE: 15
```

```
Gln Asp Ser Thr Ser Asp Leu Ile Pro Ala Pro Pro Leu Ser Lys Val
1               5                   10                  15
```

```
Pro Leu Gln Gln Asn Phe Gln Asp Asn Gln Phe His Gly Lys Trp Tyr
            20                  25                  30

Val Val Gly Glu Ala Gly Asn Leu Leu Arg Glu Asp Lys Asp Pro
            35                  40                  45

Arg Lys Met Thr Ala Thr Ile Tyr Glu Leu Lys Glu Asp Lys Ser Tyr
 50                  55                  60

Asn Val Thr Arg Val Glu Phe Gly Val Lys Thr Lys Tyr Gln Ile
 65                  70                  75                  80

Gly Thr Phe Val Pro Gly Ser Gln Pro Gly Glu Phe Thr Leu Gly Gly
            85                  90                  95

Ile Lys Ser Met Pro Gly Met Thr Ser Phe Leu Val Arg Val Val Ser
            100                 105                 110

Thr Asn Tyr Asn Gln His Ala Met Val Phe Phe Lys Tyr Val Tyr Gln
            115                 120                 125

Asn Arg Glu Tyr Phe Glu Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Ala Ile
                    165                 170                 175

Asp Gly

<210> SEQ ID NO 16
<211> LENGTH: 338
<212> TYPE: PRT
<213> ORGANISM: Artificial
<220> FEATURE:
<223> OTHER INFORMATION: Fusion protein

<400> SEQUENCE: 16

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Met Ala Gly Asn Leu Met Leu Arg Glu Asp Lys Asp Pro
            35                  40                  45

Thr Lys Met Ser Ala Thr Ile Tyr Glu Leu Lys Glu Asp Lys Ser Tyr
 50                  55                  60

Asn Val Thr Trp Val Asp Phe Arg Phe Lys Lys Cys Lys Tyr Gln Ile
 65                  70                  75                  80

Gly Thr Phe Val Pro Gly Ser Gln Pro Gly Glu Phe Thr Leu Gly Gly
            85                  90                  95

Ile Lys Ser Met Pro Gly Met Thr Ser Phe Leu Val Arg Val Val Ser
            100                 105                 110

Thr Asn Tyr Asn Gln His Ala Met Val Phe Phe Lys Tyr Val Tyr Gln
            115                 120                 125

Asn Arg Glu Tyr Phe Glu Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly Gly Gly Gly Ser Gly Gly Gly Ser Ala Ser Asp Glu Glu
            180                 185                 190
```

```
Ile Gln Asp Val Ser Gly Thr Trp Tyr Leu Lys Ala Met Thr Val Asp
            195                 200                 205

Phe Trp Cys Ser Gly Ile His Glu Glu Ser Val Thr Pro Met Thr Leu
    210                 215                 220

Thr Thr Leu Glu Gly Gly Asn Leu Glu Ala Lys Val Thr Met Asp Ile
225                 230                 235                 240

Glu Gly Phe Leu Gln Glu Phe Lys Ala Val Leu Glu Lys Thr Asp Glu
                245                 250                 255

Pro Gly Lys Tyr Thr Ala Asp Gly Gly Lys His Val Ala Tyr Ile Ile
            260                 265                 270

Arg Ser His Val Lys Asp His Tyr Ile Phe Tyr Ser Glu Gly Asp Cys
    275                 280                 285

Pro Gly Pro Val Pro Gly Val Trp Leu Val Gly Arg Asp Pro Lys Asn
290                 295                 300

Asn Leu Glu Ala Leu Glu Asp Phe Glu Lys Ala Ala Gly Ala Arg Gly
305                 310                 315                 320

Leu Ser Thr Glu Ser Ile Leu Ile Pro Arg Gln Ser Glu Thr Ser Ser
                325                 330                 335

Pro Gly

<210> SEQ ID NO 17
<211> LENGTH: 341
<212> TYPE: PRT
<213> ORGANISM: Artificial
<220> FEATURE:
<223> OTHER INFORMATION: Fusion protein

<400> SEQUENCE: 17

Ala Ser Asp Glu Glu Ile Gln Asp Val Ser Gly Thr Trp Tyr Leu Lys
1               5                   10                  15

Ala Met Thr Val Asp Phe Trp Cys Ser Gly Ile His Glu Glu Ser Val
                20                  25                  30

Thr Pro Met Thr Leu Thr Thr Leu Glu Gly Gly Asn Leu Glu Ala Lys
            35                  40                  45

Val Thr Met Asp Ile Glu Gly Phe Leu Gln Glu Phe Lys Ala Val Leu
        50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Asp Cys Pro Gly Pro Val Pro Gly Val Trp Leu Val Gly
            100                 105                 110

Arg Asp Pro Lys Asn Asn Leu Glu Ala Leu Glu Asp Phe Glu Lys Ala
        115                 120                 125

Ala Gly Ala Arg Gly Leu Ser Thr Glu Ser Ile Leu Ile Pro Arg Gln
130                 135                 140

Ser Glu Thr Ser Ser Pro Gly Ser Gly Ala Gly Gly Ser Gly Gly
145                 150                 155                 160

Gly Gly Ser Gln Asp Ser Thr Ser Asp Leu Ile Pro Ala Pro Pro Leu
                165                 170                 175

Ser Lys Val Pro Leu Gln Gln Asn Phe Gln Asp Asn Gln Phe His Gly
            180                 185                 190

Lys Trp Tyr Val Val Gly Met Ala Gly Asn Leu Met Leu Arg Glu Asp
        195                 200                 205

Lys Asp Pro Thr Lys Met Ser Ala Thr Ile Tyr Glu Leu Lys Glu Asp
```

```
                    210                 215                 220
Lys Ser Tyr Asn Val Thr Trp Val Asp Phe Arg Phe Lys Cys Lys
225                 230                 235                 240

Tyr Gln Ile Gly Thr Phe Val Pro Gly Ser Gln Pro Gly Glu Phe Thr
                245                 250                 255

Leu Gly Gly Ile Lys Ser Met Pro Gly Met Thr Ser Phe Leu Val Arg
                260                 265                 270

Val Val Ser Thr Asn Tyr Asn Gln His Ala Met Val Phe Phe Lys Tyr
                275                 280                 285

Val Tyr Gln Asn Arg Glu Tyr Phe Glu Ile Thr Leu Tyr Gly Arg Thr
                290                 295                 300

Lys Glu Leu Thr Ser Glu Leu Lys Glu Asn Phe Ile Arg Phe Ser Lys
305                 310                 315                 320

Ser Leu Gly Leu Pro Glu Asn His Ile Val Phe Pro Val Pro Ile Asp
                325                 330                 335

Gln Cys Ile Asp Gly
                340

<210> SEQ ID NO 18
<211> LENGTH: 10
<212> TYPE: PRT
<213> ORGANISM: Artificial
<220> FEATURE:
<223> OTHER INFORMATION: Peptide bond

<400> SEQUENCE: 18

Gly Gly Gly Gly Ser Gly Gly Gly Gly Ser
1               5                   10

<210> SEQ ID NO 19
<211> LENGTH: 457
<212> TYPE: PRT
<213> ORGANISM: Artificial
<220> FEATURE:
<223> OTHER INFORMATION: Heavy chain of benchmark antibody 1

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Trp Met Asn Trp Val Arg Gln Ala Pro Gly Lys Gly Leu Glu Trp Val
            35                  40                  45

Ala Ala Ile Asn Gln Asp Gly Ser Glu Lys Tyr Tyr Val Gly Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Tyr Ile His Tyr Trp
                100                 105                 110

Tyr Phe Asp Leu Trp Gly Arg Gly Thr Leu Val Thr Val Ser Ser Ala
            115                 120                 125

Ser Thr Lys Gly Pro Ser Val Phe Pro Leu Ala Pro Ser Ser Lys Ser
        130                 135                 140

Thr Ser Gly Gly Thr Ala Ala Leu Gly Cys Leu Val Lys Asp Tyr Phe
145                 150                 155                 160
```

```
Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
            290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
            355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
    450                 455

<210> SEQ ID NO 20
<211> LENGTH: 215
<212> TYPE: PRT
<213> ORGANISM: Artificial
<220> FEATURE:
<223> OTHER INFORMATION: Light chain of benchmark antibody 1

<400> SEQUENCE: 20

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60
```

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Cys Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 21
<211> LENGTH: 446
<212> TYPE: PRT
<213> ORGANISM: Artificial
<220> FEATURE:
<223> OTHER INFORMATION: Heavy chain of benchmark antibody 2

<400> SEQUENCE: 21

Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Ser Phe Thr Asp Tyr
             20                  25                  30

His Ile Ser Trp Val Arg Gln Ala Pro Gly Gln Gly Leu Glu Trp Met
         35                  40                  45

Gly Val Ile Asn Pro Glu Tyr Gly Thr Thr Asp Tyr Asn Gln Arg Phe
     50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Tyr Phe Thr Gly Thr Gly Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205
```

Ser Asn Thr Lys Val Asp Lys Arg Val Glu Ser Lys Tyr Gly Pro Pro
210             215                 220

Cys Pro Ser Cys Pro Ala Pro Glu Phe Leu Gly Gly Pro Ser Val Phe
225             230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 22
<211> LENGTH: 219
<212> TYPE: PRT
<213> ORGANISM: Artificial
<220> FEATURE:
<223> OTHER INFORMATION: Light chain of benchmark antibody 2

<400> SEQUENCE: 22

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Lys His Ser
            20                  25                  30

Arg Gly Asn Thr Phe Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Tyr Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

```
Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 23
<211> LENGTH: 456
<212> TYPE: DNA
<213> ORGANISM: artificial
<220> FEATURE:
<223> OTHER INFORMATION: DNA sequence for the mutein shown in SEQ ID
      NO: 2

<400> SEQUENCE: 23

```
gcctcagacg aggagattca ggatgtgtca gggacgtggt atctgaaggc catgacggtg      60
gattttggt gttctggggt gcatgaggag tctgttacgc caatgactct gactaccctt     120
gaaggcggca atctggaggc taaggtcacc atggatatag gggggttcct gcaagaggtg     180
aaagcagtgt tagagaagac agatgaaccg ggtaaatata cggccgatgg cggtaaacat     240
gttgcctata tcattcgcag ccatgtgaaa gatcattaca tcttttatag cgagggcgat     300
tgccctgggc tgcctgttcc aggggtgtgg ctcgtgggca gagaccccaa gaacaacctg     360
gaagccttgg aggactttga gaaagccgca ggagcccgcg gactcagcac ggagagcatc     420
ctcatcccca ggcagagcga aaccagctct ccaggg                              456
```

<210> SEQ ID NO 24
<211> LENGTH: 453
<212> TYPE: DNA
<213> ORGANISM: artificial
<220> FEATURE:
<223> OTHER INFORMATION: DNA sequence for the mutein shown in SEQ ID
      NO: 3

<400> SEQUENCE: 24

```
gcctcagacg aggagattca ggatgtgtca gggacgtggt atctgaaggc catgacggtg      60
gattttggt gttcgggtat tcatgatgag tctgttacgc caatgactct gactaccctt     120
gaaggcggca atctggaggc taaggtcacc atggatattg ctggatttct tcaagaggtt     180
aaggcagtgt tagagaagac agatgaaccg ggtaaatata cggccgatgg cggtaaacat     240
gttgcctata tcattcgcag ccatgtgaaa gatcattaca tcttttatag cgagggagat     300
tgtcctgggc cggttccagg ggtgtggctc gtgggcagag accccaagaa caacctggaa     360
gccttggagg actttgagaa agccgcagga gcccgcggac tcagcacgga gcatcctc      420
atccccaggc agagcgaaac cagctctcca ggg                                 453
```

<210> SEQ ID NO 25
<211> LENGTH: 456
<212> TYPE: DNA
<213> ORGANISM: artificial
<220> FEATURE:
<223> OTHER INFORMATION: DNA sequence for the mutein shown in SEQ ID

NO: 4

<400> SEQUENCE: 25

```
gcctcagacg aggagattca ggatgtgtca gggacgtggt atctgaaggc catgacggtg      60
gatttttggt gttcggggat tcatgaggag tctgttacgc caatgactct gactaccctt     120
gaaggcggca atctggaggc taaggtcacc atggatattc ggggatttct tcaagagttt     180
aaggcagtgt tagagaagac agatgaaccg ggtaaatata cggccgatgg cggtaaacat     240
gttgcctata tcattcgcag ccatgtgaaa gatcattaca tcttttatag cgagggagat     300
tgtcctgatt ctccggttcc aggggtgtgg ctcgtgggca gagacccaa gaacaacctg      360
gaagccttgg aggactttga gaaagccgca ggagcccgcg gactcagcac ggagagcatc     420
ctcatcccca ggcagagcga aaccagctct ccaggg                              456
```

<210> SEQ ID NO 26
<211> LENGTH: 453
<212> TYPE: DNA
<213> ORGANISM: artificial
<220> FEATURE:
<223> OTHER INFORMATION: DNA sequence for the mutein shown in SEQ ID
      NO: 5

<400> SEQUENCE: 26

```
gcctcagacg aggagattca ggatgtgtca gggacgtggt atctgaaggc catgacggtg      60
gatttttggt gttctgggat tcatgaggag tctgttacgc caatgactct gactaccctt     120
gaaggcggca atctggaggc taaggtcacc atggatattg agggatttct tcaagagttt     180
aaggcagtgt tagagaagac agatgaaccg ggtaaatata cggccgatgg cggtaaacat     240
gttgcctata tcattcgcag ccatgtgaaa gatcattaca tcttttatag cgagggagat     300
tgtcctggtc cggttccagg ggtgtggctc gtgggcagag accccaagaa caacctggaa     360
gccttggagg actttgagaa agccgcagga gcccgcggac tcagcacgga gagcatcctc     420
atccccaggc agagcgaaac cagctctcca ggg                                 453
```

<210> SEQ ID NO 27
<211> LENGTH: 456
<212> TYPE: DNA
<213> ORGANISM: artificial
<220> FEATURE:
<223> OTHER INFORMATION: DNA sequence for the mutein shown in SEQ ID
      NO: 14

<400> SEQUENCE: 27

```
gcctcagacg aggagattca ggatgtgtca gggacgtggt atctgaaggc catgacggtg      60
gattatgggt gtaatcatcc ttctatatgg tcagttacgc caatgactct gactaccctt     120
gaaggcggca atctggaggc taaggtcacc atgtattggg aggggtcccg tcaagaggat     180
aaagcagtgt tagagaagac agatgaaccg ggtaaatata cggccgatgg cggtaaacat     240
gttgcctata tcattcgcag ccatgtgaaa gatcattaca tcttttatag cgagggcata     300
tgcgaggggg caccggttcc aggggtgtgg ctcgtgggca gagacccaa gaacaacctg      360
gaagccttgg aggactttga gaaagccgca ggagcccgcg gactcagcac ggagagcatc     420
ctcatcccca ggcagagcga aaccagctct ccaggg                              456
```

<210> SEQ ID NO 28
<211> LENGTH: 534
<212> TYPE: DNA
<213> ORGANISM: artificial

```
<220> FEATURE:
<223> OTHER INFORMATION: DNA sequence for the mutein shown in SEQ ID
      NO: 9

<400> SEQUENCE: 28
caggactcca cctcagacct gatcccagcc ccacctctga gcaaggtccc tctgcagcag      60
aacttccagg acaaccaatt ccatgggaaa tggtatgtcg tgggcatggc cggaaatctg     120
atgctgcgtg aggataagga tccgaccaaa atgagcgcga ccatttacga gttgaaagaa     180
gataaatcat ataacgtcac ctgggtggac tttcgtttca agaaatgcaa ataccaaatt     240
ggaacctttg tgccggggag ccagccgggc gagtttactt taggcggaat taaaagtatg     300
ccgggcatga catcattctt ggtccgcgtc gtgagcacca actacaacca gcatgccatg     360
gtgttcttca gtacgtgta ccagaaccgc gagtactttg agatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc            534

<210> SEQ ID NO 29
<211> LENGTH: 534
<212> TYPE: DNA
<213> ORGANISM: artificial
<220> FEATURE:
<223> OTHER INFORMATION: DNA sequence for the mutein shown in SEQ ID
      NO: 10

<400> SEQUENCE: 29
caggactcca cctcagacct gatcccagcc ccacctctga gcaaggtccc tctgcagcag      60
aacttccagg acaaccaatt ccatgggaaa tggtatgtcg tgggcctggc cggaaatacc     120
atcctgcgtg aggataagga tccggacaaa atggaggcga ccatttacga gttgaaagaa     180
gataaatcat ataacgtcac cagcgtggac tttatcatga gaaatgctg gtacttcatt     240 accacctttg tgccggggag ccagccgggc gagtttactt taggccacat taaaagtatg     300
ccgggcatga catcattctt ggtccgcgtc gtgagcacca actacaacca gcatgccatg     360
gtgttcttca gtacgtgta ccagaaccgc gagttctttg agatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc            534

<210> SEQ ID NO 30
<211> LENGTH: 534
<212> TYPE: DNA
<213> ORGANISM: artificial
<220> FEATURE:
<223> OTHER INFORMATION: DNA sequence for the mutein shown in SEQ ID
      NO: 15

<400> SEQUENCE: 30
caggactcca cctcagacct gatcccagcc ccacctctga gcaaggtccc tctgcagcag      60
aacttccagg acaaccaatt ccatgggaaa tggtatgtcg tgggcgaggc cggaaatctt     120
ttgctgcgtg aggataagga tccgaggaaa atgacggcga ccatttacga gttgaaagaa     180
gataaatcat ataacgtcac ccgggtggag tttggggtta agacatacaa gtaccagatt     240
gggacctttg tgccggggag ccagccgggc gagtttactt taggcggtat taaaagtatg     300
ccgggcatga catcattttt ggtccgcgtc gtgagcacca actacaacca gcatgccatg     360
gtgttcttca gtatgtgta tcagaaccgc gagtattttg agatcacact gtacgggcgc     420
acgaaagaac tgacaagcga gctgaaggaa aattttatcc gcttttccaa atctctgggc     480
```

```
ctccctgaaa accacatcgt cttccctgtc ccaatcgacc aggctatcga cggc        534
```

<210> SEQ ID NO 31
<211> LENGTH: 456
<212> TYPE: DNA
<213> ORGANISM: artificial
<220> FEATURE:
<223> OTHER INFORMATION: DNA sequence for the mutein shown in SEQ ID
      NO: 6

<400> SEQUENCE: 31

```
gcctcagacg aggagattca ggatgtgtca gggacgtggt atctgaaggc catgacggtg   60
gattggcaat gtacttggga tgatgatcct tcagttacgc caatgactct gactacccct  120
gaaggcggca atctggaggc taaggtcacc atgcctatat ttgggctctg gcaggaggag  180
aaggcagtgt tagagaagac agatgaaccg ggtaaatata cggccgatgg cggtaaacat  240
gttgcctata tcattcgcag ccatgtgaaa gatcattaca tcttttatag cgagggagca  300
tgttatgggc aaccggttcc aggggtgtgg ctcgtgggca gagaccccaa gaacaacctg  360
gaagccttgg aggactttga gaaagccgca ggagcccgcg gactcagcac ggagagcatc  420
ctcatcccca ggcagagcga aaccagctct ccaggg                             456
```

<210> SEQ ID NO 32
<211> LENGTH: 456
<212> TYPE: DNA
<213> ORGANISM: artificial
<220> FEATURE:
<223> OTHER INFORMATION: DNA sequence for the mutein shown in SEQ ID
      NO: 12

<400> SEQUENCE: 32

```
gcctcagacg aggagattca ggatgtgtca gggacgtggt atctgaaggc catgacggtg   60
gattggcaat gtacgtgggc ggatgagccg tcagttacgc caatgactct gactacccct  120
gaaggcggca atctggaggc taaggtcacc attccaacct ttgggctcgc ggaggaggag  180
aaggcagtgt tagagaagac agatgaaccg ggtaaatata cggccgatgg cggtaaacat  240
gttgcctata tcattcgcag ccatgtgaaa gatcattaca tcttttatag cgagggacgc  300
tgttgggggc gcccggttcc aggggtgtgg ctcgtgggca gagaccccaa gaacaacctg  360
gaagccttgg aggactttga gaaagccgca ggagcccgcg gactcagcac ggagagcatc  420
ctcatcccca ggcagagcga aaccagctct ccaggg                             456
```

<210> SEQ ID NO 33
<211> LENGTH: 456
<212> TYPE: DNA
<213> ORGANISM: artificial
<220> FEATURE:
<223> OTHER INFORMATION: DNA sequence for the mutein shown in SEQ ID
      NO: 13

<400> SEQUENCE: 33

```
gcctcagacg aggagattca ggatgtgtca gggacgtggt atctgaaggc catgacggtg   60
gattgggtct gtgcgtttga tgatgatcct tcagttacgc caatgactct gactacccct  120
gaaggcggca atctggaggc taaggtcact attcctacat ttgggctcta tgaggaggag  180
aaggcagtgt tagagaagac agatgaaccg ggtaaatata cggccgatgg cggtaaacat  240
gttgcctata tcattcgcag ccatgtgaaa gatcattaca tcttttatag cgagggagcc  300
tgtcatgggc acccggttcc aggggtgtgg ctcgtgggca gagaccccaa gaacaacctg  360
```

```
gaagccttgg aggactttga gaaagccgca ggagcccgcg gactcagcac ggagagcatc      420
ctcatcccca ggcagagcga aaccagctct ccaggg                                456

<210> SEQ ID NO 34
<211> LENGTH: 1014
<212> TYPE: DNA
<213> ORGANISM: artificial
<220> FEATURE:
<223> OTHER INFORMATION: DNA sequence for the fusion protein shown in
      SEQ ID NO: 16

<400> SEQUENCE: 34
caggactcca cctcagacct gatcccagcc ccacctctga gcaaggtccc tctgcagcag       60
aacttccagg acaaccaatt ccatgggaaa tggtatgtcg tgggcatggc cggaaatctg      120
atgctgcgtg aggataagga tccgaccaaa atgagcgcga ccatttacga gttgaaagaa      180
gataaatcat ataacgtcac ctgggtggac tttcgtttca agaaatgcaa ataccaaatt      240
ggaacctttg tgccgggggag ccagccggc gagtttactt taggcggaat taaaagtatg      300
ccgggcatga catcattctt ggtccgcgtc gtgagcacca actacaacca gcatgccatg      360
gtgttcttca gtacgtgta ccagaaccgc gagtactttg atcacact gtacgggcgc         420 acgaaagaac tgacaagcga gctgaaggaa aattttatcc gcttttccaa atctctgggc      480
ctccctgaaa accacatcgt cttccctgtc ccaatcgacc agtgtatcga cggcggtggt      540
ggttctggtg gtggtggatc ggcctcagac gaggagattc aggatgtgtc agggacgtgg      600
tatctgaagg ccatgacggt ggattttgg tgttctggga ttcatgagga gtctgttacg       660
ccaatgactc tgactaccct tgaaggcggc aatctggagg ctaaggtcac catggatatt      720
gagggatttc ttcaagagtt taaggcagtg ttagagaaga cagatgaacc gggtaaatat      780
acggccgatg gcgtaaaca tgttgcctat atcattcgca gccatgtgaa agatcattac      840 atctttata gcgagggaga ttgtcctggt ccggttccag gggtgtggct cgtgggcaga       900
gaccccaaga acaacctgga agccttggag gactttgaga agccgcagg agcccgcgga      960 ctcagcacgg agagcatcct catcccagg cagagcgaaa ccagctctcc aggg           1014

<210> SEQ ID NO 35
<211> LENGTH: 1023
<212> TYPE: DNA
<213> ORGANISM: artificial
<220> FEATURE:
<223> OTHER INFORMATION: DNA sequence for the fusion protein shown in
      SEQ ID NO: 17

<400> SEQUENCE: 35
gcctcagacg aggagattca ggatgtgtca gggacgtggt atctgaaggc catgacggtg       60 gattttggt gttctgggat tcatgaggag tctgttacgc caatgactct gactacccctt     120 gaaggcggca atctggaggc taaggtcacc atggatattg agggatttct tcaagagttt      180
aaggcagtgt tagagaagac agatgaaccg ggtaaatata cggccgatgg cggtaaacat     240
gttgcctata tcattcgcag ccatgtgaaa gatcattaca tcttttatag cgagggagat      300
tgtcctggtc cggttccagg ggtgtggctc gtgggcagag accccaagaa caacctggaa      360
gccttggagg actttgagaa agccgcagga gcccgcggac tcagcacgga gagcatcctc      420
atccccaggc agagcgaaac cagctctcca gggagcgggg caggtggtgg ttctggtggt      480
ggtggatcgc aggactccac ctcagacctg atcccagccc cacctctgag caaggtccct     540
```

-continued

```
ctgcagcaga acttccagga caaccaattc catgggaaat ggtatgtcgt gggcatggcc    600
ggaaatctga tgctgcgtga ggataaggat ccgaccaaaa tgagcgcgac catttacgag    660
ttgaaagaag ataaatcata taacgtcacc tgggtggact ttcgtttcaa gaaatgcaaa    720
taccaaattg gaacctttgt gccggggagc cagccgggcg agtttacttt aggcggaatt    780
aaaagtatgc cgggcatgac atcattcttg gtccgcgtcg tgagcaccaa ctacaaccag    840
catgccatgg tgttcttcaa gtacgtgtac cagaaccgcg agtactttga gatcacactg    900
tacgggcgca cgaaagaact gacaagcgag ctgaaggaaa attttatccg cttttccaaa    960
tctctgggcc tccctgaaaa ccacatcgtc ttccctgtcc caatcgacca gtgtatcgac    1020
ggc                                                                 1023
```

<210> SEQ ID NO 36
<211> LENGTH: 11
<212> TYPE: PRT
<213> ORGANISM: Artificial
<220> FEATURE:
<223> OTHER INFORMATION: Peptide bond

<400> SEQUENCE: 36

Gly Ala Gly Gly Gly Ser Gly Gly Gly Gly Ser
1               5                   10

<210> SEQ ID NO 37
<211> LENGTH: 13
<212> TYPE: PRT
<213> ORGANISM: artificial
<220> FEATURE:
<223> OTHER INFORMATION: Peptide bond

<400> SEQUENCE: 37

Ser Gly Ala Gly Gly Gly Gly Ser Gly Gly Gly Gly Ser
1               5                   10

<210> SEQ ID NO 38
<211> LENGTH: 3
<212> TYPE: PRT
<213> ORGANISM: artificial
<220> FEATURE:
<223> OTHER INFORMATION: Peptide bond

<400> SEQUENCE: 38

Ser Ala Gly
1

<210> SEQ ID NO 39
<211> LENGTH: 52
<212> TYPE: PRT
<213> ORGANISM: artificial
<220> FEATURE:
<223> OTHER INFORMATION: residues 254-299 from Immunoglobulin G-binding
      protein G from Streptococcus dysgalactiae subsp. equisimilis
      AC-2713

<400> SEQUENCE: 39

Ala Val Asp Ala Asn Ser Leu Ala Glu Ala Lys Val Leu Ala Asn Arg
1               5                   10                  15

Glu Leu Asp Lys Tyr Gly Val Ser Asp Tyr Tyr Lys Asn Leu Ile Asn
                20                  25                  30

Asn Ala Lys Thr Val Glu Gly Val Lys Ala Leu Ile Asp Glu Ile Leu
        35                  40                  45

Ala Ala Leu Pro

<210> SEQ ID NO 40
<211> LENGTH: 315
<212> TYPE: PRT
<213> ORGANISM: artificial
<220> FEATURE:
<223> OTHER INFORMATION: Fusion protein

<400> SEQUENCE: 40

Ala Ser Asp Glu Glu Ile Gln Asp Val Ser Gly Thr Trp Tyr Leu Lys
1               5                   10                  15

Ala Met Thr Val Asp Phe Trp Cys Ser Gly Ile His Glu Glu Ser Val
            20                  25                  30

Thr Pro Met Thr Leu Thr Thr Leu Glu Gly Gly Asn Leu Glu Ala Lys
        35                  40                  45

Val Thr Met Asp Ile Glu Gly Phe Leu Gln Glu Phe Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Asp Cys Pro Gly Pro Val Pro Gly Val Trp Leu Val Gly
            100                 105                 110

Arg Asp Pro Lys Asn Asn Leu Glu Ala Leu Glu Asp Phe Glu Lys Ala
        115                 120                 125

Ala Gly Ala Arg Gly Leu Ser Thr Glu Ser Ile Leu Ile Pro Arg Gln
    130                 135                 140

Ser Glu Thr Ser Ser Pro Gly Ser Gly Ala Gly Gly Gly Ser Gly
145                 150                 155                 160

Gly Gly Gly Ser Ala Ser Asp Glu Glu Ile Gln Asp Val Ser Gly Thr
                165                 170                 175

Trp Tyr Leu Lys Ala Met Thr Val Asp Phe Trp Cys Ser Gly Ile His
            180                 185                 190

Glu Glu Ser Val Thr Pro Met Thr Leu Thr Thr Leu Glu Gly Gly Asn
        195                 200                 205

Leu Glu Ala Lys Val Thr Met Asp Ile Glu Gly Phe Leu Gln Glu Phe
    210                 215                 220

Lys Ala Val Leu Glu Lys Thr Asp Glu Pro Gly Lys Tyr Thr Ala Asp
225                 230                 235                 240

Gly Gly Lys His Val Ala Tyr Ile Ile Arg Ser His Val Lys Asp His
                245                 250                 255

Tyr Ile Phe Tyr Ser Glu Gly Asp Cys Pro Gly Pro Val Pro Gly Val
            260                 265                 270

Trp Leu Val Gly Arg Asp Pro Lys Asn Asn Leu Glu Ala Leu Glu Asp
        275                 280                 285

Phe Glu Lys Ala Ala Gly Ala Arg Gly Leu Ser Thr Glu Ser Ile Leu
    290                 295                 300

Ile Pro Arg Gln Ser Glu Thr Ser Ser Pro Gly
305                 310                 315

<210> SEQ ID NO 41
<211> LENGTH: 396
<212> TYPE: PRT
<213> ORGANISM: artificial
<220> FEATURE:
<223> OTHER INFORMATION: Fusion protein

<400> SEQUENCE: 41

```
Ala Ser Asp Glu Glu Ile Gln Asp Val Ser Gly Thr Trp Tyr Leu Lys
1               5                   10                  15

Ala Met Thr Val Asp Phe Trp Cys Ser Gly Ile His Glu Glu Ser Val
            20                  25                  30

Thr Pro Met Thr Leu Thr Thr Leu Glu Gly Gly Asn Leu Glu Ala Lys
        35                  40                  45

Val Thr Met Asp Ile Glu Gly Phe Leu Gln Glu Phe Lys Ala Val Leu
50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Asp Cys Pro Gly Pro Val Pro Gly Val Trp Leu Val Gly
            100                 105                 110

Arg Asp Pro Lys Asn Asn Leu Glu Ala Leu Glu Asp Phe Glu Lys Ala
        115                 120                 125

Ala Gly Ala Arg Gly Leu Ser Thr Glu Ser Ile Leu Ile Pro Arg Gln
130                 135                 140

Ser Glu Thr Ser Ser Pro Gly Ser Gly Ala Gly Gly Ser Gly Gly
145                 150                 155                 160

Gly Gly Ser Gln Asp Ser Thr Ser Asp Leu Ile Pro Ala Pro Pro Leu
            165                 170                 175

Ser Lys Val Pro Leu Gln Gln Asn Phe Gln Asp Asn Gln Phe His Gly
        180                 185                 190

Lys Trp Tyr Val Val Gly Glu Ala Gly Asn Leu Leu Leu Arg Glu Asp
        195                 200                 205

Lys Asp Pro Arg Lys Met Thr Ala Thr Ile Tyr Glu Leu Lys Glu Asp
        210                 215                 220

Lys Ser Tyr Asn Val Thr Arg Val Glu Phe Gly Val Lys Thr Tyr Lys
225                 230                 235                 240

Tyr Gln Ile Gly Thr Phe Val Pro Gly Ser Gln Pro Gly Glu Phe Thr
            245                 250                 255

Leu Gly Gly Ile Lys Ser Met Pro Gly Met Thr Ser Phe Leu Val Arg
        260                 265                 270

Val Val Ser Thr Asn Tyr Asn Gln His Ala Met Val Phe Phe Lys Tyr
        275                 280                 285

Val Tyr Gln Asn Arg Glu Tyr Phe Glu Ile Thr Leu Tyr Gly Arg Thr
290                 295                 300

Lys Glu Leu Thr Ser Glu Leu Lys Glu Asn Phe Ile Arg Phe Ser Lys
305                 310                 315                 320

Ser Leu Gly Leu Pro Glu Asn His Ile Val Phe Pro Val Pro Ile Asp
            325                 330                 335

Gln Ala Ile Asp Gly Ser Ala Gly Ala Val Asp Ala Asn Ser Leu Ala
        340                 345                 350

Glu Ala Lys Val Leu Ala Asn Arg Glu Leu Asp Lys Tyr Gly Val Ser
        355                 360                 365

Asp Tyr Tyr Lys Asn Leu Ile Asn Asn Ala Lys Thr Val Glu Gly Val
        370                 375                 380

Lys Ala Leu Ile Asp Glu Ile Leu Ala Ala Leu Pro
385                 390                 395
```

```
<210> SEQ ID NO 42
<211> LENGTH: 233
<212> TYPE: PRT
<213> ORGANISM: artificial
<220> FEATURE:
<223> OTHER INFORMATION: Fusion protein

<400> SEQUENCE: 42

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Leu Leu Leu Arg Glu Asp Lys Asp Pro
        35                  40                  45

Arg Lys Met Thr Ala Thr Ile Tyr Glu Leu Lys Glu Asp Lys Ser Tyr
50                  55                  60

Asn Val Thr Arg Val Glu Phe Gly Val Lys Thr Tyr Lys Tyr Gln Ile
65                  70                  75                  80

Gly Thr Phe Val Pro Gly Ser Gln Pro Gly Glu Phe Thr Leu Gly Gly
                85                  90                  95

Ile Lys Ser Met Pro Gly Met Thr Ser Phe Leu Val Arg Val Val Ser
            100                 105                 110

Thr Asn Tyr Asn Gln His Ala Met Val Phe Phe Lys Tyr Val Tyr Gln
        115                 120                 125

Asn Arg Glu Tyr Phe Glu Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Ala Ile
                165                 170                 175

Asp Gly Ser Ala Gly Ala Val Asp Ala Asn Ser Leu Ala Glu Ala Lys
            180                 185                 190

Val Leu Ala Asn Arg Glu Leu Asp Lys Tyr Gly Val Ser Asp Tyr Tyr
        195                 200                 205

Lys Asn Leu Ile Asn Asn Ala Lys Thr Val Glu Gly Val Lys Ala Leu
210                 215                 220

Ile Asp Glu Ile Leu Ala Ala Leu Pro
225                 230

<210> SEQ ID NO 43
<211> LENGTH: 214
<212> TYPE: PRT
<213> ORGANISM: artificial
<220> FEATURE:
<223> OTHER INFORMATION: Arm of fusion protein (antibody and lipocalin
      mutein)

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln His His Tyr Gly Ile Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 44
<211> LENGTH: 609
<212> TYPE: PRT
<213> ORGANISM: artificial
<220> FEATURE:
<223> OTHER INFORMATION: Arm of fusion protein (antibody and lipocalin
      mutein)

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ile Thr Tyr
            20                  25                  30

Trp Met Thr Trp Val Arg Gln Ala Pro Gly Gln Gly Leu Glu Trp Met
        35                  40                  45

Gly Gln Ile Phe Pro Ala Ser Gly Ser Ala Asp Tyr Asn Glu Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Gly Gly Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr

```
            210                 215                 220
Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys Gly Gly
        435                 440                 445

Gly Gly Ser Gly Gly Gly Gly Ser Ala Ser Asp Glu Glu Ile Gln Asp
    450                 455                 460

Val Ser Gly Thr Trp Tyr Leu Lys Ala Met Thr Val Asp Phe Trp Cys
465                 470                 475                 480

Ser Gly Ile His Glu Glu Ser Val Thr Pro Met Thr Leu Thr Thr Leu
                485                 490                 495

Glu Gly Gly Asn Leu Glu Ala Lys Val Thr Met Asp Ile Glu Gly Phe
            500                 505                 510

Leu Gln Glu Phe Lys Ala Val Leu Glu Lys Thr Asp Glu Pro Gly Lys
        515                 520                 525

Tyr Thr Ala Asp Gly Gly Lys His Val Ala Tyr Ile Ile Arg Ser His
    530                 535                 540

Val Lys Asp His Tyr Ile Phe Tyr Ser Glu Gly Asp Cys Pro Gly Pro
545                 550                 555                 560

Val Pro Gly Val Trp Leu Val Gly Arg Asp Pro Lys Asn Asn Leu Glu
                565                 570                 575

Ala Leu Glu Asp Phe Glu Lys Ala Ala Gly Ala Arg Gly Leu Ser Thr
            580                 585                 590

Glu Ser Ile Leu Ile Pro Arg Gln Ser Glu Thr Ser Ser Pro Gly Ser
        595                 600                 605

Asp

<210> SEQ ID NO 45
<211> LENGTH: 945
```

```
<212> TYPE: DNA
<213> ORGANISM: artificial
<220> FEATURE:
<223> OTHER INFORMATION: Nucleic acid sequence coding for fusion protein
      shown in SEQ ID NO:40

<400> SEQUENCE: 45
gcctcagacg aggagattca ggatgtgtca gggacgtggt atctgaaggc catgacggtg      60
gattttggt gttctgggat tcatgaggag tctgttacgc caatgactct gactacccct     120
gaaggcggca atctggaggc taaggtcacc atggatattg agggatttct tcaagagttt     180
aaggcagtgt tagagaagac agatgaaccg ggtaaatata cggccgatgg cggtaaacat     240
gttgcctata tcattcgcag ccatgtgaaa gatcattaca tcttttatag cgagggagat     300
tgtcctggtc cggttccagg ggtgtggctc gtgggcagag accccaagaa caacctggaa     360
gccttggagg actttgagaa agccgcagga gcccgcggac tcagcacgga gagcatcctc     420
atccccaggc agagcgaaac cagctctcca gggagcgggg caggtggtgg tggttctggt     480
ggtggtggat cggcctcaga cgaggagatt caggatgtgt cagggacgtg gtatctgaag     540
gccatgacgg tggattttt gtgttctggg attcatgagg agtctgttac gccaatgact     600
ctgactaccc ttgaaggcgg caatctggag gctaaggtca ccatggatat tgagggattt     660
cttcaagagt ttaaggcagt gttagagaag acagatgaac cgggtaaata tacggccgat     720
ggcggtaaac atgttgccta tatcattcgc agccatgtga agatcatta catcttttat     780
agcgagggag attgtcctgg tccggttcca ggggtgtggc tcgtgggcag agaccccaag     840
aacaacctgg aagccttgga ggactttgag aaagccgcag gagcccgcgg actcagcacg     900
gagagcatcc tcatccccag gcagagcgaa accagctctc caggg                     945

<210> SEQ ID NO 46
<211> LENGTH: 1188
<212> TYPE: DNA
<213> ORGANISM: artificial
<220> FEATURE:
<223> OTHER INFORMATION: Nucleotide sequence coding for fusion protein
      shown in SEQ ID NO: 41

<400> SEQUENCE: 46
gcctcagacg aggagattca ggatgtgtca gggacgtggt atctgaaggc catgacggtg      60
gattttggt gttctgggat tcatgaggag tctgttacgc caatgactct gactacccct     120
gaaggcggca atctggaggc taaggtcacc atggatattg agggatttct tcaagagttt     180
aaggcagtgt tagagaagac agatgaaccg ggtaaatata cggccgatgg cggtaaacat     240
gttgcctata tcattcgcag ccatgtgaaa gatcattaca tcttttatag cgagggagat     300
tgtcctggtc cggttccagg ggtgtggctc gtgggcagag accccaagaa caacctggaa     360
gccttggagg actttgagaa agccgcagga gcccgcggac tcagcacgga gagcatcctc     420
atccccaggc agagcgaaac cagctctcca gggagcgggg caggtggtgg ttctggtggt     480
ggtggatcgc aggactccac ctcagacctg atcccagccc cacctctgag caaggtccct     540
ctgcagcaga acttccagga caaccaattc catgggaaat ggtatgtcgt gggcgaggcc     600
ggaaatcttt tgctgcgtga ggataaggat ccgaggaaaa tgacggcgac catttacgag     660
ttgaaagaag ataaatcata taacgtcacc cgggtggagt ttgggttaa gacatacaag     720
taccagattg gacctttgt gccggggagc cagccgggcg agtttacttt aggcggtatt     780
aaagtatgc cgggcatgac atcattttg gtccgcgtcg tgagcaccaa ctacaaccag     840
```

```
catgccatgg tgttcttcaa gtatgtgtat cagaaccgcg agtattttga gatcacactg    900
tacgggcgca cgaaagaact gacaagcgag ctgaaggaaa attttatccg cttttccaaa    960
tctctgggcc tccctgaaaa ccacatcgtc ttccctgtcc aatcgacca ggctatcgac    1020 ggcagcgctg gtgccgtcga cgctaactct ctggctgaag ctaaagttct ggctaaccgt    1080
gaactggaca aatacggtgt tccgactac tacaaaaacc tcatcaacaa cgctaaaacc    1140
gttgaaggtg ttaaagctct gatcgacgaa attctcgcag cactgccg                1188
```

<210> SEQ ID NO 47
<211> LENGTH: 699
<212> TYPE: DNA
<213> ORGANISM: artificial
<220> FEATURE:
<223> OTHER INFORMATION: Nucleotide sequence coding for fusion protein
      shwon in SEQ ID NO:42

<400> SEQUENCE: 47

```
caggactcca cctcagacct gatcccagcc ccacctctga gcaaggtccc tctgcagcag    60
aacttccagg acaaccaatt ccatgggaaa tggtatgtcg tgggcgaggc cggaaatctt    120
ttgctgcgtg aggataagga tccgaggaaa atgacggcga ccatttacga gttgaaagaa    180
gataaatcat ataacgtcac ccgggtggag tttggggtta agacatacaa gtaccagatt    240 ggacctttg tgccggggag ccagccgggc gagtttactt taggcggtat taaaagtatg    300
ccgggcatga catcattttt ggtccgcgtc gtgagcacca actacaacca gcatgccatg    360
gtgttcttca gtatgtgta tcagaaccgc gagtattttg agatcacact gtacgggcgc    420
acgaaagaac tgacaagcga gctgaaggaa aattttatcc gcttttccaa atctctgggc    480
ctccctgaaa accacatcgt cttccctgtc ccaatcgacc aggctatcga cggcagcgct    540
ggtgccgtcg acgctaactc tctggctgaa gctaaagttc tggctaaccg tgaactggac    600
aaatacggtg tttccgacta ctacaaaaac ctcatcaaca acgctaaaac cgttgaaggt    660
gttaaagctc tgatcgacga aattctcgca gcactgccg                          699
```

<210> SEQ ID NO 48
<211> LENGTH: 645
<212> TYPE: DNA
<213> ORGANISM: artificial
<220> FEATURE:
<223> OTHER INFORMATION: Nucleotide sequence coding for one arm of
      fusion protein shown in SEQ ID NO: 43

<400> SEQUENCE: 48

```
gacatccaga tgacccagag cccatcctcc ctgtctgcct ctgtgggaga cagggtgacc    60
atcacttgta ggacctctga gaacatctac tcctacctgg cttggtatca acagaagcct    120
ggcaaggctc caaaactgct gatttacaat gccaagaccc tggctgaggg agtgccaagc    180
aggttctctg gctctggctc tggcacagac ttcaccctga ccatctcctc cctccaacct    240
gaggactttg ccacctacta ctgtcaacac cactatggca tcccattcac ctttggacaa    300
ggcaccaagg tggagattaa gcgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                   645
```

<210> SEQ ID NO 49
<211> LENGTH: 1830
<212> TYPE: DNA
<213> ORGANISM: artificial
<220> FEATURE:
<223> OTHER INFORMATION: Nucleotide sequence coding for one arm of
       fusion protein shown in SEQ ID NO: 44

<400> SEQUENCE: 49

| | | | | | |
|---|---|---|---|---|---|
| caggtccaac | ttgtccagtc | tggagcagag | gtgaagaagc | ctggagcctc | tgtgaaggtg | 60 |
| tcctgtaagg | catctggcta | catcttcatc | acctactgga | tgacctgggt | gagacaggct | 120 |
| cctggacaag | gattggagtg | gatgggacaa | atctttcctg | cctctggctc | tgctgactac | 180 |
| aatgagaagt | ttgagggcag | ggtgacaatg | accacagaca | ccagcaccag | cacagcctat | 240 |
| atggaactga | ggtccctgag | gtctgatgac | acagcagtct | actactgtgc | caggggagga | 300 |
| ggaggctttg | cctactgggg | acaaggcacc | ctggtacag | tgtcctctgc | tagcaccaag | 360 |
| ggcccatcgg | tcttccccct | ggcaccctcc | tccaagagca | cctctggggg | cacagcggcc | 420 |
| ctgggctgcc | tggtcaagga | ctacttcccc | gaaccggtga | cggtgtcgtg | gaactcaggc | 480 |
| gccctgacca | gcggcgtgca | caccttcccg | gctgtcctac | agtcctcagg | actctactcc | 540 |
| ctcagcagcg | tggtgaccgt | gccctccagc | agcttgggca | cccagaccta | catctgcaac | 600 |
| gtgaatcaca | agcccagcaa | caccaaggtg | gacaagagag | ttgagcccaa | atcttgtgac | 660 |
| aaaactcaca | catgcccacc | gtgcccagca | cctgaactcc | tggggggacc | gtcagtcttc | 720 |
| ctcttccccc | caaaacccaa | ggacaccctc | atgatctccc | ggacccctga | ggtcacgtgc | 780 |
| gtggtggtgg | acgtgagcca | cgaagacccc | gaggtcaagt | tcaactggta | cgtggacggc | 840 |
| gtggaggtgc | ataatgccaa | gacaaagccg | cgggaggagc | agtacaacag | cacgtaccgt | 900 |
| gtggtcagcg | tcctcaccgt | cctgcaccag | gactggctga | atggcaagga | gtacaagtgc | 960 |
| aaggtctcca | acaaagccct | cccagccccc | atcgagaaaa | ccatctccaa | agccaaaggg | 1020 |
| cagccccgag | aaccacaggt | gtacaccctg | cccccatccc | gggaagagat | gaccaagaac | 1080 |
| caggtcagcc | tgacctgcct | ggtcaaaggc | ttctatccca | gcgacatcgc | cgtggagtgg | 1140 |
| gagagcaatg | ggcagccgga | gaacaactac | aagaccacgc | ctcccgtgct | ggactccgac | 1200 |
| ggctccttct | tcctctacag | caagctcacc | gtggacaaga | gcaggtggca | gcaggggaac | 1260 |
| gtcttctcat | gctccgtgat | gcatgaggct | ctgcacaacc | actacacgca | gaagagcctc | 1320 |
| tccctgtctc | cgggtaaagg | tgaggaggc | tctggaggtg | gaggcagcgc | tctgatgag | 1380 |
| gagattcagg | atgtgtctgg | cacctggtat | ctgaaagcta | tgacagtgga | cttctggtgt | 1440 |
| tctggcatcc | atgaggagtc | tgtgacacct | atgaccctga | ccaccttgga | gggaggcaac | 1500 |
| ttggaggcta | aggtgacaat | ggacattgag | ggcttcctcc | aagagttcaa | ggctgtgttg | 1560 |
| gagaagacag | atgaacctgg | caaatacaca | gcagatggag | gcaaacatgt | ggcttacatc | 1620 |
| atcaggtctc | atgtgaagga | ccactacatc | ttctactctg | agggagactg | tcctggacct | 1680 |
| gtgcctggag | tgtggctggt | gggcagggac | ccaaagaaca | acttggaggc | tttggaggac | 1740 |
| tttgagaagg | ctgctggagc | caggggactg | agcacagaga | gcatcctgat | tccaagacag | 1800 |
| tctgagacct | ccagccctgg | ctctgactaa | | | | 1830 |

<210> SEQ ID NO 50
<211> LENGTH: 156
<212> TYPE: DNA
<213> ORGANISM: artificial

<220> FEATURE:
<223> OTHER INFORMATION: Nucleotide sequence coding for to residues
254-299 from Immunoglobulin G-binding protein G from Streptococcus
dysgalactiae subsp. equisimilis AC-2713 shown in SEQ ID NO:39

<400> SEQUENCE: 50

```
gccgtcgacg ctaactctct ggctgaagct aaagttctgg ctaaccgtga actggacaaa      60
tacggtgttt ccgactacta caaaaacctc atcaacaacg ctaaaaccgt tgaaggtgtt     120
aaagctctga tcgacgaaat tctcgcagca ctgccg                               156
```

<210> SEQ ID NO 51
<211> LENGTH: 446
<212> TYPE: PRT
<213> ORGANISM: artificial
<220> FEATURE:
<223> OTHER INFORMATION: Heavy chain of an IgG antibody

<400> SEQUENCE: 51

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ile Phe Ile Thr Tyr
            20                  25                  30

Trp Met Thr Trp Val Arg Gln Ala Pro Gly Gln Gly Leu Glu Trp Met
        35                  40                  45

Gly Gln Ile Phe Pro Ala Ser Gly Ser Ala Asp Tyr Asn Glu Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Gly Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
    435                 440                 445

<210> SEQ ID NO 52
<211> LENGTH: 214
<212> TYPE: PRT
<213> ORGANISM: artificial
<220> FEATURE:
<223> OTHER INFORMATION: Light chain of an IgG antibody

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Ile Pro Phe
            85                  90                  95

Thr Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210
```

<210> SEQ ID NO 53
<211> LENGTH: 341
<212> TYPE: PRT
<213> ORGANISM: artificial
<220> FEATURE:
<223> OTHER INFORMATION: Fusion protein

<400> SEQUENCE: 53

```
Ala Ser Asp Glu Glu Ile Gln Asp Val Ser Gly Thr Trp Tyr Leu Lys
1               5                   10                  15

Ala Met Thr Val Asp Phe Trp Cys Ser Gly Ile His Glu Glu Ser Val
            20                  25                  30

Thr Pro Met Thr Leu Thr Thr Leu Glu Gly Gly Asn Leu Glu Ala Lys
        35                  40                  45

Val Thr Met Asp Ile Glu Gly Phe Leu Gln Glu Phe Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Asp Cys Pro Gly Pro Val Pro Gly Val Trp Leu Val Gly
            100                 105                 110

Arg Asp Pro Lys Asn Asn Leu Glu Ala Leu Glu Asp Phe Glu Lys Ala
        115                 120                 125

Ala Gly Ala Arg Gly Leu Ser Thr Glu Ser Ile Leu Ile Pro Arg Gln
    130                 135                 140

Ser Glu Thr Ser Ser Pro Gly Ser Asp Gly Gly Gly Ser Gly Gly
145                 150                 155                 160

Gly Gly Ser Gln Asp Ser Thr Ser Asp Leu Ile Pro Ala Pro Pro Leu
                165                 170                 175

Ser Lys Val Pro Leu Gln Gln Asn Phe Gln Asp Asn Gln Phe His Gly
            180                 185                 190

Lys Trp Tyr Val Val Gly Glu Ala Gly Asn Leu Leu Leu Arg Glu Asp
        195                 200                 205

Lys Asp Pro Arg Lys Met Thr Ala Thr Ile Tyr Glu Leu Lys Glu Asp
    210                 215                 220

Lys Ser Tyr Asp Val Thr Arg Val Glu Phe Gly Val Lys Thr Tyr Lys
225                 230                 235                 240

Tyr Gln Ile Gly Thr Phe Val Pro Gly Ser Gln Pro Gly Glu Phe Thr
                245                 250                 255

Leu Gly Gly Ile Lys Ser Met Pro Gly Met Thr Ser Phe Leu Val Arg
            260                 265                 270

Val Val Ser Thr Asn Tyr Asn Gln His Ala Met Val Phe Phe Lys Tyr
        275                 280                 285

Val Tyr Gln Asn Arg Glu Tyr Phe Glu Ile Thr Leu Tyr Gly Arg Thr
    290                 295                 300

Lys Glu Leu Thr Ser Glu Leu Lys Glu Asn Phe Ile Arg Phe Ser Lys
305                 310                 315                 320

Ser Leu Gly Leu Pro Glu Asn His Ile Val Phe Pro Val Pro Ile Asp
                325                 330                 335

Gln Ala Ile Asp Gly
            340
```

<210> SEQ ID NO 54

<211> LENGTH: 1023
<212> TYPE: DNA
<213> ORGANISM: artificial
<220> FEATURE:
<223> OTHER INFORMATION: Nucleotide sequence encoding fusion protein shown in SEQ ID NO: 53

<400> SEQUENCE: 54

```
gcctcagacg aggagattca ggatgtgtca gggacgtggt atctgaaggc catgacggtg    60
gatttttggt gttctgggat tcatgaggag tctgttacgc caatgactct gactaccctt   120
gaaggcggca atctggaggc taaggtcacc atggatattg agggatttct tcaagagttt   180
aaggcagtgt tagagaagac agatgaaccg ggtaaatata cggccgatgg cggtaaacat   240
gttgcctata tcattcgcag ccatgtgaaa gatcattaca tcttttatag cgagggagat   300
tgtcctggtc cggttccagg ggtgtggctc gtgggcagag accccaagaa caacctggaa   360
gccttggagg actttgagaa agccgcagga gcccgcggac tcagcacgga gagcatcctc   420
atccccaggc agagcgaaac cagctctcca ggatccgacg tggtggtggt ttctggtggt   480
ggtggatcgc aggactccac ctcagacctg atcccagccc cacctctgag caaggtccct   540
ctgcagcaga cttccagga caaccaattc catgggaaat ggtatgtcgt gggcgaggcc   600
ggaaatcttt tgctgcgtga ggataaggat ccgaggaaaa tgacggcgac catttacgag   660
ttgaaagaag ataaatcata tgatgtcacc cgggtggagt ttggggttaa gacatacaag   720
taccagattg gacctttgt gccggggagc cagccgggcg agtttacttt aggcggtatt   780
aaaagtatgc cgggcatgac atcatttttg gtccgcgtcg tgagcaccaa ctacaaccag   840
catgccatgg tgttcttcaa gtatgtgtat cagaaccgcg agtattttga gatcacactg   900
tacgggcgca cgaaagaact gacaagcgag ctgaaggaaa atttatccg cttttccaaa   960
tctctgggcc tccctgaaaa ccacatcgtc ttccctgtcc caatcgacca ggctatcgac  1020
ggc                                                                1023
```

<210> SEQ ID NO 55
<211> LENGTH: 504
<212> TYPE: PRT
<213> ORGANISM: Artificial
<220> FEATURE:
<223> OTHER INFORMATION: Fusion protein

<400> SEQUENCE: 55

```
Ala Ser Asp Glu Glu Ile Gln Asp Val Ser Gly Thr Trp Tyr Leu Lys
 1               5                  10                  15

Ala Met Thr Val Asp Phe Trp Cys Ser Gly Ile His Glu Glu Ser Val
                20                  25                  30

Thr Pro Met Thr Leu Thr Thr Leu Glu Gly Gly Asn Leu Glu Ala Lys
            35                  40                  45

Val Thr Met Asp Ile Glu Gly Phe Leu Gln Glu Phe Lys Ala Val Leu
        50                  55                  60

Glu Lys Thr Asp Glu Pro Gly Lys Tyr Thr Ala Asp Gly Gly Lys His
 65                  70                  75                  80

Val Ala Tyr Ile Ile Arg Ser His Val Lys Asp His Tyr Ile Phe Tyr
                85                  90                  95

Ser Glu Gly Asp Cys Pro Gly Pro Val Pro Gly Val Trp Leu Val Gly
               100                 105                 110

Arg Asp Pro Lys Asn Asn Leu Glu Ala Leu Glu Asp Phe Glu Lys Ala
           115                 120                 125
```

Ala Gly Ala Arg Gly Leu Ser Thr Glu Ser Ile Leu Ile Pro Arg Gln
130                 135                 140

Ser Glu Thr Ser Ser Pro Gly Ser Asp Gly Gly Gly Ser Gly Gly
145                 150                 155                 160

Gly Gly Ser Ala Ser Asp Glu Glu Ile Gln Asp Val Ser Gly Thr Trp
            165                 170                 175

Tyr Leu Lys Ala Met Thr Val Asp Phe Trp Cys Ser Gly Ile His Glu
        180                 185                 190

Glu Ser Val Thr Pro Met Thr Leu Thr Thr Leu Glu Gly Gly Asn Leu
    195                 200                 205

Glu Ala Lys Val Thr Met Asp Ile Glu Gly Phe Leu Gln Glu Phe Lys
210                 215                 220

Ala Val Leu Glu Lys Thr Asp Glu Pro Gly Lys Tyr Thr Ala Asp Gly
225                 230                 235                 240

Gly Lys His Val Ala Tyr Ile Ile Arg Ser His Val Lys Asp His Tyr
            245                 250                 255

Ile Phe Tyr Ser Glu Gly Asp Cys Pro Gly Pro Val Pro Gly Val Trp
        260                 265                 270

Leu Val Gly Arg Asp Pro Lys Asn Asn Leu Glu Ala Leu Glu Asp Phe
    275                 280                 285

Glu Lys Ala Ala Gly Ala Arg Gly Leu Ser Thr Glu Ser Ile Leu Ile
290                 295                 300

Pro Arg Gln Ser Glu Thr Ser Ser Pro Gly Ser Asp Gly Gly Gly Gly
305                 310                 315                 320

Ser Gly Gly Gly Gly Ser Gln Asp Ser Thr Ser Asp Leu Ile Pro Ala
            325                 330                 335

Pro Pro Leu Ser Lys Val Pro Leu Gln Gln Asn Phe Gln Asp Asn Gln
        340                 345                 350

Phe His Gly Lys Trp Tyr Val Val Gly Glu Ala Gly Asn Leu Leu Leu
    355                 360                 365

Arg Glu Asp Lys Asp Pro Arg Lys Met Thr Ala Thr Ile Tyr Glu Leu
370                 375                 380

Lys Glu Asp Lys Ser Tyr Asp Val Thr Arg Val Glu Phe Gly Val Lys
385                 390                 395                 400

Thr Tyr Lys Tyr Gln Ile Gly Thr Phe Val Pro Gly Ser Gln Pro Gly
            405                 410                 415

Glu Phe Thr Leu Gly Gly Ile Lys Ser Met Pro Gly Met Thr Ser Phe
        420                 425                 430

Leu Val Arg Val Val Ser Thr Asn Tyr Asn Gln His Ala Met Val Phe
    435                 440                 445

Phe Lys Tyr Val Tyr Gln Asn Arg Glu Tyr Phe Glu Ile Thr Leu Tyr
450                 455                 460

Gly Arg Thr Lys Glu Leu Thr Ser Glu Leu Lys Glu Asn Phe Ile Arg
465                 470                 475                 480

Phe Ser Lys Ser Leu Gly Leu Pro Glu Asn His Ile Val Phe Pro Val
            485                 490                 495

Pro Ile Asp Gln Ala Ile Asp Gly
        500

<210> SEQ ID NO 56
<211> LENGTH: 1512
<212> TYPE: DNA
<213> ORGANISM: artificial
<220> FEATURE:
<223> OTHER INFORMATION: Nucleotide sequence encoding fusion protein shown in SEQ ID NO: 55

<400> SEQUENCE: 56

```
gcctcagacg aggagattca ggatgtgtca gggacgtggt atctgaaggc catgacggtg      60
gatttttggt gttctgggat tcatgaggag tctgttacgc caatgactct gactacccct     120
gaaggcggca atctggaggc taaggtcacc atggatattg agggatttct tcaagagttt     180
aaggcagtgt tagagaagac agatgaaccg ggtaaatata cggccgatgg cggtaaacat     240
gttgcctata tcattcgcag ccatgtgaaa gatcattaca tcttttatag cgagggagat     300
tgtcctggtc cggttccagg ggtgtggctc gtgggcagag accccaagaa caacctggaa     360
gccttggagg actttgagaa agccgcagga gcccgcggac tcagcacgga gagcatcctc     420
atccccaggc agagcgaaac cagctctcca gggagcgacg gtggtggtgg ttctggtggt     480
ggtggatcgg cctcagacga ggagattcag gatgtgtcag ggacgtggta tctgaaggcc     540
atgacggtgg atttttggtg ttctgggatt catgaggagt ctgttacgcc aatgactctg     600
actacccttg aaggcggcaa tctggaggct aaggtcacca tggatattga gggatttctt     660
caagagttta aggcagtgtt agagaagaca gatgaaccgg gtaaatatac ggccgatggc     720
ggtaaacatg ttgcctatat cattcgcagc catgtgaaag atcattacat cttttatagc     780
gagggagatt gtcctggtcc ggttccaggg gtgtggctcg tgggcagaga ccccaagaac     840
aacctggaag ccttggagga ctttgagaaa gccgcaggag cccgcggact cagcacggag     900
agcatcctca tccccaggca gagcgaaacc agctctccag gatccgacgg tggtggtggt     960
tctggtggtg gtggatcgca ggactccacc tcagacctga tcccagcccc acctctgagc    1020
aaggtccctc tgcagcagaa cttccaggac aaccaattcc atgggaaatg gtatgtcgtg    1080
ggcgaggccg gaaatctttt gctgcgtgag gataaggatc cgaggaaaat gacggcgacc    1140
atttacgagt tgaaagaaga taatcatat gatgtcaccc gggtggagtt tggggttaag    1200
acatacaagt accagattgg gacctttgtg ccggggagcc agccgggcga gtttacttta    1260
ggcggtatta aagtatgccg ggcatgaca tcattttttgg tccgcgtcgt gagcaccaac    1320
tacaaccagc atgccatggt gttcttcaag tatgtgtatc agaaccgcga gtattttgag    1380
atcacactgt acgggcgcac gaaagaactg acaagcgagc tgaaggaaaa ttttatccgc    1440
ttttccaaat ctctgggcct ccctgaaaac cacatcgtct ccctgtccc aatcgaccag    1500
gctatcgacg gc                                                        1512
```

<210> SEQ ID NO 57
<211> LENGTH: 339
<212> TYPE: PRT
<213> ORGANISM: artificial
<220> FEATURE:
<223> OTHER INFORMATION: Fusion protein

<400> SEQUENCE: 57

```
Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
             20                  25                  30

Val Val Gly Glu Ala Gly Asn Leu Leu Leu Arg Glu Asp Lys Asp Pro
         35                  40                  45

Arg Lys Met Thr Ala Thr Ile Tyr Glu Leu Lys Glu Asp Lys Ser Tyr
     50                  55                  60

Asp Val Thr Arg Val Glu Phe Gly Val Lys Thr Tyr Lys Tyr Gln Ile
```

```
                65                  70                  75                  80
Gly Thr Phe Val Pro Gly Ser Gln Pro Gly Glu Phe Thr Leu Gly Gly
                    85                  90                  95
Ile Lys Ser Met Pro Gly Met Thr Ser Phe Leu Val Arg Val Val Ser
                100                 105                 110
Thr Asn Tyr Asn Gln His Ala Met Val Phe Lys Tyr Val Tyr Gln
                115                 120                 125
Asn Arg Glu Tyr Phe Glu Ile Thr Leu Tyr Gly Arg Thr Lys Glu Leu
                130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Ala Ile
                    165                 170                 175
Asp Gly Gly Gly Gly Ser Gly Gly Gly Ser Ala Ser Asp Glu
                180                 185                 190
Glu Ile Gln Asp Val Ser Gly Thr Trp Tyr Leu Lys Ala Met Thr Val
                195                 200                 205
Asp Phe Trp Cys Ser Gly Ile His Glu Glu Ser Val Thr Pro Met Thr
210                 215                 220
Leu Thr Thr Leu Glu Gly Gly Asn Leu Glu Ala Lys Val Thr Met Asp
225                 230                 235                 240
Ile Glu Gly Phe Leu Gln Glu Phe Lys Ala Val Leu Glu Lys Thr Asp
                    245                 250                 255
Glu Pro Gly Lys Tyr Thr Ala Asp Gly Gly Lys His Val Ala Tyr Ile
                260                 265                 270
Ile Arg Ser His Val Lys Asp His Tyr Ile Phe Tyr Ser Glu Gly Asp
                275                 280                 285
Cys Pro Gly Pro Val Pro Gly Val Trp Leu Val Gly Arg Asp Pro Lys
                290                 295                 300
Asn Asn Leu Glu Ala Leu Glu Asp Phe Glu Lys Ala Ala Gly Ala Arg
305                 310                 315                 320
Gly Leu Ser Thr Glu Ser Ile Leu Ile Pro Arg Gln Ser Glu Thr Ser
                    325                 330                 335
Ser Pro Gly

<210> SEQ ID NO 58
<211> LENGTH: 1023
<212> TYPE: DNA
<213> ORGANISM: artificial
<220> FEATURE:
<223> OTHER INFORMATION: Nucleotide sequence encoding fusion protein
      shown in SEQ ID NO: 57

<400> SEQUENCE: 58
caggactcca cctcagacct gatcccagcc ccacctctga gcaaggtccc tctgcagcag      60
aacttccagg acaaccaatt ccatgggaaa tggtatgtcg tgggcgaggc cggaaatctt     120
ttgctgcgtg aggataagga tccgaggaaa atgacggcga ccatttacga gttgaaagaa     180
gataaatcat atgatgtcac ccgggtggag tttggggtta agacatacaa gtaccagatt     240
gggacctttg tgccggggag ccagccgggc gagtttactt taggcggtat taaaagtatg     300
ccgggcatga catcatttt ggtccgcgtc gtgagcacca actacaacca gcatgccatg     360
gtgttcttca gtatgtgta tcagaaccga gagtattttg agatcacact gtacgggcgc     420
acgaaagaac tgacaagcga gctgaaggaa aattttatcc gcttttccaa atctctgggc     480
```

```
ctccctgaaa accacatcgt cttccctgtc ccaatcgacc aggctatcga cggcggcggt      540
ggtggttctg gtggtggtgg atcggcctca gacgaggaga ttcaggatgt gtcagggacg      600
tggtatctga aggccatgac ggtggatttt tggtgttctg ggattcatga ggagtctgtt      660
acgccaatga ctctgactac ccttgaaggc ggcaatctgg aggctaaggt caccatggat      720
attgagggat ttcttcaaga gtttaaggca gtgttagaga agacagatga accgggtaaa      780
tatacggccg atggcggtaa acatgttgcc tatatcattc gcagccatgt gaaagatcat      840
tacatctttt atagcgaggg agattgtcct ggtccggttc caggggtgtg gctcgtgggc      900
agagacccca agaacaacct ggaagccttg gaggactttg agaaagccgc aggagcccgc      960
ggactcagca cggagagcat cctcatcccc aggcagagcg aaaccagctc tccaggatcc     1020
gac                                                                   1023
```

INTERLEUKIN-17A-SPECIFIC AND INTERLEUKIN-23-SPECIFIC BINDING POLYPEPTIDES AND USES THEREOF

I. BACKGROUND

Muteins of various lipocalins are a rapidly expanding class of therapeutics. Indeed, lipocalin muteins can be constructed to exhibit a high affinity and specificity against a target that is different than a natural ligand of wild type lipocalins (e.g., WO 99/16873, WO 00/75308, WO 03/029463, WO 03/029471 and WO 05/19256), such as Interleukin-17A or Interleukin-23.

A. Interleukin-17A

Interleukin-17A (IL-17A, synonymous with IL-17) is a cytokine produced from the Th17 lineage of T cells. IL-17 was originally designated "CTL-associated antigen 8" (CTLA-8) (Rouvier et al., J. Immunol, 150 5445-5556 (1993); Yao et al., Immunity, 3: 811-821 (1995)). The human equivalent of CTLA-8 was later cloned and designated "IL-17" (Yao et al., J. Immunol, 155(12): 5483-5486 (1995); Fossiez et al., J. Exp. Med., 183(6): 2593-2603 (1996)).

Human IL-17A (CTLA-8, further named as IL-17, Swiss Prot Q16552) is a glycoprotein with a Mr of 17,000 daltons (Spriggs et al., J. Clin. Immunol, 17: 366-369 (1997)). IL-17A may exist as either a homodimer IL-17 A/A or as a heterodimer complexed with the homolog IL-17F to form heterodimeric IL-17 A/F. IL-17F (IL-24, ML-1) shares a 55% amino acid identity with IL-17A. IL-17A and IL-17F also share the same receptor (IL-17RA), which is expressed on a wide variety of cells including vascular endothelial cells, peripheral T cells, B cells, fibroblast, lung cells, myelomonocytic cells, and marrow stromal cells (Kolls et al., Immunity, 21: 467-476 (2004); Kawaguchi et al., J. Allergy Clin. Immunol, 114(6): 1267-1273 (2004); Moseley et al., Cytokine Growth Factor Rev., 14(2): 155-174 (2003)). Additional IL-17 homologs have been identified (IL-17B, IL-17C, IL-17D, IL-17E). These other family members share less than 30% amino acid identity with IL-17A (Kolls et al., 2004).

IL-17A is mainly expressed by Th17 cells and is present at elevated levels in synovial fluid of patients with rheumatoid arthritis (RA) and has been shown to be involved in early RA development. IL-17A is also over-expressed in the cerebrospinal fluid of multiple sclerosis (MS) patients. In addition, IL-17 is an inducer of TNF-α and IL-1, the latter being mainly responsible for bone erosion and the very painful consequences for affected patients (Lubberts E. (2008) Cytokine, 41, p. 84-91). Furthermore, inappropriate or excessive production of IL-17A is associated with the pathology of various other diseases and disorders, such as osteoarthritis, loosening of bone implants, acute transplant rejection (Antonysamy et al., (1999) J. Immunol, 162, p. 577-584; van Kooten et al. (1998) J. Am. Soc. Nephrol., 9, p. 1526-1534), septicemia, septic or endotoxic shock, allergies, asthma (Molet et al., (2001) J. Allergy Clin. Immunol., 108, p. 430-438), bone loss, psoriasis (Teunissen et al. (1998) J. Invest. Dermatol, 111, p. 645-649), ischemia, systemic sclerosis (Kurasawa et al., (2000) Arthritis Rheum., 43, p. 2455-2463), stroke, and other inflammatory disorders.

Although a variety of inhibitors of IL-17A have been described, since the discovery of this critical proinflammatory cytokine, current approaches are not optimal, such as the necessity of complex mammalian cell production systems, a dependency on disulfide bond stability, the tendency of some antibody fragments to aggregate, limited solubility and last but not least, they may elicit undesired immune responses even when humanized. There remains a need, therefore, to develop proteins such as lipocalin muteins with binding-affinity for IL-17A.

B. Interleukin-23

Interleukin-23 (also known as IL-23) is a heterodimeric cytokine comprised of two subunits, i.e., p19 and p40 (B. Oppmann et al, Immunity 13, 715 (2000)). The p19 (Swiss Prot Q9NPF7, herein referred to interchangeably as "IL-23p19") subunit is structurally related to IL-6, granulocyte-colony stimulating factor (G-CSF), and the p35 subunit of IL-12. IL-23 mediates signaling by binding to a heterodimeric receptor, comprised of IL-23R and IL-12beta1. The IL-12beta1 subunit is shared by the IL-12 receptor, which is composed of IL-12beta1 and IL-12beta2. Transgenic p19 mice have been recently described to display profound systemic inflammation and neutrophilia (M. T. Wiekowski et al, J Immunol 166, 7563 (2001)).

Human IL-23 has been reported to promote the proliferation of T cells, in particular memory T cells and can contribute to the differentiation and/or maintenance of Th17 cells (D. M. Frucht, Sci STKE 2002 Jan. 8; 2002(114):PE1).

Although a variety of selective inhibitors of IL-23 (via binding to the p19 subunit) have been described, since the discovery of this critical heterodimeric cytokine, these current approaches still have a number of serious drawbacks, such as the necessity of complex mammalian cell production systems, a dependency on disulfide bond stability, the tendency of some antibody fragments to aggregate, limited solubility and last but not least, they may elicit undesired immune responses even when humanized. There is an unmet need to, therefore, to develop proteins such as lipocalin muteins with binding-affinity for IL-23.

II. DEFINITIONS

The following list defines terms, phrases, and abbreviations used throughout the instant specification. All terms listed and defined herein are intended to encompass all grammatical forms.

As used herein, "IL-17A" (including IL-17 A/A as well as IL-17A in complex with IL-17F, also termed as IL-17 A/F) means a full-length protein defined by Swiss Prot Q16552, a fragment thereof, or a variant thereof.

As used herein, "IL-23p19" means a full-length protein defined by Swiss Prot Q9NPF7, a fragment thereof, or a variant thereof.

As used herein, "detectable affinity" means the ability to bind to a selected target with an affinity constant of generally at least about $10^{-5}$ M. Lower affinities are generally no longer measurable with common methods such as ELISA and therefore of secondary importance. For example, binding affinities of lipocalin muteins according to the disclosure may in some embodiments be of a $K_D$ below 800 nM, in some embodiments be of a $K_D$ below 30 nM and in some embodiments about 50 picomolar (pM) or below.

As used herein, "binding affinity" of a protein of the disclosure (e.g. a mutein of a lipocalin) or a fusion polypeptide thereof to a selected target (in the present case, IL-17A or IL-23p19), can be measured (and thereby KD values of a mutein-ligand complex be determined) by a multitude of methods known to those skilled in the art. Such methods include, but are not limited to, fluorescence titration, competition ELISA, calorimetric methods, such as isothermal titration calorimetry (ITC), and surface plasmon resonance (BIAcore). Such methods are well established in the art and examples thereof are also detailed below.

It is also noted that the complex formation between the respective binder and its ligand is influenced by many different factors such as the concentrations of the respective binding partners, the presence of competitors, pH and the ionic strength of the buffer system used, and the experimental method used for determination of the dissociation constant $K_D$ (for example fluorescence titration, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective binder and its target/ligand) may vary within a certain experimental range, depending on the method and experimental setup that is used for determining the affinity of a particular lipocalin mutein for a given ligand. This means that there may be a slight deviation in the measured $K_D$ values or a tolerance range depending, for example, on whether the $K_D$ value was determined by surface plasmon resonance (Biacore), by competition ELISA, or by "direct ELISA."

As used herein, a "mutein," a "mutated" entity (whether protein or nucleic acid), or "mutant" refers to the exchange, deletion, or insertion of one or more nucleotides or amino acids, compared to the naturally occurring (wild-type) nucleic acid or protein "reference" scaffold.

The term "fragment" as used herein in connection with the muteins of the disclosure relates to proteins or peptides derived from full-length mature human tear lipocalin that are N-terminally and/or C-terminally shortened, i.e. lacking at least one of the N-terminal and/or C-terminal amino acids. Such fragments may include at least 10, more such as 20 or 30 or more consecutive amino acids of the primary sequence of the mature lipocalin and are usually detectable in an immunoassay of the mature lipocalin. In general, the term "fragment", as used herein with respect to the corresponding protein ligand IL-17A (including IL-17 A/A and IL-17 A/F) or IL-23p19 of a lipocalin mutein of the disclosure or of the combination according to the disclosure or of a fusion protein described herein, relates to N-terminally and/or C-terminally shortened protein or peptide ligands, which retain the capability of the full length ligand to be recognized and/or bound by a mutein according to the disclosure.

The term "mutagenesis" as used herein means that the experimental conditions are chosen such that the amino acid naturally occurring at a given sequence position of the mature lipocalin can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the disclosure that, for example, one amino acid at a chosen sequence position is replaced by a stretch of three random mutations, leading to an insertion of two amino acid residues compared to the length of the respective segment of the wild type protein. Such an insertion of deletion may be introduced independently from each other in any of the peptide segments that can be subjected to mutagenesis in the disclosure. In one exemplary embodiment of the disclosure, an insertion of several mutations may be introduced into the loop AB of the chosen lipocalin scaffold (cf. International Patent Application WO 2005/019256 which is incorporated by reference its entirety herein).

The term "random mutagenesis" means that no predetermined single amino acid (mutation) is present at a certain sequence position but that at least two amino acids can be incorporated with a certain probability at a predefined sequence position during mutagenesis.

"Identity" is a property of sequences that measures their similarity or relationship. The term "sequence identity" or "identity" as used in the present disclosure means the percentage of pair-wise identical residues—following (homologous) alignment of a sequence of a polypeptide of the disclosure with a sequence in question—with respect to the number of residues in the longer of these two sequences. Identity is measured by dividing the number of identical residues by the total number of residues and multiplying the product by 100.

The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of a polypeptide of the disclosure (e.g., any lipocalin mutein of the disclosure).

The percentage of sequence homology or sequence identity can, for example, be determined herein using the program BLASTP, version blastp 2.2.5 (Nov. 16, 2002; cf. Altschul, S. F. et al. (1997) Nucl. Acids Res. 25, 3389-3402). In this embodiment the percentage of homology is based on the alignment of the entire polypeptide sequences (matrix: BLOSUM 62; gap costs: 11.1; cutoff value set to $10^{-3}$) including the propeptide sequences, preferably using the wild type protein scaffold as reference in a pairwise comparison. It is calculated as the percentage of numbers of "positives" (homologous amino acids) indicated as result in the BLASTP program output divided by the total number of amino acids selected by the program for the alignment.

Specifically, in order to determine whether an amino acid residue of the amino acid sequence of a lipocalin (mutein) different from a wild-type lipocalin corresponds to a certain position in the amino acid sequence of a wild-type lipocalin, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a wild-type lipocalin can serve as "subject sequence" or "reference sequence", while the amino acid sequence of a lipocalin different from the wild-type lipocalin described herein serves as "query sequence". The terms "reference sequence" and "wild type sequence" are used interchangeably herein.

"Gaps" are spaces in an alignment that are the result of additions or deletions of amino acids. Thus, two copies of exactly the same sequence have 100% identity, but sequences that are less highly conserved, and have deletions, additions, or replacements, may have a lower degree of identity. Those skilled in the art will recognize that several computer programs are available for determining sequence identity using standard parameters, for example Blast (Altschul, et al. (1997) Nucleic Acids Res. 25, 3389-3402), Blast2 (Altschul, et al. (1990) J. Mol. Biol. 215, 403-410), and Smith-Waterman (Smith, et al. (1981) J. Mol. Biol. 147, 195-197).

The term "variant" as used in the present disclosure relates to derivatives of a protein or peptide that include modifications of the amino acid sequence, for example by substitution, deletion, insertion or chemical modification. Such modifications do in some embodiments not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. The term "variant", as used herein with respect to the corresponding protein ligand IL-17A (including IL-17 A/A and IL-17 A/F) or IL-23p19 of a lipocalin mutein of the disclosure or of the combination according to the disclosure or of a fusion protein described herein, relates to a IL-17 protein or fragment thereof or IL-23 protein or fragment thereof, respectively, that has one or more such as 1, 2, 3, 4, 5, 6, 7, 8, 9, 10, 12, 14, 16, 18, 20, 22, 24, 26, 28, 30, 40, 50, 60, 70, 80 or more amino acid substitutions, deletions and/or insertions in comparison to a wild-type IL-17A or IL-23p19 protein, respectively, such as a IL-17A or IL-23p19 reference protein as deposited with SwissProt as described herein. A IL-17A or IL-23p19 variant, respectively, has preferably an amino acid identity of at least 50%, 60%, 70%, 80%, 85%, 90% or 95% with a wild-type IL-17A or IL-23p19 protein, respectively, such as a IL-17A or IL-23p19 reference protein as deposited with SwissProt as described herein.

By a "native sequence" lipocalin is meant a lipocalin that has the same amino acid sequence as the corresponding polypeptide derived from nature. Thus, a native sequence lipocalin can have the amino acid sequence of the respective naturally-occurring lipocalin from any organism, in particular a mammal. Such native sequence polypeptide can be isolated from nature or can be produced by recombinant or synthetic means. The term "native sequence" polypeptide specifically encompasses naturally-occurring truncated or secreted forms of the lipocalin, naturally-occurring variant forms such as alternatively spliced forms and naturally-occurring allelic variants of the lipocalin. A polypeptide "variant" means a biologically active polypeptide having at least about 50%, 60%, 70%, 80% or at least about 85% amino acid sequence identity with the native sequence polypeptide. Such variants include, for instance, polypeptides in which one or more amino acid residues are added or deleted at the N- or C-terminus of the polypeptide. Generally a variant has at least about 70%, including at least about 80%, such as at least about 85% amino acid sequence identity, including at least about 90% amino acid sequence identity or at least about 95% amino acid sequence identity with the native sequence polypeptide. As an illustrative example, the first 4 N-terminal amino acid residues (HHLA) and the last 2 C-terminal amino acid residues (Ser, Asp) can be deleted, for example, in a tear lipocalin (Tlc) mutein of the disclosure without affecting the biological function of the protein, e.g. SEQ ID NOs: 2-7 and 12-13.

The term "position" when used in accordance with the disclosure means the position of either an amino acid within an amino acid sequence depicted herein or the position of a nucleotide within a nucleic acid sequence depicted herein. To understand the term "correspond" or "corresponding" as used herein in the context of the amino acid sequence positions of one or more lipocalin muteins, a corresponding position is not only determined by the number of the preceding nucleotides/amino acids. Accordingly, the position of a given amino acid in accordance with the disclosure which may be substituted may vary due to deletion or addition of amino acids elsewhere in a (mutant or wild-type) lipocalin. Similarly, the position of a given nucleotide in accordance with the present disclosure which may be substituted may vary due to deletions or additional nucleotides elsewhere in a mutein or wild type lipocalin 5'-untranslated region (UTR) including the promoter and/or any other regulatory sequences or gene (including exons and introns).

Thus, for a corresponding position in accordance with the disclosure, it is preferably to be understood that the positions of nucleotides/amino acids may differ in the indicated number than similar neighbouring nucleotides/amino acids, but said neighbouring nucleotides/amino acids, which may be exchanged, deleted, or added, are also comprised by the one or more corresponding positions.

In addition, for a corresponding position in a lipocalin mutein based on a reference scaffold in accordance with the disclosure, it is preferably to be understood that the positions of nucleotides/amino acids are structurally corresponding to the positions elsewhere in a (mutant or wild-type) lipocalin, even if they may differ in the indicated number, as appreciated by the skilled in light of the highly-conserved overall folding pattern among lipocalins.

The term "albumin" includes all mammal albumins such as human serum albumin or bovine serum albumin or rat serum albumin.

The term "organic molecule" or "small organic molecule" as used herein for the non-natural target denotes an organic molecule comprising at least two carbon atoms, but preferably not more than 7 or 12 rotatable carbon bonds, having a molecular weight in the range between 100 and 2000 Dalton, preferably between 100 and 1000 Dalton, and optionally including one or two metal atoms.

The word "detect", "detection", "detectable" or "detecting" as used herein is understood both on a quantitative and a qualitative level, as well as a combination thereof. It thus includes quantitative, semi-quantitative and qualitative measurements of a molecule of interest.

A "subject" is a vertebrate, preferably a mammal, more preferably a human. The term "mammal" is used herein to refer to any animal classified as a mammal, including, without limitation, humans, domestic and farm animals, and zoo, sports, or pet animals, such as sheep, dogs, horses, cats, cows, rats, pigs, apes such as cynomolgous monkeys and etc., to name only a few illustrative examples. Preferably, the mammal herein is human.

An "effective amount" is an amount sufficient to effect beneficial or desired results. An effective amount can be administered in one or more administrations.

A "sample" is defined as a biological sample taken from any subject. Biological samples include, but are not limited to, blood, serum, urine, feces, semen, or tissue.

III. DESCRIPTIONS OF FIGURES

FIG. 1: demonstrates that the lipocalin mutein SEQ ID NO: 5 is capable of blocking the interaction between hIL-17A and its receptor hIL-17RA with an IC50 of 50 pM. Biotinylated hIL-17A was pre-incubated with variable concentrations of said mutein and non-neutralized hIL-17A was quantified on an ELISA plate with immobilized soluble hIL17-RA. Negative control SEQ ID NO: 7 has no competitive effect. Data were fitted with a single-site binding model.

Figure 2:
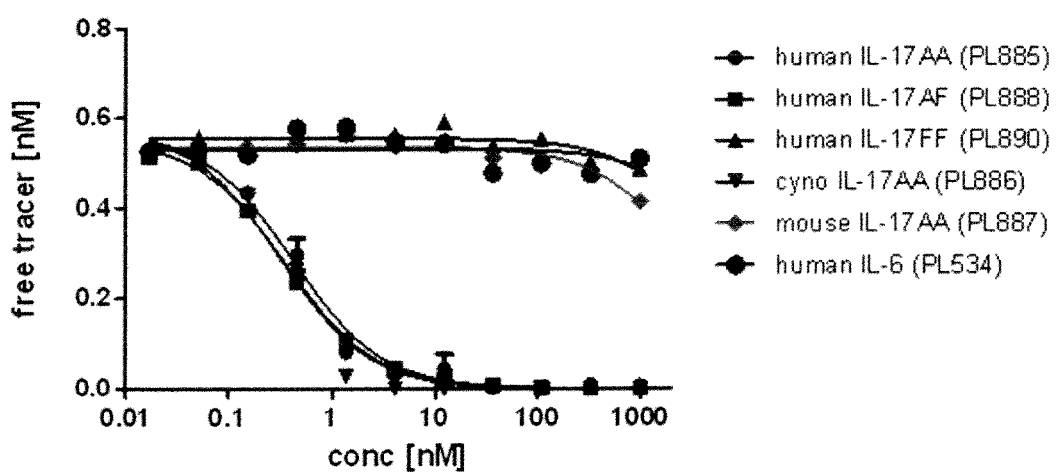

FIG. 2: shows the crossreactivity profile of the lipocalin mutein SEQ ID NO: 5 as measured in a competition ELISA format. Specificity of said lipocalin mutein to the IL-17A subunit of IL-17A and IL-17 A/F is demonstrated by identical 1050 values for binding to hIL-17A and hIL-17 A/F (IC50=0.4 nM), while binding to hIL-17F is not detectable. Full crossreactivity to cynomolgus monkey IL-17 is evident from nearly identical IC50 values of hIL-17A and cIL-17A. Within the concentration range tested, there is no crossreactivity to mouse IL-17A, and no binding to hIL-6, which serves as negative control. Data were fitted with a single-site binding model.

Figure 3:
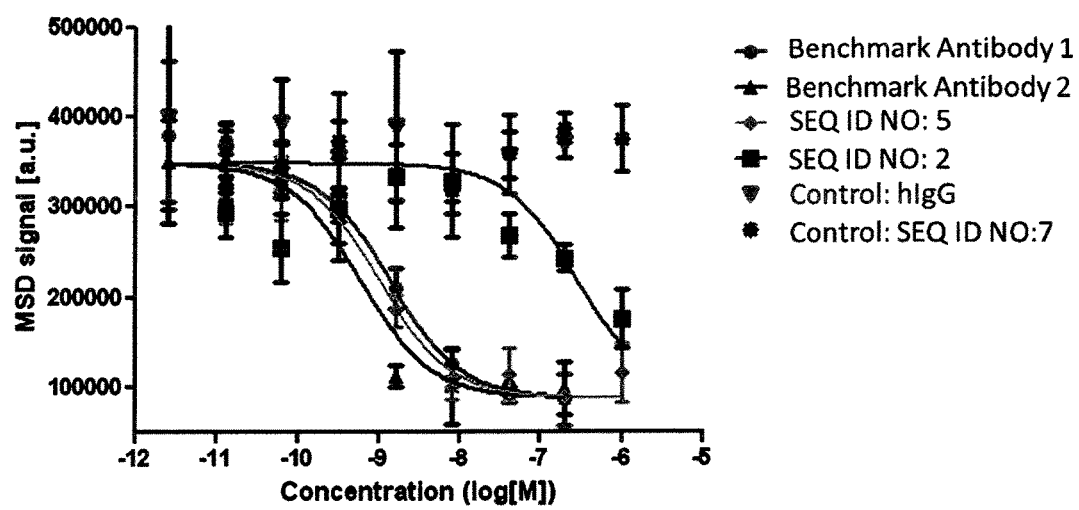

FIG. 3: illustrates that the lipocalin mutein SEQ ID NO: 5 is highly effective in blocking hIL-17A binding to its receptor hIL-17RA in a cell-based assay. The assay is based on hIL-17A-induced secretion of G-CSF in U87-MG cells. Cells are incubated with a fixed concentration of hIL-17A and titrated with muteins SEQ ID NOs: 2, 5 and 7 or, for comparison, benchmark antibody molecules. Plotted is the concentration of G-CSF in arbitrary units as measured by MSD (Meso Scale Discovery®, hereafter "MSD") against the concentration of lipocalin muteins or antibody molecules. The resulting IC50 value for the lipocalin mutein of SEQ ID NO: 5 is 1.0 nM, in a similar range as benchmark antibody molecules, benchmark antibody 1 (whose heavy chain and light chain are described in SEQ ID NOs: 19 and 20, respectively) and benchmark antibody 2 (whose heavy chain and light chain are described in SEQ ID NOs: 21 and 22, respectively), with IC50=1.4 nM and 0.6 nM, respectively. The lipocalin mutein of SEQ ID NO: 2 has an IC50 value of 289 nM. Negative controls, consisting of the Tlc mutein of SEQ ID NO: 7 and a human IgG isotype antibody (Dianova, CAT#009-000-002), have no effect. Binding of SEQ ID NO: 5 and SEQ ID NO: 2 or benchmark antibody molecules to IL-17A blocks IL-17A's binding to cell-surface IL-17RA and, thus, prevents induction of G-CSF secretion. Data were fitted with a single-site binding model, assuming equal G-CSF concentration plateaus for all molecules.

Figure 4:
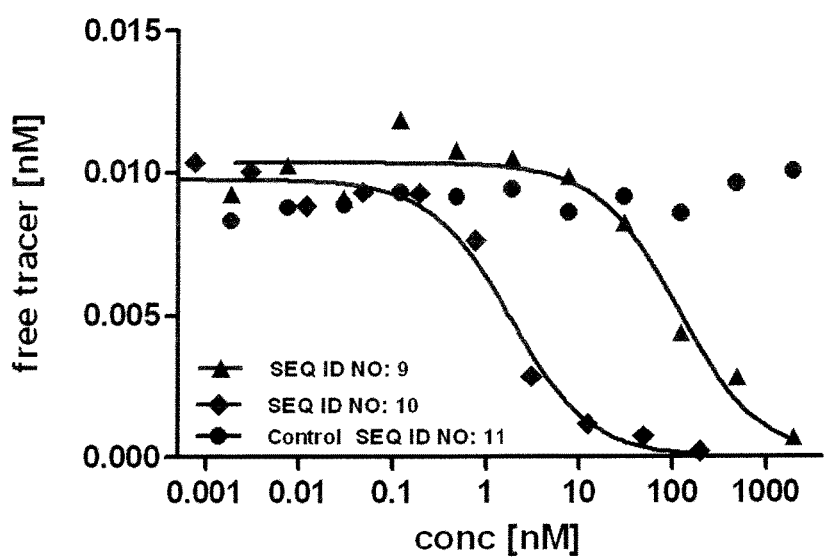

FIG. 4: demonstrates that the lipocalin muteins SEQ ID NO: 9 and SEQ ID NO: 10 are capable of blocking the interaction between hIL-23 and its receptor hIL-23R with an IC50 of 119 nM (SEQ ID NO: 9) and 1.9 nM (SEQ ID NO: 10), respectively. Biotinylated hIL-23 was pre-incubated with variable concentrations of said lipocalin muteins and non-neutralized hIL-23 was quantified on an ELISA plate with immobilized soluble hIL-23R. Negative control SEQ ID NO: 11 has no competitive effect. Data were fitted with a single-site binding model.

Figure 5:
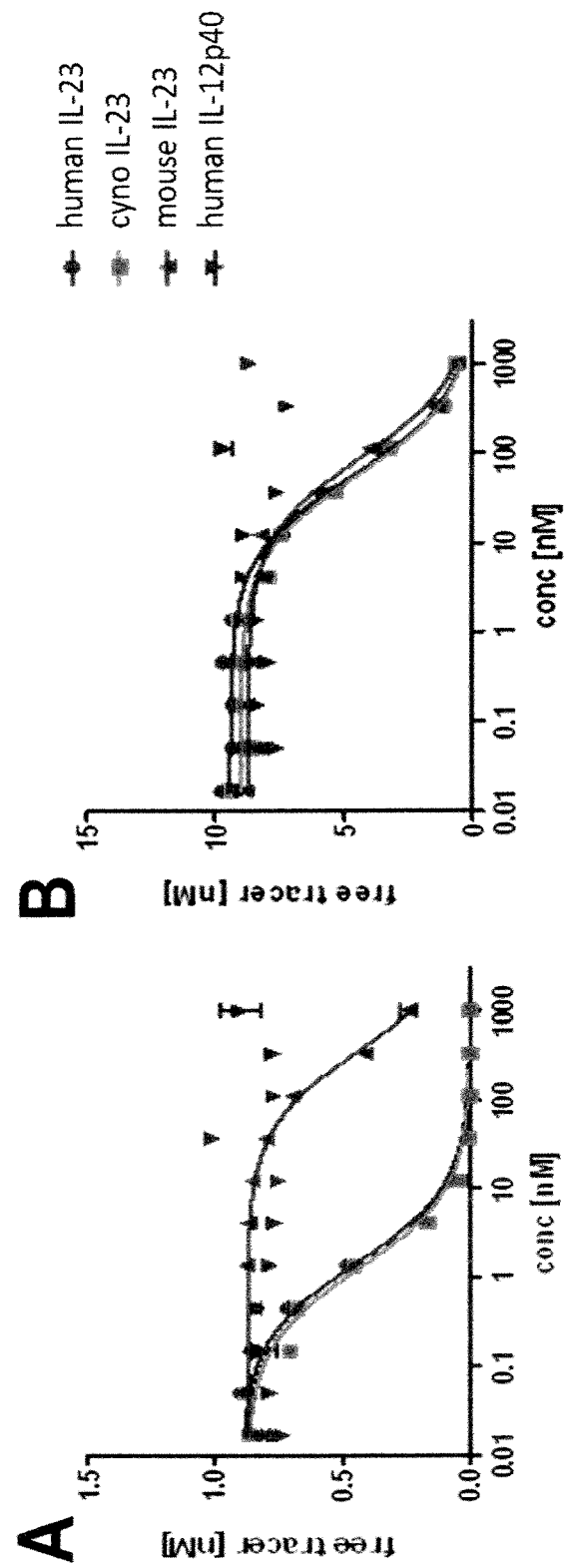

FIG. 5: shows the crossreactivity profile and specificity of the lipocalin muteins SEQ ID NO: 10 (FIG. 5A) and SEQ ID NO: 9 (FIG. 5B) as measured in a competition ELISA format. While the lipocalin mutein of SEQ ID NO: 9 is fully crossreactive for human, cynomolgus monkey and mouse IL-23, the lipocalin mutein of SEQ ID NO: 10 is fully crossreactive for hIL-23 and cIL-23 but displays a reduced affinity towards mIL-23. As desired, specific binding of both muteins to the IL-23p19 subunit of IL-23, is demonstrated by lack of binding to IL-12p40, the second subunit of IL23. Data were fitted with a single-site binding model.

Figure 6:
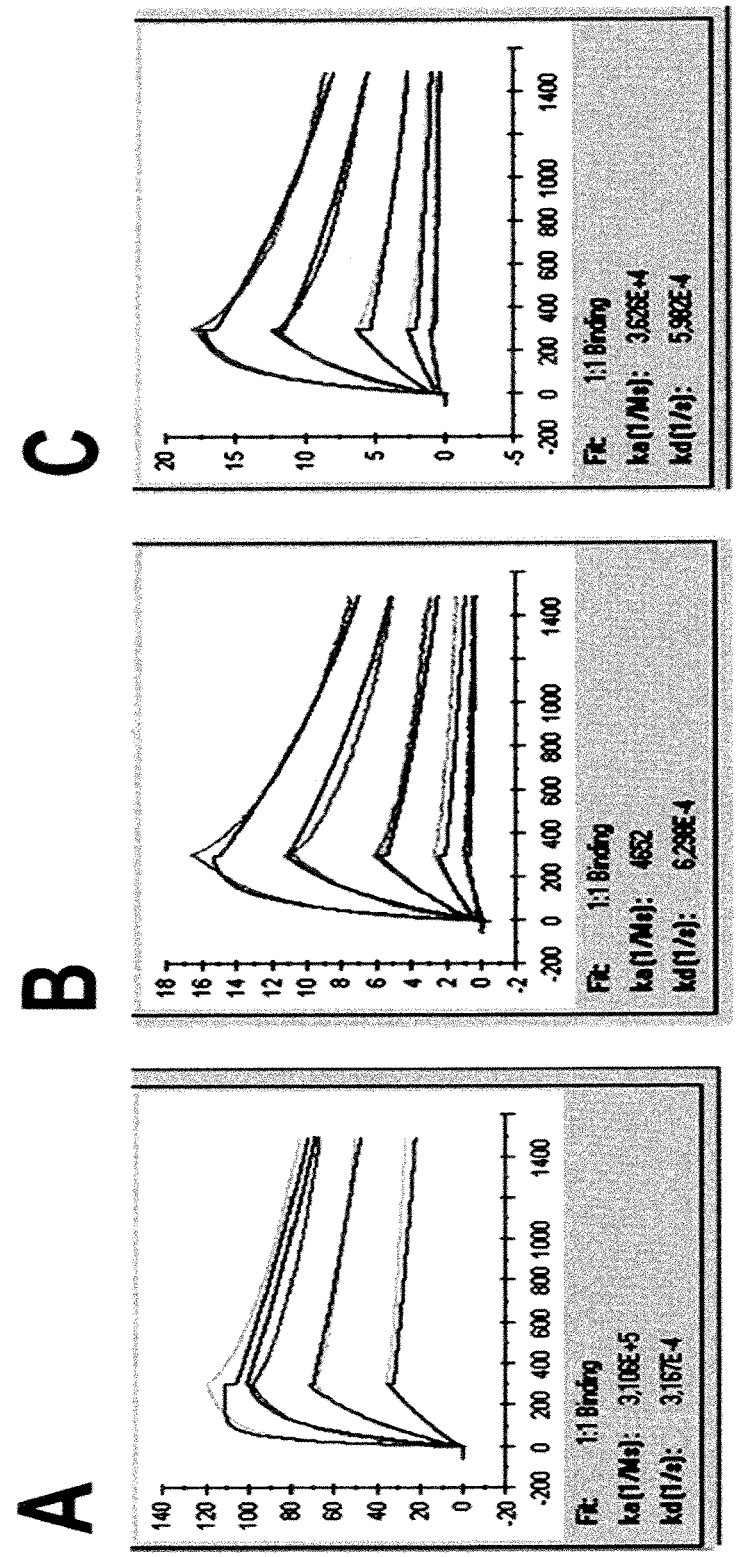

FIG. 6: provides typical measurements of on-rate and off-rate by Surface Plasmon Resonance for the lipocalin muteins SEQ ID NO: 5 (FIG. 6A), SEQ ID NO: 9 (FIG. 6B), and SEQ ID NO: 10 (FIG. 6C). The resulting dissociation constants (KD) are 1 nM to hIL-17A (SEQ ID NO: 5), 135 nM to hIL-23 (SEQ ID NO: 9) and 11 nM to hIL-23 (SEQ ID NO: 10), respectively.

Figure 7:
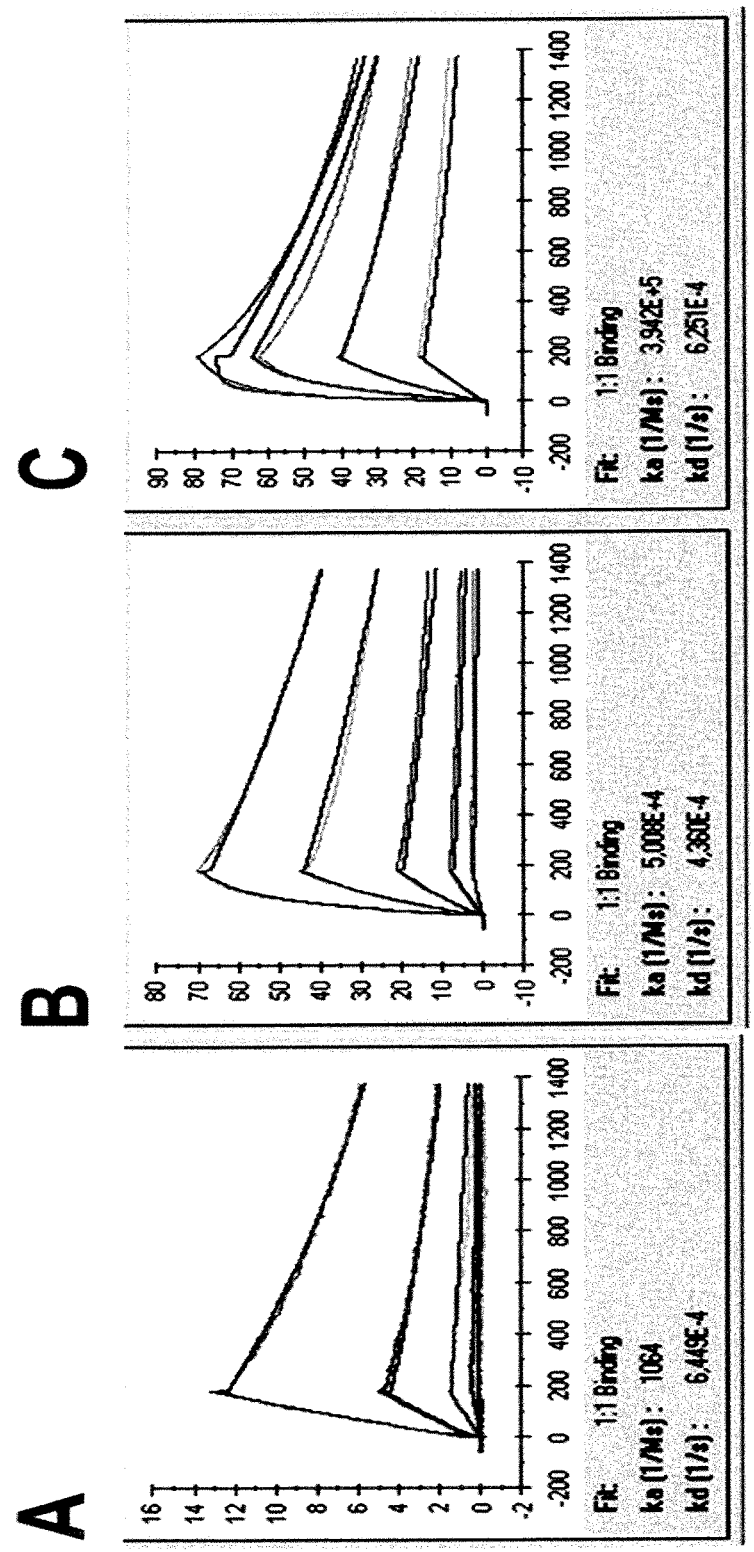

FIG. 7: provides typical measurements of on-rate and off-rate for binding and unbinding of lipocalin muteins to hIL-17A as measured by Surface Plasmon Resonance for the lipocalin muteins SEQ ID NO: 14 (FIG. 7A), SEQ ID NO: 3 (FIG. 7B), and SEQ ID NO: 4 (FIG. 7C). The resulting dissociation constants (KD) are 0.6 µM (SEQ ID NO: 14), 8.7 nM (SEQ ID NO: 3) and 1.6 nM (SEQ ID NO: 4), respectively.

Figure 8:
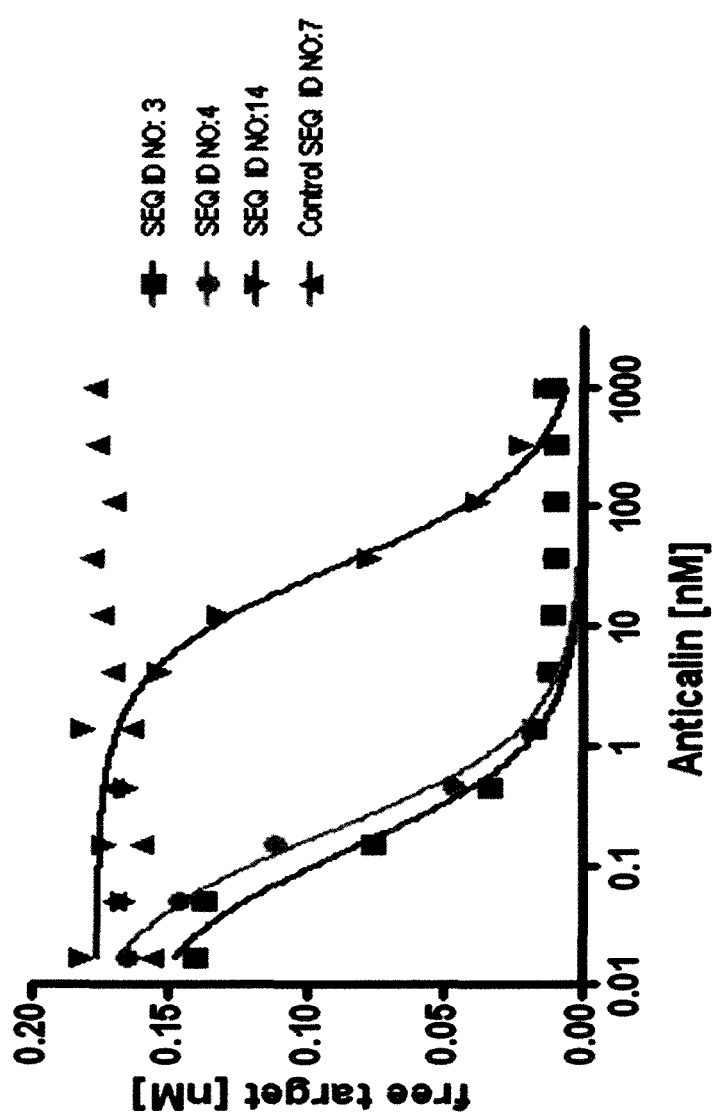

FIG. 8: demonstrates that the lipocalin muteins SEQ ID NO: 14, SEQ ID NO: 3 and SEQ ID NO: 4 are capable of blocking the interaction between hIL-17A and its receptor hIL-17RA with an IC50 of 33 nM, 0.15 nM and 0.2 nM, respectively. Biotinylated hIL-17A was pre-incubated with variable concentrations of said muteins and non-neutralized hIL-17A was quantified on an ELISA plate with immobilized soluble hIL-17-RA. Negative control SEQ ID NO: 7 has no competitive effect. Data were fitted with a single-site binding model.

Figure 9:
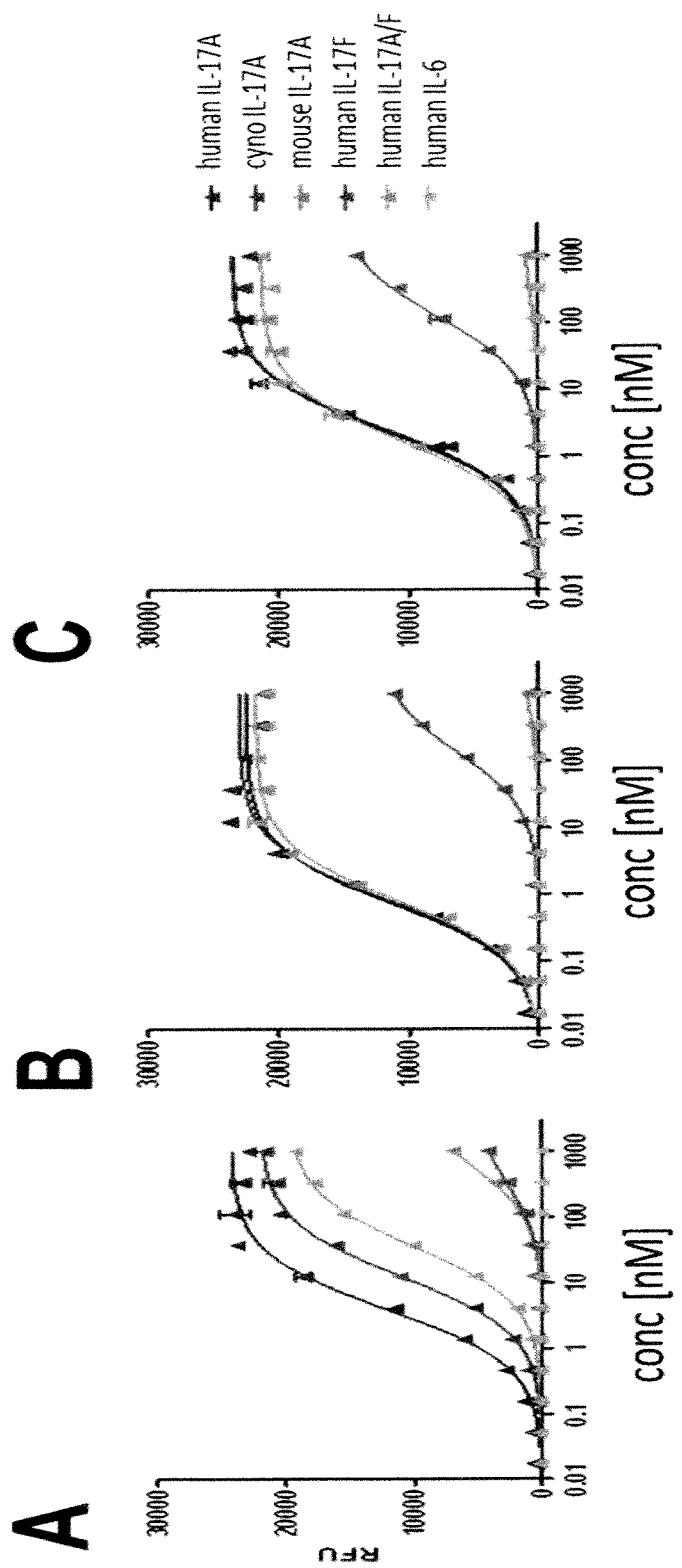

FIG. 9: shows the crossreactivity profile of the lipocalin muteins SEQ ID NO: 14, SEQ ID NO: 3 and SEQ ID NO: 4 as measured in a competition ELISA format. For all molecules, there is only weak binding to hIL-17F, no relevant crossreactivity to mouse IL-17A, and no binding to hIL-6, which serves as negative control. For SEQ ID NO: 3, strong binding to hIL-17A, hIL-17 A/F and species crossreactivity to cIL-17 A/F is shown by an apparent affinity $K_{D,app}$ of around 0.8 nM for all three ligands. The same applies to SEQ ID NO: 4, with a $K_{D,app}$ of around 2 nM for all three ligands. SEQ ID NO: 14 binds to all three ligands with fitted values of $K_{D,app/hIL-17A}$=4.0 nM, $K_{D,app/hIL-17\ NE}$=12.5 nM and $K_{D,app/cIL-17A}$=35.1 nM. Data were fitted with a single-site binding model.

Figure 10:
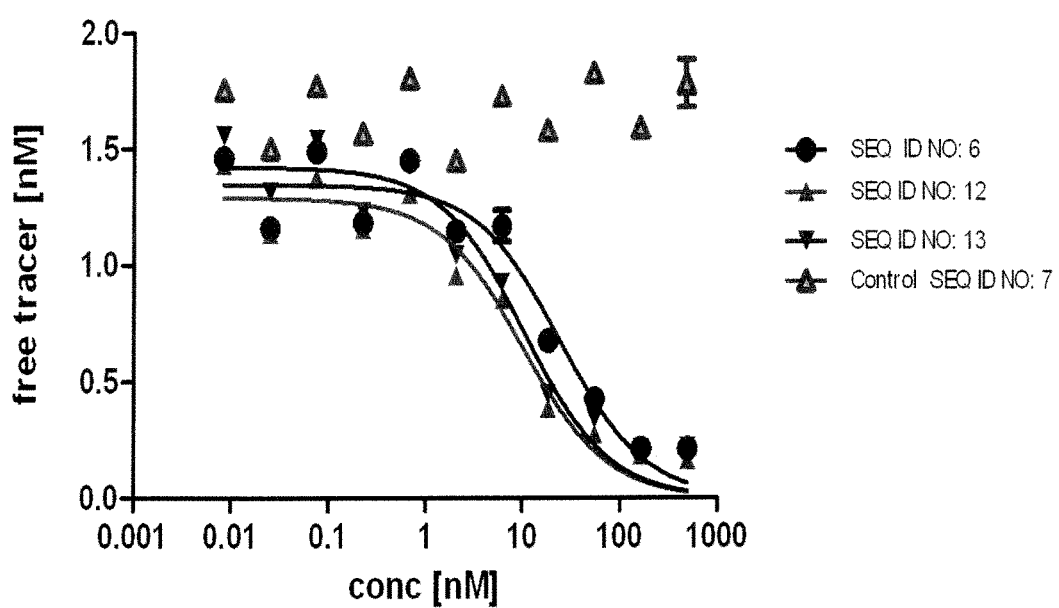

FIG. 10: demonstrates that the lipocalin muteins SEQ ID NO: 6, SEQ ID NO: 12 and SEQ ID NO: 13 are capable of blocking the interaction between hIL-23 and its receptor hIL-23R with an IC50 of 25 nM (SEQ ID NO: 6), 10 nM (SEQ ID NO: 12), and 11 nM (SEQ ID NO: 13), respectively. Biotinylated hIL-23 was pre-incubated with variable concentrations of said lipocalin muteins and non-neutralized hIL-23 was quantified on an ELISA plate with immobilized soluble hIL-23R. Negative control SEQ ID NO: 7 has no competitive effect. Data were fitted with a single-site binding model.

Figure 11:
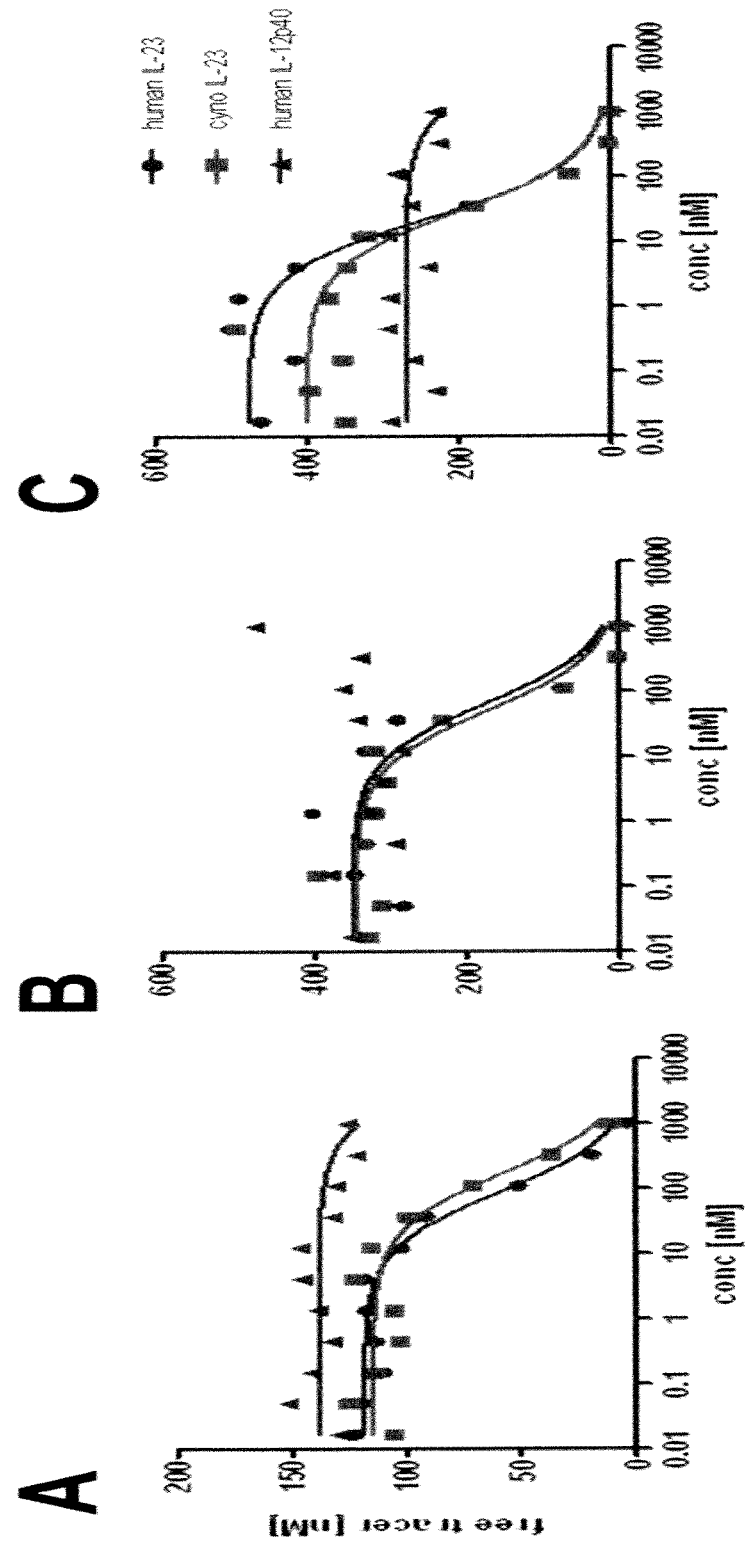

FIG. 11: shows the crossreactivity profile and specificity of the lipocalin muteins SEQ ID NO: 6 (FIG. 11A), SEQ ID NO: 12 (FIG. 11B) and SEQ ID NO: 13 (FIG. 11C), as measured in a competition ELISA format. All lipocalin muteins are fully crossreactive for human and cynomolgus monkey IL-23. As desired, specific binding of both muteins to the IL-23p19 subunit of IL-23, is demonstrated by lack of binding to IL-12p40, the second subunit of IL-23. Data were fitted with a single-site binding model.

Figure 12:
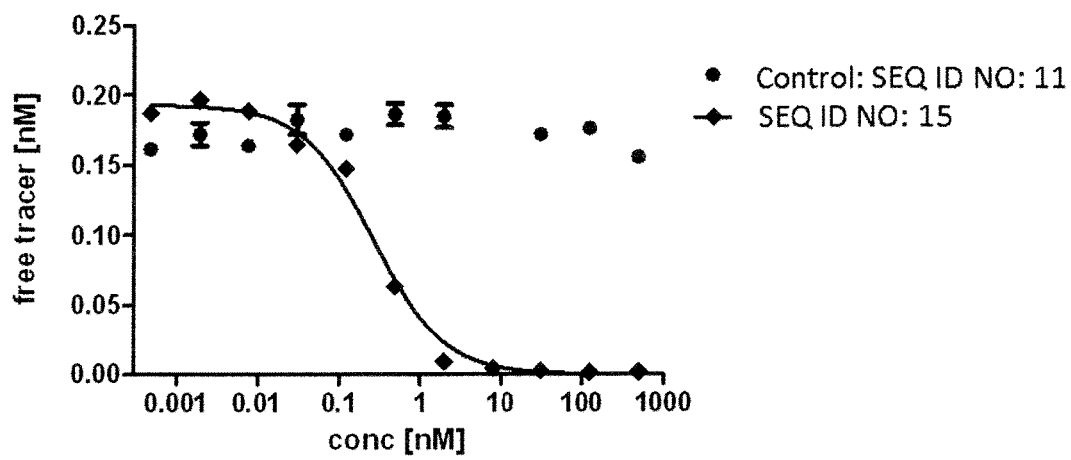

FIG. 12: demonstrates that the lipocalin mutein SEQ ID NO: 15 is capable of blocking the interaction between hIL-23 and its receptor hIL-23R in vitro with an IC50 of 0.3 nM. Biotinylated hIL-23 was pre-incubated with variable concentrations of said lipocalin mutein and non-neutralized hIL-23 was quantified on an ELISA plate with immobilized soluble hIL-23R. Negative control SEQ ID NO: 11 has no competitive effect. Data were fitted with a single-site binding model.

Figure 13:
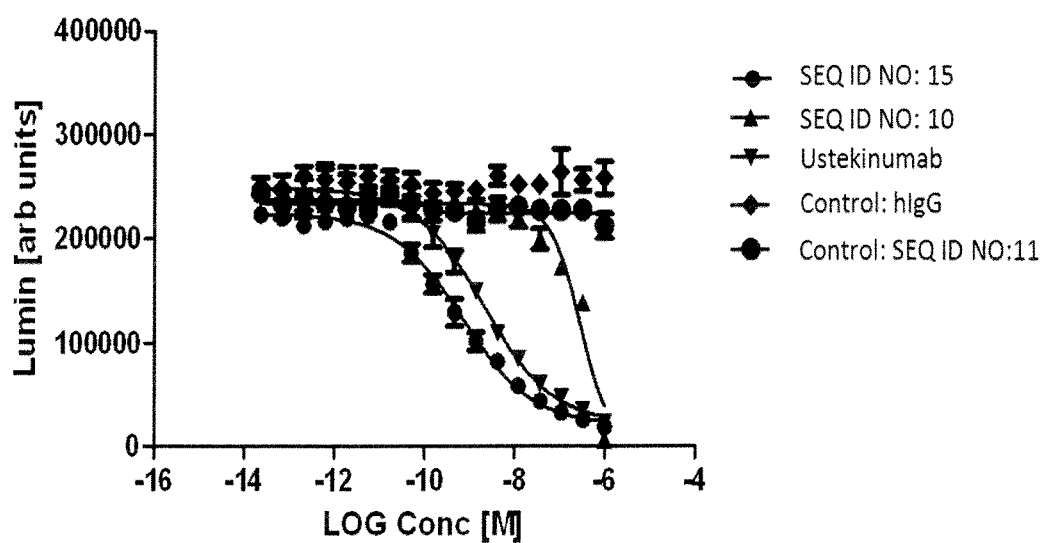

FIG. 13: demonstrates that the lipocalin muteins SEQ ID NO: 10 and SEQ ID NO: 15 are capable of blocking biological activity of hIL-23 in a cell-based proliferation assay. In the assay, SEQ ID NO: 10, SEQ ID NO: 15, negative control SEQ ID NO:11, the benchmark antibody ustekinumab as its corresponding negative control hIgG were preincubated with hIL-23 and subsequently added to Ba/F3 cells transfected with hIL-23R and hIL-12Rβ1. The transfected Ba/F3 cells proliferate in response to human IL-23. The experiment shows that this biological activity is blocked by SEQ ID NO: 10, SEQ ID NO: 15 and the benchmark antibody ustekinumab with IC50 values of 296 nM, 0.7 nM and 2.0 nM, respectively. SEQ ID NO: 15 is therefore more effective than the ustekinumab in blocking hIL-23 activity. Negative controls SEQ ID NO: 11 and hIgG have no effect on cell proliferation. Data were fitted with a sigmoidal dose-response model.

Figure 14:
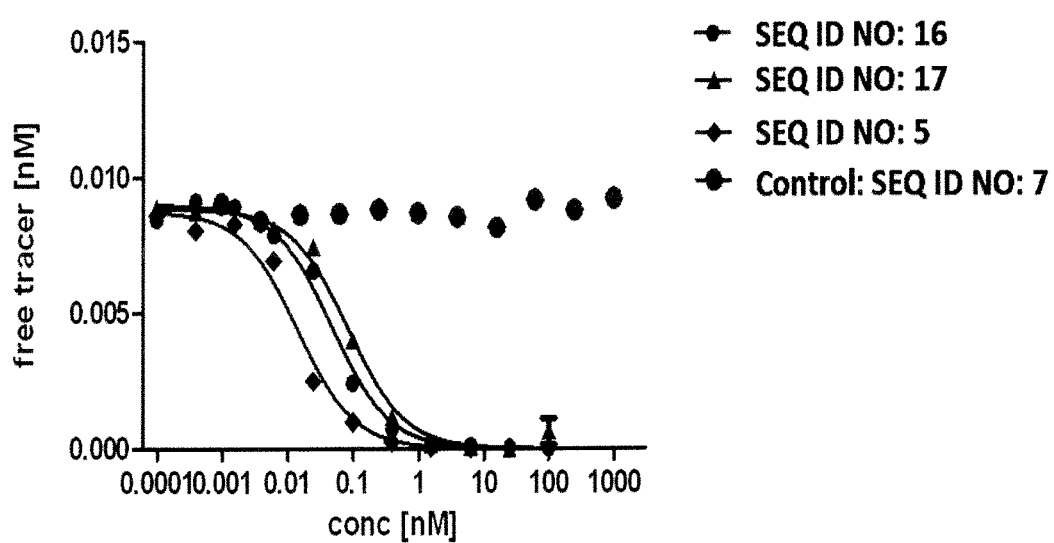

FIG. 14: demonstrates that the fusion proteins SEQ ID NO: 16 and SEQ ID NO: 17 are capable of blocking the interaction between hIL-17A and its receptor hIL-17RA in vitro with an IC50 of 0.08 nM and 0.05 nM, respectively, similar to the lipocalin mutein SEQ ID NO: 5, which displays an IC50 of 0.01 nM. Biotinylated hIL-17A was pre-incubated with variable concentrations of said muteins and non-neutralized hIL-17A was quantified on an ELISA plate with immobilized hIL-17-RA. Negative control SEQ ID NO: 7 has no competitive effect. Data were fitted with a single-site binding model.

Figure 15:
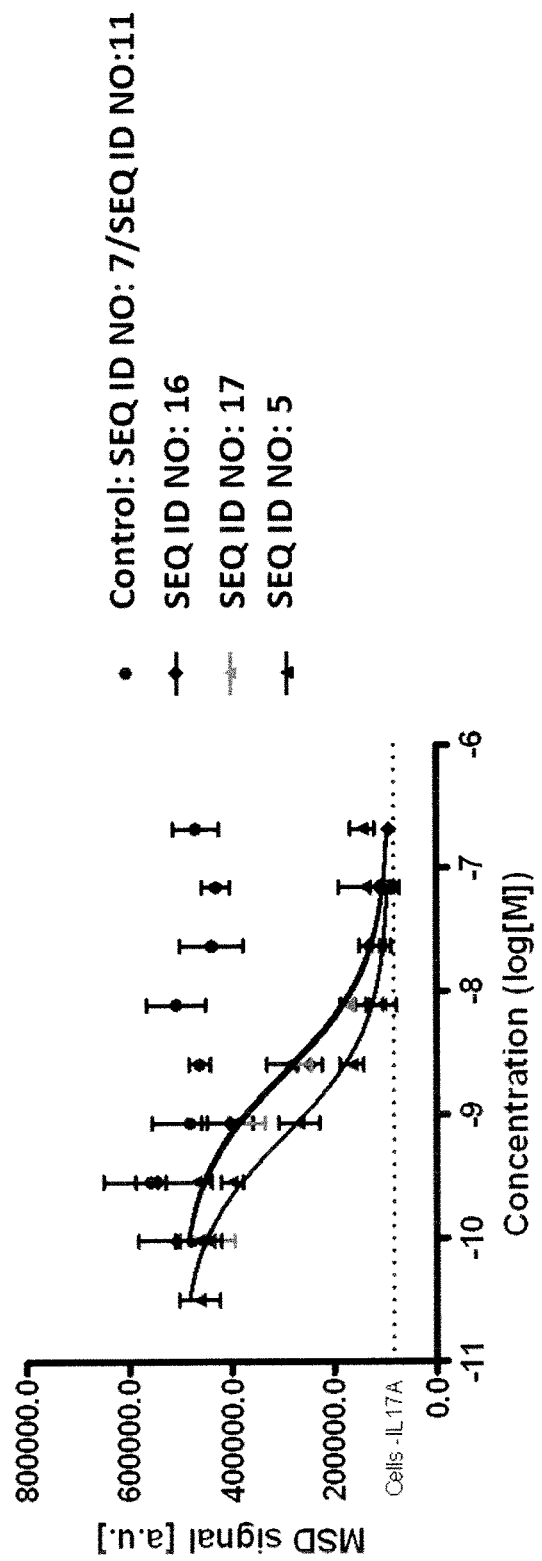

FIG. 15: illustrates that the fusion proteins SEQ ID NO: 16 and SEQ ID NO: 17 are highly effective in blocking hIL-17A binding to its receptor hIL-17RA in a cell-based assay, with a potency that is comparable to the lipocalin mutein SEQ ID NO: 5. The assay is based on hIL-17A-induced secretion of G-CSF in U87-MG cells. Cells are incubated with a fixed concentration of hIL-17A and titrated with muteins SEQ ID NOs: 16, 17, 5 and 7. Plotted is the concentration of G-CSF in arbitrary units as measured by MSD against the concentration of fusion protein(s), lipocalin mutein(s), or antibody molecule(s). The fusion proteins (SEQ ID NO: 16 and SEQ ID NO: 17) and the lipocalin mutein SEQ ID NO: 5 display the following 1050 values: IC50=2.2 nM for SEQ ID NO: 16, IC50=1.7 nM for SEQ ID NO: 17, and IC50=0.7 nM for SEQ ID NO: 5, respectively. Negative control SEQ ID NO: 7 has no effect. Data were fitted with a single-site binding model, assuming equal G-CSF concentration plateaus for all molecules.

FIG. 16: depicts an alignment of amino acid sequences of certain human tear lipocalin based muteins in comparison with the polypeptide sequence of the mature human tear lipocalin. Compared to the linear polypeptide sequence of the mature human tear lipocalin (SEQ ID NO: 1), the first 4 N-terminal amino acid residues (His, His, Leu, Ala) and the last 2 C-terminal amino acid residues (Ser, Asp) are deleted in these muteins (listed as SEQ ID NOs: 2-7 and 12-14).

FIG. 17: depicts an alignment of amino acid sequences of certain human neutrophil gelatinase-associated lipocalin based muteins (listed as SEQ ID NOs: 9-11 and 15) in comparison with the polypeptide sequence of the mature neutrophil gelatinase-associated lipocalin (SEQ ID NO: 8).

Figure 18:
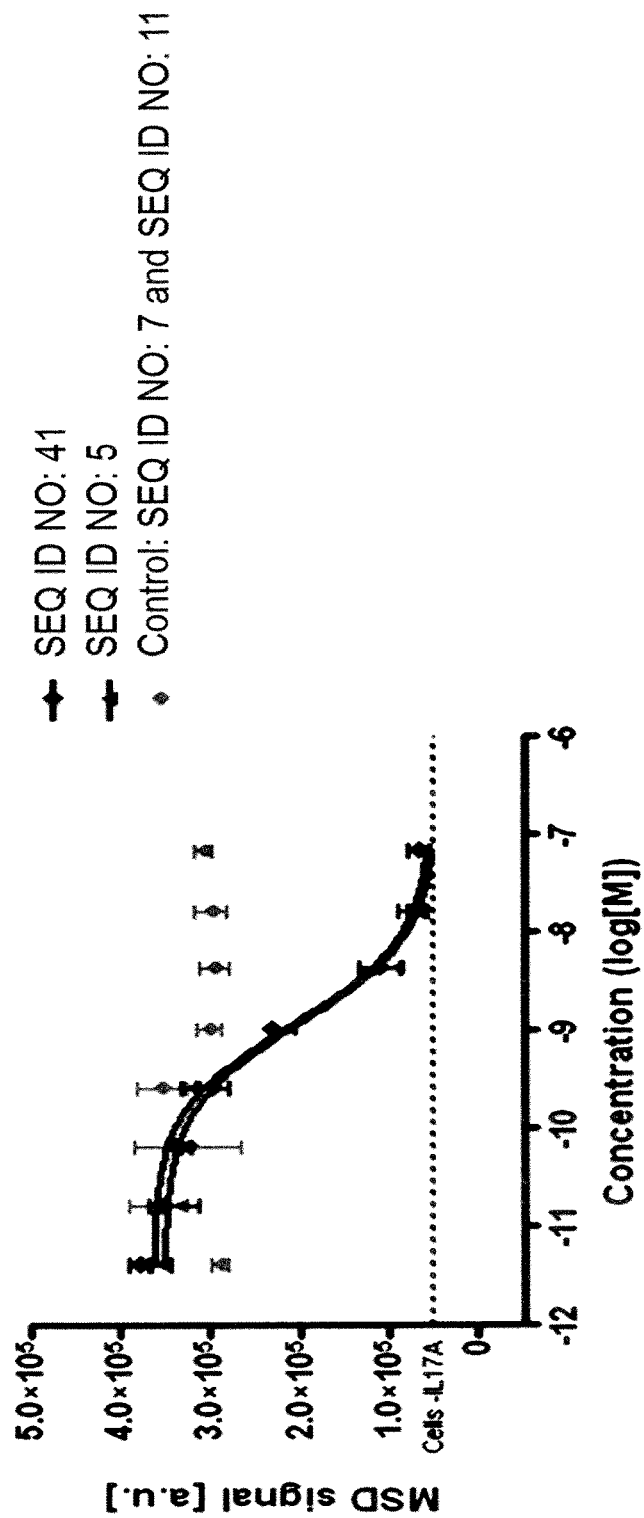

FIG. 18: illustrates that the ABD fusion (SEQ ID NO: 41) is as effective as its IL-17A-binding building block (lipocalin mutein, SEQ ID NO: 5) alone in blocking hIL-17A binding to its receptor hIL-17RA in a cell-based assay. The assay is based on hIL-17A-induced secretion of G-CSF in U87-MG cells. Cells are incubated with a fixed concentration of hIL-17A and titrated with the ABD fusion (diamonds) or SEQ ID NO: 5 (triangles) as a positive control. Plotted is the concentration of G-CSF in arbitrary units as measured by MSD against the concentration of the two molecules. The resulting IC50 values for the ABD fusion and its building block SEQ ID NO: 5 alone are identical and both amount to IC50=1.2 nM. Negative control (circles), consisting of a mixture of SEQ ID NO: 11 and SEQ ID NO: 7, has no effect. Binding of the ABD fusion and SEQ ID NO: 5 to IL-17A blocks IL-17A's binding to cell-surface IL-17RA and, thus, prevents induction of G-CSF secretion.

Figure 19:
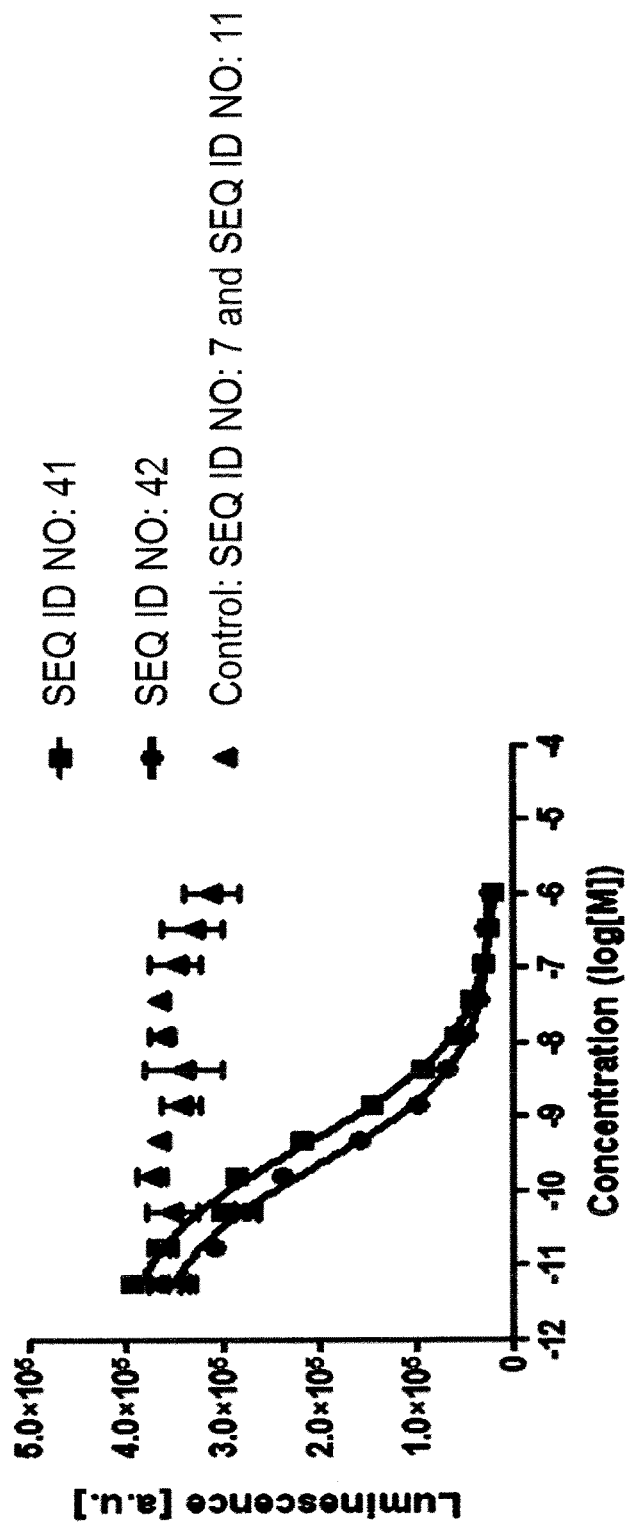

FIG. 19: illustrates that the ABD fusion (SEQ ID NO: 41) is as effective as its IL-23-binding building block (ABD fusion, SEQ ID NO: 42) alone in antagonising biological activity of hIL-23 in a cell-based proliferation assay. In the assay, the ABD fusion of SEQ ID NO: 41 (squares), the building block of SEQ ID NO: 42 (circles), and negative control (triangles) consisting a mixture of SEQ ID NO: 11 and SEQ ID NO: 7, were preincubated with hIL-23 and subsequently added to Ba/F3 cells transfected with hIL-23R and hIL-12Rβ1. The transfected Ba/F3 cells proliferate in response to human IL-23. The experiment shows that this biological activity is blocked by SEQ ID NO: 41 and its building block SEQ ID NO: 42 with comparable potency, with IC50 values of 0.42 nM and 0.22 nM, respectively. Negative control has no effect on cell proliferation.

Figure 20:
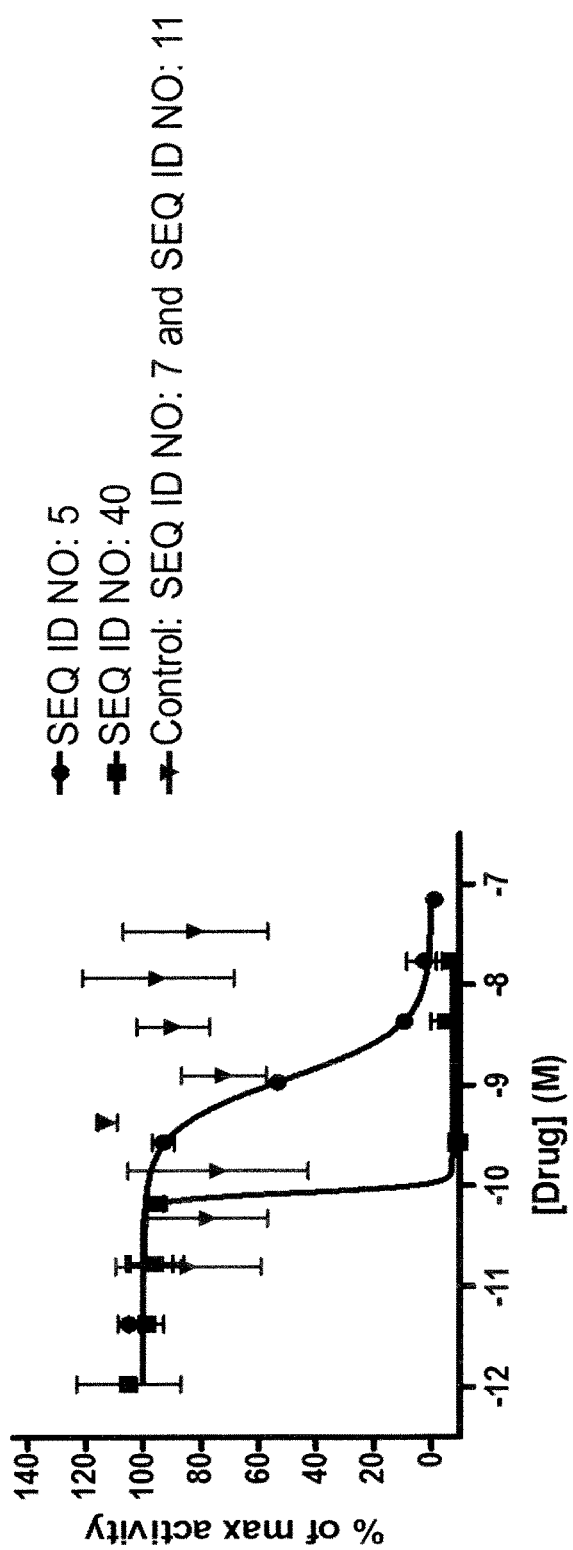

FIG. 20: illustrates that the bivalent fusion protein (SEQ ID NO: 40) displays an avidity effect to its homodimeric target IL-17A, and is therefore considerably more effective than its IL-17A-binding building block (lipocalin mutein, SEQ ID NO: 5) alone in antagonising hIL-17A binding to its receptor hIL-17RA in a cell-based assay. The assay is based on hIL-17A-induced secretion of G-CSF in U87-MG cells. Cells were incubated with a fixed concentration of hIL-17A and titrated with the fusion protein (squares) or the single building block SEQ ID NO: 5 (circles) as a positive control. The concentration of G-CSF in arbitrary units as measured by MSD is plotted against the concentration of the two molecules. The resulting IC50 value for the bivalent fusion protein lies at 0.12 nM, and therefore close to the limit of the assay which is governed by the employed concentration of IL-17A, which lies at about 100 pM. The bivalent fusion protein therefore has a much lower IC50 value than the IC50 value of the building block of SEQ ID NO: 5 alone, which is 1.2 nM. Negative control, consisting of a mixture of SEQ ID NO: 11 and SEQ ID NO: 7 (triangles), has no effect. Binding of the fusion protein and SEQ ID NO: 5 to IL-17A blocks IL-17A's binding to cell-surface IL-17RA and, thus, prevents induction of G-CSF secretion.

Figure 21:
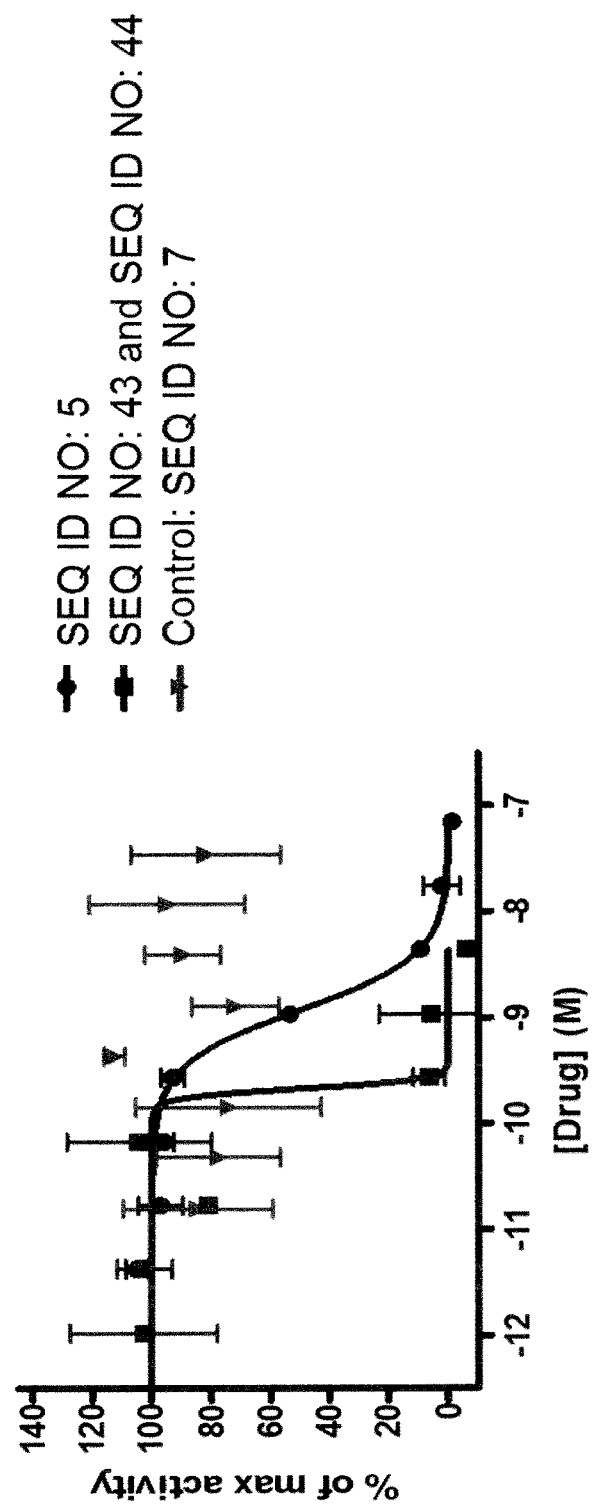

FIG. 21: illustrates that the fusion protein ((comprising the amino acids shown in SEQ ID NOs: 43 and 44) is effective in antagonising hIL-17A binding to its receptor hIL-17RA in a cell-based assay. Moreover, there is a prominent avidity effect showing the enhanced potency of the fusion protein in the cell-based assay compared to the IL-17A-binding building block of SEQ ID NO: 5 alone. The assay is based on hIL-17A-induced secretion of G-CSF in U87-MG cells. Cells were incubated with a fixed concentration of hIL-17A and titrated with the fusion protein (squares) or the single building block of SEQ ID NO: 5 (circles) as a positive control. The concentration of G-CSF in arbitrary units as measured by MSD is plotted against the concentration of lipocalin muteins and the resulting IC50 value for the fusion protein lies at 0.17 nM, which was rather close to the limit of the assay which is governed by the employed concentration of IL-17A (about 100 pM). Therefore, the fusion protein has a much lower IC50 value than the IC50 value the building block of SEQ ID NO: 5 alone, which was 1.2 nM. Negative control, consisting of a mixture of human IgG (CAT#. 009-000-003, Dianova) and SEQ ID NO: 7 (triangles), has no effect. Binding of the fusion protein and SEQ ID NO: 5 to IL-17A blocks IL-17A's binding to cell-surface IL-17RA and, thus, prevents induction of G-CSF secretion.

Figure 22:
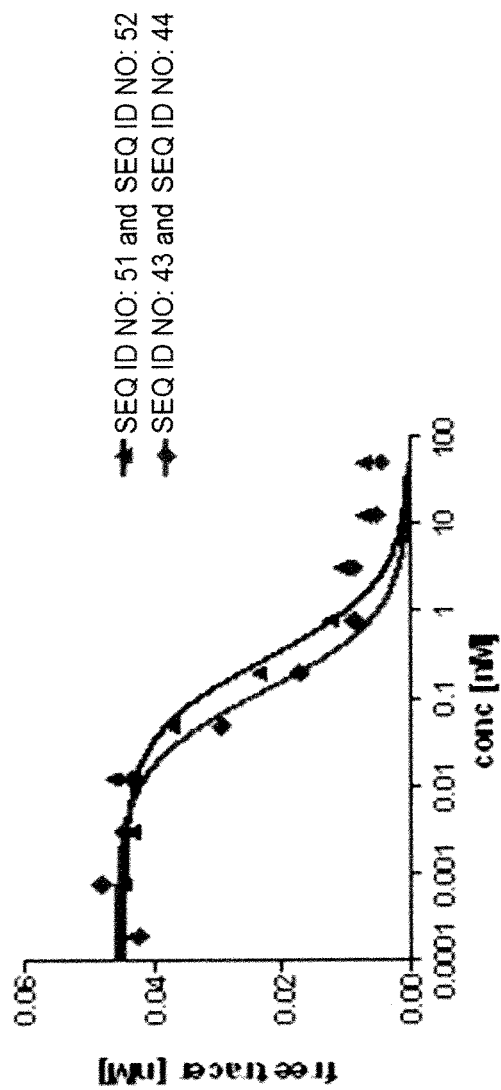

FIG. 22: illustrates that the fusion protein (comprising the amino acids shown in SEQ ID NOs: 43 and 44) (diamonds) is as effective as the IL-23-binding building block (an IgG antibody, comprising the amino acids shown in SEQ ID NOs: 51 and 52) alone (triangles) in blocking the interaction between hIL-23 and its receptor hIL-23R in vitro, yielding an IC50 value of 0.16 nM for for the fusion protein and an IC50 value of 0.22 nM for the IL-23-binding building block. Biotinylated hIL-23 was pre-incubated with variable concentrations of said two molecules and non-neutralized hIL-23 was quantified on an ELISA plate with immobilized soluble hIL-23R.

Figure 23:
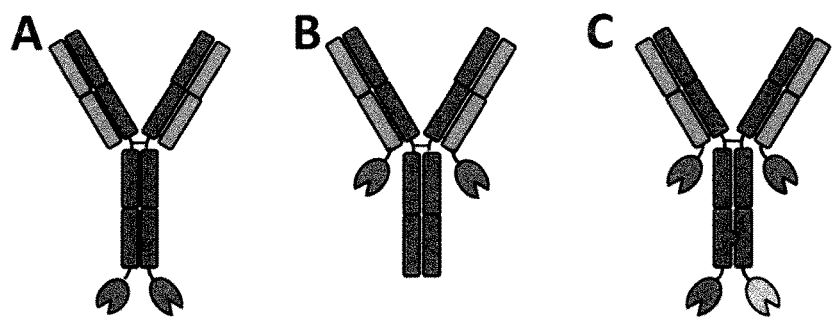

FIG. 23: provides examples of potential fusion protein variants comprising at least an antibody and at least a lipocalin mutein. FIG. 23A shows that the lipocalin mutein could be fused to the C-terminus of the antibody heavy chain. FIG. 23B shows that the lipocalin mutein could be fused to the C-terminus of the antibody light chain. FIG. 23C shows that one lipocalin muteins could be fused to the C-terminus of an antibody heavy chain, while one lipocalin mutein could be simultaneously fused to the C-terminus of the antibody light chain, with preferential pairing induced by a knob-in-hole approach (Ridgway et al. (1996), Protein Eng. 9/7), 617-621).

Figure 24:
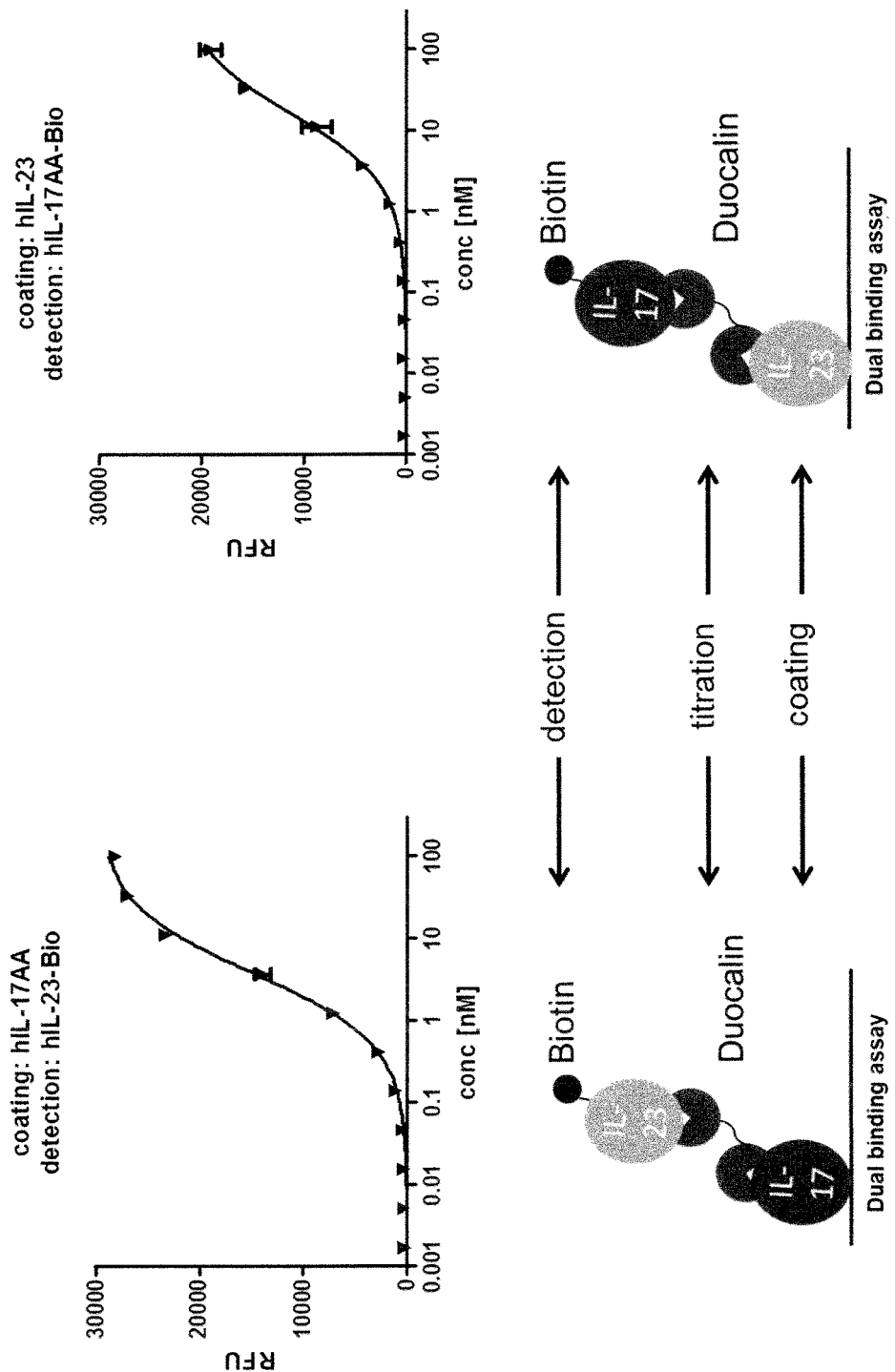

FIG. 24: demonstrates that the ABD fusion of SEQ ID NO: 41 is capable of engaging both hIL-17A and hIL-23 simultaneously. The titration of the ABD fusion on coated hIL-17A following detection with biotinylated hIL-23 resulted in an EC50 of 4 nM, while no full saturation was achieved for titration of the ABD fusion on coated hIL-23 and detection via biotinylated hIL-17A. Fitted EC50 values from this assay format do not reflect binding affinities.

Figure 25:
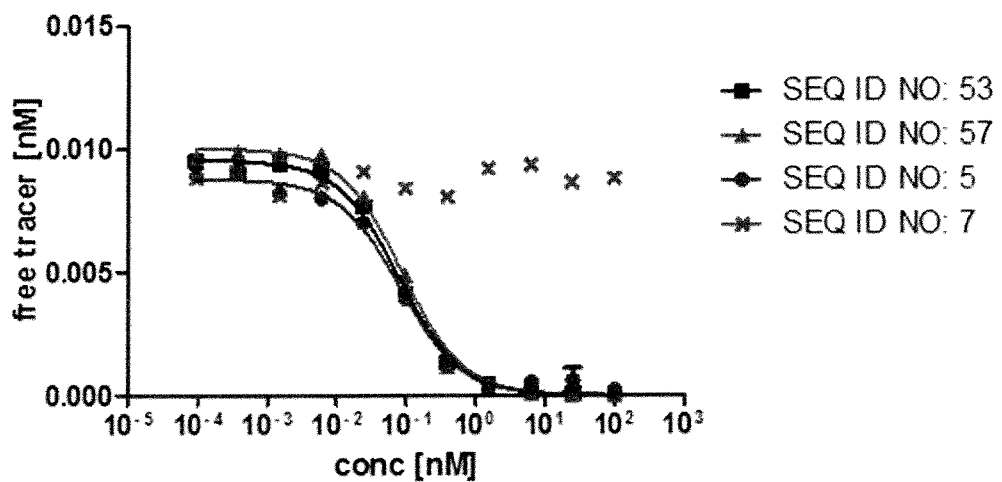

FIG. 25: demonstrates that the fusion proteins (SEQ ID NO: 53 and SEQ ID NO: 57) are capable of blocking the interaction between hIL-17A and its receptor hIL-17RA in vitro with an IC50 of 0.08 nM and 0.09 nM, respectively; similar to the lipocalin mutein of SEQ ID NO: 5, which displays an IC50 of 0.08 nM. Biotinylated hIL-17A was pre-incubated with variable concentrations of the fusion proteins and non-neutralized hIL-17A was quantified on an ELISA plate with immobilized soluble hIL-17-RA. Negative control SEQ ID NO: 7 has no competitive effect. Data were fitted with a single-site binding model.

Figure 26:
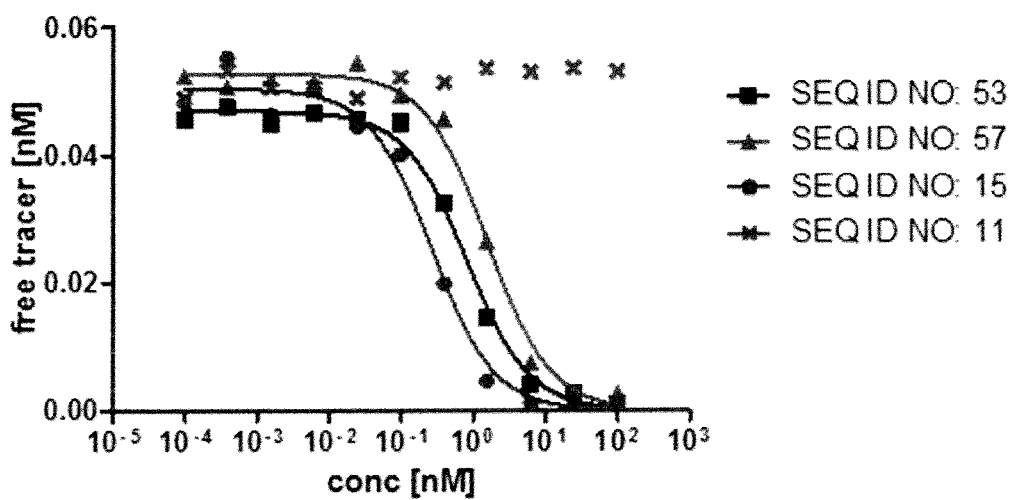

FIG. 26: illustrates that the fusion proteins (SEQ ID NO: 53 and SEQ ID NO: 57) are capable of blocking the interaction between hIL-23 and its receptor hIL-23R in vitro, yielding IC50 values of 0.8 nM for SEQ ID NO: 53, 1.6 nM for SEQ ID NO: 57; while the lipocalin mutein of SEQ ID NO: 15 displays an IC50 of 0.27 nM. Biotinylated hIL-23 was pre-incubated with variable concentrations of the fusion proteins and non-neutralized hIL-23 was quantified on a microtiter plate with immobilized soluble hIL-23R. Negative control SEQ ID NO: 11 does not show any effect on the IL23/IL23R interaction.

Figure 27:
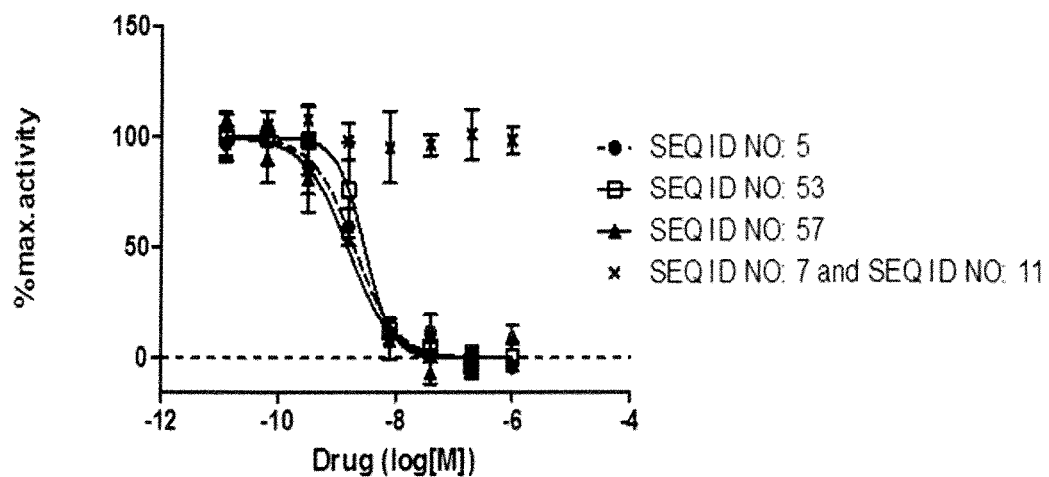

FIG. 27: illustrates that the fusion proteins (SEQ ID NO: 53 and SEQ ID NO: 57) are highly effective in blocking hIL-17A binding to its receptor hIL-17RA in a cell-based assay, with a potency that is comparable to the lipocalin mutein of SEQ ID NO: 5. The assay is based on hIL-17A-induced secretion of G-CSF in U87-MG cells. Cells were incubated with a fixed concentration of hIL-17A and titrated with the fusion proteins, the lipocalin mutein and a mixture of SEQ ID NO: 11 and SEQ ID NO: 7. The fusion proteins and the lipocalin mutein display the following IC50 values: 2.0 nM for SEQ ID NO: 5, 2.9 nM for SEQ ID NO: 53, and 1.5 nM for SEQ ID NO: 57, respectively. Negative control, consisting of a mixture of SEQ ID NO: 11 and SEQ ID NO: 7, has no effect. Data were fitted with a sigmoidal binding model.

Figure 28:
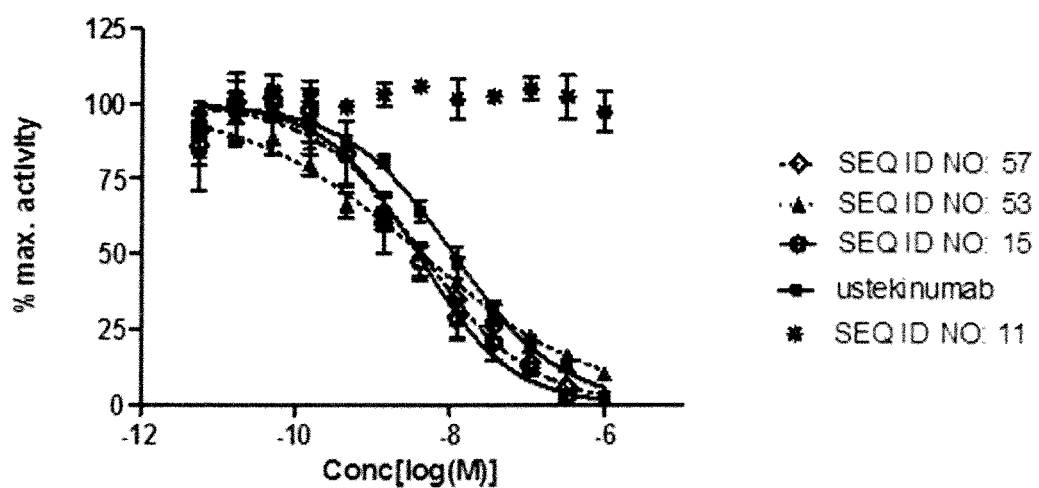

FIG. 28: demonstrates that the fusion proteins (SEQ ID NO: 53 and SEQ ID NO: 57) are capable of blocking biological activity of hIL-23 in a cell-based proliferation assay. In the assay, SEQ ID NO: 53, SEQ ID NO: 57, SEQ ID NO: 15, negative control (SEQ ID NO: 11), as well as the benchmark antibody ustekinumab and its corresponding negative control human IgG (CAT#. 009-000-003, Dianova), were preincubated with hIL-23 and subsequently added to Ba/F3 cells transfected with hIL-23R and hIL-12Rβ1. The transfected Ba/F3 cells proliferated in response to hIL-23. The experiment shows that this biological activity is blocked by SEQ ID NO: 53 and SEQ ID NO: 57 with 1050 values of 4.3 nM and 4.4 nM, respectively. For SEQ ID NO: 5, an IC50 value of 3.8 nM was determined; and for the benchmark antibody ustekinumab, an IC50 value of 11.1 nM was determined. SEQ ID NO: 53, SEQ ID NO: 57, SEQ ID NO: 15 are therefore more effective than the benchmark antibody in blocking hIL-23 activity. Negative controls (SEQ ID NO: 11 and hIgG) have no effect on cell proliferation. Data were fitted with a sigmoidal dose-response model.

Figure 29:
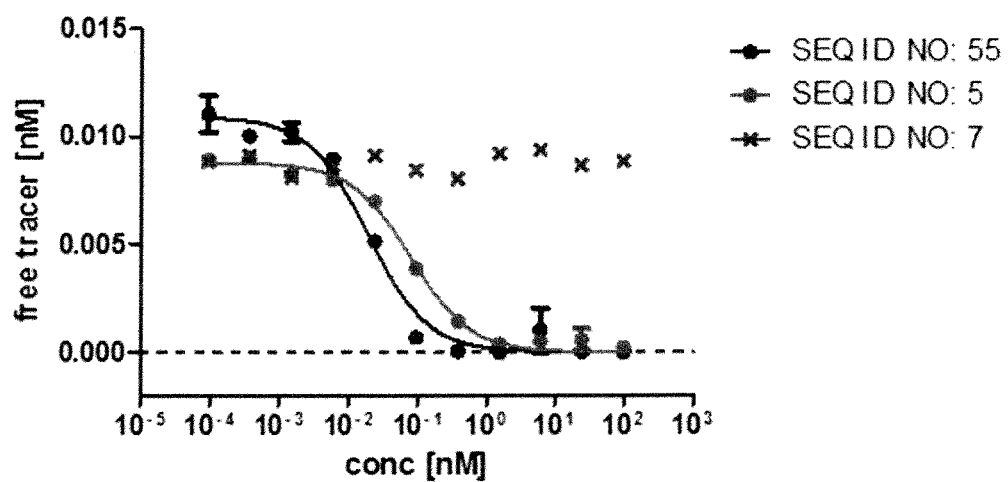

FIG. 29: demonstrates that the fusion protein (SEQ ID NO: 55) is capable of blocking the interaction between hIL-17A and its receptor hIL-17RA in vitro with an improved IC50 of 0.019 nM compared to the lipocalin mutein of SEQ ID NO: 5, which displays an IC50 of 0.08 nM. The bivalent fusion protein (SEQ ID NO: 55) displays an avidity effect to the homodimeric target IL-17A, and is, therefore, considerably more effective than the lipocalin mutein of SEQ ID NO: 5 in antagonising hIL-17A binding to its receptor hIL-17RA. Biotinylated hIL-17A was pre-incubated with variable concentrations of the fusion protein and the lipocalin mutein and non-neutralized hIL-17A was quantified on an ELISA plate with immobilized soluble hIL-17-RA. Negative control (SEQ ID NO: 7)) has no competitive effect. Data were fitted with a single-site binding model.

Figure 30:
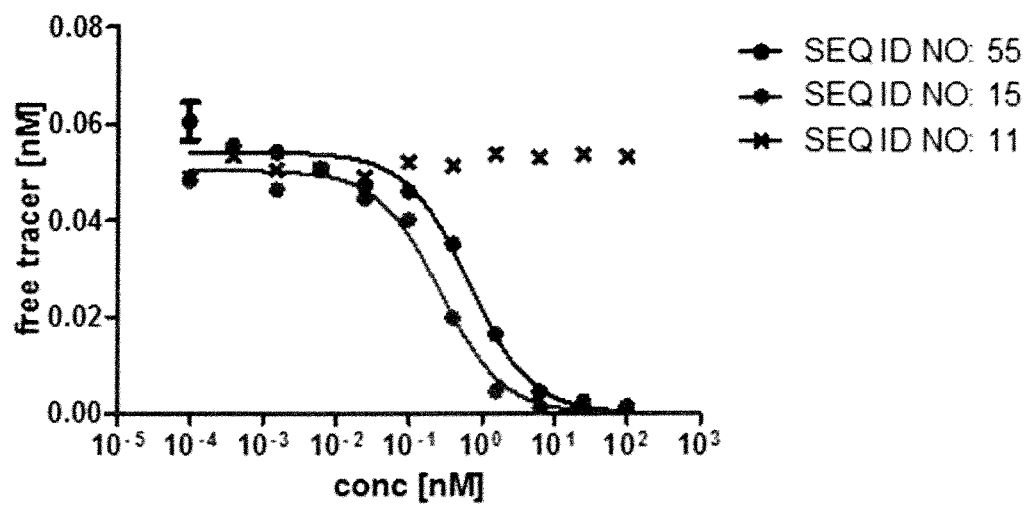

FIG. 30: illustrates that the fusion protein (SEQ ID NO: 55) is capable of blocking the interaction between hIL-23 and its receptor hIL-23R in vitro, yielding an IC50 value of 0.65 nM; while the lipocalin mutein of SEQ ID NO: 15 displays an IC50 value of 0.27 nM. Biotinylated hIL-23 was pre-incubated with variable concentrations of said two molecules and non-neutralized hIL-23 was quantified on a microtiter plate with immobilized soluble hIL-23R. Negative control (SEQ ID NO: 11) does not show any effect on the IL23/IL23R interaction.

IV. DETAILED DESCRIPTION OF THE DISCLOSURE

The present disclosure contributes to the state of art a polypeptide having binding specificity for IL-17A and/or IL-23p19, wherein the polypeptide comprises a lipocalin mutein that binds with at least a detectable affinity to IL-17A or IL-23p19.

In some embodiments, the polypeptide is a lipocalin mutein that is capable of binding IL-17A with at least a detectable affinity. In some embodiments, the polypeptide is a lipocalin mutein that is capable of binding IL-23p19 with at least a detectable affinity. The present disclosure also relates to use of both polypeptides, for the binding of IL-17A and IL-23p19 in a subject.

In some aspects, the polypeptide is a fusion protein comprising at least two subunits, wherein one subunit has binding specificity for IL-17A and another subunit has binding specificity for IL-23p19. In some further embodiments, the fusion protein may further comprise a subunit, wherein the subunit has binding specificity for IL-23p19 or IL-17A. In some still further embodiments, the fusion protein may comprise one subunit specific for IL-17A, one subunit specific for IL-23p19, and one subunit containing a bacterial albumin binding domain (ABD).

In some other aspects, a polypeptide of the disclosure may also be a fusion protein comprising at least two subunits specific for IL-17A, or a fusion protein comprising at least two subunits specific for IL-23p19.

In some embodiments, the subunit of the fusion protein having binding specificity for IL-17A comprises a lipocalin mutein specific for IL-17A of the disclosure. In some embodiments, the subunit of the fusion protein having binding specificity for IL-23p19 comprises an antibody that binds to IL-23p19. In some other embodiments, the subunit of the fusion protein having binding specificity for IL-23p19 comprises a lipocalin mutein specific for IL-23p19 of the disclosure. In some embodiments, the subunit of the fusion protein having binding specificity for IL-17A comprises an antibody that binds to IL-17A.

A. Lipocalin Muteins with Binding-Affinity for Interleukin-17A (IL-17A, Synonymous with IL-17).

In one aspect, the present disclosure provides human lipocalin muteins that bind human IL-17A (same as "IL-17") and useful applications therefor. Binding proteins described herein may bind human IL-17A homodimer (same as "IL-17 A/A") and/or heterodimers of human IL-17A and the human IL-17F homolog (same as "IL-17 A/F"). The disclosure also provides methods of making IL-17A binding proteins described herein as well as compositions comprising such proteins. IL-17A binding proteins of the disclosure as well as compositions thereof may be used in methods of detecting IL-17A (including IL-17 A/A and IL-17 A/F) in a sample or in methods of binding of IL-17A (including IL-17 A/A and IL-17 A/F) in a subject. No such human lipocalin muteins having these features attendant to the uses provided by present disclosure have been previously described.

1. Exemplary Lipocalin Muteins with Binding-Affinity for Interleukin-17A (IL-17A).

One embodiment of the current disclosure relates to a lipocalin mutein that is capable of binding Interleukin-17A (IL-17A) with an affinity measured by a KD of about 600 nM or lower. More preferably, the lipocalins can have an affinity measured by a KD of about 10 nM or lower, i.e., in the picomolar range. In another embodiment, the lipocalin mutein is capable of binding to human IL-17A in a competition assay preferably with an EC50 value of about 30 nM, 0.2 nM, 0.15 nM, 50 pM or lower.

A lipocalin mutein of the disclosure can be capable of blocking IL-17A binding to its receptor IL-17RA. In some further embodiments, the lipocalin muetin has an IC50 value at least as good as or superior to the IC50 value of a benchmark antibody, when said lipocalin mutein and the benchmark antibody are measured in an assay essentially as described in Example 4. The lipocalin mutein may have an IC50 value of 1 nM or less in the assay when at the same time the benchmark antibody has an IC50 value of 1.4 nM or less in the assay; the benchmark antibody can be a polypeptide comprising (i) SEQ ID NO: 19 or 21 as the first subunit and (ii) SEQ ID NO: 20 or 22 as the second subunit.

A lipocalin is a polypeptide defined by its supersecondary structure, namely cylindrical β-pleated sheet supersecondary structural region comprising eight β-strands connected pair-wise by four loops at one end to define thereby a binding pocket. The present disclosure is not limited to lipocalin muteins specifically disclosed herein. In this regard, the disclosure relates to a lipocalin mutein having a cylindrical β-pleated sheet supersecondary structural region comprising eight β-strands connected pair-wise by four loops at one end to define thereby a binding pocket, wherein at least one amino acid of each of at least three of said four loops has been mutated and wherein said lipocalin muetein is effective to bind IL-17 with detectable affinity.

A lipocalin mutein binding IL-17 with detectable affinity may include at least one amino acid substitution of a native cysteine residue by another amino acid, e.g. by a serine residue. A lipocalin mutein binding IL-17 with detectable affinity may include one or more non-native cysteine residues, substituting one or more amino acids of a wild type lipocalin with a cysteine residue. This also includes at least two amino acid substitutions of a native amino acid by a cysteine residue, hereby to form one or more cysteine briges between two cysteine residues. The cysteine residues may be situated in a manner that a resulting cysteine bridge can "connect" two loop regions of the lipocalin mutein, which may enhance stability of such polypeptide. The definition of these regions is used herein in accordance with Flower (Flower, 1996, supra, Flower, et al., 2000, supra) and Breustedt et al. (2005, supra).

A polypeptide or protein of the disclosure can be a mutein of a lipocalin, preferably a lipocalin selected from the group consisting of retinol-binding protein (RBP), bilin-binding protein (BBP), apolipoprotein D (APO D), neutrophil gelatinase associated lipocalin (NGAL), tear lipocalin (TLPC or Tlc), $\alpha_2$-microglobulin-related protein (A2m), 24p3/uterocalin (24p3), von Ebners gland protein 1 (VEGP 1), von Ebners gland protein 2 (VEGP 2), and Major allergen Can f1 precursor (ALL-1), with Tlc and NGAL each being a preferred lipocalin.

As used herein, a "lipocalin" is defined as a monomeric protein of approximately 18-20 kDA in weight, having a cylindrical β-pleated sheet supersecondary structural region comprising a plurality of (preferably eight) β-strands connected pair-wise by a plurality of (preferably four) loops at one end to define thereby a binding pocket. It is the diversity of the loops in the otherwise rigid lipocalin scaffold that gives rise to a variety of different binding modes among the lipocalin family members, each capable of accommodating targets of different size, shape, and chemical character (reviewed, e.g., in Flower, D. R. (1996), supra; Flower, D. R. et al. (2000), supra, or Skerra, A. (2000) Biochim. Biophys. Acta 1482, 337-350). Indeed, the lipocalin family of proteins have naturally evolved to bind a wide spectrum of ligands, sharing unusually low levels of overall sequence conservation (often with sequence identities of less than 20%) yet retaining a highly conserved overall folding pattern. The correspondence between positions in various lipocalins is well known to one of skill in the art. See, for example, U.S. Pat. No. 7,250,297.

In one preferred embodiment, a protein disclosed herein is a mutein of human tear lipocalin (TLPC or Tlc), also termed lipocalin-1, tear pre-albumin or von Ebner gland protein. The term "human tear lipocalin" or "Tlc" or "lipocalin-1" as used herein refers to the mature human tear lipocalin with the SWISS-PROT/UniProt Data Bank Accession Number P31025 (Isoform 1). The amino acid sequence shown in SWISS-PROT/UniProt Data Bank Accession Number P31025 may be used as a preferred "reference sequence".

In one aspect, the present disclosure relates to novel, specific-binding human tear lipocalin muteins directed against or specific for Interleukin-17A (IL-17A). Human tear lipocalin muteins disclosed herein may be used for therapeutic and/or diagnostic purposes. A human tear lipocalin mutein of the disclosure may also be designated herein as "a Tlc mutein". As used herein, a Tlc mutein of the disclosure "specifically binds" a target (e.g. here, IL-17A) if it is able to discriminate between that target and one or more reference targets, since binding specificity is not an absolute, but a relative property. "Specific binding" can be determined, for example, in accordance with Western blots, ELISA-, RIA-, ECL-, IRMA-tests, FACS, IHC and peptide scans.

In this regard, the disclosure provides one or more Tlc muteins that are capable of binding Interleukin-17A (IL-17A) with an affinity measured by a KD of about 100 nM, about 10 nM, about 1 nM or lower. More preferably, the Tlc muteins can have an affinity measured by a KD of about 1 nM, 0.8 nM, 0.6 nM, 100 pM or lower.

In some embodiments, a Tlc mutein of the disclosure includes at least two amino acid substitutions, which are located at one or more sequence positions of the positions 26-34, 55-58, 60-61, 64, 101, 104-108, 111, 114 and 153 of the linear polypeptide sequence of the mature human tear lipocalin.

In further particular embodiments, the Tlc muteins of the disclosure may further comprise a mutated amino acid residue at one or more positions corresponding to position 26-34, 55-58, 60-61, 64, 104-108 of the linear polypeptide sequence of the mature human tear lipocalin (SWISS-PROT Data Bank Accession Number P31025).

In further particular embodiments, the Tlc muteins of the disclosure may further include a mutated amino acid residue at one or more positions corresponding to positions 101, 111, 114 and 153 of the linear polypeptide sequence of the mature human tear lipocalin.

In particular embodiments, the Tlc muteins of the disclosure comprise at least 1, 2, 3, 4, 5, 6, 7, 8, 9, 10, 11, 12, 13, 14, 15, 16, 17, 18, 19, 20 or 21, sometimes even more, mutated amino acid residues at one or more sequence positions corresponding to sequence positions 26, 27, 28, 29, 30, 31, 32, 33, 34, 55, 56, 57, 58, 60, 61, 64, 101, 104, 105, 106, 107, 108, 111, 114 and 153 of the linear polypeptide sequence of the mature human tear lipocalin.

Similarly, the disclosure relates to a polypeptide comprising a tear lipocalin shown in SEQ ID NO: 1, wherein said tear lipocalin comprises at least 2, 3, 4, 5, 6, 7, 8, 9, 10, 11, 12, 13, 14, 15, 16, 17, 18, 19, 20 or 21, sometimes even more, mutated amino acid residues at the sequence positions 26, 27, 28, 29, 30, 31, 32, 33, 34, 55, 56, 57, 58, 60, 61, 64, 101, 104, 105, 106, 107, 108, 111, 114 and/or 153. Said polypeptide is preferably a lipocalin mutein.

In further particular embodiments, a Tlc mutein according to the current disclosure comprises an amino acid sequence selected from the group consisting of SEQ ID NOs: 2-5 and 14. In another embodiment, the mutein has at least 70% identity or at least 70% sequence homology to the sequence of a wild-type human lipocalin, including the human tear lipocalin. Preferably, said mutein comprises at least 2, 3, 4, 5, 6, 7, 8, 9, 10, 11, 12, 13, 14, 15, 16, 17, 18, 19, 20 or 21, sometimes even more, mutated amino acid residues at the sequence positions 26, 27, 28, 29, 30, 31, 32, 33, 34, 55, 56, 57, 58, 60, 61, 64, 101, 104, 105, 106, 107, 108, 111, 114 and/or 153 of the linear polypeptide sequence of tear lipocalin (SEQ ID NO: 1).

As two illustrative examples, the mutein of the SEQ ID NO: 2 has an amino acid sequence identity or a sequence homology of approximately 85.44% with the amino acid sequence of mature human tear lipocalin, and the mutein of the SEQ ID NO: 4 has an amino acid sequence identity or a sequence homology of approximately 84.8% with mature human tear lipocalin.

In some embodiments, a lipocalin mutein according to the disclosure may include at least one amino acid substitution of a native cysteine residue by e.g. a serine residue. In some embodiments, a Tlc mutein according to the disclosure includes an amino acid substitution of a native cysteine residue at positions 61 and/or 153 by a serine residue. In this context it is noted that it has been found that removal of the structural disulfide bond (on the level of a respective naïve nucleic acid library) of wild type tear lipocalin that is formed by the cysteine residues 61 and 153 (cf. Breustedt, et al., 2005, supra) may providetear lipocalin muteins that are not only stably folded but are also able to bind a given non-natural ligand with high affinity. Without wishing to be bound by theory, it is also believed that the elimination of the structural disulde bond provides the further advantage of allowing for the (spontaneous) generation or deliberate introduction of non-natural artificial disulfide bonds into muteins of the disclosure, thereby increasing the stability of the muteins. For example, in some embodiments, a Tlc mutein according to the disclosure includes an amino acid substitution of a native cysteine residue at position 101 by a serine residue. Further, in some embodiments, a mutein according to the disclosure includes an amino acid substitution of a native arginine residue at positions 111 by a proline residue. In some embodiments a mutein according to the disclosure includes an amino acid substitution of a native lysine residue at positions 114 by a tryptophan residue.

A Tlc mutein according to the disclosure may further include, with respect to the amino acid sequence of the mature human tear lipocalin (SWISS-PROT Data Bank Accession Number P31025), one or more, including at least two, at least three, at least four, at least five, at least six, at least seven, at least eight, at least nine, at least ten, at least eleven, at least twelve, at least thirteen or at least fourteen amino acid substitutions of native amino acid residues by cysteine residues at any of positions 26-34, 55-58, 60-61, 64, 101, 104-106, 108, 111, 114 and 153 of the mature human tear lipocalin.

In some embodiments, a mutein according to the disclosure includes an amino acid substitution of a native amino acid by a cysteine residue at positions 28 or 105 with respect to the amino acid sequence of mature human tear lipocalin. In some embodiments a mutein according to the disclosure includes an amino acid substitution of a native amino acid by a cysteine residue at positions 28 or 105 with respect to the amino acid sequence of mature human tear lipocalin. In a further particular embodiment, a mutein according to the disclosure includes an amino acid substitution of a native amino acid by two cysteine residues at positions 28 and 105 with respect to the amino acid sequence of mature human tear lipocalin.

In some embodiments, a Tlc mutein according to the disclosure includes a substituted amino acid of at least one or of both of the cysteine residues occurring at each of the sequences positions 61 and 153 by another amino acid and the mutation of at least three amino acid residue at any one of the sequence positions 26-34, 55-58, 60-61, 64, 101, 104-108, 111, 114 and 153 of the linear polypeptide sequence of the mature human tear lipocalin (SWISS-PROT Data Bank Accession Number P31025). The positions 26-34 are included in the AB loop, the position 55 is located at the very end of a beta-sheet and following positions 56-58 as well as 60-61 and 64 are included in the CD loop. The positions 104-108 are included in the GH loop in the binding site at the open end of the β-barrel structure of the mature human tear lipocalin. The definition of these regions is used herein in accordance with Flower (Flower, 1996, supra, Flower, et al., 2000, supra) and Breustedt et al. (2005, supra). In some embodiments, the Tlc mutein according to the disclosure includes the amino acid substitutions Cys 61→Ala, Phe, Lys, Arg, Thr, Asn, Gly, Gln, Asp, Asn, Leu, Tyr, Met, Ser, Pro or Trp and Cys 153→Ser or Ala. Such a substitution has proven useful to prevent the formation of the naturally occurring disulphide bridge linking Cys 61 and Cys 153, and thus to facilitate handling of the mutein. However, tear lipocalin muteins that binds IL-17A and that have the disulphide bridge formed between Cys 61 and Cys 153 are also part of the present disclosure.

In some embodiments, the Tlc mutein according to the disclosure includes at least one amino acid substitution, which may be an additional amino acid substitution, selected from Arg 111→Pro and Lys 114→Trp. A Tlc mutein of the disclosure may further include the cysteine at position 101 of the sequence of the mature human tear lipocalin substituted by another amino acid. This substitution may, for example, be the mutation Cys 101→Ser or Cys 101→Thr.

As defined above, a Tlc mutein of the disclosure includes at least two amino acid substitutions, which are located at one or more sequence positions of the positions 26-34, 55-58, 60-61, 64, 101, 104-108, 111, 114 and 153 of the linear polypeptide sequence of the mature human tear lipocalin. In some embodiments, a mutein of the disclosure includes two or more, such as 3, 4, 5, 6, 7, 8, 9, 10, 11, 12, 13, 14, 16, 18, 19, 20 or 21 amino acid substitutions of these sequence positions of the mature human tear lipocalin. In one embodiment, the Tlc mutein has a mutated amino acid residue at each of the sequence positions 26-34, 55-58, 60-61, 64, 101, 104-108, 111, 114 and 153 of the linear polypeptide sequence of the mature human tear lipocalin.

In some embodiments, a Tlc mutein of the disclosure has at any one or more of the sequence positions 26-34, 55-58, 60-61, 64, 101, 104-108, 111, 114 and 153 of the linear polypeptide sequence of the mature human tear lipocalin one or more of the following mutated amino acid residues: Arg 26→Asp, Thr, Ser, Gly, Phe, Tyr, Val or Glu, Pro 29→Arg, Lys, Ser, Glu, Leu or Phe, Asn 32→Tyr, Trp, Gln, His, Leu, Ser, Phe or Arg, Glu 34→Gly, Asn, Pro, Trp, Arg or His, Leu 56→Pro, Ser, Phe, Tyr, Arg, Asn, Ala, Val, Asp, Gln, Glu or Thr, Ser 58→Asp, Trp, Phe, Ala, Glu, His, Arg, Pro or Gly, Cys 61→Arg, Ser, Gly, Ala, Trp, Lys, Tyr, Asp, Thr, Val, Ile, Thr, Phe, Asn, Leu, Gln or Glu, Glu 104→Trp, Thr, Ser, His, Ile, Asp or Ala and His 106→Ala, Tyr, Phe, Pro, Thr or Glu. In some embodiments, a Tlc mutein of the disclosure includes two or more, such as 3, 4, 5, 6, 7, 8 or all mutated amino acid residues at these sequence positions of the mature human tear lipocalin.

In some embodiments, a Tlc mutein according to the disclosure includes at least one of the following substitutions: Glu 27→Thr, Asn, Asp, Trp, Arg, Leu, Gly or Val, Glu 30→Gly, Lys, Phe, His, Trp or Asn, Met 31→Ala, His, Leu, Val, Trp, Gly, Pro or Arg, Leu 33→Gln, Asp, Gly, Val, Glu, Ile or Phe, Met 55→Gln, Asn, Ile, Thr, Ser or Leu, Ile 57→Leu, Trp or Ser, Arg 60→Tyr, Asp, Thr, Phe, Ile, Ser or Arg, Gly 107→Leu or Asp and Lys 108→Leu, Ser, Phe, Ala or Trp. In some embodiments, a Tlc mutein according to the disclosure includes two or more, such as 3, 4, 5, 6, 7 or all of the substitutions amino acid substitutions of these sequence positions of the mature human tear lipocalin.

In some embodiments, a Tlc mutein according to the disclosure includes one of the substitutions selected from the group consisting Val 64→Phe, Val 64→Leu, Val 64→Asp or Val 64→Ala.

Additionally, a Tlc mutein according to the disclosure may further include an amino acid substitution Arg 111→Pro. A Tlc mutein according to the disclosure may also include a substitution Lys 114→Trp. It may also comprise a substitution Cys 101→Ser or Cys 101→Thr. In some preferred embodiments, a Tlc mutein according to the disclosure may also comprise a substitution Cys 153→Ser.

In some embodiments, the Tlc mutein binding IL-17A includes at least one, including 2, 3, 4, 5, 6 or 7 of the following the amino acid substitutions: Arg 26→Phe; Glu 27→Trp; Phe 28→Cys; Pro 29→Ser; Glu 30→Gly; Leu 33→Glu; Leu 56→Asp; Ser 58→Arg; Cys 101→Ser; Glu 104→Asp; Leu 105→Cys; Arg 111→Pro; Lys 114→Trp and Cys 153→Ser.

In some embodiments, the Tlc mutein binding IL-17A includes with respect to the amino acid sequence of mature human tear lipocalin at least 1, 2, 3, 4, 5, 6 or 7 amino acid substitutions selected from the group consisting of Arg 26→Phe; Glu 27→Trp; Phe 28→Cys; Pro 29→Ser; Glu 30→Gly; Leu 33→Asp; Leu 56→Asp; Ser 58→Glu; Cys 101→Ser; Glu 104→Asp; Leu 105→Cys; Arg 111→Pro; Lys 114→Trp and Cys 153→Ser. In some embodiments, the Tlc mutein includes all of these amino acid substitutions.

Additionally, such a Tlc mutein further comprising one of the following sets of amino acid substitutions:
1. Met 31→Val, Asn 32→His, Leu 56→Asp, Ser 58→Gly, Arg 60→Phe; Cys 61→Leu; His 106→Pro; and Lys 108→Ser; or
2. Met 31→Ile, Asn 32→His, Leu 56→Asp, Ser 58→Ala, Arg 60→Phe; Cys 61→Leu; His 106→pro; and Lys 108→Leu.

In some embodiments the Tlc mutein binding IL-17A includes one of the following sets of amino acid substitutions:
1. Arg 26→Phe; Glu 27→Trp; Glu 30→Gly; Met 31→Val; Asn 32→His; Leu 33→Glu; Leu 56→Asp; Ser 58→Gly; Arg 60→Phe; Cys 61→Leu; His 106→Pro; Lys 108→Leu;
2. Arg 26→Thr; Glu 27→Trp; Glu 30→Gly; Met 31→Ile; Asn 32→His; Leu 33→Asp; Leu 56→Asp; Ser 58→Ala; Arg 60→Phe; Cys 61→Leu; His 106→Pro;
3. Arg 26→Phe; Glu 27→Trp; Glu 30→Gly; Met 31→Ile; Asn 32→His; Leu 33→Glu; Leu 56→Asp; Ser 58→Arg; Arg 60→Phe; Cys 61→Leu; His 106→Pro; Lys 108→Ser; or
4. Arg 26→Thr; Glu 27→Trp; Glu 30→Gly; Met 31→Ile; Asn 32→His; Leu 33→Glu; Leu 56→Asp; Ser 58→Glu; Arg 60→Phe; Cys 61→Leu; His 106→Pro.

In the residual region, i.e. the region differing from sequence positions 26-34, 55-58, 60-61, 64, 101, 104-106, 108, 111, 114 and 153, a Tlc mutein of the disclosure may include the wild type (natural) amino acid sequence outside the mutated amino acid sequence positions. A protein of the disclosure may include the wild type (natural) amino acid sequence of the "parental" protein scaffold (such as a lipocalin) outside the mutated amino acid sequence positions. In some embodiments, a lipocalin mutein according to the disclosure may also carry one or more amino acid mutations at a sequence position/positions as long as such a mutation does, at least essentially not hamper or not interfere with the binding activity and the folding of the mutein. Such mutations can be accomplished very easily on DNA level using established standard methods (Sambrook, J. et al. (2001) Molecular Cloning: A Laboratory Manual, 3rd Ed., Cold Spring Harbor Laboratory Press, Cold Spring Harbor, N.Y.). Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of the human tear lipocalin as long as these deletions or insertion result in a stable folded/functional mutein (for example, Tlc muteins with truncated N- and C-terminus). In such mutein, for instance, one or more amino acid residues are added or deleted at the N- or C-terminus of the polypeptide. Generally such a mutein may have about at least 70%, including at least about 80%, such as at least about 85% amino acid sequence identity, with the amino acid sequence of the mature human tear lipocalin. As an illustrative example, the first 4 N-terminal amino acid residues (His, His, Leu, Ala) and the last 2 C-terminal amino acid residues (Ser, Asp) can be deleted in a tear lipocalin mutein of the disclosure without affecting the biological function of the protein, e.g. SEQ ID NOs: 2-5. In addition, one GH loop amino acid residue (Lys) corresponding to sequence position 108 of the linear polypeptide sequence of the mature human tear lipocalin (SWISS-PROT Data Bank Accession Number P31025) can be deleted in a tear lipocalin mutein of the disclosure without affecting the biological function of the protein, e.g. SEQ ID NO: 3 and SEQ ID NO: 5.

Such modifications of the amino acid sequence include directed mutagenesis of single amino acid positions in order to simplify sub-cloning of the mutated lipocalin gene or its parts by incorporating cleavage sites for certain restriction enzymes. In addition, these mutations can also be incorporated to further improve the affinity of a Tlc mutein for IL-17A. Furthermore, mutations can be introduced in order to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation. Exemplary possibilities of such a mutation to introduce a cysteine residue into the amino acid sequence of a Tlc mutein include the substitutions Thr 40→Cys, Glu 73→Cys, Arg 90→Cys, Asp 95→Cys, and Glu 131→Cys. The generated thiol moiety at the side of any of the amino acid positions 40, 73, 90, 95 and/or 131 may be used to PEGylate or HESylate the mutein, for example, in order to increase the serum half-life of a respective Tlc mutein.

The present disclosure also encompasses Tlc muteins as defined above, in which the first four N-terminal amino acid residues of the sequence of mature human tear lipocalin (His-His-Leu-Leu; positions 1-4) and/or the last two C-terminal amino acid residues (Ser-Asp; positions 157-158) of the linear polypeptide sequence of the mature human tear lipocalin (SWISS-PROT Data Bank Accession Number P31025) have been deleted (SEQ ID NOs: 2-5). In addition, the present disclosure encompasses Tlc muteins as defined above, in which one GH loop amino acid residue (Lys) corresponding to sequence position 108 of the linear polypeptide sequence of the mature human tear lipocalin has been deleted (SEQ ID NO: 3 and SEQ ID NO: 5). Another possible mutation of the wild type polypeptide sequence of the mature human tear lipocalin is to change the amino acid sequence at sequence positions 5 to 7 (Ala Ser Asp) to Gly Gly Asp as described in PCT application WO 2005/019256.

The Tlc muteins of the disclosure may include, consist essentially of or consist of any one of the amino acid sequences set forth in SEQ ID NOs: 2-5 and 14 or a fragment or variant thereof.

A Tlc mutein of the disclosure may include with respect to the amino acid sequence of mature human tear lipocalin at least 6, 7, 8, 9, 10, 11, 12, 13, 14 or 15 amino acid substitutions selected from the group consisting of Arg 26→Phe; Glu 27→Trp; Pro 29→Ser; Glu 30→Gly; Met 31→Ile; Asn 32→His; Leu 33→Glu; Leu 56→Asp; Arg 60→Phe; Glu 104→Asp and His 106→Pro and may further include at least one amino acid substitution selected from the group consisting of Phe 28→Cys; Cys 61→Leu; Cys 101→Ser; Leu 105→Cys; Arg 111→Pro; Lys 114→Trp; and Cys 153→Ser.

In one specific embodiment, such Tlc mutein includes the following amino acid substitutions: Arg 26→Phe; Glu 27→Trp; Pro 29→Ser; Glu 30→Gly; Met 31→Ile; Asn 32→His; Leu 33→Glu; Leu 56→Asp; Ser 58→Glu; Arg 60→Phe; Val 64-Phe; Glu 104→Asp; His 106→Pro and Lys 108→Thr.

A Tlc mutein according to the present disclosure can be obtained by means of mutagenesis of a naturally occurring form of human tear lipocalin.

In one embodiment of the disclosure, the method for the generation of a mutein of human tear lipocalin includes mutating at least 2, 3, 4, 5, 6, 8, 10, 12, 14, 15, 16, 17, 18, 19, 20 or 21, sometimes even more, of the codons of any of the amino acid sequence positions 26, 27, 28, 29, 30, 31, 32, 33, 34, 55, 56, 57, 58, 60, 61, 64, 101, 104, 105, 106, 107, 108, 111, 114 and 153 of the linear polypeptide sequence of the mature human tear lipocalin. In one embodiment all 25 of the codons of amino acid sequence positions 26, 27, 28, 29, 30, 31, 32, 33, 34, 55, 56, 57, 58, 60, 61, 64, 101, 104, 105, 106, 107, 108, 111, 114 and 153 of the linear polypeptide sequence of the mature human tear lipocalin can be mutated.

In a further embodiment, the methods according to the disclosure include the mutation of both of the codons encoding cysteine at positions 61 and 153 in the linear polypeptide sequence of mature human tear lipocalin. In one embodiment position 61 is mutated to encode an alanine, phenylalanine, lysine, arginine, threonine, asparagine, tyrosine, methionine, serine, proline or a tryptophan residue, to name only a few possibilities. In embodiments where position 153 is mutated, an amino acid such as a serine or alanine can be introduced at position 153.

In another embodiment of the disclosure, the codons encoding amino acid sequence positions 111 and/or 114 of the linear polypeptide sequence of mature human tear lipocalin are mutated to encode for example a proline at position 111 and a tryptophan at position 114.

Another embodiment of the methods as described herein involves mutagenesis of the codon encoding the cysteine at position 101 of the linear polypeptide sequence of mature human tear lipocalin so that this codon encodes any other amino acid. In one embodiment the mutated codon encoding position 101 encodes a serine. Accordingly, in some embodiments either two or all three of the cysteine codons at position 61, 101 and 153 are replaced by a codon of another amino acid.

In further particular embodiments, a Tlc mutein of the disclosure has an amino acid sequence as set forth in any one of SEQ ID NOs: 2-5 and 14 or of a fragment or variant thereof.

In further particular embodiments, a Tlc mutein of the disclosure has at least 75%, at least 80%, at least 85% or higher identity to an amino acid sequence selected from the group consisting of SEQ ID NOs: 2-5 and 14.

In some embodiments a substitution (or replacement) is a conservative substitution. Nevertheless, any substitution—including non-conservative substitution or one or more from the exemplary substitutions below—is envisaged as long as the lipocalin mutein retains its capability to bind to IL-17A, and/or it has an identity to the then substituted sequence in that it is at least 60%, such as at least 65%, at least 70%, at least 75%, at least 80%, at least 85% or higher identity to the amino acid sequence of the mature human tear lipocalin.

2. Applications of Lipocalin Muteins with Binding-Affinity for Interleukin-17A (IL-17A)

IL-17A is a pro-inflammatory cytokine produced by a subset of memory T cells (called Th17) that has been implicated in the pathogenesis of many disorders, e.g. multiple sclerosis (MS) (Hellings, P. W. et al., Am. J. Resp. Cell Mol. Biol. 28 (2003) 42-50; Matusevicius, D. et al., Multiple Sclerosis 5 (1999) 101-104), rheumatoid arthritis (RA) (Ziolkovvska, M. et al., J. Immunol. 164 (2000) 2832-38; Kotake, S. et al., J. Clin. Invest. 103 (1999) 1345-52; Hellings, P. W. et al., Am. J. Resp. Cell Mol. Biol. 28 (2003) 42-50). IL-17A plays a role in the induction of other inflammatory cytokines, chemokines and adhesion molecules (Komiyama, Y. et al., J. Immunol. 177 (2006) 566-573), psoriasis, Crohn's disease, chronic obstructive pulmonary disease (COPD), asthma, and transplant rejection.

IL-17A is involved in the induction of proinflammatory responses and induces or mediates expression of a variety of other cytokines, factors, and mediators including tissue necrosis factor-alpha (TNF-α), IL-6, IL-8, IL-1β, granulocyte colony-stimulating factor (G-CSF), prostaglandin E2 (PGE2), IL-10, IL-12, IL-IR antagonist, leukemia inhibitory factor, and stromelysin (Yao et al., J. Immunol, 155(12): 5483-5486 (1995); Fossiez et al., J. Exp. Med., 183(6): 2593-2603 (1996); Jovanovic et al., J. Immunol, 160: 3513-3521 (1998); Teunissen et al., J. Investig. Dermatol, 111: 645-649 (1998); Chabaud et al., J. Immunol, 161: 409-414 (1998)). IL-17A also induces nitric oxide in chondrocytes and in human osteoarthritis explants (Shalom-Barak et al., J. Biol Chem., 273: 27467-27473 (1998); Attur et al., Arthritis Rheum., 40: 1050-1053 (1997)). Through its role in T cell mediated autoimmunity, IL-17A induces the release of cytokines, chemokines, and growth factors (as noted above), is an important local orchestrator of neutrophil accumulation, and plays a role in cartilage and bone destruction. There is growing evidence that targeting IL-17A signaling might prove useful in a variety of autoimmune diseases including rheumatoid arthritis (RA), psoriasis, Crohn's disease, multiple sclerosis (MS), psoriatric disease, asthma, and lupus (SLE) (see, e.g., Aggarwal et al., J. Leukoc. Biol, 71(1): 1-8 (2002); Lubberts et al., "Treatment with a neutralizing anti-murine interleukin-17 antibody after the onset of collagen-induced arthritis reduces joint inflammation, cartilage destruction, and bone erosion," Arthritis Rheum., 50: 650-659 (2004)).

In addition, it is known in the art that inflammatory and immunoregulatory processes are implicated in the pathogenesis of various forms of cardiovascular disease (Biasucci, L., et al., Circulation 1999, 99:855-860; Albert, C, et al, Circulation 2002, 105:2595-9; Buffon, A., et al, NEJM 2002, 347:55-7; Nakajima, T., et al., Circulation 2002, 105:570-5). Recent studies have established a basis for treating cardiovascular disease by reducing inflammatory and immunoregulatory responses of the disease (Blankenberg, S., et al., Circulation 2002, 106:24-30; Mallat, Z., et al, Circulation 2001, 104:1598-603; Mallat, Z., et al, Circ Res. 2001, 89:E41-5). Cardiovascular disease encompasses a number of disorders that affect the muscle and/or blood vessels of the heart, peripheral blood vessels, muscles and various organs.

Numerous possible applications for the Tlc muteins of the disclosure, therefore, exist in medicine. In one further aspect, the disclosure relates to the use of a Tlc mutein disclosed for detecting IL-17A (including IL-17 A/A and IL-17 A/F) in a sample as well as a respective method of diagnosis.

The present disclosure also involves the use of one or more Tlc muteins as described for complex formation with IL-17A.

Therefore, in another aspect of the disclosure, the disclosed muteins are used for the detection of IL-17A. Such use may include the steps of contacting one or more said muteins, under suitable conditions, with a sample suspected of containing IL-17A, thereby allowing formation of a complex between the muteins and IL-17A, and detecting the complex by a suitable signal.

The detectable signal can be caused by a label, as explained above, or by a change of physical properties due to the binding, i.e. the complex formation, itself. One example is plasmon surface resonance, the value of which is changed during binding of binding partners from which one is immobilized on a surface such as a gold foil.

The muteins disclosed herein may also be used for the separation of IL-17A. Such use may include the steps of contacting one or more said muteins, under suitable conditions, with a sample supposed to contain IL-17A, thereby allowing formation of a complex between the muteins and IL-17A, and separating the complex from the sample.

In the use of the disclosed muteins for the detection of IL-17A as well as the separation of IL-17A, the muteins and/or IL-17A or a domain or fragment thereof may be immobilized on a suitable solid phase.

In still another aspect, the present disclosure features a diagnostic or analytical kit comprising a Tlc mutein according to the disclosure.

In addition to their use in diagnostics, in yet another aspect, the disclosure encompasses the use of a mutein of the disclosure or a composition comprising such mutein for the binding of IL-17A in a subject and/or inhibiting the binding of IL-17A to its receptor in a subject.

In still another aspect, the present disclosure features a method of binding IL-17A in a subject, comprising administering to said subject an effective amount of one or more lipocalin muteins of the disclosure or of one or more compositions comprising such muteins.

In still another aspect, the present disclosure involves a method for inhibiting the binding of IL-17A to its receptor in a subject, comprising administering to said subject an effective amount of one or more lipocalin muteins of the disclosure or of one or more compositions comprising such muteins.

In the context of the present disclosure, the disclosed lipocalin muteins with binding-affinity for IL-17A can bind to IL-17A that exists as a homodimer, but such muteins can also bind to IL-17A that exists as a heterodimer complexed with the homolog IL-17F to form heterodimeric IL-17 A/F. In one preferred embodiment, one lipocalin mutein of the disclosure may bind with a detectable affinity to IL-17A in complex with IL-17F.

B. Lipocalin Muteins with Binding-Affinity for Interleukin-23p19 (IL-23p19).

In addition, the present disclosure fulfills the need for alternative inhibitors of IL-23p19 by providing human lipocalin muteins that bind human IL-23p19 and useful applications therefor. Accordingly, the disclosure also provides methods of making and using the IL-23p19 binding proteins described herein as well as compositions that may be used in methods of detecting IL-23p19 in a sample or in methods of binding of IL-23p19 in a subject. No such human lipocalin muteins having these features attendant to the uses provided by present disclosure have been previously described.

One embodiment of the current disclosure relates to a lipocalin mutein that is capable of binding Interleukin-23p19 (IL-23p19), with an affinity measured by a KD of about 140 nM or lower. More preferably, the lipocalins can have an affinity measured by a KD of about 12 nM or 1 nM or lower, i.e., in the picomolar range. In another embodiment, the lipocalin mutein is capable of binding to human IL-23p19 in a competition assay preferably with an EC50 value of about 120 nM, 25 nM, 10 nM, 2 nM or lower.

Another embodiment of the current disclosure provides a lipocalin mutein that is capable of blocking IL-23 binding to its receptor. In some further embodiments, the lipocalin muetin has an IC50 value at least as good as or superior to the IC50 value of ustekinumab, when said lipocalin mutein and ustekinumab are measured in an assay essentially as described in Example 13. In some still further embodiments, the lipocalin mutein has an IC50 value of 1 nM or less in the assay (e.g. FIG. 13) when at the same time ustekinumab has an IC50 value of 3.5 nM or less in the assay.

As noted above, a lipocalin is a polypeptide defined by its supersecondary structure, namely cylindrical β-pleated sheet supersecondary structural region comprising eight β-strands connected pair-wise by four loops at one end to define thereby a binding pocket. The present disclosure is not limited to lipocalin muteins specifically disclosed herein. In this regard, the disclosure relates to a lipocalin mutein having a cylindrical β-pleated sheet supersecondary structural region comprising eight β-strands connected pair-wise by four loops at one end to define thereby a binding pocket, wherein at least one amino acid of each of at least three of said four loops has been mutated and wherein said lipocalin is effective to bind IL-23p19 with detectable affinity.

In some embodiments, a lipocalin mutein binding IL-23p19 with detectable affinity may include at least one amino acid substitution of a native cysteine residue by another amino acid, for example, a serine residue. In some other embodiments, a lipocalin mutein binding IL-23p19 with detectable affinity may include one or more non-native cysteine residues substituting one or more amino acids of a wild type lipocalin. In a further particular embodiment, a lipocalin mutein according to the disclosure includes at least two amino acid substitutions of a native amino acid by a cysteine residue, hereby to form one or more cysteine briges. In some embodiments, said cysteine bridge may connect at least two loop regions. The definition of these regions is used herein in accordance with Flower (Flower, 1996, supra, Flower, et al., 2000, supra) and Breustedt et al. (2005, supra). In a related embodiment, the disclosure teaches one or more lipocalin muteins that are capable of inhibiting the binding of IL-23 to its receptor. In a related embodiment, the disclosure teaches one or more lipocalin muteins that are capable of inhibiting the binding of IL-23 to its receptor.

A protein of the disclosure can be a mutein of a lipocalin, preferably a lipocalin selected from the group consisting of retinol-binding protein (RBP), bilin-binding protein (BBP), apolipoprotein D (APO D), neutrophil gelatinase associated lipocalin (NGAL), tear lipocalin (TLPC), $\alpha_2$-microglobulin-related protein (A2m), 24p3/uterocalin (24p3), von Ebners gland protein 1 (VEGP 1), von Ebners gland protein 2 (VEGP 2), and Major allergen Can f1 precursor (ALL-1), with NGAL being a preferred lipocalin. As used herein, a "lipocalin" is defined as monomeric protein of approximately 18-20 kDA in weight, having a cylindrical β-pleated sheet supersecondary structural region comprising a plurality of (preferably eight) β-strands connected pair-wise by a plurality of (preferably four) loops at one end to define thereby a binding pocket. It is the diversity of the loops in the otherwise rigid lipocalin scaffold that gives rise to a variety of different binding modes among the lipocalin family members, each capable of accommodating targets of different size, shape, and chemical character (reviewed, e.g., in Flower, D. R. (1996), supra; Flower, D. R. et al. (2000), supra, or Skerra, A. (2000) *Biochim. Biophys. Acta* 1482, 337-350). Indeed, the lipocalin family of proteins have naturally evolved to bind a wide spectrum of ligands, sharing unusually low levels of overall sequence conservation (often with sequence identities of less than 20%) yet retaining a highly conserved overall folding pattern. The correspondence between positions in various lipocalins is well known to one of skill in the art. See, for example, U.S. Pat. No. 7,250,297.

In one preferred embodiment, a protein of the disclosure is a mutein of human tear lipocalin (TLPC or Tlc), also termed lipocalin-1, tear pre-albumin or von Ebner gland protein. The term "human tear lipocalin" or "Tlc" or "lipocalin-1" as used herein refers to the mature human tear lipocalin with the SWISS-PROT/UniProt Data Bank Accession Number P31025 (Isoform 1). The amino acid sequence shown in SWISS-PROT/UniProt Data Bank Accession Number P31025 may be used as a preferred "reference sequence".

In yet another preferred embodiment, a protein of the disclosure is a mutein of Lipocalin 2 (Lcn 2; also known as human neutrophil gelatinase-associated lipocalin, hNGAL, or as siderocalin). The term "human neutrophil gelatinase-associated lipocalin" or "hNGAL" or "lipocalin 2" or "Lcn2" as used herein refers to the mature hNGAL with the SWISS-PROT/UniProt Data Bank Accession Number P80188 (Isoform 1). The amino acid sequence shown in SWISS-PROT/UniProt Data Bank Accession Number P80188 may be used as a preferred "reference sequence".

1. Exemplary Lipocalin Muteins with Binding-Affinity for Interleukin-23p19 (IL-23p19)

In one aspect, the present disclosure relates to novel, specific-binding human tear lipocalin muteins directed against or specific for Interleukin-23 (IL-23p19). Human tear lipocalin muteins disclosed herein may be used for therapeutic and/or diagnostic purposes. A human tear lipocalin mutein of the disclosure may also be designated herein as "a Tlc mutein". As used herein, a Tlc mutein of the disclosure "specifically binds" a target (here, IL-23p19) if it is able to discriminate between that target and one or more reference targets, since binding specificity is not an absolute, but a relative property. "Specific binding" can be determined, for example, in accordance with Western blots, ELISA-, RIA-, ECL-, IRMA-tests, FACS, IHC and peptide scans.

In some embodiments, a Tlc mutein binds IL-23p19 with a $K_D$ of 50 nM or less, 25 nM or less, 10 nM or less.

In this regard, the disclosure provides one or more Tlc muteins that are capable of binding Interleukin-23p19 (IL-23p19) with an affinity measured by a KD of about 25 nM or lower. More preferably, the Tlc muteins can have an affinity measured by a KD of about 10 nM or lower.

In some embodiments, a Tlc mutein of the disclosure includes at least two amino acid substitutions, which are located at one or more sequence positions of the positions 26-34, 55-58, 60-61, 64, 101, 104-108, 111, 114 and 153 of the linear polypeptide sequence of the mature human tear lipocalin.

In further particular embodiments, the Tlc muteins of the disclosure may further comprise a mutated amino acid residue at one or more positions corresponding to position 26-34, 55-58, 60-61, 64, 104-108 of the linear polypeptide sequence of the mature human tear lipocalin (SWISS-PROT Data Bank Accession Number P31025).

In further particular embodiments, the Tlc muteins of the disclosure may further include a mutated amino acid residue at one or more positions corresponding to positions 101, 111, 114 and 153 of the linear polypeptide sequence of the mature human tear lipocalin.

In particular embodiments, the Tlc muteins of the disclosure comprise at least 1, 2, 3, 4, 5, 6, 7, 8, 9, 10, 11, 12, 13, 14, 15, 16, 17, 18, 19, 20 or 21, sometimes even more, mutated amino acid residues at one or more sequence positions corresponding to sequence positions 26, 27, 28, 29, 30, 31, 32, 33, 34, 56, 58, 60, 61, 64, 101, 104, 105, 106, 108, 111, 114 and 153 of the linear polypeptide sequence of the mature human tear lipocalin.

Similarly, the disclosure relates to a polypeptide comprising tear lipocalin shown in SEQ ID NO: 1, wherein said tear lipocalin comprises at least 2, 3, 4, 5, 6, 7, 8, 9, 10, 11, 12, 13, 14, 15, 16, 17, 18, 19, 20 or 21, sometimes even more, mutated amino acid residues at the sequence positions 26, 27, 28, 29, 30, 31, 32, 33, 34, 56, 58, 60, 61, 64, 101, 104, 105, 106, 108, 111, 114 and/or 153. Said polypeptide is preferably a lipocalin mutein.

In further particular embodiments, a Tlc mutein according to the current disclosure comprises an amino acid sequence selected from the group consisting of SEQ ID NOs: 6, 12, 13 and 15. In another embodiment, the mutein has at least 70% identity or at least 70% sequence homology to the sequence of a wild-type human lipocalin, including the human tear lipocalin. Preferably, said mutein comprises at least 2, 3, 4, 5, 6, 7, 8, 9, 10, 11, 12, 13, 14, 15, 16, 17, 18, 19, 20 or 21, sometimes even more, mutated amino acid residues at the sequence positions 26, 27, 28, 29, 30, 31, 32, 33, 34, 55, 56, 57, 58, 60, 61, 64, 101, 104, 105, 106, 107, 108, 111, 114 and/or 153 of the linear polypeptide sequence of tear lipocalin (SEQ ID NO: 1).

In another embodiment, the current disclosure relates to a nucleic acid molecule comprising a nucleotide sequence encoding a Tlc mutein disclosed herein.

In yet another embodiment, the disclosure encompasses a host cell containing said nucleic acid molecule.

The amino acid sequence of a Tlc mutein disclosed herein has a high sequence identity to mature human tear lipocalin (SWISS-PROT Data Bank Accession Number P31025) when compared to sequence identities with other lipocalins. In this general context, the amino acid sequence of a Tlc mutein of the disclosure is at least substantially similar to the amino acid sequence of mature human tear lipocalin, with the proviso that possibly there are gaps (as defined below) in an alignment that are the result of additions or deletions of amino acids. A respective sequence of a mutein of the disclosure, being substantially similar to the sequences of mature human tear lipocalin, has, in some embodiments, at least 70% identity or sequence homology, at least 75% identity or sequence homology, at least 80% identity or sequence homology, at least 82% identity or sequence homology, at least 85% identity or sequence homology, at least 87% identity or sequence homology, or at least 90% identity or sequence homology including at least 95% identity or sequence homology, to the sequence of mature human tear lipocalin, with the proviso that the altered position or sequence is retained and that one or more gaps are possible.

As three illustrative examples, the mutein of the SEQ ID NO: 6 has an amino acid sequence identity or a sequence homology of approximately 84.8% with the amino acid sequence of mature human tear lipocalin; the mutein of the SEQ ID NO: 12 has an amino acid sequence identity or a sequence homology of approximately 83.54% with the amino acid sequence of mature human tear lipocalin; and the mutein of the SEQ ID NO: 13 has an amino acid sequence identity or a sequence homology of approximately 84.18% with the amino acid sequence of mature human tear lipocalin.

In some embodiments, a Tlc mutein according to the disclosure includes an amino acid substitution of a native cysteine residue at positions 61 and/or 153 by a serine residue. In this context it is noted that it has been found that removal of the structural disulfide bond (on the level of a respective naïve nucleic acid library) of wild type tear lipocalin that is formed by the cysteine residues 61 and 153 (cf. Breustedt, et al., 2005, supra) provides tear lipocalin muteins that are not only stably folded but in addition are also able to bind a given non-natural ligand with high affinity. Without wishing to be bound by theory, it is also believed that the elimination of the structural disulde bond provides the further advantage of allowing for the (spontaneous) generation or deliberate introduction of non-natural artificial disulfide bonds into muteins of the disclosure, thereby increasing the stability of the muteins. For example, in some embodiments, a Tlc mutein according to the disclosure includes an amino acid substitution of a native cysteine residue at position 101 by a serine residue. Further, in some embodiments, a mutein according to the disclosure includes an amino acid substitution of a native arginine residue at positions 111 by a proline residue. In some embodiments a mutein according to the disclosure includes an amino acid substitution of a native lysine residue at positions 114 by a tryptophan residue.

A Tlc mutein according to the disclosure may further include, with respect to the amino acid sequence of the mature human tear lipocalin (SWISS-PROT Data Bank Accession Number P31025), one or more, including at least two, at least three, at least four, at least five, at least six, at least seven, at least eight, at least nine, at least ten, at least eleven, at least twelve, at least thirteen or at least fourteen amino acid substitutions of native amino acid residues by cysteine residues at any of positions 26-34, 55-58, 60-61, 64, 101, 104-106, 108, 111, 114 and 153 of the mature human tear lipocalin.

In some embodiments, a mutein according to the disclosure includes an amino acid substitution of a native amino acid by a cysteine residue at positions 28 or 105 with respect to the amino acid sequence of mature human tear lipocalin. In some embodiments a mutein according to the disclosure includes an amino acid substitution of a native amino acid by a cysteine residue at positions 28 or 105 with respect to the amino acid sequence of mature human tear lipocalin.

In some embodiments, a Tlc mutein according to the disclosure includes a substituted amino acid of at least one or of both of the cysteine residues occurring at each of the sequences positions 61 and 153 by another amino acid and the mutation of at least three amino acid residue at any one of the sequence positions 26-34, 55-58, 60-61, 64, 101, 104-108, 111, 114 and 153 of the linear polypeptide sequence of the mature human tear lipocalin (SWISS-PROT Data Bank Accession Number P31025). The positions 26-34 are included in the AB loop, the position 55 is located at the very end of a beta-sheet and following positions 56-58 as well as 60-61 and 64 are included in the CD loop. The positions 104-108 are included in the GH loop in the binding site at the open end of the β-barrel structure of the mature human tear lipocalin. The definition of these regions is used herein in accordance with Flower (Flower, 1996, supra, Flower, et al., 2000, supra) and Breustedt et al. (2005, supra). In some embodiments, the Tlc mutein according to the disclosure includes the amino acid substitutions Cys 61→Ala, Phe, Lys, Arg, Thr, Asn, Gly, Gln, Asp, Asn, Leu, Tyr, Met, Ser, Pro or Trp and Cys 153→Ser or Ala. Such a substitution has proven useful to prevent the formation of the naturally occurring disulphide bridge linking Cys 61 and Cys 153, and thus to facilitate handling of the mutein. However, tear lipocalin muteins that binds IL-23p19 and that have the disulphide bridge formed between Cys 61 and Cys 153 are also part of the present disclosure.

In some embodiments, the Tlc mutein according to the disclosure includes at least one amino acid substitution, which may be an additional amino acid substitution, selected from Arg 111→Pro and Lys 114→Trp. A Tlc mutein of the disclosure may further include the cysteine at position 101 of the sequence of the mature human tear lipocalin substituted by another amino acid. This substitution may, for example, be the mutation Cys 101→Ser or Cys 101→Thr.

As defined above, a Tlc mutein of the disclosure includes at least two amino acid substitutions, which are located at one or more sequence positions of the positions 26-34, 55-58, 60-61, 64, 101, 104-108, 111, 114 and 153 of the linear polypeptide sequence of the mature human tear lipocalin. In some embodiments, a mutein of the disclosure includes two or more, such as 3, 4, 5, 6, 7, 8, 9, 10, 11, 12, 13, 14, 16, 18, 19, 20 or 21 amino acid substitutions of these sequence positions of the mature human tear lipocalin. In one embodiment, the Tlc mutein has a mutated amino acid residue at each of the sequence positions 26-34, 55-58, 60-61, 64, 101, 104-108, 111, 114 and 153 of the linear polypeptide sequence of the mature human tear lipocalin.

In some embodiments, the mutated amino acid residues at any one or more of the sequence positions 26-34, 55-58, 60-61, 64, 101, 104-108, 111, 114 and 153 of the linear polypeptide sequence of the mature human tear lipocalin include one or more of the following substitutions: Arg 26→Asp, Thr, Ser, Gly, Phe, Tyr, Val or Trp, Pro 29→Arg, Ala, Ser, Glu, Leu or Thr, Asn 32→Tyr, Trp, Gln, His, Leu, Ser, Phe or Asp, Glu 34→Gly, Asn, Pro, Trp, Arg or His, Leu 56→Pro, Ser, Phe, Tyr, Arg, Asn, Ala, Val, Asp, Gln, Glu or Thr, Ser 58→Asp, Trp, Phe, Ala, Glu, His, Arg, Pro or Gly, Cys 61→Arg, Ser, Gly, Ala, Trp, Lys, Tyr, Asp, Thr, Val, Ile, Thr, Phe, Asn, Leu, Gln or Glu, Glu 104→Trp, Thr, Ser, His, Ile, Arg or Ala and His 106→Ala, Tyr, Phe, His, Thr or Glu. In some embodiments, a Tlc mutein of the disclosure includes two or more, such as 3, 4, 5, 6, 7, 8 or all amino acid substitutions of these sequence positions of the mature human tear lipocalin.

In some embodiments, a Tlc mutein according to the disclosure includes at least one of the following substitutions: Glu 27→Thr, Asn, Asp, Trp, Arg, Val, Phe or Gln, Glu 30→Gly, Lys, Phe, His, Trp or Asn, Met 31→Ala, His, Leu, Val, Trp, Gly, Pro or Asp, Leu 33→Gln, Asp, Gly, Val, Glu, Ile or Phe, Met 55→Gln, Asn, Ile, Thr, Ser or Leu, Ile 57→Leu, Trp or Ser, Arg 60→Tyr, Asp, Thr, Phe, Ile, Ser or Leu, Gly 107→Leu or Asp and Lys 108→Arg, Ser, His, Gln or Trp. In some embodiments, a Tlc mutein according to the disclosure includes two or more, such as 3, 4, 5, 6, 7 or all of the substitutions amino acid substitutions of these sequence positions of the mature human tear lipocalin.

In some embodiments, a Tlc mutein according to the disclosure includes one of the substitutions selected from the group consisting Val 64→Glu, Val 64→Leu, Val 64→Asp or Val 64→Ala.

Additionally, a Tlc mutein according to the disclosure may further include an amino acid substitution Arg 111→Pro. A Tlc mutein according to the disclosure may also include a substitution Lys 114→Trp. It may also comprise a substitution Cys 101→Ser or Cys 101→Thr. In some preferred embodiments, a Tlc mutein according to the disclosure may also comprise a substitution Cys 153→Ser.

In the residual region, i.e. the region differing from sequence positions 26-34, 55-58, 60-61, 64, 101, 104-106, 108, 111, 114 and 153, a Tlc mutein of the disclosure may include the wild type (natural) amino acid sequence outside the mutated amino acid sequence positions. In some embodiments a lipocalin mutein according to the disclosure may also carry one or more amino acid mutations at a sequence position/positions as long as such a mutation does, at least essentially not hamper or not interfere with the binding activity and the folding of the mutein. Such mutations can be accomplished very easily on DNA level using established standard methods. Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. On the other hand, it is also possible to introduce non-conservative alterations in the amino acid sequence. In addition, instead of replacing single amino acid residues, it is also possible to either insert or delete one or more continuous amino acids of the primary structure of the human tear lipocalin as long as these deletions or insertion result in a stable folded/functional mutein (for example, Tlc muteins with truncated N- and C-terminus). In such mutein, for instance, one or more amino acid residues are added or deleted at the N- or C-terminus of the polypeptide. Generally such a mutein may have about at least 70%, including at least about 80%, such as at least about 85% amino acid sequence identity, with the amino acid sequence of the mature human tear lipocalin. As an illustrative example, the first 4 N-terminal amino acid residues (His, His, Leu, Ala) and the last 2 C-terminal amino acid residues (Ser, Asp) can be deleted in a tear lipocalin mutein of the disclosure without affecting the biological function of the protein, e.g. SEQ ID NOs: 6, 12, 13 and 15.

Such modifications of the amino acid sequence include directed mutagenesis of single amino acid positions in order to simplify sub-cloning of the mutated lipocalin gene or its parts by incorporating cleavage sites for certain restriction enzymes. In addition, these mutations can also be incorporated to further improve the affinity of a Tlc mutein for IL-23p19. Furthermore, mutations can be introduced in order to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation. Exemplary possibilities of such a mutation to introduce a cysteine residue into the amino acid sequence of a Tlc mutein include the substitutions Thr 40→Cys, Glu 73→Cys, Arg 90→Cys, Asp 95→Cys, and Glu 131→Cys. The generated thiol moiety at the side of any of the amino acid positions 40, 73, 90, 95 and/or 131 may be used to PEGylate or HESylate the mutein, for example, in order to increase the serum half-life of a respective Tlc mutein.

The present disclosure also encompasses Tlc muteins as defined above, in which, e.g., the first four N-terminal amino acid residues of the sequence of mature human tear lipocalin (His-His-Leu-Leu; positions 1-4) and/or the last two C-terminal amino acid residues (Ser-Asp; positions 157-158) of the linear polypeptide sequence of the mature human tear lipocalin (SWISS-PROT Data Bank Accession Number P31025) have been deleted (SEQ ID NOs: 6, 12, 13 and 15). Another possible mutation of the wild type polypeptide sequence of the mature human tear lipocalin is to change the amino acid sequence at sequence positions 5 to 7 (Ala Ser Asp) to Gly Gly Asp as described in PCT application WO 2005/019256.

The Tlc muteins of the disclosure may include, consist essentially of or consist of any one of the amino acid sequences set forth in SEQ ID NOs: 6, 12, 13 and 15 or a fragment or variant thereof.

In some embodiments, the Tlc muteins binding IL-23p19 may include with respect to the amino acid sequence of mature human tear lipocalin at least 1, 2, 3, 4, 5, 6 or 7 amino acid substitutions selected from the group consisting of Arg 26→Trp; Glu 27→Gln; Pro 29→Thr; Glu 30→Trp; Met 31→Asp; Asn 32→Asp; Leu 33→Asp; Glu 32→Pro; Leu 56→Pro; Ser 58→Phe; Arg 60→Leu; Val 64→Glu; Glu 104→Ala; His 106→Tyr and Lys 108→Gln. In some embodiments, the Tlc muteins include all of these amino acid substitutions. In some embodiments, the Tlc muteins may further include at least one amino acid substitution selected from the group consisting of Phe 28→Cys; Cys 101→Ser; Leu 105→Cys; Arg 111→Pro; Lys 114→Trp; and Cys 153→Ser.

In some embodiments, the Tlc muteins binding IL-23p19 may include with respect to the amino acid sequence of mature human tear lipocalin at least 1, 2, 3, 4, 5, 6 or 7 amino acid substitutions selected from the group consisting of Arg 26→Trp; Glu 27→Val; Pro 29→Ala; Glu 30→Phe; Met 31→Ala; Asn 32→Asp; Leu 33→Glu; Glu 32→Pro; Met 55→Ile; Leu 56→Pro; Ile 57→Thr; Ser 58→Phe; Arg 60→Leu; Val 64→Glu; Glu 104→Arg; His 106→Trp and Lys 108→His or Arg. In some embodiments, the Tlc muteins include all of these amino acid substitutions. In some embodiments, the Tlc muteins may further include at least one amino acid substitution selected from the group consisting of Phe 28→Cys; Cys 101→Ser; Leu 105→Cys; Arg 111→Pro; Lys 114→Trp; and Cys 153→Ser.

In further particular embodiments, a Tlc mutein of the disclosure has an amino acid sequence as set forth in any one of SEQ ID NOs: 6, 12, 13 and 15 or of a fragment or variant thereof.

In further particular embodiments, a Tlc mutein of the disclosure has at least 75%, at least 80%, at least 85% or higher identity to an amino acid sequence selected from the group consisting of SEQ ID NOs: 6, 12, 13 and 15.

In some embodiments a substitution (or replacement) is a conservative substitution. Nevertheless, any substitution—including non-conservative substitution or one or more from the exemplary substitutions below—is envisaged as long as the lipocalin mutein retains its capability to bind to IL-23p19, and/or it has an identity to the then substituted sequence in that it is at least 60%, such as at least 65%, at least 70%, at least 75%, at least 80%, at least 85% or higher identity to the amino acid sequence of the mature human tear lipocalin.

In one aspect, the present disclosure relates to novel, specific-binding human lipocalin 2 (Lcn2 or NGAL) muteins directed against or specific for Interleukin-23p19 (IL-23p19). Human lipocalin 2 muteins disclosed herein may be used for therapeutic and/or diagnostic purposes. A human lipocalin 2 mutein of the disclosure may also be designated herein as "a NGAL mutein". As used herein, a Tlc mutein of the disclosure "specifically binds" a target (here, IL-23p19) if it is able to discriminate between that target and one or more reference targets, since binding specificity is not an absolute, but a relative property. "Specific binding" can be determined, for example, in accordance with Western blots, ELISA-, RIA-, ECL-, IRMA-tests, FACS, IHC and peptide scans.

In some embodiments, a NGAL mutein binds IL-23p19 with a $K_D$ of 200 nM or less, 140 nM or less, 20 nM or less, 2 nM or less.

In this regard, the disclosure provides one or more NGAL muteins that are capable of binding Interleukin-23p19 (IL-23p19) with an affinity measured by a KD of about 140 nM or lower. More preferably, the NGAL muteins can have an affinity measured by a KD of about 12 nM or lower.

In some embodiments, a NGAL mutein of the disclosure includes at one or more positions corresponding to position 28, 36, 40-41, 49, 52, 68, 70, 72-73, 75, 77, 79, 81, 87, 96, 100, 103, 106, 125, 127, 132 and 134 of the linear polypeptide sequence of SEQ ID NO: 8 a substitution.

In particular embodiments, a lipocalin mutein of the disclosure comprises at least 1, 2, 3, 4, 5, 6, 7, 8, 9, 10, 11 or 12, sometimes even more, substitution(s) at a sequence position corresponding to sequence position 28, 36, 40-41, 49, 52, 68, 70, 72-73, 75, 77, 79, 81, 87, 96, 100, 103, 106, 125, 127, 132 and 134 of the linear polypeptide sequence of the mature human NGAL (SWISS-PROT Data Bank Accession Number P80188, SEQ ID NO: 8). Preferably, it is envisaged that the disclosure relates to a lipocalin mutein which comprises, in addition to one or more substitutions at positions corresponding to positions 36, 87 and/or 96 of the linear polypeptide sequence of human NGAL (SEQ ID NO: 8), at one or more positions corresponding to positions 28, 40-41, 49, 52, 68, 70, 72-73, 77, 79, 81, 100, 103, 106, 125, 127, 132 and 134 of the linear polypeptide sequence of human NGAL (SEQ ID NO: 8) a substitution. More preferably, the latter one or more positions correspond to positions 28, 36, 40, 41, 49, 52, 68, 70, 72, 73, 77, 79, 81, 87, 96, 100, 103, 106, 125, 127, 132 and/or 134 of the linear polypeptide sequence of human NGAL (SEQ ID NO: 8). Said lipocalin muteins are preferably NGAL muteins which bind IL-23p19, in particular human IL-23p19.

Similarly, the disclosure relates to a polypeptide comprising SEQ ID NO: 8, wherein said polypeptide comprises at least 1, 2, 3, 4, 5, 6, 7, 8, 9, 10, 11 o 12 mutated amino acid residues at the sequence positions 28, 36, 40-41, 49, 52, 68, 70, 72-73, 75, 77, 79, 81, 87, 96, 100, 103, 106, 125, 127, 132 and 134. Said polypeptide is preferably a NGAL mutein which binds IL-23p19, in particular human IL-23p19.

In further particular embodiments, a lipocalin mutein according to the current disclosure comprises an amino acid sequence selected from the group consisting of SEQ ID NOs: 9-10. In another embodiment, the mutein has at least 70% identity to the sequence of a wild-type human lipocalin, including human Lipocalin 2 (Lcn 2 or NGAL). Preferably, said mutein comprises 1, 2, 3, 4, 5, 6, 7, 8, 9, 10, 11 or 12 mutated amino acid residues at the sequence positions 28, 36, 40-41, 49, 52, 68, 70, 72-73, 75, 77, 79, 81, 87, 96, 100, 103, 106, 125, 127, 132 and 134 of the linear polypeptide sequence of human NGAL (SEQ ID NO: 8).

Specifically, in order to determine whether a nucleotide residue or amino acid residue of the amino acid sequence of a lipocalin different from a NGAL lipocalin mutein of the disclosure corresponds to a certain position in the nucleotide sequence or the amino acid sequence of a NGAL lipocalin mutein as described, in particular any of SEQ ID NOs: 8-11 or that having one or more amino acid substitutions at position 28, 36, 40-41, 49, 52, 68, 70, 72-73, 75, 77, 79, 81, 87, 96, 100, 103, 106, 125, 127, 132 and 134 of the linear polypeptide sequence of SEQ ID NO: 8, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a lipocalin mutein of any of SEQ ID NOs: 8-11 or that having one or more amino acid substitutions at position 28, 36, 40-41, 49, 52, 68, 70, 72-73, 75, 77, 79, 81, 87, 96, 100, 103, 106, 125, 127, 132 and 134 of the linear polypeptide sequence of SEQ ID NO: 8 can serve as "subject sequence" or "reference sequence", while the amino acid sequence of a lipocalin different from any of the NGAL muteins described herein serves as "query sequence".

Given the above, a skilled artisan is thus readily in a position to determine which amino acid position mutated in Lcn2 as described herein corresponds to an amino acid of a scaffold other than Lcn2, preferably such as one of those described herein. Specifically, a skilled artisan can align the amino acid sequence of a mutein as described herein, in particular a NGAL mutein of the disclosure with the amino acid sequence of a different lipocalin to determine which amino acid(s) of said mutein correspond(s) to the respective amino acid(s) of the amino acid sequence of said different lipocalin. More specifically, a skilled artisan can thus determine which amino acid of the amino acid sequence of said different lipocalin corresponds to the amino acid at position (s) 28, 36, 40-41, 49, 52, 68, 70, 72-73, 75, 77, 79, 81, 87, 96, 100, 103, 106, 125, 127, 132 and 134 of the linear polypeptide sequence of SEQ ID NO: 8.

Proteins of the disclosure, which are directed against or specific for IL-23p19, include any number of specific-binding protein muteins that are based on a defined protein scaffold. Preferably, the number of nucleotides or amino acids, respectively, that is exchanged, deleted or inserted is 1, 2, 3, 4, 5, 6, 7, 8, 9, 10, 11, 12, 13, 14, 15, 16, 17, 18, 19, 20 or more such as 25, 30, 35, 40, 45 or 50, with 1, 2, 3, 4, 5, 6, 7, 8, 9, 10, or 11 being preferred and 9, 10 or 11 being even more preferred. However, it is preferred that a lipocalin mutein of the disclosure is still capable of binding IL-23p19, in particular human IL-23p19.

The amino acid sequence of a protein of the disclosure may have a high sequence identity to mature human Lipocalin 2 or other lipocalins. In this context, a protein of the disclosure may have at least 70%, at least 75%, at least 80%, at least 82%, at least 85%, at least 87%, at least 90% identity, including at least 95% identity to a protein selected from the group consisting of the sequence of SEQ ID NOs: 8-11.

The disclosure also includes structural homologues of the proteins selected from the group consisting of the sequence of SEQ ID NOs: 8-11, which have an amino acid sequence homology or sequence identity of more than about 60%, preferably more than 65%, more than 70%, more than 75%, more than 80%, more than 85%, more than 90%, more than 92% and most preferably more than 95% in relation thereto.

In yet another aspect, the present disclosure includes various lipocalin muteins, including muteins of human Lipocalin 2 that specifically bind IL-23p19. In this sense, IL-23p19 can be regarded a non-natural ligand of wild type human Lipocalin 2, where "non-natural ligand" refers to a compound that does not bind to wildtype lipocalins, including human Lipocalin 2 under physiological conditions. By engineering wildtype lipocalins such as human Lipocalin 2 with mutations at certain positions, the present inventors have demonstrated that high affinity and high specificity for a non-natural ligand is possible. In one aspect at least at 1, 2, 3, 4, 5, 6, 7, 8, 9, 10, 11 or 12 nucleotide triplet(s) encoding for any of the sequence positions 28, 36, 40-41, 49, 52, 68, 70, 72-73, 75, 77, 79, 81, 87, 96, 100, 103, 106, 125, 127, 132 and 134 of the linear polypeptide sequence of SEQ ID NO: 8, or other parallel sites on lipocalins, a random mutagenesis can be carried out by allowing substitution at this positions by a subset of nucleotide triplets.

Further, the lipocalins can be used to generate muteins that have a mutated amino acid residue at any one or more, including at least at any one, two, three, four, five, six, seven, eight, nine, ten, eleven or twelve, of the sequence positions of the sequence positions corresponding to the sequence positions 28, 36, 40-41, 49, 52, 68, 70, 72-73, 75, 77, 79, 81, 87, 96, 100, 103, 106, 125, 127, 132 and 134 of the linear polypeptide sequence of SEQ ID NO: 8.

In some embodiments, a NGAL mutein of the disclosure has at any one or more of the sequence positions 28, 36, 40-41, 49, 52, 68, 70, 72-73, 75, 77, 79, 81, 87, 96, 100, 103, 106, 125, 127, 132 and 134 of the linear polypeptide sequence of the mature human NGAL (SEQ ID NO: 8) one or more of the following mutated amino acid residues: Gln 28→His, Asp or Ala, Leu 36→Asp, Gln, Glu, Met or Ser, Lys 50→Asn, Asp, Leu, Pro or Arg, Tyr 52→Ser, Thr or Glu, Trp 79→Thr, Pro, Ser or Gln, Arg 81→Ala, Gly or Thr, Asn 96→Arg, Gly or His, Thr 104→Trp, Val, Glu, or Thr, Tyr 106→Phe, Lys 125→Leu, His, or Tyr, Ser 127→Glu, Tyr or Asp and Lys 134→Ala, Glu or Ser. In some embodiments, a NGAL mutein of the disclosure includes two or more, such as 3, 4, 5, 6, 7 or all mutated amino acid residues at these sequence positions of the mature human NGAL.

In some embodiments, a NGAL mutein according to the disclosure includes at least one of the following substitutions of these sequence positions of the mature human NGAL: Ala 40→Arg, Leu or Tyr, Ile 41→Met or Leu, Gln 49→Met, Thr, Arg or Asp, Met 51→Val or Ile, Ser 68→Trp, Arg or Thr, Leu 70→Ile, Glu or Asp, Phe 71→Ser or Leu, Arg 72→Ser, Pro, Ile or Asp, Lys 73→His, Phe, Met or Thr, Asp 77→Glu, Lys, Trp or Leu, Tyr 100→Gly or Met, Gly 102→Asp or Met, Leu 103→Lys, Met or Asp, Val 126→Ala and Tyr 132→Ser, Phe or His. In some embodiments, a NGAL mutein according to the disclosure includes two or more, such as 3, 4, 5, 6, 7 or all of the s amino acid substitutions of these sequence positions of the mature human NGAL.

Additionally, a NGAL mutein according to the disclosure may also comprise a substitution Cys 87→Ser or Cys 87→Thr.

Additionally, a NGAL mutein according to the disclosure may also comprise a substitution Cys 76→Ser, Tyr, Arg or Phe. In a further embodiment, the mutein may also comprise a substitution Cys 175→Lys, Arg, Ser, Trp or Ala.

Additionally, a NGAL mutein according to the disclosure may also comprise a substitution Lys 75→Thr or Arg.

In some embodiments, the NGAL mutein binding IL-23p19 includes at least one, including 2, 3, 4 or 5 of the following amino acid substitutions: Tyr 100→Met, Leu 103→Met, Tyr 106→Phe, Lys 125→Tyr, Ser 127→Tyr and Lys 134→Glu. In some embodiments, the NGAL mutein includes all of these amino acid substitutions.

In some embodiments, the NGAL mutein binding IL-23p19 includes with respect to the amino acid sequence of mature human NGAL at least 1, 2, 3 or 4 amino acid substitutions selected from the group consisting of Leu 36→Met, Ile 41→Met, Ser 68→Trp, Arg 72→Ile and Tyr 132→Phe.

Additionally, such a Tlc mutein further comprising one of the following sets of amino acid substitutions:
1. Ala 40→Leu, Arg 49→Thr, Lys 52→Ser, Leu 70→Asp, Lys 73→Phe, Asp 77→Lys, Trp 79→Gln, Arg 81→Gly, Asn 96→Gly; or
2. Ala 40→Thr, Arg 49→Asp, Lys 52→Glu, Leu 70→Asp, Lys 73→Met, Asp 77→Trp, Trp 79→Phe, Arg 81→Thr, Asn 96→His.

In one embodiment, a mutein of the disclosure, which binds to IL-23p19 includes the following amino acid replacements:
(a) Leu 36→Met, Ala 40→Leu, Ile 41→Met, Arg 49→Thr, Lys 52→Ser, Ser 68→Trp, Leu 70→Asp, Lys 73→Phe, Asp 77→Lys, Trp 79→Gln, Arg 81→Gly, Asn 96→Gly, Tyr 100→Met, Leu 103→Met, Tyr 106→Phe, Lys 125→Tyr, Ser 127→Tyr, Lys 134→Glu; or
(b) Ala 40→Thr, Arg 49→Asp, Lys 52→Glu, Leu 70→Asp, Arg 72-Ile, Lys 73→Met, Asp 77→Trp, Trp 79→Phe, Arg 81→Thr, Asn 96→His, Tyr 100→Met, Leu 103→Met, Tyr 106→Phe, Lys 125→Tyr, Ser 127→Tyr, Tyr 132→Phe, Lys 134→Glu.

In addition, the muteins referred to in (a) to (b) may have the amino acid substitutions in comparison to wild type human NGAL (Lcn2) which are apparent from the sequence alignment shown in FIG. 17. These substitutions may be at position 28, 36, 40, 41, 49, 52, 68, 70, 72, 73, 77, 79, 81, 87, 96, 100, 103, 106, 125, 127, 132 and/or 134. For example, when the wild type sequence has at position 100 a Tyrosine residue, then each of the muteins has a Methionine residue at the corresponding position. The disclosure also includes structural homologues of the proteins selected from the group consisting of the sequences shown in FIG. 17, which have an amino acid sequence homology or sequence identity of more than about 60%, preferably more than 65%, more than 70%, more than 75%, more than 80%, more than 85%, more than 90%, more than 92% and most preferably more than 95% in relation thereto.

In some embodiments a substitution (or replacement) is a conservative substitution. Nevertheless, any substitution—including non-conservative substitution or one or more from the exemplary substitutions below—is envisaged as long as the lipocalin mutein retains its capability to bind to IL-23p19, and/or it has an identity to the then substituted sequence in that it is at least 60%, such as at least 65%, at least 70%, at least 75%, at least 80%, at least 85% or higher identity to the amino acid sequence of the mature human lipocalin 2.

2. Applications of Lipocalin Muteins with Binding-Affinity for Interleukin-23p19 (IL-23p19)

Interleukin-23 (IL-23) is a heterodimeric cytokine composed of a unique subunit, p19 (herein referred to interchangeably as "IL-23p19"), and the p40 subunit, which is shared with interleukin-12 (IL-12) (Oppmann, Immunity 13:115 (2000)). IL-23 has been found to stimulate the production and/or maintenence of IL-17A and IL-17F from activated CD4 T cells in what has now been termed as a "new" T-helper (Th) subset, designated Th1 7. A review of IL-23 cytokine and receptor biology is reviewed in Holscher, Curr. Opin. Invest. Drugs 6:489 (2005) and Langrish et al. Immunol Rev. 202:96 (2004). Similar to Th1 and Th2 lineages, Th17 cells have most likely evolved to provide adaptive immunity to specific classes of pathogens, such as extracellular bacteria. However, inappropriate Th 17 responses have been strongly implicated in a growing list of autoimmune disorders, including multiple sclerosis, rheumatoid arthritis, inflammatory bowel disease, and psoriasis.

In this regard, IL-23 promotes a distinct CD4 T cell activation state characterized by the production of interleukin-17 (J. Biol. Chem. 278:1910-191 (2003); see also Langrish et al). IL-23 drives a pathogenic T cell population that induces autoimmune inflammation (J. Exp. Med. 201: 233-240 (2005); Starnes et al. "Cutting edge: IL-17F, a novel cytokine selectively expressed in activated T cells and monocytes, regulates angiogenesis and endothelial cell cytokine production" J. Immunol. 167:4137-4140 (2001)).

Numerous possible applications for the muteins with binding-affinity for IL-23p19 of the disclosure, therefore, exist in medicine. In one further aspect, the disclosure relates to the use of such a mutein disclosed for detecting IL-23p19 in a sample as well as a respective method of diagnosis.

The present disclosure also involves the use of one or more muteins with binding-affinity for IL-23p19 as described for complex formation with IL-23p19.

Therefore, in another aspect of the disclosure, the disclosed muteins are used for the detection of IL-23p19. Such use may include the steps of contacting one or more said muteins, under suitable conditions, with a sample suspected of containing IL-23p19, thereby allowing formation of a complex between the muteins and IL-23p19, and detecting the complex by a suitable signal.

The detectable signal can be caused by a label, as explained above, or by a change of physical properties due to the binding, i.e. the complex formation, itself. One example is plasmon surface resonance, the value of which is changed during binding of binding partners from which one is immobilized on a surface such as a gold foil.

The muteins disclosed herein may also be used for the separation of IL-23p19. Such use may include the steps of contacting one or more said muteins, under suitable conditions, with a sample supposed to contain IL-23p19, thereby allowing formation of a complex between the muteins and IL-23p19, and separating the complex from the sample.

In the use of the disclosed muteins for the detection of IL-23p19 as well as the separation of IL-23p19, the muteins and/or IL-23p19 or a domain or fragment thereof may be immobilized on a suitable solid phase.

Accordingly, the presence or absence of a molecule such as IL-23p19, e.g., in a sample, as well as its concentration or level may be determined.

In still another aspect, the present disclosure features a diagnostic or analytical kit comprising a mutein with binding-affinity for IL-23p19 according to the disclosure.

In addition to their use in diagnostics, in yet another aspect, the disclosure encompasses the use of such a mutein of the disclosure or a composition comprising such mutein for the binding of IL-23p19 in a subject and/or inhibiting the binding of IL-23 to its receptor in a subject.

In still another aspect, the present disclosure features a method of binding IL-23p19 in a subject, comprising administering to said subject an effective amount of one or more lipocalin muteins with binding-affinity for IL-23p19 of the disclosure or of one or more compositions comprising such a mutein.

In still another aspect, the present disclosure involves a method for inhibiting the binding of IL-23 to its receptor in a subject, comprising administering to said subject an effective amount of one or more lipocalin muteins with binding-affinity for IL-23p19 of the disclosure or of one or more compositions comprising such a mutein.

C. Compositions Comprising an IL-17A Binding Lipocalin Mutein and/or an IL-23p19 Binding Lipocalin Mutein and Uses of the Lipocalin Muteins IL-17A and IL-23 are cytokines involved in inflammation. Human interleukin-17A (also known as "IL-17", including IL-17 A/A and IL-17 A/F) is a cytokine which stimulates the expression of interleukin-6 (IL-6), intracellular adhesion molecule 1 (ICAM-I), interleukin-8 (IL-8), granulocyte macrophage colony-stimulating factor (GM-CSF), and prostaglandin E2 expression, and plays a role in the preferential maturation of CD34+ hematopoietic precursors into neutrophils (Yao et al, J. Immunol 755:5483 (1995); Fossiez et al, J. Exp. Med. 183:2593 (1996)). Human interleukin-23 (also known as "IL-23") is a cytokine which has been reported to promote the proliferation of T cells, in particular memory T cells.

Both IL-17A (including IL-17A in complex with IL-17F, also termed as IL-17 A/F) and IL-23 have been reported to play important roles in many autoimmune diseases, such as multiple sclerosis, rheumatoid arthritis, Crohn's disease, and psoriasis. Both IL-23 and IL-17A are overexpressed in the centralnervous system of humans with multiple sclerosis and in mice undergoing an animal model of multiple sclerosis, experimental autoimmune encephalomyelitis (EAE). The overexpression is observed in mice when the EAE is induced by either myelinoligodendrocyte glycoprotein (MOG) 35-55 peptide- or proteolipid peptide (PLP). Furthermore, neutralization of either IL-23p19 or IL-17A results in amelioration of EAE symptoms in mice (Park et al., Immunol 6:1133 (2005); Chen et al., J Clin Invest. 116:1317 (2006)).

It has also been demonstrated that IL-17A and Th17 cells can be produced from IL-23-independent sources, and the in vivo development of an IL-17 effector response has been shown to be IL-23-independent (Mangan et al., Nature 441:231 (2006)). Neutralization of IL-23 would theoretically eliminate existing IL-17A producing cells, but would not completely prevent the development of new Th17 cells.

The present disclosure, therefore, concerns the binding of both of these proinflammatory cytokines, IL-17A and IL-23p19, since binding both IL-23 (via p19) and IL-17A is more effective therapeutically than neutralization of IL-23p19 alone or IL-17A alone and thus, beneficial for the effective treatment of inflammatory diseases.

Although antibodies against IL-17A and/or IL-23p19 have been described, these antibody-based approaches still have a number of serious drawbacks such as the necessity of complex mammalian cell production systems, a dependency on disulfide bond stability, the tendency of some antibody fragments to aggregate, limited solubility and last but not least, they may elicit undesired immune responses even when humanized. There is an unmet need to, therefore, to develop small globular proteins such as lipocalins as scaffolds for the generation of a novel class of IL-17A or IL-23p19 binding proteins, e.g. lipocalin muteins with binding-affinity for IL-17A or IL-23p19.

Accordingly, it is an object of the present disclosure to provide human lipocalin muteins that bind IL-17A (including IL-17 A/A and IL-17 A/F) and/or IL-23p19 and can be used in pharmaceutical applications. The disclosure also provides one or more compositions comprising such lipocalin muteins and, optionally, one or more pharmaceutically or diagnostically acceptable excipients (e.g. adjuvants, diluents or carriers). Lipocalin muteins of the disclosure as well as compositions thereof may be used in methods of detecting IL-17A (including IL-17 A/A and IL-17 A/F) and/or IL-23p19 in a sample or in methods of binding of IL-17A (including IL-17 A/A and IL-17 A/F) and/or IL-23p19 in a subject.

As discussed above, binding IL-17A (including IL-17 A/A and IL-17 A/F) and IL-23p19 concomitantly with lipocalin muteins specific for IL-17A (including IL-17 A/A and IL-17 A/F) or IL-23p19, respectively, could overcome some of the hypoxia-mediated effects that binding IL-17A (including IL-17 A/A and IL-17 A/F) alone or binding IL-23p19 alone, respectively, might induce. The present disclosure, therefore, encompasses use of (i) a first lipocalin mutein specific for IL-17A and (ii) a second lipocalin mutein specific for IL-23p19, for the binding of IL-17A and IL-23p19 in a subject. Such use includes a step of administering to a subject an effective amount of (i) a first lipocalin mutein specific for IL-17A and (ii) a second lipocalin mutein specific for IL-23p19.

In the context of the present disclosure, the lipocalin mutein specific for IL-17A can binds to IL-17A that exists as a homodimer (i.e. IL-17 A/A), but it can also binds to IL-17A that exists as a heterodimer complexed with the homolog IL-17F to form heterodimeric IL-17 A/F. In one preferred embodiment, said lipocalin mutein binds to IL-17A and IL-17F complex.

The first lipocalin mutein and the second lipocalin mutein may be administered in combination, including concurrently, concomitantly or in series. In some embodiments, the first lipocalin mutein and the second lipocalin mutein may be included in a composition that may be administered. The composition may include an effective amount of the first and the second lipocalin mutein as active ingredients, in association with at least one pharmaceutically acceptable adjuvant, diluent or carrier. The first lipocalin mutein and the second lipocalin mutein may also be administered independent from each other, including at individual intervals at independent points of time.

In some embodiments, the present disclosure also relates to a composition comprising a first lipocalin mutein specific for IL-17A and (ii) a second lipocalin mutein specific for IL-23p19, which composition can be used in a method of binding of IL-17A and IL-23p19 e.g. in a subject. In addition, such composition may be used in a method of detecting IL-17A (including IL-17 A/A and IL-17 A/F) and IL-23p19 e.g. in a sample.

In some other embodiments, the present disclosure relates to a combination of a first lipocalin mutein and a second lipocalin mutein. One of these lipocalin muteins can bind to IL-17A as a given non-natural target with detectable affinity. The other lipocalin mutein can bind to IL-23p19 as a given non-natural target with detectable affinity. The respective lipocalin mutein thus binds to IL-17A or to IL-23p19, respectively, as a given non-natural target. The term "non-natural target" refers to a compound, which does not bind to the corresponding lipocalin under physiological conditions. For example, the first lipocalin mutein can bind to IL-17A and the second lipocalin mutein can bind to IL-23p19, or vice versa. The combination of the first lipocalin mutein and the second lipocalin mutein may be provided in various forms.

In some embodiments, the lipocalin mutein specific for IL-17A as used in the disclosure is able to bind IL-17A with detectable affinity, i.e. with a dissociation constant of at least 200 nM, including about 100 nM, about 50 nM, about 25 nM or about 15 nM. In some embodiments, the lipocalin mutein specific for IL-23p19 as used in the disclosure is able to bind IL-23p19 with detectable affinity, i.e. with a dissociation constant of at least 200 nM including about 100 nM, about 50 nM, about 25 nM or about 15 nM. In some further preferred embodiments, a lipocalin mutein of the combination according to the disclosure binds IL-17A or IL-23p19, respectively, with a dissociation constant for IL-17A or IL-23p19 of at least about 10 nM, about 1 nM, about 0.1 nM, about 10 pM, or even less. The present disclosure, thus, provides a combination of (i) a mutein of a lipocalin that has a particularly high affinity to IL-17A and (ii) a mutein of a lipocalin that has a particularly high affinity to IL-23p19.

In some embodiments, the lipocalin muteins with a detectable affinity for IL-17A are muteins of human tear lipocalin. These and further details on lipocalin muteins with a detectable affinity for IL-17A can be found in Section A of the current disclosure.

In a particularly preferred embodiment, a lipocalin mutein that is specific for IL-17A is shown in any one of SEQ ID NOs: 2-5.

In some embodiments, the lipocalin muteins with a detectable affinity for IL-23p19 are muteins of human tear lipocalin or muteins of human neutrophil gelatinase associated lipocalin. These and further details of lipocalin muteins with a detectable affinity for IL-23p19 have been disclosed in in Section B of the current disclosure.

In a particular preferred embodiment, the lipocalin mutein that is specific for IL-23p19 is shown in any one of SEQ ID NOs: 6, 9, 10, 12, 13 and 15.

In still another aspect, the present disclosure features a method of binding IL-17A and IL-23 in a subject comprising administering to said subject an effective amount of (i) a first lipocalin mutein specific for IL-17A and (ii) a second lipocalin mutein specific for IL-23p19.

In still another aspect, the present disclosure involves a method for inhibiting the binding of IL-17A and IL-23 to their respective receptor(s) in a subject comprising administering to said subject an effective amount of (i) a first lipocalin mutein specific for IL-17A and (ii) a second lipocalin mutein specific for IL-23p19.

The present disclosure also involves the use of (i) a first lipocalin mutein specific for IL-17A and (ii) a second lipocalin mutein specific for IL-23p19 for complex formation with IL-17A and IL-23p19.

Therefore, in another aspect of the disclosure, the disclosed muteins can be used for the detection of IL-17A and IL-23p19. Such use may include the steps of contacting two or more said muteins, under suitable conditions, with a sample suspected of containing IL-17A and IL-23p19, thereby allowing formation of a complex between the muteins and IL-17A or between the muteins and IL-23p19, respectively, and detecting the complex by a suitable signal.

The detectable signal can be caused by a label, as explained above, or by a change of physical properties due to the binding, i.e. the complex formation, itself. One example is plasmon surface resonance, the value of which is changed during binding of binding partners from which one is immobilized on a surface such as a gold foil.

The muteins disclosed herein may also be used for the separation of IL-17A and IL-23p19. Such use may include the steps of contacting one or more said muteins, under suitable conditions, with a sample supposed to contain IL-17A and IL-23p19, thereby allowing formation of a complex between the muteins and IL-17A or between the muteins and IL-23, respectively, and separating the complex from the sample.

In the use of the disclosed muteins for the detection of IL-17A and IL-23p19 as well as the separation of IL-17A and IL-23p19, the muteins and/or IL-17A and IL-23p19 or a domain or fragment thereof may be immobilized on a suitable solid phase.

Accordingly, the presence or absence of IL-17A and/or IL-23p19, e.g., in a sample, as well as their concentration or level may be determined.

In another aspect, the disclosure provides for a kit of parts. The kit includes a first and a second container. The first container includes the first lipocalin mutein and the second container includes the second lipocalin mutein. In one aspect, the disclosure relates to a kit that includes, in one or more containers, separately or in admixture, a lipocalin mutein specific for IL-17A. In yet another aspect, the disclosure also relates to a kit that includes, in one or more containers, separately or in admixture, a lipocalin mutein specific for IL-23p19. In some embodiments, the disclosure relates to a kit that includes, in one or more containers, separately or in admixture, a lipocalin mutein specific for IL-17A and a lipocalin mutein specific for IL-23p19. In some further preferred embodiments, the kid comprises a first container that includes a first lipocalin mutein specific for IL-17A and a second container that includes a second lipocalin mutein specific for IL-23p19. In some embodiments the kit further includes integrally thereto or as one or more separate documents, information pertaining to the contents or the kit and the use of the lipocalin muteins. The kit may include in some embodiments one or more compositions that are formulated for reconstitution in a diluent. Such a diluent, e.g. a sterile diluent, may also be included in the kit, for example within a container.

D. Fusion Proteins with Binding Affinity for IL-17A and/or IL-23p19 and Uses Thereof In one aspect, the present disclosure relates to a fusion protein comprising at least two subunits: one subunit has binding specificity for IL-17A and another subunit has binding specificity for IL-23p19.

For example, the present disclosure provides a fusion protein that has protein moieties with binding specificity for IL-17A (including IL-17 A/A and IL-17 A/F) and IL-23p19, respectively. In this regard, one subunit of said fusion protein may comprise a lipocalin mutein of the disclosure specific for IL-17A (including IL-17 A/A and IL-17 A/F) while another subunit of said fusion protein may comprise a lipocalin mutein of the disclosure specific for IL-23p19.

In another aspect, the present disclosure is pertinent to a fusion protein comprising at least two subunits, where each has a binding specificity for IL-17A (including IL-17 A/A and IL-17 A/F). In some embodiments, at least one subunit comprises a lipocalin mutein specific for IL-17A. In some embodiments, the fusion protein has a binding affinity for IL-17A by a KD of 10 nM or lower. In some further embodiments, each of the two subunits comprises a lipocalin mutein specific for IL-17 A/A. In some further embodiments, each of the two subunits comprises a lipocalin mutein specific for IL-17 A/F. The two lipocalin muteins may have a different amino acid sequence. Hence, in some embodiment, the two lipocalin muteins bind to a different epitope on IL-17A. In some other embodiments, however, the two lipocalin muteins may be identical to each other. For example, such a fusion protein may comprise two lipocalin muteins of SEQ ID NO: 5. In this regard, the fusion protein may have the amino acids shown in SEQ ID NO: 40.

In some embodiments, a fusion protein of the disclosure having two subunits that have binding specificity to IL-17A (including IL-17 A/A and IL-17 A/F) may exhibit a higher potency than a single subunit, due to an avidity effect of the two subunits, which is brought about by the dimeric nature of the target (e.g. IL17 A/A). In this regard, the fusion protein can be a bivalent fusion protein. In still another aspect, the present disclosure also encompasses a fusion protein comprising at least two subunits that have binding specificity for IL-23p19. In some embodiments, at least one subunit comprises a lipocalin mutein specific for IL-23p19. In some embodiments, the fusion protein has a binding affinity for IL-23p19 by a KD of 50 nM or lower. In some further embodiments, each of the two subunits comprises a lipocalin mutein specific for IL-23p19. The two lipocalin muteins may have a different amino acid sequence. Hence, in some embodiment, the two lipocalin muteins bind to a different epitope on IL-23p19. In some other embodiments, however, the two lipocalin muteins may be identical to each other.

In one further aspect, the present application discloses a fusion protein comprising (i) an antibody (for example, a full-length IgG) or antibody-derived protein that binds to IL23 and (ii) a lipocalin mutein specific for IL-17A.

In another aspect, the present application discloses a fusion protein comprising (i) an antibody (for example, a full-length IgG) or antibody-derived protein that binds to IL-17A and (ii) a lipocalin mutein specific for IL-23p19.

Exemplary lipocalin muteins specific for IL-17A (including IL-17 A/A and IL-17 A/F) include those disclosed in Section A of the current disclosure. In a particularly preferred embodiment, the lipocalin mutein is shown in any one of the SEQ ID NOs: 2-5 and 14.

In some further embodiments, an antibody that binds to IL-23 may be an antibody disclosed in WO 2008/103432. Such an antibody has the heavy chain and light chain as shown in SEQ ID NOs: 6 and 14 of WO 2008/103432, respectively. SEQ ID NO: 6 of WO 2008/103432 corresponds to SEQ ID NO: 51 of the present application and SEQ ID NO: 14 of WO 2008/103432 corresponds to SEQ ID NO: 52 of the present application.

Exemplary lipocalin muteins specific for IL-23p19 include those disclosed in Section B of the current disclosure. In a particularly preferred embodiment, the lipocalin mutein is shown in any one of the SEQ ID NOs: 6, 9, 10, 12, 13 and 15.

In some further embodiments, an antibody that binds to IL-17A (including IL-17 A/A and IL-17 A/F) may be benchmark antibody 1 (whose heavy chain and light chain are described in SEQ ID NOs: 19 and 20, respectively) or benchmark antibody 2 (whose heavy chain and light chain are described in SEQ ID NOs: 21 and 22, respectively).

In some particular embodiments, the lipocalin mutein can be linked, for example, via a peptide bond, to the C-terminus of the antibody heavy chain domain (VH), the N-terminus of the VH, the C-terminus of the antibody light chain (VL), and/or the N-terminus of the VL (see FIG. 23). In a particular embodiment, a fusion protein of the disclosure may comprise a lipocalin mutein attached to the C-terminus of each VH of an IgG antibody. For example, such an IgG antibody may be an IgG antibody disclosed in WO 2008/103432. Specifically, SEQ ID NOs: 6 and 14 of WO 2008/103432 show the heavy chain and light chain of such an IgG antibody, respectively. In this regard, one of such fusion proteins comprises the amino acids shown in SEQ ID NOs: 43 and 44.

There may be distinct advantages in choosing one construct over another (e.g., as between an antibody-lipocalin mutein fusion protein and a bivalent lipocalin mutein fusion protein), as will become apparent to the skilled person in the art through routine testing, for example, by comparing the IC50 values of different molecules (such as the IC50 values of the fusion protein of SEQ ID NO: 40 and the fusion protein comprises the amino acids shown in SEQ ID NOs: 43 and 44, as generated in Examples 23 and 24, respectively).

In a related embodiment, one or more fusion proteins of the disclosure are capable of inhibiting the binding of IL-17A and the binding of IL-23 to their respective receptor(s). In some further embodiments, one or more fusion proteins of the disclosure are capable of engaging IL-17A and IL-23p19 simultaneously, and, hence, thereby are capable of inhibiting the binding of IL-17A and the binding of IL-23 to their respective receptor(s) at the same time.

In this aspect, the present disclosure relates to a fusion polypeptide comprising at least two subunits in any order, including one subunit comprises a lipocalin mutein specific for IL-17A (including IL-17 A/A and IL-17 A/F) and one subunit comprises a lipocalin mutein specific for IL-23p19. In some further embodiments, the fusion polypeptide may contain an additional subunit, which subunit comprises a lipocalim mutein specific for IL-17A (including IL-17 A/A and IL-17 A/F) or IL-23p19. In some embodiments, two IL-17A-specific lipocalin muteins, as included in two different subunits of the fusion polypeptide, may bind to different epitopes on the IL-17A target; alternatively, the two IL-17A-specific lipocalin muteins, as included in two different subunits of the fusion polypeptide, may have the same amino acid sequence and, hence, have the specificity for the same epitope on the IL-17A target. A fusion polypeptide of the disclosure having two subunits binding to IL-17A may exhibit a stronger binding to IL-17A than a fusion polypeptide having only one subunit binding to IL-17A, due to an avidity effect brought about by the dimeric nature of the target. Likewise, two IL-23p19-specific lipocalin muteins, as included in two different subunits of the fusion polypeptide, may bind to different epitopes on the IL-23p19 target; alternatively, the two IL-23p19-specific lipocalin mutein, as included in two different subunits of the fusion polypeptide, may have the same amino acid sequence and, hence, the specificity for the same epitope on the IL-23p19 target. A fusion polypeptide may also include a linker that links one subunit to another subunit.

In some embodiments, one subunit of a fusion protein of the disclosure comprises a lipocalin mutein disclosed in Section A of the current disclosure. In a particularly preferred embodiment, the subunit comprises a lipocalin mutein shown in any one of the SEQ ID NOs: 2-5 and 14.

In some embodiments, one subunit of a fusion protein of the disclosure comprises a lipocalin mutein disclosed in in Section B of the current disclosure. In a particular preferred embodiment, the subunit comprises a lipocalin mutein shown in any one of the SEQ ID NOs: 6, 9, 10, 12, 13 and 15.

In a particular embodiment, one subunit of a fusion protein of the disclosure comprises the amino acids shown in SEQ ID NO: 5.

In a particular embodiment, one subunit a fusion protein of the disclosure comprises the amino acids shown in SEQ ID NO: 9 or SEQ ID NO: 15.

In a still preferred embodiment, a fusion protein of the disclosure comprises the amino acids shown in SEQ ID NO: 16, SEQ ID NO: 17, SEQ ID NO: 53, SEQ ID NO: 57 or SEQ ID NO: 55.

In another aspect, the present application discloses a fusion protein comprising at least two subunits, wherein one subunit has binding specificity for IL-17A or IL-23p19 and another subunit contains a bacterial albumin binding domain (ABD). In some embodiments, the subunit has binding specificity for IL-17A or IL-23p19 comprises a lipocalin mutein specific for IL-17A or IL-23p19 of the disclosure. Furthermore, the fusion protein may comprise in any order (i) one subunit specific for IL-17A, (ii) one subunit specific for IL-23p19 and (iii) one subunit that contains a bacterial albumin binding domain. In some embodiments, the subunit has binding specificity for IL-17A comprises a lipocalin mutein specific for IL-17A of the disclosure. In some other embodiments, the subunit has binding specificity for IL-23p19 comprises a lipocalin mutein specific for IL-23p19 of the disclosure.

In some embodiments, the bacterial albumin binding domain may be a streptococcal protein G (König, T., & Skerra, A. (1998) *J. Immunol. Methods* 218, 73-83) e.g. as shown in SEQ ID NO: 39.

In particular, the present disclosure provides an ABD fusion protein of SEQ ID NO: 42, which is capable of binding to IL-23p19. In addition, the present application features an ABD fusion protein of SEQ ID NO: 41, which have binding specificity to both IL-17A and IL-23p19.

In some embodiments, a fusion protein of the disclosure has a binding affinity for IL-17A (including IL-17 A/A and IL-17 A/F) measured by a KD of 600 nM or less. More preferably, said fusion protein may have an affinity measured by a KD of at least 10 nM. In some further embodiments, the IL-17A-binding moiety (or moieties) of a fusion protein of the disclosure may have a binding affinity for IL-17A (including IL-17 A/A and IL-17 A/F) as good as that of such moiety as a stand-alone polypeptide.

In some embodiments, a fusion protein of the disclosure has a binding affinity for IL-23p19 measured by a KD of 140 nM or lower. More preferably, said fusion protein may have an affinity measured by a KD of 50 nM or lower. In some further embodiments, the IL-23p19-binding moiety (or moieties) of a fusion protein of the disclosure may have a binding affinity for IL-23p19 as good as that of such moiety as a stand-alone polypeptide.

In a related embodiment, one or more fusion proteins of the disclosure are capable of inhibiting the binding of IL-17A to its receptor.

In a related embodiment, a fusion protein of the disclosure is capable of inhibiting the binding of IL-23 to its receptor.

In some embodiments, a fusion protein of the disclosure may also include a linker (e.g. a peptide bond) that covalently links a lipocalin mutein of the disclosure and another lipocalin mutein of the disclosure to each other. This can be achieved, for example, by expression of the linked lipocalin muteins as a single polypeptide connected by a peptide linker. A suitable peptide linker can be comprised of a stretch of amino acids of arbitrary length containing any amino acids. A preferred linker design utilizes a repeated stretch of amino acids of glycines and serines following the formula (GxSy)n, where x is the number of glycine repeats and y the number of serine repeats in a building block that is repeated n times. The values of each of the variables x, y, and n can range from 0 to 100, preferably from 0 to 10. Two non-limiting examples are hereby provided with SEQ ID NO: 18 and SEQ ID NOs: 36-38.

In some other embodiments, chemical methods of covalently linking may be applied to link a lipocalin mutein of the disclosure to another lipocalin mutein of the disclosure. One example is the use of bifunctional linkers that allow reactive chemistry between the linker and an amino acid side chain, for example, between a maleimide and and a free cysteine in a lipocalin mutein, or an activated carboxylic acid ester and a primary amine in the lipocalin mutein. This includes reaction with non-natural amino acid side chains that may be included during protein expression, and which provide a functionality that can be selectively derivatised. In some still further embodiments, "click" chemistry, such as the cycloaddition of an azide and an alkine, may be used to link one or more subunits of a fusion polypeptide of the disclosure.

In some further preferred embodiments, a fusion protein of the disclosure further comprises the amino acids shown in SEQ ID NO: 18 or SEQ ID NOs: 36-38.

In some further embodiments, one subunit comprising a lipocalin mutein of the disclosure may be, directly or via a chemical linker attached, to another subunit comprising a lipocalin mutein of the disclosure in a fusion protein as disclosed herein.

In some still further embodiments, a lipocalin mutein of the disclosure can be fused either to the N- or C-terminus or to both the N- and the C-termini of another lipocalin mutein.

In some embodiments, each of the subunits as comprised in a fusion polypeptide of disclosure, stay thermostable (e.g. can resist a melting temperature at a $T_m$ of at least 40° C.). In some embodiments, each of said three subunits, comprised in a fusion polypeptide of disclosure, are with high cooperativity of unfolding with respect to one or more other subunits (e.g. eliminate partial unfolding, and thus significantly reducing their rate of degradation). This elimination of partial unfolding is termed "cooperative," because unfolding is an all-or-none process. In some further embodiments, one or more lipocalin muteins as included in the fusion polypeptide can resist a melting temperature at a Tm of at least 50° C., at least 55° C., at least 60° C. or even higher. In some still further embodiments, one or more HSA component as included in the fusion polypeptide can resist a melting temperature at a $T_m$ of at least 30° C., at least 35° C., at least 40° C. or even higher.

In some embodiments, the one or more fusion proteins of the disclosure comprise multimers: e.g., tetramers, trimers or dimers of the lipocalin muteins of the disclosure, wherein at least one lipocalin mutein is fused to at least one side (e.g. to the N-terminus) of another lipocalin mutein. In some further embodiments, multimeric fusion proteins may be preferred to the corresponding monomeric fusion protein. For example, a dimeric fusion protein of the disclosure binding to IL-17A may exhibit a stronger binding to IL-17A due to an avidity effect brought about by the dimeric nature of the target.

In some further embodiment, one or more fusion proteins of the disclosure result in the formation of "Duocalins" as described in Schlehuber, S., and Skerra, A. (2001), Duocalins, engineered ligand-binding proteins with dual specificity derived from the lipocalin fold. *Biol. Chem.* 382, 1335-1342, the disclosure of which is hereby incorporated by reference in its entirety.

In still another aspect, the disclosure encompasses the use of one or more fusion proteins of the disclosure or of one or more compositions comprising such proteins for the binding of IL-17A and/or IL-23p19 in a subject and/or inhibiting the binding of IL-17 and/or IL-23 to their respective receptor(s) in a subject.

In still another aspect, the present disclosure features a method of binding IL-17A and/or IL-23p19 in a subject, comprising administering to said subject an effective amount of one or more fusion proteins of the disclosure or of one or more compositions comprising such proteins.

In still another aspect, the present disclosure involves a method for inhibiting the binding of IL-17 and/or IL-23 to their respective receptor(s) in a subject, comprising administering to said subject an effective amount of one or more fusion proteins of the disclosure or of one or more compositions comprising such proteins.

Fusion proteins of the disclosure may also include a signal sequence. Signal sequences at the N-terminus of a polypeptide direct this polypeptide to a specific cellular compartment, for example the periplasm of E. coli or the endoplasmatic reticulum of eukaryotic cells. A large number of signal sequences are known in the art. An illustrative signal sequence for secretion a polypeptide into the periplasm of E. coli is the OmpA-signal sequence.

The present disclosure also involves the use of one or more fusion proteins of the disclosure for complex formation with IL-17A and/or IL-23p19.

Therefore, in another aspect of the disclosure, one or more fusion proteins of the disclosure can be used for the detection of IL-17A and/or IL-23p19. Such use may include the steps of contacting one or more fusion proteins of the disclosure, under suitable conditions, with a sample suspected of containing IL-17A and/or IL-23p19, thereby allowing formation of a complex between the proteins and IL-17A and/or between the proteins and IL-23p19, respectively, and detecting the complex by a suitable signal.

The detectable signal can be caused by a label, as explained above, or by a change of physical properties due to the binding, i.e. the complex formation, itself. One example is plasmon surface resonance, the value of which is changed during binding of binding partners from which one is immobilized on a surface such as a gold foil.

The one or more fusion proteins disclosed herein may also be used for the separation of IL-17A and/or IL-23p19 from a sample that contains other substances. Such use may include the steps of contacting one or more said fusion proteins, under suitable conditions, with a sample supposed to contain IL-17A and/or IL-23p19, thereby allowing formation of a complex between the proteins and IL-17A and/or between the proteins and IL-23, respectively, and separating the complex from the sample.

In the use of a disclosed fusion proteins for the detection of IL-17A and/or IL-23p19 as well as the separation of IL-17A and/or IL-23p19, the fusion protein, IL-17A, IL-23p19 and/or a domain or fragment thereof may be immobilized on a suitable solid phase.

Accordingly, the presence or absence of molecules such as IL-17A and/or IL-23p19, e.g., in a sample, as well as its concentration or level may be determined.

In another aspect, the disclosure provides for a kit comprising at least one fusion protein of the disclosure and one or more instructions for using the kit.

In some embodiments the kit further includes integrally thereto or as one or more separate documents, information pertaining to the contents or the kit and the use of the fusion proteins. The kit may include in some embodiments one or more fusion proteins of the disclosure that are formulated for reconstitution in a diluent. Such a diluent, e.g. a sterile diluent, may also be included in the kit, for example within a container.

E. Lipocalin Mueteins and Fusion Proteins of the Disclosure

Lipocalins are proteinaceous binding molecules that have naturally evolved to bind ligands. Lipocalins occur in many organisms, including vertebrates, insects, plants and bacteria. The members of the lipocalin protein family (Pervaiz, S., & Brew, K. (1987) FASEB J. 1, 209-214) are typically small, secreted proteins and have a single polypeptide chain. They are characterized by a range of different molecular-recognition properties: their ability to bind various, principally hydrophobic molecules (such as retinoids, fatty acids, cholesterols, prostaglandins, biliverdins, pheromones, tastants, and odorants), their binding to specific cell-surface receptors and their formation of macromolecular complexes. Although they have, in the past, been classified primarily as transport proteins, it is now clear that the lipocalins fulfill a variety of physiological functions. These include roles in retinol transport, olfaction, pheromone signalling, and the synthesis of prostaglandins. The lipocalins have also been implicated in the regulation of the immune response and the mediation of cell homoeostasis (reviewed, for example, in Flower, D. R. (1996) Biochem. J. 318, 1-14 and Flower, D. R. et al. (2000) Biochim. Biophys. Acta 1482, 9-24).

The lipocalins share unusually low levels of overall sequence conservation, often with sequence identities of less than 20%. In strong contrast, their overall folding pattern is highly conserved. The central part of the lipocalin structure consists of a single eight-stranded anti-parallel β-sheet closed back on itself to form a continuously hydrogen-bonded β-barrel. This β-barrel forms a central cavity. One end of the barrel is sterically blocked by the N-terminal peptide segment that runs across its bottom as well as three peptide loops connecting the β-strands. The other end of the β-barrel is open to the solvent and encompasses a target-binding site, which is formed by four flexible peptide loops. It is this diversity of the loops in the otherwise rigid lipocalin scaffold that gives rise to a variety of different binding modes each capable of accommodating targets of different size, shape, and chemical character (reviewed, e.g., in Flower, D. R. (1996), supra; Flower, D. R. et al. (2000), supra, or Skerra, A. (2000) Biochim. Biophys. Acta 1482, 337-350).

A lipocalin mutein according to the present disclosure may be a mutein of any chosen lipocalin. Examples of suitable lipocalins (also sometimes designated as "protein 'reference' scaffolds" or simply "scaffolds") of which a mutein may be used include, but are not limited to, tear lipocalin (lipocalin-1, von Ebner gland protein), retinol binding protein, neutrophil, lipocalin-type prostaglandin D-synthase, β-lactoglobulin, bilin-binding protein (BBP), apolipoprotein D (APO D), neutrophil gelatinase associated lipocalin (NGAL), tear lipocalin (Tlc), α2-microglobulin-related protein (A2m), 24p3/uterocalin (24p3), von Ebners gland protein 1 (VEGP 1), von Ebners gland protein 2 (VEGP 2), and Major allergen Can f1 precursor (ALL-1). In related embodiments, the lipocalin mutein is selected from the group consisting of human neutrophil gelatinase associated lipocalin (NGAL), human tear lipocalin (Tlc), human apolipoprotein D (APO D) and the bilin-binding protein of Pieris brassicae.

When used herein in the context of the lipocalin muteins of the present disclosure that bind to IL-17A or IL-23p19, the term "specific for" includes that the lipocalin mutein is directed against, binds to, or reacts with IL-17A or IL-23p19, respectively. Thus, being directed to, binding to or reacting with includes that the lipocalin mutein specifically binds to IL-17A or IL-23p19, respectively. The term "specifically" in this context means that the lipocalin mutein reacts with an IL-17A protein or an IL-23p19 protein, as described herein, but essentially not with another protein. The term "another protein" includes any non-IL-17A or non-IL-23p19 protein, respectively, including proteins closely related to or being homologous to IL-17A or IL-23p19 against which the lipocalins disclosed herein are directed to. However, IL-17A or IL-23p19 proteins, fragments and/or variants from species other than human such as those described in the context of the definition "subject" are not excluded by the term "another protein". The term "does not essentially bind" means that the lipocalin mutein of the present disclosure does not bind another protein, i.e., shows a cross-reactivity of less than 30%, preferably 20%, more preferably 10%, particularly preferably less than 9, 8, 7, 6 or 5%. Whether the lipocalin specifically reacts as defined herein above can easily be tested, inter alia, by comparing the reaction of a lipoclin mutein of the present disclosure with IL-17A or IL-23p19 and the reaction of said lipocalin with (an) other protein(s). "Specific binding" can also be determined, for example, in accordance with Western blots, ELISA-, RIA-, ECL-, IRMA-tests, FACS, IHC and peptide scans.

The amino acid sequence of a lipocalin mutein according to the disclosure has a high sequence identity to respective lipocalin when compared to sequence identities with another lipocalin (see also above). In this general context the amino acid sequence of a lipocalin mutein of the combination according to the disclosure is at least substantially similar to the amino acid sequence of the corresponding lipocalin (the wild-type or reference lipocalin). A respective sequence of a lipocalin mutein of the combination according to the disclosure, being substantially similar to the sequences of the corresponding lipocalin, has in some to the wild-type (or reference) lipocalin, one or more amino acid embodiments at least 65%, at least 70%, at least 75%, at least 80%, at least 82%, at least 85%, at least 87%, at least 90% identity, including at least 95% identity to the sequence of the corresponding lipocalin. In this regard, a lipocalin mutein of the disclosure of course may contain, in comparison substitutions as described herein which renders the lipocalin mutein capable of binding to IL-17A or IL-23p19, respectively. Typically a mutein of a lipocalin includes one or more mutations—relative to the native sequence lipocalin—of amino acids in the four loops at the open end of the ligand binding site of the lipocalin (cf. above). As explained above, these regions are essential in determining the binding specificity of a lipocalin mutein for a desired target. As an illustrative example, a mutein derived from a polypeptide of tear lipocalin, NGAL lipocalin or a homologue thereof, may have one, two, three, four or more mutated amino acid residues at any sequence position in the N-terminal region and/or in the three peptide loops BC, DE, and FG arranged at the end of the β-barrel structure that is located opposite to the natural lipocalin binding pocket. As a further illustrative example, a mutein derived from a polypeptide of tear lipocalin or a homologue thereof, may have no mutated amino acid residues in peptide loop DE arranged at the end of the β-barrel structure, compared to wild type sequence of tear lipocalin.

A lipocalin mutein according to the disclosure includes one or more, such as two, three, four, five, six, seven, eight, nine, ten, eleven, twelve, thirteen, fourteen, fifteen, sixteen, seventeen, eighteen, nineteen or even twenty substitutions in comparison to the corresponding native lipocalin, provided that such a lipocalin mutein should be capable of binding to IL-17A or IL-23p19, respectively. For example, a lipocalin mutein can have a substitution at a position corresponding to a distinct position (i.e. at a corresponding position) of the wild-type lipocalin having the wild-type sequence of, for example, tear lipocalin, NGAL lipocalin, or any other lipocalin disclosed herein. In some embodiments a lipocalin mutein of the combination according to the disclosure includes at least two amino acid substitutions, including 2, 3, 4 or 5, sometimes even more, amino acid substitutions of a native amino acid by an arginine residue. Accordingly, the nucleic acid of a protein 'reference' scaffold as described herein is subject to mutagenesis with the aim of generating a lipocalin mutein which is capable of binding to IL-17A or IL-23p19, respectively.

Also, a lipocalin mutein of the present disclosure can comprise a heterologous amino acid sequence at its N- or C-Terminus, preferably C-terminus, such as a Strep-tag, e.g., Strep II tag without affecting the biological activity (binding to its target e.g. IL-17A or IL-23p19, respectively) of the lipocalin mutein.

Likewise, a lipocalin mutein of the present disclosure may lack 1, 2, 3, 4 or more amino acids at its N-terminal end and/or 1, 2 or more amino acids at its C-terminal end, in comparison to the respective wild-type lipocalin; for example, SEQ ID NOs: 2-7 and 12-14.

Specifically, in order to determine whether an amino acid residue of the amino acid sequence of a lipocalin mutein different from a wild-type lipocalin corresponds to a certain position in the amino acid sequence of a wild-type lipocalin, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a wild-type lipocalin can serve as "subject sequence" or "reference sequence", while the amino acid sequence of a lipocalin different from the wild-type lipocalin described herein serves as "query sequence". The terms "reference sequence" and "wild type sequence" are used interchangeably herein.

In some embodiments a substitution (or replacement) is a conservative substitution. Nevertheless, any substitution—including non-conservative substitution or one or more from the exemplary substitutions listed below—is envisaged as long as the lipocalin mutein retains its capability to bind to IL-17A or IL-23p19, respectively, and/or it has an identity to the then substituted sequence in that it is at least 60%, such as at least 65%, at least 70%, at least 75%, at least 80%, at least 85% or higher identical to the "original" sequence.

Conservative substitutions are generally the following substitutions, listed according to the amino acid to be mutated, each followed by one or more replacement(s) that can be taken to be conservative: Ala→Gly, Ser, Val; Arg→Lys; Asn→Gln, His; Asp→Glu; Cys→Ser; Gln→Asn; Glu→Asp; Gly→Ala; His→Arg, Asn, Gln; Ile→Leu, Val; Leu→Ile, Val; Lys→Arg, Gln, Glu; Met→Leu, Tyr, Ile; Phe→Met, Leu, Tyr; Ser→Thr; Thr→Ser; Trp→Tyr; Tyr→Trp, Phe; Val→Ile, Leu. Other substitutions are also permissible and can be determined empirically or in accord with other known conservative or non-conservative substitutions. As a further orientation, the following eight groups each contain amino acids that can typically be taken to define conservative substitutions for one another:

b. Alanine (Ala), Glycine (Gly);
c. Aspartic acid (Asp), Glutamic acid (Glu);
d. Asparagine (Asn), Glutamine (Gln);
e. Arginine (Arg), Lysine (Lys);
f. Isoleucine (Ile), Leucine (Leu), Methionine (Met), Valine (Val);
g. Phenylalanine (Phe), Tyrosine (Tyr), Tryptophan (Trp);
h. Serine (Ser), Threonine (Thr); and
i. Cysteine (Cys), Methionine (Met)

If such substitutions result in a change in biological activity, then more substantial changes, such as the following, or as further described below in reference to amino acid classes, may be introduced and the products screened for a desired characteristic. Examples of such more substantial changes are: Ala→Leu, Ile; Arg→Gln; Asn→Asp, Lys, Arg, His; Asp→Asn; Cys→Ala; Gln→Glu; Glu→Gln; His→Lys; Ile→Met, Ala, Phe; Leu→Ala, Met, Norleucine; Lys→Asn; Met→Phe; Phe→Val, Ile, Ala; Trp→Phe; Tyr→Thr, Ser; Val→Met, Phe, Ala.

Substantial modifications in the biological properties of the lipocalin are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, methionine, alanine, valine, leucine, iso-leucine; (2) neutral hydrophilic: cysteine, serine, threonine; (3) acidic: aspartic acid, glutamic acid; (4) basic: asparagine, glutamine, histidine, lysine, arginine; (5) residues that influence chain orientation: glycine, proline; and (6) aromatic: tryptophan, tyrosine, phenylalanine.

Non-conservative substitutions will entail exchanging a member of one of these classes for another class. Any cysteine residue not involved in maintaining the proper conformation of the respective lipocalin also may be substituted, generally with serine, to improve the oxidative stability of the molecule and prevent aberrant crosslinking. Conversely, cysteine bond (s) may be added to the lipocalin to improve its stability.

Any mutation, including an insertion as discussed above, can be accomplished very easily on the nucleic acid, e.g. DNA level using established standard methods. Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) iso-leucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of tear lipocalin as long as these deletions or insertion result in a stable folded/functional mutein.

Modifications of the amino acid sequence include directed mutagenesis of single amino acid positions in order to simplify sub-cloning of the mutated lipocalin gene or its parts by incorporating cleavage sites for certain restriction enzymes. In addition, these mutations can also be incorporated to further improve the affinity of a lipocalin mutein or a fusion protein for a given target. Furthermore, mutations can be introduced in order to modulate certain characteristics of the mutein or fusion protein such as to improve folding stability, serum stability, protein resistance or water solubility or to reduce aggregation tendency, if necessary. For example, naturally occurring cysteine residues may be mutated to other amino acids to prevent disulphide bridge formation. It is also possible to deliberately mutate other amino acid sequence position to cysteine in order to introduce new reactive groups, for example for the conjugation to other compounds, such as polyethylene glycol (PEG), hydroxyethyl starch (HES), biotin, peptides or proteins, or for the formation of non-naturally occurring disulphide linkages. The generated thiol moiety may be used to PEGylate or HESylate the mutein or the fusion protein, for example, in order to increase the serum half-life of a respective lipocalin mutein or fusion protein.

In some embodiments, if one of the above moieties is conjugated to a lipocalin mutein or a fusion protein of the disclosure, conjugation to an amino acid side chain can be advantageous. Suitable amino acid side chains may occur naturally in the amino acid sequence of a human lipocalin or may be introduced by mutagenesis. In case a suitable binding site is introduced via mutagenesis, one possibility is the replacement of an amino acid at the appropriate position by a cysteine residue.

For example, such mutation includes at least one of Thr 40→Cys, Glu 73→Cys, Arg 90→Cys, Asp 95→Cys or Glu 131→Cys substitution in the wild type sequence of human tear lipocalin. The newly created cysteine residue at any of these positions can in the following be utilized to conjugate the mutein or the fusion protein to a moiety prolonging the serum half-life of the mutein or a fusion protein thereof, such as PEG or an activated derivative thereof.

With respect to a mutein of human Lipocalin 2, exemplary possibilities of such a mutation to introduce a cysteine residue into the amino acid sequence of a lipocalin including human Lipocalin 2 mutein to include the introduction of a cysteine (Cys) residue at at least at one of the sequence positions that correspond to sequence positions 14, 21, 60, 84, 88, 116, 141, 145, 143, 146 or 158 of the wild type sequence of human NGAL. In some embodiments where a human Lipocalin 2 mutein of the disclosure has a sequence in which, in comparison to the sequence of the SWISS-PROT/UniProt Data Bank Accession Number P80188, a cysteine has been replaced by another amino acid residue, the corresponding cysteine may be reintroduced into the sequence. As an illustrative example, a cysteine residue at amino acid position 87 may be introduced in such a case by reverting to a cysteine as originally present in the sequence of SWISS-PROT accession No P80188. The generated thiol moiety at the side of any of the amino acid positions 14, 21, 60, 84, 88, 116, 141, 145, 143, 146 and/or 158 may be used to PEGylate or HESylate the mutein, for example, in order to increase the serum half-life of a respective human Lipocalin 2 mutein or a fusion protein thereof.

In another embodiment, in order to provide suitable amino acid side chains for conjugating one of the above moieties to a lipocalin mutein or a fusion protein according to the present disclosure, artificial amino acids may be introduced by mutagenesis. Generally, such artificial amino acids are designed to be more reactive and thus to facilitate the conjugation to the desired compound. One example of such an artificial amino acid that may be introduced via an artificial tRNA is para-acetyl-phenylalanine.

For several applications of the muteins or fusion proteins disclosed herein it may be advantageous to use them in the form of conjugates, for example, as fused to a moiety which is a protein, or a protein domain or a peptide. In some embodiments, a lipocalin mutein or a fusion protein thereof is fused at the N-terminus or the C-terminus of the lipocalin mutein (including as comprised in a fusion protein of the disclosure) to a protein, a protein domain or a peptide, for instance, a signal sequence and/or an affinity tag.

Affinity tags such as the Strep-Tag® or Strep-Tag® II (Schmidt, T. G. M. et al. (1996) *J. Mol. Biol.* 255, 753-766), the myc-tag, the FLAG-tag, the $His_6$-tag or the HA-tag or proteins such as glutathione-S-transferase also allow easy detection and/or purification of recombinant proteins are further examples of suitable fusion partners. Finally, proteins with chromogenic or fluorescent properties such as the green fluorescent protein (GFP) or the yellow fluorescent protein (YFP) are suitable fusion partners for lipocalin muteins of the disclosure as well.

In general, it is possible to label the lipocalin muteins or fusion proteins of the disclosure with a compound including any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation or the emission of X-rays when using a radioactive label. Alkaline phosphatase, horseradish peroxidase and β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the lipocalin muteins or fusion proteins of the disclosure. The lipocalin muteins or fusion proteins of the disclosure may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). The lipocalin muteins or fusion proteins of the disclosure may, however, also be conjugated with therapeutically active nucleic acids such as antisense nucleic acid molecules, small interfering RNAs, micro RNAs or ribozymes. Such conjugates can be produced by methods well known in the art.

As indicated above, a lipocalin mutein or a fusion protein of the disclosure may in some embodiments be conjugated to a moiety that extends the serum half-life of the mutein or the fusion protein (in this regard see also PCT publication WO 2006/56464 where such conjugation strategies are described with references to muteins of human neutrophil gelatinase-associated lipocalin with binding affinity for CTLA-4). The moiety that extends the serum half-life may be a polyalkylene glycol molecule, hydroxyethyl starch, fatty acid molecules, such as palmitic acid (Vajo & Duckworth 2000, *Pharmacol. Rev.* 52, 1-9), an Fc part of an immunoglobulin, a CH3 domain of an immunoglobulin, a CH4 domain of an immunoglobulin, an albumin binding peptide, or an albumin binding protein, transferrin to name only a few. The albumin binding protein may be a bacterial albumin binding protein, an antibody, an antibody fragment including domain antibodies (see U.S. Pat. No. 6,696,245, for example), or a lipocalin mutein with binding activity for albumin. Accordingly, suitable conjugation partner for extending the half-life of a lipocalin mutein or a fusion protein of the disclosure includes a bacterial albumin binding domain, such as the one of streptococcal protein G (König, T., & Skerra, A. (1998) *J. Immunol. Methods* 218, 73-83) or the one as shown in SEQ ID NO: 39. In addition, examples of albumin binding peptides that can be used as conjugation partner are, for instance, those having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr as described in US patent application 2003/0069395 or Dennis et al. (Dennis, M. S., Zhang, M., Meng, Y. G., Kadkhodayan, M., Kirchhofer, D., Combs, D. & Damico, L. A. (2002) *J Biol Chem* 277, 35035-35043).

In other embodiments, albumin itself (Osborn, B. L. et al., 2002, *J. Pharmacol. Exp. Ther.* 303, 540-548), or a biological active fragment of albumin can be used as conjugation partner of a lipocalin mutein or a fusion protein of the disclosure. The term "albumin" includes all mammal albumins such as human serum albumin or bovine serum albumin or rat albumine If the albumin-binding protein is an antibody fragment it may be a domain antibody. Domain Antibodies (dAbs) are engineered to allow precise control over biophysical properties and in vivo half-life to create the optimal safety and efficacy product profile. Domain Antibodies are for example commercially available from Domantis Ltd. (Cambridge, UK and MA, USA).

When transferrin is used as a moiety to extend the serum half-life of the lipocalin muteins or the fusion proteins of the disclosure, the muteins or the fusion proteins can be genetically fused to the N or C terminus, or both, of non-glycosylated transferrin. Non-glycosylated transferrin has a half-life of 14-17 days, and a transferrin-conjugated mutein or fusion protein will similarly have an extended half-life. The transferrin carrier also provides high bioavailability, biodistribution and circulating stability. This technology is commercially available from BioRexis (BioRexis Pharmaceutical Corporation, PA, USA). Recombinant human transferrin (DeltaFerrin™) for use as a protein stabilizer/half-life extension partner is also commercially available from Novozymes Delta Ltd. (Nottingham, UK).

If an Fc part of an immunoglobulin is used for the purpose to prolong the serum half-life of the lipocalin muteins or fusion proteins of the disclosure, the SynFusion™ technology, commercially available from Syntonix Pharmaceuticals, Inc (MA, USA), may be used. The use of this Fc-fusion technology allows the creation of longer-acting biopharmaceuticals and may, for example, consist of two copies of a mutein linked to the Fc region of an antibody to improve pharmacokinetics, solubility, and production efficiency.

Yet another alternative to prolong the half-life of the lipocalin muteins or fusion proteins of the disclosure is to fuse to the N- or C-terminus of the muteins (including as comprised in fusion proteins of the disclosure) long, unstructured, flexible glycine-rich sequences (for example, poly-glycine with about 20 to 80 consecutive glycine residues). This approach disclosed in WO2007/038619, for example, has also been term "rPEG" (recombinant PEG).

If polyalkylene glycol is used as conjugation partner, the polyalkylene glycol can be substituted, unsubstituted, linear or branched. It can also be an activated polyalkylene derivative. Examples of suitable compounds are polyethylene glycol (PEG) molecules as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) The Clinical Efficacy of Poly(Ethylene Glycol)-Modified Proteins *J. Control. Release* 11, 139-148). The molecular weight of such a polymer, such as polyethylene glycol, may range from about 300 to about 70.000 Dalton, including, for example, polyethylene glycol with a molecular weight of about 10.000, of about 20.000, of about 30.000 or of about 40.000 Dalton. Moreover, as e.g. described in U.S. Pat. No. 6,500,930 or 6,620,413, carbohydrate oligo- and polymers such as starch or hydroxyethyl starch (HES) can be conjugated to a mutein or a fusion protein of the disclosure for the purpose of serum half-life extension.

In addition, a lipocalin mutein or fusion protein disclosed herein may be conjugated to a moiety that may confer new characteristics to the lipocalin muteins or fusion proteins of the disclosure such as enzymatic activity or binding affinity for other molecules. Examples of suitable moieties include alkaline phosphatase, horseradish peroxidase, gluthation-S-transferase, the albumin-binding domain of protein G, protein A, antibody fragments, oligomerization domains or toxins.

In addition, it may be possible to fuse a lipocalin mutein or fusion protein disclosed herein with a separate enzyme active site such that both "components" of the resulting fusion protein together act on a given therapeutic target. For example, the binding domain of the lipocalin mutein (including as comprised in a fusion protein of the disclosure) may attach to the disease-causing target, allowing the enzyme domain to abolish the biological function of the target.

In some embodiments, a lipocalin mutein or a fusion protein of the disclosed may be conjugated to a moiety via a linker (e.g. a peptide bond) that covalently links a lipocalin mutein of the disclosure and another disclosed moiety to each other. This can be achieved, for example, by expression of the linked lipocalin muteins as a single polypeptide connected by a peptide linker. A suitable peptide linker can be comprised of a stretch of amino acids of arbitrary length containing any amino acids. A preferred linker design utilizes a repeated stretch of amino acids of glycines and serines following the formula (GxSy)n, where x is the number of glycine repeats and y the number of serine repeats in a building block that is repeated n times. The values of each of the variables x, y, and n can range from 0 to 100, preferably from 0 to 10. Non-limiting examples are hereby provided with SEQ ID NO: 18 and SEQ ID NOs: 36-38.

In some other embodiments, chemical methods of covalently linking may be applied to link a lipocalin mutein of the disclosure to another disclosed moiety. One example is the use of bifunctional linkers that allow reactive chemistry between the linker and an amino acid side chain, for example, between a maleimide and and a free cysteine in a lipocalin mutein, or an activated carboxylic acid ester and a primary amine in the lipocalin mutein. This includes reaction with non-natural amino acid side chains that may be included during protein expression, and which provide a functionality that can be selectively derivatised. In some still further embodiments, "click" chemistry, such as the cycloaddtion of an azide and an alkine, may be used to link one or more subunits of a fusion polypeptide of the disclosure.

The present disclosure also relates to nucleic acid molecules (DNA and RNA) that include nucleotide sequences encoding the lipocalin muteins and the fusion proteins of the disclosure. Since the degeneracy of the genetic code permits substitutions of certain codons by other codons specifying the same amino acid, the disclosure is not limited to a specific nucleic acid molecule encoding a lipocalin mutein or a fusion protein as described herein but encompasses all nucleic acid molecules that include nucleotide sequences encoding a functional mutein or a functional fusion protein. In this regard, the present disclosure provides nucleotide sequences encoding some exemplary lipocalin muteins, some exemplary fusion proteins generic as shown in SEQ ID NOs: 23-35, 45-49 and 54.

In one embodiment of the disclosure, the method includes subjecting the nucleic acid molecule to mutagenesis at nucleotide triplets coding for at least one, sometimes even more, of the sequence positions corresponding to the sequence positions 28, 36, 40-41, 49, 52, 68, 70, 72-73, 75, 77, 79, 81, 87, 96, 100, 103, 106, 125, 127, 132 and 134 of the linear polypeptide sequence of human NGAL (SEQ ID NO: 8).

In another embodiment of the method according to the disclosure, a nucleic acid molecule encoding a human tear lipocalin is firstly subjected to mutagenesis at one or more of the amino acid sequence positions 26-34, 55-58, 60-61, 64, 104-108 of the linear polypeptide sequence of human tear lipocalin (SEQ ID NO: 1). Secondly, the nucleic acid molecule encoding a human tear lipocalin is also subjected to mutagenesis at one or more of the amino acid sequence positions 101, 111, 114 and 153 of the linear polypeptide sequence of the mature human tear lipocalin.

The disclosure also includes nucleic acid molecules encoding the lipocalin muteins and fusion proteins of the disclosure, which include additional mutations outside the indicated sequence positions of experimental mutagenesis. Such mutations are often tolerated or can even prove to be advantageous, for example if they contribute to an improved folding efficiency, serum stability, thermal stability or ligand binding affinity of the muteins and the fusion proteins.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it includes sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the disclosure can include a regulatory sequence, such as a promoter sequence. In some embodiments a nucleic acid molecule of the disclosure includes a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the disclosure can also be part of a vector or any other kind of cloning vehicle, such as a plasmid, a phagemid, a phage, a baculovirus, a cosmid or an artificial chromosome.

In one embodiment, the nucleic acid molecule is included in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (see e.g. Lowman, H. B. (1997) *Annu. Rev. Biophys. Biomol. Struct.* 26, 401-424, or Rodi, D. J., and Makowski, L. (1999) *Curr. Opin. Biotechnol.* 10, 87-93).

Such cloning vehicles can include, aside from the regulatory sequences described above and a nucleic acid sequence encoding a lipocalin mutein or a fusion protein as described herein, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding a lipocalin mutein or a fusion protein as described herein, and in particular a cloning vector containing the coding sequence of such a mutein can be transformed into a host cell capable of expressing the gene. Transformation can be performed using standard techniques. Thus, the disclosure is also directed to a host cell containing a nucleic acid molecule as disclosed herein.

The transformed host cells are cultured under conditions suitable for expression of the nucleotide sequence encoding a lipocalin mutein or a fusion protein of the disclosure. Suitable host cells can be prokaryotic, such as *Escherichia coli* (*E. coli*) or *Bacillus subtilis*, or eukaryotic, such as *Saccharomyces cerevisiae, Pichia pastoris*, SF9 or High5 insect cells, immortalized mammalian cell lines (e.g., HeLa cells or CHO cells) or primary mammalian cells.

The disclosure also relates to a method for the production of a polypeptide as described herein, wherein the lipocalin mutein or the fusion protein is produced starting from the nucleic acid coding for the lipocalin mutein or the fusion protein by means of genetic engineering methods. The method can be carried out in vivo, the lipocalin mutein or the fusion protein can for example be produced in a bacterial or eucaryotic host organism and then isolated from this host organism or its culture. It is also possible to produce a protein in vitro, for example by use of an in vitro translation system.

When producing the lipocalin mutein, the fusion protein or the fragment in vivo, a nucleic acid encoding such mutein is introduced into a suitable bacterial or eukaryotic host organism by means of recombinant DNA technology (as already outlined above). For this purpose, the host cell is first transformed with a cloning vector that includes a nucleic acid molecule encoding a lipocalin mutein or a fusion protein as described herein using established standard methods. The host cell is then cultured under conditions, which allow expression of the heterologous DNA and thus the synthesis of the corresponding polypeptide. Subsequently, the polypeptide is recovered either from the cell or from the cultivation medium.

In some embodiments, a nucleic acid molecule, such as DNA, disclosed in this application may be "operably linked" to another nucleic acid molecule of the disclosure to allow expression of a fusion proteion of the disclosure. In this regard, an operable linkage is a linkage in which the sequence elements of the first nucleic acid molecule and the sequence elements of the second nucleic acid molecule are connected in a way that enables expression of the fusion protein as a single polypeptide.

In addition, in some embodiments, the naturally occurring disulfide bond between Cys 76 and Cys 175 may be removed in NGAL muteins of the disclosure (including as comprised in fusion proteins of the disclosure). In some embodiments for Tlc muteins of the disclosure as well (including as comprised in fusion proteins of the disclosure), the naturally occurring disulfide bond between Cys 61 and Cys 153 may be removed. Accordingly, such muteins or fusion proteins can be produced in a cell compartment having a reducing redox milieu, for example, in the cytoplasma of Gram-negative bacteria.

In case a lipocalin mutein or a fusion protein of the disclosure includes intramolecular disulfide bonds, it may be preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds.

It is, however, also possible to produce a lipocalin mutein or a fusion protein of the disclosure in the cytosol of a host cell, preferably *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi et al. (2002) *J. Mol. Biol.* 315, 1-8).

However, a lipocalin mutein or a fusion protein as described herein may not necessarily be generated or produced only by use of genetic engineering. Rather, such a lipocalin mutein or a fusion protein can also be obtained by chemical synthesis such as Merrifield solid phase polypeptide synthesis or by in vitro transcription and translation. It is for example possible that promising mutations are identified using molecular modeling and then to synthesize the wanted (designed) polypeptide in vitro and investigate the binding activity for IL-17A. Methods for the solid phase and/or solution phase synthesis of proteins are well known in the art (see e.g. Bruckdorfer, T. et al. (2004) *Curr. Pharm. Biotechnol.* 5, 29-43).

In another embodiment, the lipocalin muteins or the fusion proteins of the disclosure may be produced by in vitro transcription/translation employing well-established methods known to those skilled in the art.

The skilled worker will appreciate methods useful to prepare lipocalin muteins contemplated by the present disclosure but whose protein or nucleic acid sequences are not explicity disclosed herein. As an overview, such modifications of the amino acid sequence include, e.g., directed mutagenesis of single amino acid positions in order to simplify sub-cloning of a mutated lipocalin gene or its parts by incorporating cleavage sites for certain restriction enzymes. In addition, these mutations can also be incorporated to further improve the affinity of a lipocalin mutein or a fusion protein for its target (e.g. IL-17A or IL-23p19, respectively). Furthermore, mutations can be introduced to modulate certain characteristics of the mutein or the fusion protein, such as, to improve folding stability, serum stability, protein resistance or water solubility or to reduce aggregation tendency, if necessary. For example, naturally occurring cysteine residues may be mutated to other amino acids to prevent disulphide bridge formation.

The lipocalin muteins and fusion proteins, disclosed herein, as well as their derivatives can be used in many fields similar to antibodies or fragments thereof. For example, the lipocalin muteins and/or fusion proteins, as well as their respective derivatives, can be used for labeling with an enzyme, an antibody, a radioactive substance or any other group having biochemical activity or defined binding characteristics. By doing so, their respective targets thereof can be detected or brought in contact with them. In addition, lipocalin muteins and/or fusion proteins of the disclosure can serve to detect chemical structures by means of established analytical methods (e.g., ELISA or Western Blot) or by microscopy or immunosensorics. In this regard, the detection signal can either be generated directly by use of a suitable mutein, or a suitable fusion protein; or indirectly by immunochemical detection of the bound mutein via an antibody.

Other protein scaffolds that can be engineered in accordance with the present invention to provide protein muteins that bind IL-17 and/or IL-23 with detectable affinity include: an EGF-like domain, a Kringle-domain, a fibronectin type I domain, a fibronectin type II domain, a fibronectin type III domain, a PAN domain, a G1a domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (Ill. et al. "Design and construction of a hybrid immunoglobulin domain with properties of both heavy and light chain variable regions" Protein Eng 10:949-57 (1997)), "Minibodies" (Martin et al. "The affinity-selection of a minibody polypeptide inhibitor of human interleukin-6" EMBO J 13:5303-9 (1994)), "Diabodies" (Holliger et al. "'Diabodies': small bivalent and bispecific antibody fragments" PNAS USA 90:6444-6448 (1993)), "Janusins" (Traunecker et al. "Bispecific single chain molecules (Janusins) target cytotoxic lymphocytes on HIV infected cells" EMBO J 10:3655-3659 (1991) and Traunecker et al. "Janusin: new molecular design for bispecific reagents" Int J Cancer Suppl 7:51-52 (1992), a nanobody, an adnectin, a tetranectin, a microbody, an affilin, an affibody an ankyrin, a crystallin, a knottin, ubiquitin, a zinc-finger protein, an autofluorescent protein, an ankyrin or ankyrin repeat protein or a leucine-rich repeat protein, an avimer (Silverman, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P 2005, Nat Biotech, December; 23(12):1556-61, E-Publication in Nat Biotech. 2005 Nov. 20 edition); as well as multivalent avimer proteins evolved by exon shuffling of a family of human receptor domains as also described in Silverman J, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P, Nat Biotech, December; 23(12):1556-61, E-Publication in Nat. Biotechnology. 2005 Nov. 20 edition).

Additional objects, advantages, and features of this disclosure will become apparent to those skilled in the art upon examination of the following Examples and the attached Figures thereof, which are not intended to be limiting. Thus, it should be understood that although the present disclosure is specifically disclosed by exemplary embodiments and optional features, modification and variation of the disclosures embodied therein herein disclosed may be resorted to by those skilled in the art, and that such modifications and variations are considered to be within the scope of this disclosure.

V. EXAMPLES

Example 1: Affinity of a Lipocalin Mutein to IL-17A

To measure the binding affinity of the lipocalin mutein SEQ ID NO: 5 to IL-17A, a Surface Plasmon Resonance (SPR) based assay was employed utilizing a Biacore T200 instrument (GE Healthcare). In the SPR affinity assay (FIG. 6A), IL-17A was immobilized on a CM5 sensor chip using standard amine chemistry: The surface of the chip was activated using EDC and NHS. Subsequently, 5 μg/mL of IL-17A solution in 10 mM Acetate pH 5 was applied at a flow rate of 10 μL/min until an immobilization level of 279 resonance units (RU) was achieved. Residual activated groups were quenched with ethanolamine. The reference channels underwent blank immobilization by treatment with EDC/NHS following ethanolamine.

To determine the affinity, four dilutions of SEQ ID NO: 5 were prepared in HBS-EP+ buffer and applied to the prepared chip surface, using concentrations of 111, 37, 12 and 4 nM. The binding assay was carried out with a contact time of 300 s, dissociation time of 1200 s and applying a flow rate of 30 μL/min. All measurements were performed at 25° C. Regeneration of the immobilized IL-17A surface was achieved with consecutive injections of 10 mM aqueous $H_3PO_4$ (30 s) and 10 mM glycine-HCl pH 1.5 (15 s) followed by an extra wash with running buffer and a stabilization period of 30 s. Prior to the protein measurements three startup cycles were performed for conditioning purposes. Data were evaluated with Biacore T200 Evaluation software (V 1.0). Double referencing was used. The 1:1 Binding model was used to fit the raw data.

The resulting fit curves are shown in FIG. 6A. The data shows that SEQ ID NO: 5 bound with high affinity to IL-17A, with an association rate constant of $k_a$=3.1×10$^5$ M$^{-1}$ sec$^{-1}$ and a dissociation rate constant of $k_d$=3.2×10$^{-4}$ sec$^{-1}$, resulting in a dissocation constant of $K_d$=1.0 nM.

Example 2: Competitive Mode of Action of a Lipocalin Mutein to IL-17A

Whether SEQ ID NO: 5 binds to IL-17A in a competitive mode was tested in vitro using a competition ELISA format (FIG. 1). In this experiment, a constant concentration of biotinylated IL-17A was incubated with variable concentrations of SEQ ID NO: 5 for 1 h. After this pre-incubation in solution, an aliquot of the lipocalin mutein/IL-17A mixture was transferred to an ELISA plate coated with human IL-17RA receptor to measure the concentration of hIL-17A that was not blocked to bind to the IL-17RA receptor (FIG. 1).

All incubation steps were performed with shaking at 300 rpm, and the plate was washed after each incubation step with 80 µl PBS-T buffer (PBS, 0.05% Tween 20) for five times using a Biotek ELx405 select CW washer. In the first step, a 384 well MSD plate was directly coated with 20 µl of soluble human IL-17RA receptor at a concentration of 1 µg/ml in PBS over night at 4° C. After washing, the receptor coated wells were blocked with 60 µl PBS-T/BSA (2% BSA in PBS containing 0.1% Tween 20) for 1 h at room temperature.

A fixed concentration of 0.01 nM human IL-17A was incubated in solution with varying concentrations of SEQ ID NO: 5, or with SEQ ID NO: 7 as a negative control, using a starting concentration of SEQ ID NO: 5 of 100 nM (negative control SEQ ID NO: 7: 1000 nM) which was serially diluted at a 1:4 ratio down to 1 pM in PBS-T/BSA buffer (negative control: 10 pM). After 1 h incubation at room temperature, 20 µl of the reaction mixture was transferred to the IL-17RA receptor-coated MSD plate to capture unbound (free) or non-competitively bound hIL-17A for 20 min at RT. To allow for transformation of ELISA readout results into absolute free hIL-17A concentrations (cf. below), a standard curve containing varying concentrations of hIL-17A starting with 25 nM (1:4 serially diluted in 11 steps) was prepared in PBS-T/BSA and incubated for 20 min on the same MSD plate as well.

To allow for detection and quantitation of bound biotinylated hIL-17A, the residual supernatants were discarded and 20 µl Strepavidin Sulfo-tag was added at a concentration of 1 µg/mL in PBS-T/BSA and incubated for 1 h at RT. After washing, 60 µl MSD Read Buffer T (2×) was added to each well and the plate was read within 15 min.

The resulting Electrochemoluminescence (ECL) signal was measured using the SECTOR Imager 2400 (Meso Scale Discovery). The evaluation was performed as follows: free IL-17A concentration $c(IL-17A)_{free}$ was calculated (from the standard curve determined in parallel) and plotted versus SEQ ID NO: 5 concentration, c(SEQ ID NO: 5). To obtain the SEQ ID NO: 5 concentration at which formation of the IL-17A/IL-17RA-complex was blocked by 50% (1050), the curves were fitted by nonlinear regression with a single-sites binding model according to $c(IL-17A)_{free}=c(IL-17A)_{tot}/(1+c(SEQ\ ID\ NO:\ 5)/IC50))$, with the total tracer concentration $c(IL-17A)_{tot}$ and the IC50 value as free parameters. Curve fitting was performed using GraphPad Prism 4 software.

In summary, the negative control SEQ ID NO: 7 did not bind to hIL-17A; in contrast, SEQ ID NO: 5 showed a strong competitive binding to hIL-17A, with a fitted IC50 value of 50 pM.

Example 3: Specificity and Species Crossreactivity of a Lipocalin Mutein to IL-17A Specificity and species crossreactivity (FIG. 2) of SEQ ID NO: 5 were assayed by a "Solution competition ELISA", the principle of which was as follows: A constant concentration of SEQ ID NO: 5 was incubated with variable concentrations of ligands (hIL-17A, hIL-17 A/F, hIL-17F, cIL-17A, mIL-17A, and hIL-6 as a negative control) for 1 h. After this pre-incubation in solution, an aliquot of the mutein/ligand mixture was transferred to an ELISA plate coated with hIL-17A to measure the remaining concentration of free SEQ ID NO: 5. The concentration of free (non ligand-bound) SEQ ID NO: 5 was determined via a quantitative ELISA setup (FIG. 2). Note that this assay relies on all ligands targeting the same binding site in the SEQ ID NO: 5, i.e. the ligands bind to the SEQ ID NO: 5 in competition with each other.

In the following detailed experimental protocol, incubation and washing steps were performed as described above in the competition ELISA protocol. A 384-well plate suitable for fluorescence measurements (Greiner FLUOTRAC™ 600, black flat bottom, high-binding) was coated with 20 µl of Neutravidin at a concentration of 5 µg/ml in PBS over night at 4° C. After washing, the Neutravidin-coated wells were blocked with 100 µl blocking buffer (PBS-T/BSA) for 1 h at room temperature. After washing again, 20 µl biotinylated hIL-17A at a concentration of 1 µg/mL in PBS was added for 1 h at room temperature, and excess reagent was removed.

A fixed concentration of 0.5 nM SEQ ID NO: 5 was incubated in solution with varying concentrations of ligands (hIL-17A, hIL-17 A/F, hIL-17F, cIL-17A, mIL-17A, and hIL-6 as a negative control), using a starting concentration of 1000 nM which was serially diluted at a 1:3 ratio down to 17 pM in PBS-T/BSA. After 1 h incubation at room temperature, 20 µl of the reaction mixture was transferred to the 384-well plate upon which biotinylated hIL-17A was immobilized to capture unbound (free) SEQ ID NO: 5 for 20 min at RT. To allow for transformation of ELISA readout results into absolute free SEQ ID NO: 5 concentrations (cf. below), a standard curve containing varying concentrations of SEQ ID NO: 5 starting with 200 nM (1:3 serially diluted in 11 steps) was prepared in PBS-T/BSA and incubated for 20 min on the same ELISA plate as well.

The residual supernatants were discarded and 20 µl HRP-labeled anti-lipocalin antibody was added at a predetermined optimal concentration in PBS-T/BSA and incubated for 1 h at RT. The anti-lipocalin antibody had been obtained by immunization of rabbits with a mixture of lipocalin muteins, and was subsequently coupled to HRP using a kit (EZ-link Plus Activated Peroxidase, Thermo Scientific) according to the manufacturer's intructions, to obtain the antibody-HRP conjugate. After washing, 20 µl fluorogenic HRP substrate (Quantablue, Pierce) was added to each well, and the reaction allowed to proceed for 60 minutes. The fluorescence intensity of every well on the plate was read using a Genios Plus Microplate reader (Tecan). To evaluate the data, free SEQ ID NO: 5 concentration, $c(SEQ\ ID\ NO:\ 5)_{free}$, was calculated based on the standard curve results, and plotted versus ligand concentration, c(Ligand). To obtain the ligand concentration at which formation of the IL-17A/SEQ ID NO: 5 complex was blocked by 50% (IC50), the curves were fitted by nonlinear regression with a single-sites binding model according to $c(SEQ\ ID\ NO:\ 5)_{free}=c(SEQ\ ID\ NO:\ 5)_{tot}/(1+c(Ligand)/IC50))$, with the total tracer concentration $c(SEQ\ ID\ NO:\ 5)_{tot}$ and the IC50 value as free parameters. Curve fitting was performed using GraphPad Prism 4 software.

In summary, binding of SEQ ID NO: 5 to hIL-17F, mIL-17A, and the negative control hIL-6 could not be detected. The remaining ligands evidently were bound with high affinity, and curve fitting yielded the following results: $IC50_{hIL-17A}=0.4$ nM, $IC50_{hIL-17\ A/F}=0.4$ nM and $IC50_{cIL-17A}=0.3$ nM. The identical IC50 values for human IL-17A and human IL-17 A/F in the absence of binding to human IL-17F demonstrate that SEQ ID NO: 5 bound specifically to the IL-17A subunit of IL-17A and IL-17 A/F. Binding to the IL-17A subunit is evidently in no way influenced or disturbed by the nature of the second subunit in a dimer containing IL-17A. Further, the result shows that SEQ ID NO: 5 was fully crossreactive to cynomolgus monkey IL-17A.

Example 4: Lipocalin-Mutein-Mediated Blockade of IL-17A Induced G-CSF Secretion in a Cell-Based Assay We employed a cell-based assay to demonstrate the ability of SEQ ID NO: 5 to block the biological activity of IL-17A. The assay was based on IL-17A-induced secretion of G-CSF in U87-MG cells (ATCC catalog# HTB-14). In this assay, recombinant hIL-17A was preincubated with SEQ ID NO: 5, SEQ ID NO: 2, benchmark antibody molecules or controls and added to the cells. Besides SEQ ID NO: 5, the following benchmarks and controls were included in the assay: antibody molecules (benchmark antibody 1 and benchmark antibody 2 as described above), and the lipocalin mutein SEQ ID NO: 2 as benchmarks and positive controls, and SEQ ID NO: 7 and a human IgG isotype antibody (Dianova, CAT#009-000-002) as negative controls. The concentration of G-CSF in the supernatant was then measured by ELISA.

U87-MG cells were cultured in cell culture flasks under standard conditions (Dulbecco's Modified Eagle Medium DMEM (PAN Biotech GmbH) containing 10% fetal calf serum FCS (PAA Laboratories), 37° C., 5% $CO_2$ atmosphere).

On day 1 of the experiment, the adherent cells were dissociated from their substrate with Accutase (PAA Laboratories) according to the manufacturer's instructions. Subsequently, cells were centrifuged down for 5 minutes at 1000 rpm, resuspended in medium and filtered through a 100 μm cell strainer (Falcon) to remove cell aggregates. Cells were then seeded in 96-well flat bottom tissue culture plates (Greiner) at a density of 8000 cells per well using an end volume of 100 μl. They were incubated overnight under standard conditions.

SEQ ID NO: 5, SEQ ID NO: 2, SEQ ID NO: 7, a human IgG isotype antibody (Dianova, CAT#009-000-002), benchmark antibody 1 and benchmark antibody 2 (as described above) were the molecules under study ("MUS"). On day 2, a fixed concentration of 0.5 nM recombinant hIL-17A was preincubated with a dilution series of MUS for 30 minutes at 37° C., with concentrations ranging from 5000 nM to 13 nM (dilution steps were carried out at a ratio of 1:5). The medium of the cells grown in the 96-well plate was replaced by 80 μl fresh medium, to which 20 μl of the preincubated IL-17A/MUS solutions were subsequently added. This was done in triplicate for each MUS or control. The cells were incubated for a further 20-24 hours under standard conditions. Before collection of the supernatants for measurement of G-CSF levels, wells were visually inspected with a microscope. Wells that exhibited considerable cell death or the presence of cellular aggregates were excluded from evaluation. G-CSF levels were determined using the G-CSF Ultra-Sensitive Kit from MSD. To evaluate the data, the G-CSF concentration in arbitrary units was plotted versus the MUS concentration, c(MUS). To obtain the MUS concentration at which induction of G-CSF production by U-87 MG cells was reduced to 50% (I050), the curves were fitted by nonlinear regression with a single-sites binding model according to $c(G-CSF)=c(G-CSF)_{Min}+[c(G-CSF)_{Max}-c(G-CSF)_{Min}]/[1+c(MUS)/IC50]$, with free parameters being IC50, the induced G-CSF concentration $c(G-CSF)_{Max}$, and the uninduced G-CSF concentration $c(G-CSF)_{Min}$. Here, it was assumed that $c(G-CSF)_{Max}$ and $c(G-CSF)_{Min}$ were independent of the antagonist or control molecule under study, and they were therefore fitted to common values for all molecules.

As shown in FIG. 3, the resulting IC50 value for SEQ ID NO: 5 was 1.0 nM, in a similar range as benchmark antibody molecules (benchmark antibody 1 and benchmark antibody 2 as described above), with IC50=1.4 nM and 0.6 nM, respectively. SEQ ID NO: 2 had an I050 value of 289 nM. This is also evidence of the broad dynamic range of the assay. Negative controls, consisting of SEQ ID NO: 7 and a human IgG isotype antibody (Dianova, CAT#009-000-002), had no effect on IL-17A-induced G-CSF production of the cells.

Example 5: Affinity of Lipocalin Muteins to IL-23

To measure the binding affinity of the lipocalin muteins SEQ ID NO: 9 and SEQ ID NO: 10 to IL-23, a Surface Plasmon Resonance (SPR) based assay was employed utilizing a Biacore T200 instrument (GE Healthcare). In the SPR affinity assay (FIG. 6B and FIG. 6C), IL-23 was immobilized on a CM5 sensor chip using standard amine chemistry: The surface of the chip was activated using EDC and NHS. Subsequently, 5 μg/mL of IL-23 solution in 10 mM acetate pH 4.5 was applied at a flow rate of 10 μL/min until an immobilization level of 169 resonance units (RU) was achieved. Residual activated groups were quenched with ethanolamine. The reference channels were treated with EDC/NHS following ethanolamine (blank immobilization).

To determine the respective mutein affinities, five dilutions of SEQ ID NO: 10 and SEQ ID NO: 9, respectively, were prepared in HBS-EP+ buffer and applied to the prepared chip surface, using concentrations of 3000, 600, 120, 24 and 4.8 nM (SEQ ID NO: 10) and 3000, 1000, 333, 111 and 37 nM (SEQ ID NO: 9). The binding assay was carried out with a contact time of 300 s, dissociation time of 1200 s and applying a flow rate of 30 μL/min. All measurements were performed at 25° C. Regeneration of the immobilized IL-23 surface was achieved by injection of 10 mM aqueous $H_3PO_4$ (30 s) followed by an extra wash with running buffer and a stabilization period of 30 s. Prior to the protein measurements three startup cycles were performed for conditioning purposes. Data were evaluated with Biacore T200 Evaluation software (V 1.0). Double referencing was used. The 1:1 Binding model was used to fit the raw data.

As shown in FIG. 6C, the resulting fit curves demonstrate that SEQ ID NO: 10 bound with high affinity to IL-23, with an association rate constant of $k_a=4.2\times10^4$ $M^{-1}$ $sec^{-1}$ and a dissociation rate constant of $k_d=4.8\times10^{-4}$ $sec^{-1}$, resulting in a dissocation constant of $K_d=11.5$ nM. Similarly, as shown in FIG. 6B, SEQ ID NO: 9 bound with moderate affinity to IL-23, with an association rate constant of ka=$4.7\times10^3$ $M^{-1}$ $sec^{-1}$ and a dissociation rate constant of kd=$6.3\times10^{-4}$ $sec^{-1}$, resulting in a dissocation constant of $K_d=135.4$ nM. The rates of complex formation and complex dissociation are in a typical range of biomolecular interactions.

Example 6: Competitive Mode of Action of Several Lipocalin Muteins to IL-23

Whether the lipocalin muteins SEQ ID NO: 9 and SEQ ID NO: 10 bind to IL-23 in a competitive mode was tested in vitro using a competition ELISA format (FIG. 4), in analogy to Example 2, but using IL-23 as the target.

All incubation steps were performed with shaking 300 rpm, and the plate was washed after each incubation step with 80 µl PBS/0.05% Tween 20 for five times using a Biotek ELx405 select CW washer. A 384 well MSD plate was directly coated with 20 µl of soluble human IL-23 receptor at a concentration of 1 µg/ml in PBS over night at 4° C. After washing, the receptor-coated wells were blocked with 60 µl PBS-T/BSA for 1 h at room temperature.

A fixed concentration of 0.01 nM biotinylated human IL-23 was incubated in solution with varying concentrations of SEQ ID NO: 10 or SEQ ID NO: 9, or with SEQ ID NO: 11 as a negative control, using starting concentrations of 200 nM (SEQ ID NO: 10) and 2000 nM (SEQ ID NO: 9 and SEQ ID NO: 11) which were serially diluted at a 1:4 ratio down to 0.2 pM (SEQ ID NO: 10) and 2 pM (SEQ ID NO: 9 and SEQ ID NO: 11) in PBS-T/BSA. After 1 h incubation at room temperature, 20 µl of the reaction mixture was transferred to the IL-23 receptor-coated MSD plate to capture unbound (free) or non-competitively bound hIL-23 for 20 min at RT. To allow for transformation of ELISA readout results into absolute free hIL-23 concentrations (cf. below), a standard curve containing varying concentrations of hIL-23 starting with 100 nM (1:4 serially diluted in 11 steps) was prepared in PBS-T/BSA and incubated for 20 min on the same MSD plate as well. To allow for detection and quantitation of bound biotinylated hIL-23, the residual supernatants were discarded and 20 µl Strepavidin Sulfo-tag was added at a concentration of 1 µg/mL in PBS-T/BSA and incubated for 1 h at RT. After washing, 60 µl MSD Read Buffer T (2×) was added to each well and the plate was read within 15 min.

The resulting ECL signal was measured using the SECTOR Imager 2400 (Meso Scale Discovery). The evaluation was performed in analogy to Example 2. As shown in FIG. 4, the negative control SEQ ID NO: 11 did not bind to hIL-23, in contrast, SEQ ID NO: 10 showed a competitive binding to hIL23, with a fitted IC50 value of 1.9 nM, and SEQ ID NO: 9 showed competitive binding, with a fitted IC50 value of 119 nM.

Example 7: Specificity and Species Crossreactivity of Lipocalin Muteins to IL-23

Specificity and species crossreactivity of the lipocalin muteins SEQ ID NO: 10 (FIG. 5A) and SEQ ID NO: 9 (FIG. 5B) were assayed by a "Solution competition ELISA", in analogy to Example 3, but studying different ligands, namely, hIL-23, cIL-23, mIL-23 and hIL-12p40.

In the following detailed experimental protocol, incubation and washing steps were performed as described above in the competition ELISA protocol. A 384-well plate suitable for fluorescence measurements (Greiner FLUOTRAC™ 600, black flat bottom, high-binding) was coated with 20 µl of Neutravidin at a concentration of 5 µg/ml in PBS over night at 4° C. After washing, the Neutravidin-coated wells were blocked with 100 µl PBS-T/BSA for 1 h at room temperature. After washing again, 20 µl biotinylated hIL-23-Bio at a concentration of 0.25 µg/mL in PBS was added for 1 h at room temperature, and excess reagent was removed.

A fixed concentration of 10 nM SEQ ID NO: 9 or 1 nM SEQ ID NO: 10 was incubated in solution with varying concentrations of ligands (hIL-23, cIL-23, mIL-23 and hIL-12p40), using a starting concentration of 1000 nM which was serially diluted at a 1:3 ratio down to 17 pM in PBS-T/BSA. After 20 minutes incubation at room temperature, 20 µl of the reaction mixture was transferred to the hIL-23 coated 384-well plate to capture unbound (free) SEQ ID NO: 10 and SEQ ID NO: 9, for 20 min at RT. To allow for transformation of ELISA readout results into absolute free SEQ ID NO: 10 and SEQ ID NO: 9 concentrations (cf. below), a standard curve containing varying concentrations of SEQ ID NO: 10 and SEQ ID NO: 9 starting with 100 nM (SEQ ID NO: 10) or 1000 nM (SEQ ID NO: 9)—1:3 serially diluted in 11 steps—was prepared in PBS-T/BSA and incubated for 20 min on the same MSD plate as well.

To quantitate plate-captured SEQ ID NO: 10 and SEQ ID NO: 9, the residual supernatants were discarded and 20 µl HRP-labeled anti-lipocalin antibody was added at a predetermined optimal concentration in PBS-T/BSA and incubated for 1 h at RT. The anti-lipocalin antibody had been obtained by immunization of rabbits with a mixture of lipocalin muteins, and was subsequently coupled to HRP using a kit (EZ-link Plus Activated Peroxidase, Thermo Scientific) according to the manufacturer's intructions, to obtain the antibody-HRP conjugate. Further handling of the plates, data acquisition and evaluation were performed as described in Example 3.

As shown in FIG. 5, the result demonstrates that SEQ ID NO: 9 was fully crossreactive for human, cynomolgus monkey and mouse IL-23, with $IC50_{hIL-23}$=55 nM, $IC50_{cIL-23}$=56 nM and $IC50_{mIL-23}$=88 nM, while SEQ ID NO: 10 was fully crossreactive only for hIL-23 and cIL-23, with a much reduced affinity towards mIL-23, with $IC50_{hIL-23}$=1.4 nM, $IC50_{cIL-23}$=1.3 nM and $IC50_{mIL-23}$=361 nM. As desired, specific binding of both muteins to the IL-23p19 subunit of IL-23 is demonstrated by lack of binding to IL-12p40, the second subunit of IL23.

Example 8: Competitive Mode of Action of Additional Lipocalin Muteins to IL-23

Whether SEQ ID NO: 6, SEQ ID NO: 12 and SEQ ID NO: 13 bind to human IL-23 in a competitive manner was tested in vitro using a competition ELISA format (FIG. 10). The experiment was carried out in analogy to Example 2, with modifications as described below.

All incubation steps were performed with shaking at 300 rpm, and the plate was washed after each incubation step with 80 µl PBS-T buffer (PBS, 0.05% Tween 20) for five times using a Biotek ELx405 select CW washer. In the first step, a 384-well plate suitable for fluorescence measurements (Greiner FLUOTRAC™ 600, black flat bottom, high-binding) was coated with 20 µl of a an anti-human IgG-Fc antibody raised from mouse at a concentration of 5 µg/ml in PBS over night at 4° C. After washing, the receptor coated wells were blocked with 100 µl PBS-T/BSA (2% BSA in PBS containing 0.1% Tween 20) for 2.5 h at room temperature, and blocking solution was removed again by washing. Subsequently, 20 µl of an Fc-fusion of soluble human IL-23 receptor at a concentration of 1 µg/mL was added to the wells of the antibody-coated 384 well plate, resulting in capture of the receptor.

A fixed concentration of 1.6 nM human IL-23 was incubated in solution with varying concentrations of SEQ ID NO: 6, SEQ ID NO: 12 and SEQ ID NO: 13, or with SEQ ID NO: 7 as a negative control, using a starting concentration of 500 nM which was serially diluted at a 1:3 ratio down to 8 pM in PBS-T/BSA buffer. After 20 minutes incubation at room temperature, 20 µl of the reaction mixture was transferred to the IL-23 receptor-coated 384 well plate to capture unbound (free) or non-competitively bound hIL-23 for 20 min at RT. To allow for transformation of ELISA readout results into absolute free hIL-23 concentrations, a standard curve containing varying concentrations of hIL-23 starting with 500 nM (1:3 serially diluted in 10 steps) was prepared in PBS-T/BSA and incubated for 20 min on the same 384 well plate as well.

To allow for detection and quantitation of bound biotinylated hIL-23, the residual supernatants were discarded and 20 µl HRP-labeled Extravidin (Sigma) was added at a predetermined optimal concentration in PBS-T/BSA and incubated for 1 h at RT. After washing, 20 µl fluorogenic HRP substrate (Quantablue, Pierce) was added to each well, and the reaction allowed to proceed for 2 minutes. Further handling of the plates, data acquisition and evaluation were performed in analogy to Example 3, with exception of the instrument used for fluorescence reading, which in the current example was a Safire Microplate reader (Tecan).

In FIG. 10, it clearly demonstrates that SEQ ID NO: 6, SEQ ID NO: 12 and SEQ ID NO: 13 all bound to hIL-23 in competition with the soluble hIL-23 receptor. The result of data fitting as shown in FIG. 10 is as follows: SEQ ID NO: 6 displayed an IC50 value of 25 nM, SEQ ID NO: 12 displayed an IC50 value of 10 nM, and SEQ ID NO: 13 displayed an IC50 value of 11 nM. As expected, the negative control SEQ ID NO: 7 did not bind to hIL-23.

Example 9: Specificity and Species Crossreactivity of Lipocalin Muteins to IL-23 Subunit Specificity and species crossreactivity of SEQ ID NO: 6 (FIG. 11A), SEQ ID NO: 12 (FIG. 11B) and SEQ ID NO: 13 (FIG. 11C) were assayed by a "Solution competition ELISA", in analogy to Example 3, but assaying the targets human IL-23, cynomolgus monkey IL-23 and human IL-12p40.

In the following detailed experimental protocol, incubation and washing steps were performed as described above in the competition ELISA protocol. A 384-well plate suitable for fluorescence measurements (Greiner FLUOTRAC™ 600, black flat bottom, high-binding) was coated with 20 µl of Neutravidin at a concentration of 5 µg/ml in PBS over night at 4° C. After washing, the Neutravidin-coated wells were blocked with 100 µl blocking buffer (PBS-T/BSA) for 1 h at room temperature. After washing again, 20 µl biotinylated hIL-23 at a concentration of 1 µg/mL in PBS was added for 1 h at room temperature, and excess reagent was removed.

In separate experiments, a fixed concentration of 100 nM SEQ ID NO: 6, SEQ ID NO: 12 or SEQ ID NO: 13 was incubated in solution with varying concentrations of ligands (hIL-23, cIL-23, hIL-12p40), using a starting concentration of 1000 nM which was serially diluted at a 1:3 ratio down to 17 pM in PBS-T/BSA. Note that the lipocalein muteins contained a C-terminal Streptag fusion to allow binding and subsequent detection with the aid of an anti-Streptag antibody. After 20 minutes incubation at room temperature, 20 µl of the reaction mixture was transferred to the 384-well plate upon which biotinylated hIL-23 was immobilized to capture unbound (free) SEQ ID NO: 6, SEQ ID NO: 12 or SEQ ID NO: 13, respectively, for 20 min at RT. To allow for transformation of ELISA readout results into absolute free SEQ ID NO: 6, SEQ ID NO: 12 or SEQ ID NO: 13 concentrations, a standard curve containing varying concentrations of each lipocalin mutein starting with 1000 nM (1:3 serially diluted in 11 steps) was prepared in PBS-T/BSA and incubated for 20 min on the same ELISA plate as well.

The residual supernatants were discarded and 20 µl of HRP-conjugated anti-Streptag IgG antibody (Genscript) was added at a predetermined optimal concentration in PBS-T/BSA and incubated for 1 h at RT. After washing, 20 µl fluorogenic HRP substrate (Quantablue, Pierce) was added to each well, and the reaction allowed to proceed for 30 minutes. Data acquisition, handling and fitting were performed in analogy to Example 3.

As shown in FIG. 11, the analysis of the data demonstrates that SEQ ID NO: 6, SEQ ID NO: 12 or SEQ ID NO: 13 were fully crossreactive for human, and cynomolgus monkey IL-23. The fitted 1050 values for SEQ ID NO: 6 (FIG. 11A) were $IC50_{hIL-23}$=89 nM and $IC50_{cIL-23}$=177 nM; for SEQ ID NO: 12 (FIG. 11B), were $IC50_{hIL-23}$=66 nM and $IC50_{cIL-23}$=51 nM; and for SEQ ID NO: 13 (FIG. 11C), were $IC50_{hIL-23}$=24 nM and $IC50_{cIL-23}$=30 nM. As desired, specific binding of all three muteins to the IL-23p19 subunit of IL-23 is demonstrated by lack of binding to IL-12p40, the second subunit of IL-23.

Example 10: Affinity of Additional Lipocalin Muteins to IL-17A

To measure the binding affinity of the lipocalin muteins of SEQ ID NO: 3, SEQ ID NO: 4 and SEQ ID NO: 14 to IL-17A, a SPR-based assay was employed in analogy to Example 1.

The SPR traces and resulting fit curves are shown in FIG. 7(A-C). The results are as follows: SEQ ID NO: 3 bound to IL-17A with an association rate constant of $k_a$=5.0×10$^4$ M$^{-1}$ sec$^{-1}$ and a dissociation rate constant of $k_d$=4.4×10$^{-4}$ sec$^{-1}$, resulting in a dissocation constant of $K_d$=8.7 nM; SEQ ID NO: 4 bound to IL-17A with an association rate constant of $k_a$=5.0×10$^4$ M$^{-1}$ sec$^{-1}$ and a dissociation rate constant of $k_d$=4.4×10$^{-4}$ sec$^{-1}$, resulting in a dissocation constant of $K_d$=8.7 nM; and SEQ ID NO: 14 bound to IL-17A with an association rate constant of $k_a$=1.1×10$^3$ M$^{-1}$ sec$^{-1}$ and a dissociation rate constant of $k_d$=6.5×10$^{-4}$ sec$^{-1}$, resulting in a dissocation constant of $K_d$=0.6 µM.

Example 11: Competitive Mode of Action of Additional Lipocalin Muteins to IL-17A Whether SEQ ID NO: 3, SEQ ID NO: 4 and SEQ ID NO: 14 bind to IL-17A in a competitive mode was tested in vitro using a competition ELISA format (FIG. 8). The experiment was carried out in analogy to Example 2, with modifications as described below.

All incubation steps were performed with shaking at 300 rpm, and the plate was washed after each incubation step with 80 µl PBS-T buffer (PBS, 0.05% Tween 20) for five times using a Biotek ELx405 select CW washer. In the first step, a 384-well plate suitable for fluorescence measurements (Greiner FLUOTRAC™ 600, black flat bottom, high-binding) was coated with 20 µl of a an anti-human IgG-Fc antibody raised from goat at a concentration of 5 µg/ml in PBS over night at 4° C. After washing, the receptor coated wells were blocked with 60 µl PBS-T/BSA (2% BSA in PBS containing 0.1% Tween 20) for 1 h at room temperature. Subsequently, 20 µl of an Fc-fusion of soluble human IL-17RA receptor at a concentration of 1 µg/mL was added to the wells of the antibody-coated 384 well plate, resulting in capture of the receptor.

A fixed concentration of 0.2 nM human IL-17A was incubated in solution with varying concentrations of SEQ ID NO: 3, SEQ ID NO: 4 and SEQ ID NO: 14, or with SEQ ID NO: 7 as a negative control, using a starting concentration of 1000 nM which was serially diluted at a 1:3 ratio down to 17 pM in PBS-T/BSA buffer. After 1 h incubation at room temperature, 20 µl of the reaction mixture was transferred to the IL-17RA receptor-coated 384 well plate to capture unbound (free) or non-competitively bound hIL-17A for 20 min at RT. To allow for transformation of ELISA readout results into absolute free hIL-17A concentrations, a standard curve containing varying concentrations of hIL-17A starting with 500 nM (1:3 serially diluted in 10 steps) was prepared in PBS-T/BSA and incubated for 20 min on the same 384 well plate as well.

To allow for detection and quantitation of bound biotinylated hIL-17A, the residual supernatants were discarded and 20 µl HRP-labeled Extravidin (Sigma) was added at a predetermined optimal concentration in PBS-T/BSA and incubated for 1 h at RT. After washing, 20 µl fluorogenic HRP substrate (Quantablue, Pierce) was added to each well, and the reaction allowed to proceed for 30 minutes. Further handling of the plates, data acquisition and evaluation were performed in analogy to Example 3.

The data in FIG. 8 clearly demonstrates that SEQ ID NO: 3, SEQ ID NO: 4 and SEQ ID NO: 14 all bound to hIL-17A in competition with the soluble hIL-17RA receptor. The result of data fitting as shown in FIG. 8 is as follows: SEQ ID NO: 3 displayed an IC50 value of 0.15 nM, SEQ ID NO: 4 displayed an IC50 value of 0.2 nM, and SEQ ID NO: 14 displayed an IC50 value of 33 nM in this assay. As expected, the negative control SEQ ID NO: 7 did not bind to hIL-17A.

Example 12: Specificity and Species Crossreactivity of Additional Lipocalin Muteins to IL-17A As shown in FIG. 9 (A-C), specificity and species cross-reactivity of SEQ ID NO: 3, SEQ ID NO: 4 and SEQ ID NO: 14 were assayed by an Affinity ELISA, the principle of which was as follows: All ligands to be assayed (hIL-17-A, hIL-17 A/F, hIL-17-F, cIL-17-A, mIL-17A, and hIL-6 as a negative control) were directly coated on a 384-well plate suitable for fluorescence measurements for 1 h. Then, varying concentrations of the three lipocalin muteins or SEQ ID NO: 7 as a negative control were added to the ELISA plate, and bound lipocalin muteins were detected by fluorescence using HRP-conjugated anti-lipocalin antibody and a fluorogenic HRP substrate as described in detail below.

In the following detailed experimental protocol, incubation and washing steps were performed as described above in Example 2. A 384-well plate (Greiner FLUOTRAC™ 600, black flat bottom, high-binding) was coated with each respective ligand by addition of 20 µl of PBS containing hIL-17A, hIL-17 A/F, hIL-17F, cIL-17A, mIL-17A, or hIL-6 at a concentration of 5 µg/mL and incubation overnight at 4° C. Neutravidin at a concentration of 5 µg/ml in PBS over night at 4° C. After washing, the ligand-coated wells were blocked with 100 µl blocking buffer (PBS-T/BSA) for 1 h at room temperature.

After washing again, a lipocalin-mutein dilution series in 20 µl PBS-T/BSA was added to the ligand-coated wells, containing a range of concentrations of SEQ ID NO: 3, SEQ ID NO: 4 and SEQ ID NO: 14 (1000 nM starting concentration, 1:3 dilution in 11 steps). After 1 h incubation at room temperature, the residual supernatants were discarded and 20 µl HRP-conjugated anti-lipocalin antibody (cf. Example 3) was added at a predetermined optimal concentration in PBS-T/BSA and incubated for 1 h at RT. After washing, 20 µl fluorogenic HRP substrate (Quantablue, Pierce) was added to each well, and the reaction allowed to proceed for 30 minutes. The fluorescence intensity of every well on the plate was read using a Genios Plus Microplate reader (Tecan). To determine the apparent affinity $K_{D,app}$ of the lipocalin mutein to each ligand as a measure of target specificity, the fluorescence F was plotted against the lipocalin concentration c(Lipocalin) (FIG. 9) and fitted by nonlinear regression with a single-sites binding model according to $F=F_{MAX}/(1+K_{D,app}/c(Lipocalin))$, with the maximum fluorescence signal in arbitrary units $F_{MAX}$ and $K_{D,app}$ as free parameters. Curve fitting was performed using Graph Pad Prism 4 software.

In summary, binding of SEQ ID NO: 3, SEQ ID NO: 4 and SEQ ID NO: 14 to mIL-17A and hIL-17F was in all cases too low to allow a meaningful fit of the data, and binding to the negative control hIL-6 could not be detected. The remaining ligands were bound with high affinity. For SEQ ID NO: 3, the results were $K_{D,app/hIL-17A}=0.7$ nM, $K_{D,app/hIL-17\ A/F}=0.8$ nM and $K_{D,app/cIL-17A}=0.8$ nM. For SEQ ID NO: 4, the results were $K_{D,app/hIL-17A}=2.4$ nM, $K_{D,app/hIL-17\ A/F}=1.8$ nM and $K_{D,app/cIL-17A}=2.6$ nM. For SEQ ID NO: 14, the results were $K_{D,app/hIL-17A}=4.0$ nM, $K_{D,app/hIL-17A/F}=12.5$ nM and $K_{D,app/cIL-17A}=35.1$ nM.

Example 13: Competitive Mode of Action of an Additional Lipocalin Mutein Binding to IL-23

Whether the lipocalin mutein SEQ ID NO: 15 binds to IL-23 in a competitive mode was tested in vitro using a competition ELISA format in analogy to Example 6, with the modification that biotinylated human IL-23 was employed at a concentration of 0.2 nM (FIG. 12). SEQ ID NO: 11 was used as the negative control. Both SEQ ID NO: 15 and the negative control were serially diluted (at a 1:4 ratio) down to 0.5 pM from a starting concentration of 500 nM. All other conditions of the experiment, including detection and data analysis were analogous to Example 6.

As shown in FIG. 12, the negative control SEQ ID NO: 11 did not bind to hIL-23, in contrast, SEQ ID NO: 15 showed a competitive binding to hIL23, with a fitted IC50 value of 0.3 nM.

Example 14: Lipocalin-Mutein-Mediated Blockade of IL-23 in Cell-Based Proliferation Assays The ability of the lipocalin mutein SEQ ID NO: 15 to neutralize the biological activity of hIL-23 was assessed by the application of short-term proliferation bioassays employing cells that recombinantly expressing the human IL-23 receptor. The Ba/F3 transfectant cell line expresses both subunits of the receptor, hIL-23R and hIL-12Rβ1, and is responsive to both human IL-23 and cynomolgus monkey IL-23. The Ba/F3 cells proliferate responding to hIL-23 in a dose-dependent manner, and proliferation can be inhibited by an IL-23-neutralizing agent. In the assay, SEQ ID NO: 15 was preincubated at various concentrations with a constant amount of hIL-23, and the mixtures were subsequently added to Ba/F3 cells in culture. After three days in culture, the extent of proliferation was assessed by quantifying the number of viable cells. This was performed using the CellTiter-Glo Luminescent Cell Viability Assay (Promega CAT# G7571) to measure ATP levels, which correlate with the number of metabolically active cells. The ability of SEQ ID NO: 15 to neutralize hIL-23 was assessed by its IC50 value, i.e. the concentration of the lipocalin mutein that leads to half-maximal inhibition of hIL-23 induced proliferation.

The detailed procedure of setting up the assay is hereby described in the following. Ba/F3 transfectants were maintained in RPMI-1640 medium, 10% fetal calf serum, 0.05 mM 2-mercaptoethanol, 500 µg/mL geneticin (G418), 1 ng/mL mIL-3, 2 µg/mL puromycin, and 200 µg/mL zeocin. Ba/F3 proliferation assays were carried out in RPMI-1640 medium, 10% fetal calf serum, and 0.05 mM 2-mercaptoethanol. Assays were performed in 96-well white clear flat-bottom plates (Greiner) in 100 µL per well.

On day 1, cells from a Ba/F3 suspension cell culture were counted, pelleted, washed twice in assay medium, and resuspended to $1\times10^5$/mL for plating. 140 pM of hIL-23 (CAT# HZ-1254, HumanZyme)—corresponding to the predetermined EC50 required to induce Ba/F3 cell proliferation—were preincubated for 30 minutes at room temperature with a dilution series of five samples: two lipocalin muteins SEQ ID NO: 10 and SEQ ID NO: 15, the negative control SEQ ID NO: 11, the benchmark antibody ustekinumab (Stelara, obtained from Janssen-Cilag), and a human IgG isotype antibody as another negative control (CAT#. 009-000-003, Dianova). All titration series were performed with a serial 1:3 dilution in assay medium starting with 1 µM test compound. After preincubation, the mixture of the five samples was added to $1\times10^5$ cells each (20 µl to 80 µl cells, providing to a final volume of 100p1) in a 96-well plate. Subsequently, the cells were allowed to proliferate for 72 hours at 37° C. To ensure that the potency of hIL-23 was not subject to inter- and intra-day variability, the dose-dependent proliferation response of the Ba/F3 cells to hIL-23 was checked by adding a dilution series of hIL-23 alone to Ba/F3 cells, using 1:3 dilution steps in assay medium starting with 50 nM. To quantify cell proliferation after 72 hours, 100 µL CellTiter-Glo reagents were added to the cells in each of the wells and incubated for 2 minutes on an orbital shaker to induce cell lysis, and luminescence was measured using the PheraStar FS reader.

IC50 values were determined using GraphPad Prism software (GraphPad Software Inc., San Diego, Calif., USA) by plotting Luminescence signal agains samples' concentration and non-linear regression of the data with sigmoidal dose-response model.

Outcome of the experiment is shown in FIG. 13. The proliferation assay disclosed above (Exp 4 in Table 1 below) was one typical example of the total four proliferation assays performed in accordance with the same procedure described herein, to test the potency of hIL-23-antagonising lipocalin muteins SEQ ID NO: 10 and SEQ ID NO: 15. Table 1 below shows the results of those four independent proliferation assays (Exp 1, Exp 2, Exp 3 and Exp 4). As shown in Table 1 below, the potency (average+/−standard deviation) of three tested samples was determined as following: 323+/−133 nM for SEQ ID NO: 10, 0.6+/−0.3 nM for SEQ ID NO: 15 and 2.4+/−0.7 nM for ustekinumab.

TABLE 1

| Molecule | EC50 [nM] Exp 1 | EC50 [nM] Exp 2 | EC50 [nM] Exp 3 | EC50 [nM] Exp 4 | EC50 [nM] AVERAGE | EC50 [nM] STDEV |
|---|---|---|---|---|---|---|
| SEQ ID NO: 10 | 515.0 | 199.0 | 316.0 | 296.0 | 331.5 | 132.6 |
| SEQ ID: 15 | 0.3 | 0.4 | 1.0 | 0.7 | 0.6 | 0.3 |
| Ustekinumab | 1.9 | 2.3 | 3.5 | 2.0 | 2.4 | 0.7 |

Example 15: Competitive Mode of Action of Fusion Proteins Binding to IL-17A

The performance of the fusion proteins SEQ ID NO: 16 and SEQ ID NO: 17 relative to SEQ ID NO: 5 was assessed using a competition ELISA format in analogy to Example 2. In this experiment, a constant concentration of biotinylated IL-17A was incubated with variable concentrations of four samples, SEQ ID NO: 7, SEQ ID NO: 16, SEQ ID NO: 17 and SEQ ID NO: 5, for 1 h. Among them, SEQ ID NO: 7 was used as the negative control. After this pre-incubation in solution, an aliquot of the sample/IL-17A mixture was transferred to an ELISA plate coated with human IL-17RA receptor to measure the concentration of hIL-17A that was not blocked to bind to the IL-17RA receptor. The experimental procedure, including data analysis, was performed in a manner that was identical to Example 2.

The result of the experiment is shown in FIG. 14. While the negative control SEQ ID NO: 7 did not antagonise the IL-17A/IL-17RA receptor interaction, the fusion proteins SEQ ID NO: 16 and SEQ ID NO: 17 displayed IC50 values that were close to the IC50 of the corresponding lipocalin mutein SEQ ID NO: 5. The fitted values for the experiment were 0.08 nM for SEQ ID NO: 16, 0.05 nM for SEQ ID NO: 17 and 0.01 nM for SEQ ID NO: 5, respectively.

Example 16: Fusion Protein-Mediated Blockade of IL-17A Induced G-CSF Secretion in a Cell-Based Assay A cell-based assay was employed to demonstrate the ability of fusion proteins SEQ ID NO: 16 and SEQ ID NO: 17 to block the biological activity of IL-17A. For comparison, the activity of SEQ ID NO: 5 was also assayed. The assay was based on IL-17A-induced secretion of G-CSF in U87-MG cells and was performed in analogy to Example 4. Recombinant hIL-17A was preincubated with SEQ ID NO: 5, SEQ ID NO: 16, SEQ ID NO: 17 and a negative control was subsequently added to the cells. As for said negative control, a mixture of the lipocalin muteins SEQ ID NO: 7 and SEQ ID NO: 11 was used. The concentration of G-CSF in the supernatant was then measured by ELISA. The experimental procedure, including data analysis, was performed as described for Example 4.

Outcome of the experiment is shown in FIG. 15. Three tested samples SEQ ID NO: 5, SEQ ID NO: 16 and SEQ ID NO: 17 all effectively blocked IL-17A-induced G-CSF secretion, while the negative control had no effect. The potency of SEQ ID NO: 16 and SEQ ID NO: 17 were nearly identical, showing that whether SEQ ID NO: 5 is the N-terminal part or C-terminal part of a fusion protein of the disclosure does not have an effect on potency. The potency of the fusion proteins was only slightly reduced compared to SEQ ID NO: 5 alone. The cell-based assay disclosed above (Exp 1 in Table 2 below) serves as an example of the two independent proliferation assays performed in accordance with the same procedure described herein. The average potency of three tested samples was determined as following as shown in Table 2 below: SEQ ID NO: 5 displayed an IC50 of IC50=0.7 nM, SEQ ID NO: 16 displayed an IC50 of IC50=2.2 nM, and SEQ ID NO: 17 displayed an IC50 of IC50=1.7 nM.

TABLE 2

| Molecule | EC50 [nM] Exp 1 | EC50 [nM] Exp 2 | EC50 [nM] AVERAGE |
|---|---|---|---|
| SEQ IQ NO: 17 | 2.1 | 1.3 | 1.7 |
| SEQ IQ NO: 16 | 2.3 | 2.1 | 2.2 |
| SEQ IQ NO: 5 | 0.7 | 0.7 | 0.7 |

Example 17: Competitive Mode of Action of Fusion Proteins Binding to IL-17A

A competition ELISA assay was employed to assess the competitive binding of the fusion proteins (which contain at least two subunits: one subunit comprising the lipocalin mutein of SEQ ID NO: 5, either at the N- or at the C-terminal side, is linked to another subunit comprising the lipocalin mutein of SEQ ID NO: 15, by a peptide linker (e.g. SEQ ID NO: 18 or SEQ ID NO: 36)) to human IL-17A. The performance of the fusion proteins using SEQ ID NO: 5 as a positive control is assessed using a competition ELISA format in analogy to Example 2. In this experiment, a constant concentration of biotinylated IL-17A is incubated with variable concentrations of thes test molecules, a mixture of SEQ ID NO: 7 and SEQ ID NO: 11, and SEQ ID NO: 5, for 1 h. Among them, the mixture of SEQ ID NO: 7 and SEQ ID NO: 11 is used as the negative control. After this pre-incubation in solution, an aliquot of the sample/IL-17A mixture is transferred to an ELISA plate coated with human IL-17RA receptor to measure the concentration of hIL-17A that is not blocked to bind to the IL-17RA receptor. The experimental procedure, including data analysis, was performed in a manner that is analogous to Example 2.

In the ELISA measuring binding to IL-17A in a manner that antagonises the IL-17A/IL-17RA interaction, the fusion proteins have an IC50 value of 1 nM or less. The positive controls perform as described in Example 2 and Example 15, with slight variations within experimental error; the negative control has no effect.

Example 18: Competitive Mode of Action of Fusion Proteins Binding to IL-23

A competition ELISA assay was employed to assess the competitive binding of the fusion proteins as described in Example 17 to human IL-23. The in vitro assay was performed using a competition ELISA format in analogy to Example 6, with the modification that biotinylated human IL-23 was employed at one of the following concentrations: 0.2 nM, 0.1 nM, 0.05 nM or 0.01 nM. A mixture of SEQ ID NO: 7 and SEQ ID NO: 11 is used as the negative control, while SEQ ID NO: 15 is used as the positive control. The fusion proteins, the positive and the negative control are serially diluted down to 0.5 pM from a starting concentration of 500 nM or lower. All other conditions of the experiment, including detection and data analysis are analogous to Example 6.

In the ELISA measuring binding to IL-23 in a manner that antagonises the IL-23/IL-23 receptor interaction, the fusion proteins have an IC50 value of 5 nM or less. The positive controls perform as described in Example 6 with slight variations within experimental error; the negative control has no effect.

Example 19: Fusion Protein-Mediated Blockade of IL-17A Induced G-CSF Secretion in a Cell-Based Assay A cell-based assay was employed to demonstrate the ability of the fusion proteins as described in Example 17 to block the biological activity of human IL-17A. The fusion proteins contain an IL-17A-binding lipocalin mutein linked to an IL-23-binding lipocalin mutein in both possible orders. For comparison, the IL-17A-binding lipocalin mutein was also assayed.

To assess blockade of the biological activity of human IL-17A, the cell-assay based on IL-17A-induced secretion of G-CSF in U87-MG cells was performed in analogy to Example 4. Recombinant hIL-17A is preincubated with the fusion proteins of the disclosure, a negative control as well as multiple positive controls, and the mixtures are subsequently added to the cells. As for the negative control, a mixture of the lipocalin muteins SEQ ID NO: 7 and SEQ ID NO: 11 is used. As positive controls, SEQ ID NO: 5, benchmark antibody 1 and benchmark antibody 2 are employed. The concentration of G-CSF is measured by ELISA. The experimental procedure, including data analysis, was performed as described in Example 4.

In the cell-based assay of antagonism of IL-17A induced G-CSF secretion, the fusion proteins have an IC50 value of 5 nM or less. The positive controls perform as described in Example 4 and Example 16, with slight variations within experimental error, the negative control has no effect.

Example 20: Fusion Protein-Mediated Blockade of IL-23 Induced Proliferation of Molecules in a Cell Based Assay A cell-based assay was employed to demonstrate the ability of the fusion proteins as described in Example 17 to block the biological activity of human IL-23. The fusion proteins contain an IL-17A-binding lipocalin mutein linked to an IL-23-binding lipocalin mutein in both possible orders. For comparison, the IL-23-binding lipocalin mutein was also assayed.

To assess blockade of the biological activity of human IL-23, the proliferation assay utilizing the Ba/F3 transfectant cell line expressing both hIL-23R and hIL-12Rβ1 was employed in analogy to Example 14. The fusion proteins as well as negative and positive controls are preincubated at various concentrations with a constant amount of hIL-23 and the mixtures are subsequently added to Ba/F3 cells in culture. As the negative control, a mixture of the lipocalin muteins SEQ ID NO: 7 and SEQ ID NO: 11 is used. As positive controls, SEQ ID NO: 15 and the benchmark antibody ustekinumab were employed. After three days in culture, the extent of proliferation was assessed by quantifying the number of viable cells. This can, for example, be performed using the CellTiter-Glo Luminescent Cell Viability Assay (Promega CAT# G7571) to measure ATP levels, which correlate with the number of metabolically active cells. The ability of an IL-23-neutralizing agent to neutralize hIL-23 was assessed by its IC50 value, i.e. the concentration of the agent that leads to half-maximal inhibition of hIL-23 induced proliferation.

In the cell-based assay of antagonism of IL-23 induced cell proliferation, the fusion proteins have an IC50 value of 5 nM or less. The positive control performs as described in Example 14; the negative control has no effect.

Example 21: ABD Fusion-Mediated Blockade of IL-17A Induced G-CSF Secretion in a Cell-Based Assay We employed a cell-based assay to demonstrate the ability of an ABD fusion (SEQ ID NO: 41) to block the biological activity of IL-17A. The assay was based on IL-17A-induced secretion of G-CSF in U87-MG cells (ATCC catalog# HTB-14). In this experiment, a constant concentration of biotinylated IL-17A was preincubated with variable concentrations of (i) the ABD fusion, (ii) a mixture of SEQ ID NO: 15 and SEQ ID NO: 7 or (iii) SEQ ID NO: 5. Among them, the mixture of SEQ ID NO: 15 and SEQ ID NO: 7 was used as the negative control, while and SEQ ID NO: 5 served as the positive control. The concentration of G-CSF in the supernatant was then measured by ELISA.

U87-MG cells were cultured in cell culture flasks under standard conditions (Dulbecco's Modified Eagle Medium DMEM containing 10% fetal calf serum FCS, 37° C., 5% $CO_2$ atmosphere).

On day 1 of the experiment, the adherent cells were dissociated from their substrate with Accutase. Subsequently, cells were centrifuged down for 5 minutes at 1000 rpm, resuspended in medium and filtered through a 100 µm cell strainer (e.g. Falcon) to remove cell aggregates. Cells were then seeded in 96-well flat bottom tissue culture plates (e.g. Greiner) at a density of 8000 cells per well using an end volume of 100 µl. They were incubated overnight under standard conditions.

The ABD fusion and controls: the mixture of SEQ ID NO: 15 and SEQ ID NO: 7 and SEQ ID NO: 5 were the analytes under study. On day 2, a fixed concentration of 0.5 nM recombinant hIL-17A was precincubated with a dilution series of the ABD fusion or controls for 30 minutes at 37° C., with concentrations ranging from 70 nM to the picomolar range. The medium of the cells grown in the 96-well plate was replaced by 80 µl fresh medium, to which 20 µl of the preincubated IL-17A/the ABD fusion or controls solutions were subsequently added. As a further negative control, the ABD fusion or controls were added to the cells without IL-17A. This was done in triplicate for each molecule. The cells were incubated for a further 21 hours under standard conditions. Before collection of the supernatants for measurement of G-CSF levels, wells were visually inspected with a microscope. Wells that exhibit considerable cell death or the presence of cellular aggregates were excluded from evaluation. G-CSF levels were determined using the G-CSF Ultra-Sensitive Kit from MSD. To evaluate the data, the G-CSF concentration in arbitrary units was plotted versus the analyte concentration, c(Analyte). To obtain the ABD fusion or controls concentration at which induction of G-CSF production by U-87 MG cells was reduced to 50% (1050), the curves were fitted by nonlinear regression with a single-sites binding model according to $c(G\text{-}CSF)=c(G\text{-}CSF)_{Min}+[c(G\text{-}CSF)_{Max}-c(G\text{-}CSF)_{Min}]/[1+c(Analyte)/IC50]$, with free parameters being IC50, the induced G-CSF concentration $c(G\text{-}CSF)_{Max}$, and the uninduced G-CSF concentration $c(G\text{-}CSF)_{Min}$. Here, it was assumed that $c(G\text{-}CSF)_{Max}$ and $c(G\text{-}CSF)_{Min}$ were independent of the ABD-fusion or control molecule under study, and they were therefore fitted to common values for all molecules.

In the cell-based assay of antagonism of IL-17A induced G-CSF secretion shown in FIG. 18, the ABD fusion displayed an IC50 value of 1.2 nM, a value which was confirmed in a repeat experiment, where the IC50 value was 1.1 nM. The positive control EQ ID NO: 5 displayed an identical IC50 value of 1.2 nM. The negative control had no effect.

Example 22: ABD Fusion-Mediated Blockade of IL-23 Induced Proliferation of Cells The ability of the ABD fusion, referred to in Example 21, to neutralize the biological activity of hIL-23 was assessed by the application of short-term proliferation bioassays employing cells that recombinantly express the human IL-23 receptor. The Ba/F3 transfectant cell line expresses both subunits of the receptor, hIL-23R and hIL-12Rβ1, and is responsive to both human IL-23 and cynomolgus monkey IL-23. The Ba/F3 cells proliferate responding to hIL-23 in a dose-dependent manner, and proliferation can be inhibited by an IL-23-neutralizing agent. In the assay, the ABD fusion was preincubated at various concentrations with a constant amount of hIL-23, and the mixtures were subsequently added to Ba/F3 cells in culture. After three days in culture, the extent of proliferation was assessed by quantifying the number of viable cells. This was for example performed using the CellTiter-Glo Luminescent Cell Viability Assay (Promega CAT# G7571) to measure ATP levels, which correlate with the number of metabolically active cells. The ability of the ABD fusion to neutralize hIL-23 was assessed by its IC50 value, i.e. the concentration of the protein that leads to half-maximal inhibition of hIL-23 induced proliferation.

The detailed procedure of setting up the assay is described in the following. Ba/F3 transfectants were maintained in RPMI-1640 medium, 10% fetal calf serum, 0.05 mM 2-mercaptoethanol, 500 µg/mL geneticin (G418), 1 ng/mL mIL-3, 2 µg/mL puromycin, and 200 µg/mL zeocin. Ba/F3 proliferation assays were carried out in RPMI-1640 medium, 10% fetal calf serum, and 0.05 mM 2-mercaptoethanol. Assays were performed in 96-well white clear flat-bottom plates (e.g. Greiner) in 100 µL per well.

On day 1, cells from a Ba/F3 suspension cell culture were counted, pelleted, washed twice in assay medium, and resuspended to $1\times10^5$/mL for plating. A fixed concentration of 140 pM hIL-23 (CAT# HZ-1254, HumanZyme)—corresponding to the predetermined EC50 required to induce Ba/F3 cell proliferation—was preincubated for 30 minutes at room temperature with a dilution series of three samples: the ABD fusion (SEQ ID NO: 41), the negative control consisting of a mixture of SEQ ID NO: 8 and SEQ ID NO: 7, and the positive control ABD fusion (SEQ ID NO: 42). All titration series were performed with a serial 1:3 dilution in assay medium starting with 1 µM test compound. After preincubation, the mixture of the three samples was added to $1\times10^5$ cells each (20 µl to 80 µl cells, reaching a final volume of 100 µl) in a 96-well plate. Subsequently, the cells were allowed to proliferate for 72 hours at 37° C. To ensure that the potency of hIL-23 was not subject to inter- and intra-day variability, the dose-dependent proliferation response of the Ba/F3 cells to hIL-23 was checked by adding a dilution series of hIL-23 alone to Ba/F3 cells, starting with 50 nM. To quantify cell proliferation 100 µL CellTiter-Glo reagent was added to the cells in each of the wells and incubates for 2 minutes on an orbital shaker to induce cell lysis, and luminescence was measured using a PheraStar FS reader.

IC50 values were determined by plotting Luminescence signal against the samples concentration and non-linear regression of the data with a sigmoidal dose-response model.

In three independent experiments of antagonism of IL-23 induced cell proliferation, with one example shown in FIG. 19, the ABD fusion (SEQ ID NO: 41) had an IC50 value of 0.38+/−0.04 nM. Within the experimental error, the positive control ABD fusion (SEQ ID NO: 42) had an identical IC50 value of 0.41+/−0.25 nM; the negative control had no effect.

Example 23: Fusion Protein-Mediated Blockade of IL-17A Induced G-CSF Secretion in a Cell-Based Assay We employed a cell-based assay to demonstrate the ability of a fusion protein (SEQ ID NO: 40) to block the biological activity of IL-17A. The assay was based on IL-17A-induced secretion of G-CSF in U87-MG cells (ATCC catalog# HTB-14). In this experiment, a constant concentration of biotinylated IL-17A was preincubated with variable concentrations of (i) the fusion protein, a mixture of (ii) SEQ ID NO: 15 and SEQ ID NO: 7, or (iii) SEQ ID NO: 5. Among them, the mixture of SEQ ID NO: 15 and SEQ ID NO: 7 was used as the negative control, while SEQ ID NO: 5 served as the positive control. The concentration of G-CSF in the supernatant was then measured by ELISA.

U87-MG cells were cultured in cell culture flasks under standard conditions (Dulbecco's Modified Eagle Medium DMEM containing 10% fetal calf serum FCS, 37° C., 5% $CO_2$ atmosphere).

On day 1 of the experiment, the adherent cells were dissociated from their substrate with Accutase. Subsequently, cells were centrifuged down for 5 min. at 1000 rpm, resuspended in medium and filtered through a 100 μm cell strainer (e.g. Falcon) to remove cell aggregates. Cells were then seeded in 96-well flat bottom tissue culture plates (e.g. Greiner) at a density of 8000 cells per well using an end volume of 100 μl. They were incubated overnight under standard conditions.

The fusion protein and controls: the mixture of SEQ ID NO: 15 and SEQ ID NO: 7, and SEQ ID NO: 5 were the analytes under study. On day 2, a fixed concentration of 0.5 nM recombinant hIL-17A was precincubated with a dilution series of fusion protein (or controls) for 30 minutes at 37° C., with concentrations ranging from 70 nM (controls) or 18 nM (fusion protein) to the picomolar range. The medium of the cells grown in the 96-well plate was replaced by 80 μl fresh medium, to which 20 μl of the preincubated IL-17A/fusion protein or controls solutions were subsequently added. As a further negative control, the fusion protein or controls were added to the cells without IL-17A. This was done in triplicate for each molecule. The cells were incubated for a further 21 hours under standard conditions. Before collection of the supernatants for measurement of G-CSF levels, wells were visually inspected with a microscope. Wells that exhibit considerable cell death or the presence of cellular aggregates were excluded from evaluation. G-CSF levels were determined using the G-CSF Ultra-Sensitive Kit from MSD. To evaluate the data, the G-CSF concentration in arbitrary units was plotted versus the analyte concentration, c(Analyte). To obtain the fusion protein or controls concentration at which induction of G-CSF production by U-87 MG cells was reduced to 50% (IC50), the curves were fitted by nonlinear regression with a single-sites binding model according to $c(G\text{-}CSF)=c(G\text{-}CSF)_{Min}+[c(G\text{-}CSF)_{Max}-c(G\text{-}CSF)_{Min}]/[1+c(\text{Analyte})/IC50]$, with free parameters being IC50, the induced G-CSF concentration $c(G\text{-}CSF)_{Max}$, and the uninduced G-CSF concentration $c(G\text{-}CSF)_{Min}$. Here, it was assumed that $c(G\text{-}CSF)_{Max}$ and $c(G\text{-}CSF)_{Min}$ were independent of the fusion protein or control molecule under study, and they were therefore fitted to common values for all molecules.

In the cell-based assay of antagonism of IL-17A induced G-CSF secretion shown in FIG. 20, the fusion protein (SEQ ID NO: 40) displayed an IC50 value of 120 pM. The positive control SEQ ID NO: 5 displayed an IC50 value of 1.2 nM. The negative control had no effect.

Example 24: Fusion Protein-Mediated Blockade of IL-17A Induced G-CSF Secretion in a Cell-Based Assay We employed a cell-based assay to demonstrate the ability of a fusion protein (comprising the amino acids shown in SEQ ID NOs: 43 and 44) to block the biological activity of IL-17A. The assay was based on IL-17A-induced secretion of G-CSF in U87-MG cells (ATCC catalog# HTB-14). In this experiment, a constant concentration of biotinylated IL-17A was preincubated with variable concentrations of (i) the fusion protein, (ii) a mixture of a human IgG isotype antibody (CAT#. 009-000-003, Dianova) and SEQ ID NO: 7, or (iii) SEQ ID NO: 5. Among them, the mixture of human IgG and SEQ ID NO: 7 was used as the negative control, while SEQ ID NO: 5 served as the positive control. The concentration of G-CSF in the supernatant was then measured by ELISA.

U87-MG cells were cultured in cell culture flasks under standard conditions (Dulbecco's Modified Eagle Medium DMEM containing 10% fetal calf serum FCS, 37° C., 5% $CO_2$ atmosphere).

On day 1 of the experiment, the adherent cells were dissociated from their substrate with Accutase. Subsequently, cells were centrifuged down for 5 minutes at 1000 rpm, resuspended in medium and filtered through a 100 μm cell strainer (e.g. Falcon) to remove cell aggregates. Cells were then seeded in 96-well flat bottom tissue culture plates (e.g. Greiner) at a density of 8000 cells per well using an end volume of 100 μl. They were incubated overnight under standard conditions.

The fusion protein and controls: the mixture of human IgG, SEQ ID NO: 7, and SEQ ID NO: 5 were the analytes under study. On day 2, a fixed concentration of 0.5 nM recombinant hIL-17A was precincubated with a dilution series of fusion protein or controls for 30 minutes at 37° C., with concentrations ranging from 70 nM (controls) or 4.4 nM (fusion protein) to the picomolar range. The medium of the cells grown in the 96-well plate was replaced by 80 μl fresh medium, to which 20 μl of the preincubated IL-17A/fusion protein or controls solutions were subsequently added. As a further negative control, fusion protein or controls were added to the cells without IL-17A. This was done in triplicate for each molecule. The cells were incubated for a further 21 hours under standard conditions. Before collection of the supernatants for measurement of G-CSF levels, wells were visually inspected with a microscope. Wells that exhibit considerable cell death or the presence of cellular aggregates were excluded from evaluation. G-CSF levels were determined using the G-CSF Ultra-Sensitive Kit from MSD. To evaluate the data, the G-CSF concentration in arbitrary units was plotted versus the analyte concentration, c(Analyte). To obtain the fusion protein or controls concentration at which induction of G-CSF production by U-87 MG cells was reduced to 50% (IC50), the curves were fitted by nonlinear regression with a single-sites binding model according to $c(G\text{-}CSF)=c(G\text{-}CSF)_{Min}+[c(G\text{-}CSF)_{Max}-c(G\text{-}CSF)_{Min}]/[1+c(\text{Analyte})/IC50]$, with free parameters being IC50, the induced G-CSF concentration $c(G\text{-}CSF)_{Max}$, and the uninduced G-CSF concentration $c(G\text{-}CSF)_{Min}$. Here, it was assumed that $c(G\text{-}CSF)_{Max}$ and $c(G\text{-}CSF)_{Min}$ were independent of the antagonist or control molecule under study, and they were therefore fitted to common values for all molecules.

In the cell-based assay of antagonism of IL-17A induced G-CSF secretion shown in FIG. 21, the fusion protein (comprising the amino acids shown in SEQ ID NOs: 43 and 44) displayed an IC50 value of 170 pM. The positive control SEQ ID NO: 5 displayed an IC50 value of 1.2 nM. The negative control had no effect.

Example 25: Competitive Mode of Action of Binding of Fusion Protein to IL-23

A competition ELISA assay was employed to assess the competitive binding of the fusion protein (comprising the amino acids shown in SEQ ID NOs: 43 and 44), referred to in Example 24, to human IL-23. In this experiment, a constant concentration of biotinylated IL-23 was incubated with variable concentrations of the fusion protein, or an IgG antibody (comprising the amino acids shown in SEQ ID NOs: 51 and 52), for 1 h. The IgG antibody served as the positive control. After this pre-incubation in solution, an aliquot of the sample/IL-23 mixture was transferred to an ELISA plate coated with human IL-23 receptor to measure the concentration of hIL-23 that was not blocked to bind to the IL-23 receptor. The detailed experimental procedure was described as follows.

All incubation steps were performed with shaking 300 rpm, and the plate was washed after each incubation step with 80 µl PBS/0.05% Tween 20 for five times using a Biotek ELx405 select CW washer. A 384 well MSD plate was directly coated with 20 µl of soluble human IL-23 receptor at a concentration of 1 µg/ml in PBS over night at 4° C. After washing, the receptor-coated wells were blocked with 60 µl PBS-T/BSA for 1 h at room temperature.

A fixed concentration of 0.05 nM biotinylated human IL-23 was incubated in solution with varying concentrations of the fusion protein or the positive control IgG, which two are the analytes under study, using starting concentrations of 50 nM (fusion protein) or 100 nM (control), which were serially diluted to picomolar levels in PBS-T/BSA. After 1 h incubation at room temperature, 20 µl of the reaction mixture was transferred to the IL-23 receptor-coated MSD plate to capture unbound (free) or non-competitively bound hIL-23 for 20 min at RT. To allow for transformation of ELISA readout results into absolute free hIL-23 concentrations (cf. below), a standard curve containing varying concentrations of hIL-23 starting with 100 nM (1:4 serially diluted in 11 steps) was prepared in PBS-T/BSA and incubated for 20 min on the same MSD plate as well. To allow for detection and quantitation of bound biotinylated hIL-23, the residual supernatants were discarded and 20 µl Strepavidin Sulfo-tag was added at a concentration of 1 µg/mL in PBS-T/BSA and incubated for 1 h at RT. After washing, 60 µl MSD Read Buffer T (2×) was added to each well and the plate was read within 15 min.

The resulting Electrochemoluminescence (ECL) signal was measured with a suitable instrument such as the SECTOR Imager 2400 (Meso Scale Discovery). The evaluation was performed as follows: free IL-23 concentration $c(IL-23)_{free}$ was calculated (from the standard curve determined in parallel) and plotted versus fusion protein or control concentration, c(Analyte). To obtain the fusion protein concentration at which formation of the IL-23/IL-23R-complex was blocked by 50% (IC50), the curves were fitted by nonlinear regression with a single-sites binding model according to $c(IL-23)_{free}=c(IL-23)_{tot}/(1+c(Analyte)/IC50))$, with the total tracer concentration $c(IL-23)_{tot}$ and the IC50 value as free parameters. The positive control was evaluated in the same manner.

In the ELISA measuring binding to IL-23 in a manner that antagonises the IL-23/IL-23 receptor interaction shown in FIG. 22, two measurements led to an average IC50 value of 0.14 nM (0.16; 0.12) for the fusion protein (comprising the amino acids shown in SEQ ID NOs: 43 and 44). The positive control IgG (comprising the amino acids shown in SEQ ID NOs: 51 and 52), in contrast, had an 1050 value of 0.26 nM (0.22; 0.29).

Example 26: Simultaneous Binding of ABD Fusion to IL-17A and IL-23

Simultaneous binding of an ABD fusion (SEQ ID NO: 41) to both targets (human IL-17A and human IL-23) was assayed in a binding ELISA (FIG. 24), the principle of which was as follows: One target (human IL-17A or human IL-23) was coated on an ELISA plate and variable concentrations of the ABD fusion were added. Bound ABD fusion was detected with the complementary biotinylated target (human IL-23-bio or human IL-17A-bio). Resulting binding curves prove the ABD fusion's ability to bind both targets (IL-17A and IL-23) simultaneously.

All incubation steps were performed with shaking at 300 rpm, and the plate was washed after each incubation step with 100 µL PBS-T buffer (PBS pH7.4, 0.05% Tween 20) for five times using a Biotek ELx405 select CW washer. The assay buffer was PBS-T/BSA (PBS pH7.4, 0.1% Tween 20, 2% BSA). A 384-well plate suitable for fluorescence measurements (Greiner FLUOTRAC™ 600, black flat bottom, high-binding) was coated with 20 µL of human IL-17A or human IL-23 at a concentration of 5 µg/mL in PBS over night at 4° C. After washing, the ligand-coated wells were blocked with 100 µL blocking buffer (PBS-T/BSA) for 1 h at room temperature.

Concentration of ABD fusion solutions was adjusted to 100 nM and then solutions were serially diluted at a 1:3 ratio down to 2 nM in PBS-T/BSA. A volume of 20 µL of the dilution was transferred to the 384-well plate and allowed to bind for 1 h at room temperature.

After the incubation, the residual supernatants were discarded and 20 µL of the complementary biotinylated target (human IL-23-bio or human IL-17A-bio) at 1 µg/mL in PBS-T/BSA was added and incubated for 1 h at RT. Supernatants were discarded again. To detect bound biotinylated target, 20 µL Extravidin HRP (Sigma) in PBS-T/BSA were added at a 1:5000 dilution and incubated for 1 h at room temperature.

After washing, 20 µL fluorogenic HRP substrate (Quantablue, Pierce) was added to each well, and the reaction was allowed to proceed for 5 minutes (human IL-17A coating and human IL-23-bio detection) or 15 minutes (human IL-23 coating and human IL-17A detection). The fluorescence intensity in relative fluorescence units (RFU) of every well on the plate was read using a Genios Plus Microplate reader (Tecan). To obtain the ABD fusion concentration at which the maximum fluorescence signal is reached by 50% (EC50), the curves were fitted by nonlinear regression with a single-site binding model according to $RFU=RFU_{max} \cdot c$ (ABD fusion)/(EC50+c(ABD fusion)), with the maximum relative fluorescence units $RFU_{max}$ and the EC50 value as free parameters. Curve fitting was performed using GraphPad Prism 4 software.

Simultaneous binding of the ABD fusion to human IL-23 and to human IL-17AA could be detected in both orientations of the assays. The fitted EC50 values are shown in FIG. 24.

Example 27: Competitive Mode of Action of Fusion Proteins Binding to IL-17A

The performance of the fusion proteins (SEQ ID NO: 53 and SEQ ID NO: 57) relative to the lipocalin of SEQ ID NO: 5 was assessed using a competition ELISA format in analogy to Example 2. In this experiment, a constant concentration of biotinylated IL-17A was incubated with variable concentrations of four samples, SEQ ID NO: 5, SEQ ID NO: 53, SEQ ID NO: 57 and SEQ ID NO: 7, for 1 h. Among them, SEQ ID NO: 7 was used as the negative control. After this pre-incubation in solution, an aliquot of the sample/IL-17A mixture was transferred to an ELISA plate coated with human IL-17RA receptor to measure the concentration of hIL-17A that was not blocked to bind to the IL-17RA receptor. The experimental procedure, including data analysis, was performed in a manner that was identical to Example 2.

The result of the experiment is shown in FIG. 25. While the negative control SEQ ID NO: 7 did not antagonise the IL-17A/IL-17RA receptor interaction, the fusion proteins SEQ ID NO: 53 and SEQ ID NO: 57 displayed IC50 values that were close to the IC50 of the corresponding lipocalin mutein of SEQ ID NO: 5. The fitted values for the experiment were 0.08 nM for SEQ ID NO: 53, 0.09 nM for SEQ ID NO: 57 and 0.08 nM for SEQ ID NO: 5.

Example 28: Competitive Mode of Action of Fusion Proteins Binding to IL-23

A competition ECL assay was employed to assess the competitive binding of the fusion proteins as described in Example 27 to human IL-23. The in vitro assay was performed using a competition ELISA format in analogy to Example 6, with the modification that biotinylated human IL-23 was employed at one of the following concentrations: 0.2 nM, 0.1 nM, 0.05 nM or 0.01 nM. SEQ ID NO: 11 was used as the negative control, while the lipocalin mutein of SEQ ID NO: 15 was used as positive control. The fusion proteins, the positive and the negative control were serially diluted down to 10 fM from a starting concentration of 500 nM or lower. All other conditions of the experiment, including detection and data analysis were analogous to Example 6.

The result of the experiments is shown in FIG. 26. In the ELISA measuring binding to IL-23 in a manner that antagonises the IL-23/IL-23 receptor interaction, the SEQ ID NO: 53 had an IC50 value of 0.8 nM, SEQ ID NO: 57 had an IC50 value of 1.6 nM, and SEQ ID NO: 15 had an 1050 value of 0.3 nM. The negative control showed no effect.

Example 29: Fusion Protein-Mediated Blockade of IL-17A Induced G-CSF Secretion in a Cell-Based Assay A cell-based assay was employed to demonstrate the ability of the fusion proteins as described in Example 27 to block the biological activity of human IL-17A. The fusion proteins contain an IL-17A-binding lipocalin mutein linked to an IL-23-binding lipocalin mutein in both possible orders. For comparison, the IL-17A-binding lipocalin mutein was also assayed.

A cell-based assay was employed to demonstrate the ability of fusion proteins SEQ ID NO: 53 and SEQ ID NO: 57 to block the biological activity of IL-17A. For comparison, the activity of SEQ ID NO: 5 was also assayed. The assay was based on IL-17A-induced secretion of G-CSF in U87-MG cells and was performed in analogy to Example 4. Recombinant hIL-17A was preincubated with SEQ ID NO: 53, SEQ ID NO: 57, SEQ ID NO: 5 and a negative control was subsequently added to the cells. As for said negative control, a mixture of the lipocalin muteins SEQ ID NO: 7 and SEQ ID NO: 11 was used. The concentration of G-CSF in the supernatant was then measured by ELISA. The experimental procedure, including data analysis, was performed as described for Example 4.

Outcome of the experiment is shown in FIG. 27. Three tested samples (SEQ ID NO: 53, SEQ ID NO: 57 and SEQ ID NO: 5) all effectively blocked IL-17A-induced G-CSF secretion, while the negative control had no effect. The potency of SEQ ID NO: 53 and SEQ ID NO: 57 were nearly identical. The potency of three tested samples was determined as following: SEQ ID NO: 5 displayed an IC50 of 2 nM, SEQ ID NO: 53 displayed an IC50 of 2.9 nM, and SEQ ID NO: 57 displayed an IC50 of 1.5 nM.

Example 30: Fusion Protein-Mediated Blockade of IL-23 Induced Proliferation of Molecules in a Cell Based Assay A cell-based assay was employed to demonstrate the ability of the fusion proteins as described in Example 27 to block the biological activity of human IL-23. The fusion proteins contain an IL-17A-binding lipocalin mutein linked to an IL-23-binding lipocalin mutein in both possible orders. For comparison, the IL-23-binding lipocalin mutein of was also assayed.

To assess blockade of the biological activity of human IL-23, the proliferation assay utilizing the Ba/F3 transfectant cell line expressing both hIL-23R and hIL-12Rβ1 was employed in analogy to Example 14. The fusion proteins as well as negative and positive controls were preincubated at various concentrations with a constant amount of hIL-23 and the mixtures are subsequently added to Ba/F3 cells in culture. As the negative control, a mixture of the lipocalin muteins SEQ ID NO: 7 and SEQ ID NO: 11 is used. As positive controls, SEQ ID NO: 15 and the benchmark antibody ustekinumab were employed. After three days in culture, the extent of proliferation was assessed by quantifying the number of viable cells. This can, for example, be performed using the CellTiter-Glo Luminescent Cell Viability Assay (Promega CAT# G7571) to measure ATP levels, which correlate with the number of metabolically active cells. The ability of an IL-23-neutralizing agent to neutralize hIL-23 was assessed by its IC50 value, i.e. the concentration of the agent that leads to half-maximal inhibition of hIL-23 induced proliferation.

In FIG. 28 the results of the experiment are displayed. In the cell-based assay of antagonism of IL-23 induced cell proliferation the IL23 building block, SEQ ID NO: 15 had an IC50 3.8 nM whereas the benchmark antibody ustekinumab had an IC50 of 11.1 nM. The fusions proteins SEQ ID NO: 53 and SEQ ID NO: 57 displayed comparable IC50 values of 4.3 nM and 4.4 nM, respectively. The negative control had no effect.

Example 31: Competitive Mode of Action of Fusion Proteins Binding to IL-17A

The performance of the fusion protein SEQ ID NO: 55 relative to the mutein of SEQ ID NO: 5 was assessed using a competition ELISA format in analogy to Example 2. In this experiment, a constant concentration of biotinylated IL-17A was incubated with variable concentrations of SEQ ID NO: 55, SEQ ID NO: 5 and SEQ ID NO: 7, for 1 h. Among them, SEQ ID NO: 7 was used as the negative control. After this pre-incubation in solution, an aliquot of the sample/IL-17A mixture was transferred to an ELISA plate coated with human IL-17RA receptor to measure the concentration of hIL-17A that was not blocked to bind to the IL-17RA receptor. The experimental procedure, including data analysis, was performed in a manner that was identical to Example 2.

The result of the experiment is shown in FIG. 29. While the negative control SEQ ID NO: 7 did not antagonise the IL-17A/IL-17RA receptor interaction, an 1050 of 0.019 nM was obtained for the fusion protein SEQ ID NO: 55 while SEQ ID NO: 5 displayed an IC50 of 0.08 nM.

The bivalent fusion protein (SEQ ID NO: 55) displayed an avidity effect to the homodimeric target IL-17A, and was, therefore, considerably more effective than the lipocalin mutein of SEQ ID NO: 5 in antagonising hIL-17A binding to its receptor hIL-17RA.

Example 32: Competitive Mode of Action of Fusion Proteins Binding to IL-23

A competition ECL assay was employed to assess the competitive binding of the fusion protein as described in Example 31 to human IL-23. The in vitro assay was performed using a competition ELISA format in analogy to Example 18. The fusion protein, the positive and the negative control were serially diluted down to 10 fM from a starting concentration of 500 nM or lower. All other conditions of the experiment, including detection and data analysis were analogous to Example 6.

The result of the experiments is shown in FIG. 30. In the ELISA measuring binding to IL-23 in a manner that antagonises the IL-23/IL-23 receptor interaction, the fusion protein SEQ ID NO: 55 had an IC50 value of 0.65 nM while an IC50 of 0.27 was determined for SEQ ID NO: 15.

Embodiments illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present embodiments have been specifically disclosed by preferred embodiments and optional features, modification and variations thereof may be resorted to by those skilled in the art, and that such modifications and variations are considered to be within the scope of this invention. All patents, patent applications, textbooks and peer-reviewed publications described herein are hereby incorporated by reference in their entirety. Furthermore, where a definition or use of a term in a reference, which is incorporated by reference herein is inconsistent or contrary to the definition of that term provided herein, the definition of that term provided herein applies and the definition of that term in the reference does not apply. Each of the narrower species and subgeneric groupings falling within the generic disclosure also forms part of the invention. This includes the generic description of the invention with a proviso or negative limitation removing any subject matter from the genus, regardless of whether or not the excised material is specifically recited herein. In addition, where features are described in terms of Markush groups, those skilled in the art will recognize that the disclosure is also thereby described in terms of any individual member or subgroup of members of the Markush group. Further embodiments will become apparent from the following claims.

The invention claimed is:

1. A lipocalin mutein having binding specificity for IL-17A and comprising, at positions corresponding to positions 26-34, 55-58, 60-61, 64, 101, 104-108, 111, 114 and 153 of the linear polypeptide sequence of mature human tear lipocalin (SEQ ID NO: 1), the same set of amino acid residues that one of the muteins set forth in SEQ ID NOs: 2-5 and 14 has at the respective positions, wherein the lipocalin mutein has at least 90% sequence identity to the amino acid sequence of one of the muteins set forth in SEQ ID NOs: 2-5 and 14.

2. The lipocalin mutein of claim 1, wherein the lipocalin mutein has at least 95% sequence identity to the amino acid sequence of one of the muteins set forth in SEQ ID NOs: 2-5 and 14.

3. The lipocalin mutein of claim 1, wherein the lipocalin mutein comprises, at positions corresponding to positions 26-34, 55-58, 60-61, 64, 101, 104-108, 111, 114 and 153 of the linear polypeptide sequence of mature human tear lipocalin (SEQ ID NO: 1), the same set of amino acid residues set forth in SEQ ID NO: 2 at the respective positions.

4. The lipocalin mutein of claim 1, wherein the lipocalin mutein comprises, at positions corresponding to positions 26-34, 55-58, 60-61, 64, 101, 104-108, 111, 114 and 153 of the linear polypeptide sequence of mature human tear lipocalin (SEQ ID NO: 1), the same set of amino acid residues set forth in SEQ ID NO: 3 at the respective positions.

5. The lipocalin mutein of claim 1, wherein the lipocalin mutein comprises, at positions corresponding to positions 26-34, 55-58, 60-61, 64, 101, 104-108, 111, 114 and 153 of the linear polypeptide sequence of mature human tear lipocalin (SEQ ID NO: 1), the same set of amino acid residues set forth in SEQ ID NO: 4 at the respective positions.

6. The lipocalin mutein of claim 1, wherein the lipocalin mutein comprises, at positions corresponding to positions 26-34, 55-58, 60-61, 64, 101, 104-108, 111, 114 and 153 of the linear polypeptide sequence of mature human tear lipocalin (SEQ ID NO: 1), the same set of amino acid residues set forth in SEQ ID NO: 5 at the respective positions.

7. The lipocalin mutein of claim 1, wherein the lipocalin mutein comprises, at positions corresponding to positions 26-34, 55-58, 60-61, 64, 101, 104-108, 111, 114 and 153 of the linear polypeptide sequence of mature human tear lipocalin (SEQ ID NO: 1), the same set of amino acid residues set forth in SEQ ID NO: 14 at the respective positions.

8. The lipocalin mutein of claim 1, wherein the lipocalin mutein comprises the polypeptide sequence of any of SEQ ID NOs: 2-5 and 14.

9. The lipocalin mutein of claim 1, wherein the lipocalin mutein is fused at its N-terminus and/or its C-terminus to a moiety which is a protein, or a protein domain or a peptide.

10. The lipocalin mutein of claim 1, wherein the lipocalin mutein is conjugated to a compound selected from the group consisting of an organic molecule, an enzyme label, a radioactive label, a colored label, a fluorescent label, a chromogenic label, a luminescent label, a hapten, digoxigenin, biotin, a cytostatic agent, a toxin, a metal complex, a metal, and colloidal gold.

11. The lipocalin mutein of claim 1, wherein the lipocalin mutein is conjugated to a moiety that extends the serum half-life of the mutein, wherein the moiety that extends the serum half-life is selected from the group consisting of a polyalkylene glycol molecule, a polyethylene glycol molecule, hydroxyethyl starch, a Fc part of an immunoglobulin, a CH3 domain of an immunoglobulin, a CH4 domain of an immunoglobulin, an albumin binding peptide, and an albumin binding protein.

12. A diagnostic or analytical kit comprising the lipocalin mutein of claim 1.

13. A nucleic acid molecule comprising a nucleotide sequence encoding the lipocalin mutein of claim 1.

14. A host cell containing the nucleic acid molecule of claim 13.

15. A method of producing the lipocalin mutein of claim 1, wherein the method comprises culturing a host cell transformed with a nucleic acid encoding said lipocalin mutein under conditions suitable for expression of the nucleic acid so that the lipocalin mutein is produced.

16. A method of detecting the presence of IL-17A in a sample, the method comprising contacting the sample with the lipocalin mutein of claim 1 under conditions that allow the formation of a complex of the lipocalin mutein and IL-17A and detecting the complex for the presence of IL-17A.

* * * * *